United States Patent
Vennerstrom et al.

(12) 
(10) Patent No.: US 6,825,230 B2
(45) Date of Patent: Nov. 30, 2004

(54) SPIRO AND DISPIRO 1,2,4-TRIXOLANE ANTIMALARIALS

(75) Inventors: Jonathan L. Vennerstrom, Omaha, NE (US); Yuxiang Dong, Omaha, NE (US); Jacques Chollet, Basel (CH); Hugues Matile, Basel (CH); Maniyan Padmanilayam, Woburn, MA (US); Yuanqing Tang, Omaha, NE (US); William N. Charman, Parkville (AU)

(73) Assignee: Medicines for Malaria Venture MMV (CH)

(*) Notice: Subject to any disclaimer, the term of this patent is extended or adjusted under 35 U.S.C. 154(b) by 0 days.

(21) Appl. No.: 10/642,721

(22) Filed: Aug. 18, 2003

(65) Prior Publication Data

US 2004/0039008 A1 Feb. 26, 2004

Related U.S. Application Data

(63) Continuation-in-part of application No. PCT/US02/19767, filed on Jun. 21, 2002.

(51) Int. Cl.$^7$ .................... A61K 31/357; C07D 323/02
(52) U.S. Cl. ...................................... 514/462; 549/341
(58) Field of Search ........................... 514/462; 549/341

(56) References Cited

U.S. PATENT DOCUMENTS 6,486,199 B1 * 11/2002 Vennerstrom et al. ...... 514/462

OTHER PUBLICATIONS

Kuel, Helmut: "Uber Konstitution und Entstehung der Ozonide von Bis–adamantyliden und Bis–Bicyclo '3.3.1!non–9–yliden" *Chemische Berichte,* vol. 108, No. 4, 1975, pp. 1207–1217, XP002217805.

Tabuchi, T: "Ozonolysis of vinyl ethers in the presence of α–diketones and α–keto esters", *J. Org. Chem.,* vol. 56, 1991, pp. 6591–6595, XP001117555.

Dussault, P.J.: "Selectivity in Lewis acid–mediated fragmentations of peroxides and ozonides; application to the synthesis of alkenes, homoallylethers, and 1,2–dioxolanes", *Perkin Trans,* vol. 1, 2000, pp. 3006–3013, XP001117556.

Griesbaum, Karl, "Diozonides from Coozonolyses of Suitable O–Methyl Oximes and Ketones", *Tetrahedron, Elsevier Science Publishers, Amsterdam, NL,* vol. 53, no. 15, Apr. 14, 1997, pp. 5463–5470 XP004105588.

Meshnick, S:"Artemisinin and the Antimalarial Endoperoxides: From Herbal Remedy to Targeted Chemotherapy", *Microbiological Reviews,* American Society for Microbiology, Washington, DC, U.S. vol. 60, no. 2, Jun. 1, 1996, pp. 301–315, XP002052313.

Jefford, Charles W: "Peroxidic Antimalarials", *Advances in Drug Research,* Academic Press, London, GB, vol. 29, 1997, pp. 271–325, XP002119844.

* cited by examiner

*Primary Examiner*—Ba K. Trinh
(74) *Attorney, Agent, or Firm*—McKee, Voorhees & Sease, P.L.C.

(57) ABSTRACT

A means and method for treating malaria, schistosomiasis, and cancer using a spiro or dispiro 1,2,4-trioxolane is described. The preferred 1,2,4-trioxolanes include a spiroadamantane group on one side of the trioxolane group, and a spirocyclohexyl on the other side of the trioxolane group, whereby the spirocyclohexyl ring is preferably substituted at the 4-position. In comparison to artemisinin semisynthetic derivatives, the compounds of this invention are structurally simple, easy to synthesize, non-toxic, and potent against malarial parasites.

54 Claims, No Drawings

SPIRO AND DISPIRO 1,2,4-TRIXOLANE ANTIMALARIALS

CROSS-REFERENCE TO RELATED APPLICATION

This invention is a continuation-in-part of patent application number PCT/US02/19767 filed Jun. 21, 2002, which claims priority to U.S. Pat. No. 6,486,199, the disclosures of which are hereby expressly incorporated by reference.

FIELD OF THE INVENTION

This invention relates to compositions and methods for treating malaria. Specifically, this invention relates to pharmaceutical compositions including spiro and dispiro trioxolanes, and methods of their use and manufacture.

BACKGROUND OF THE INVENTION

Malaria is an acute and often chronic infectious disease resulting from the presence of protozoan parasites within red blood cells. Caused by single-celled parasites of the genus *Plasmodium*, malaria is transmitted from person to person by the bite of female mosquitos.

Although once prevalent in North America and other temperate regions of the world, today malaria occurs mostly in tropical and subtropic countries. Each year, between 400 million and 600 million people contract the disease, and 1.5 million to 2.7 million die of the disease.

Four species of *Plasmodium* protozoan parasites are generally responsible for malaria, including *Plasmodium vivax, Plasmodium falciparum, Plasmodium malariae,* and *Plasmodium ovale*. Of the four, *Plasmodium falciparum* is the most dangerous, accounting for half of all clinical cases of malaria and 90% of deaths from the disease.

The transmission of malaria begins when a female mosquito bites a human already infected with the malaria parasite. When the infected mosquito bites another human, sporozoites in the mosquito's saliva are transferred into the blood, which then travel to the liver. In the liver, the sporozoites divide rapidly, then enter the bloodstream where they invade red blood cells. Inside these blood cells, the merozoites multiply rapidly until they cause the red blood cells to burst, releasing into the blood stream a new generation of merozoites that then infect other red blood cells.

The symptoms associated with malaria are generally associated with the bursting of the red blood cells. The destruction of the red blood cells spills wastes, toxin, and other debris into the blood. This in turn causes an intense fever that can leave the infected individual exhausted and bedridden. More severe symptoms associated with repeat infections and/or infection by *Plasmodium falciparum* include anemia, severe headaches, convulsions, delirium and, in some instances, death.

The treatment of malaria has been especially difficult due to the ability of malaria parasites to develop resistance to drugs. Quinine, an antimalarial compound that is extracted from the bark of the South American cinchona tree, is one of the oldest and most effective pharmaceuticals in existence. The downside to quinine is that it is short-acting, and fails to prevent disease relapses. Further, quinine is associated with side effects ranging from dizziness to deafness.

Chloroquine is a synthetic chemical similar to quinine. It became the drug of choice for malaria when it was developed in the 1940s due to its effectiveness, ease of manufacture, and general lack of side effects. However, in the last few decades, malaria parasites in many areas of the world have become resistant to chloroquine.

Mefloquine is another synthetic analog of quinine that has been used in the treatment of malaria. Malaria parasites have also developed resistance to mefloquine, however. Mefloquine is also associated with undesirable central nervous side effects in some patients, including hallucinations and vivid nightmares.

Antifolate drugs are effective against malaria parasites by inhibiting their reproduction. Although the parasites have also developed a resistance to antifolate drugs, the drugs can still be used effectively in combination with other types of antimalarials. The use of combination therapies in treating malaria has the drawbacks of being inconvenient and expensive, however.

More recent developments in the treatment of malaria have involved the use of the peroxide functional group, as exemplified by the drug artemisinin, which contains a unique 1,2,4-trioxane heterocyclic pharmacophore. The antimalarial action of artemisinin is due to its reaction with the iron in free heme molecules in the malaria parasite with the generation of free radicals leading to cellular destruction.

The discovery of artemisinin (qinghaosu), a naturally occurring endoperoxide sesquiterpene lactone (Meshnick et al., 1996; Vroman et al. 1999; Dhingra et al., 2000) initiated a substantial effort to elucidate its molecular mechanism of action (Jefford, 1997; Cumming et al., 1997) and to identify novel antimalarial peroxides (Dong and Vennerstrom, 2001). Many synthetic 1,2,4-trioxanes, 1,2,4,5-tetraoxanes, and other endoperoxides have been prepared.

Although the clinically useful semisynthetic artemisinin derivatives are rapid acting and potent antimalarial drugs, they have several disadvantages including recrudescence, neurotoxicity, (Wesche et al., 1994) and metabolic instability. (White, 1994). A fair number of these compounds are quite active in vitro, but most suffer from low oral activity. (White, 1994; van Agtmael et al., 1999). Although many synthetic antimalarial 1,2,4-trioxanes have since been prepared (Cumming et al., 1996; Jefford, 1997), there exists a need in the art to identify new peroxide antimalarial agents, especially those which are easily synthesized, are devoid of neurotoxicity, and which possess improved pharmacokinetic properties, e.g. improved stability, oral absorption, etc.

Accordingly, it is a primary objective of the present invention to provide compositions and methods for prophylaxis and treatment of malaria using spiro and dispiro 1,2,4-trioxolanes.

It is a further objective of the present invention to provide a composition and method for prophylaxis and treatment of malaria using spiro and dispiro 1,2,4-trioxolanes that is nontoxic.

It is a further objective of the present invention to provide a composition and method for prophylaxis and treatment of malaria using spiro and dispiro 1,2,4-trioxolanes that is metabolically stable and orally active.

It is yet a further objective of the present invention to provide a composition and method for prophylaxis and cost-effective treatment of malaria using spiro and dispiro 1,2,4-trioxolanes that do not involve a treatment regimen of more than three days.

It is a further objective of the present invention to provide compositions and methods for prophylaxis and treatment of malaria using spiro and dispiro 1,2,4-trioxolanes that can be used either as stand-alone medicaments or in combination with other agents.

It is still a further objective of the present invention to provide novel intermediates for synthesizing compositions for prophylaxis and treatment of malaria.

The method and means of accomplishing each of the above objectives as well as others will become apparent from the detailed description of the invention which follows hereafter.

SUMMARY OF THE INVENTION

The invention describes a method and composition for treating malaria with spiro and dispiro 1,2,4-trioxolanes, their prodrugs and analogues. The trioxolanes of this invention are sterically hindered on one side of the trioxolane heterocycle in order to provide chemical and metabolic stability to the trioxolane ring for better in vivo activity. In one embodiment, the spiro and dispiro trioxolanes are sterically hindered with an unsubstituted, mono-, di-, or poly-substituted $C_5$–$C_{12}$ spiro cycloalkyl group, which may be spiroadamantane. In this embodiment, the spiro and dispiro trioxolanes may include a spirocyclohexyl that is functionalized or substituted at the 4-position or a spiropiperidyl ring that is functionalized or substituted at the nitrogen atom. In another embodiment, the trioxolanes of this invention include an alkyl bridge from the 4-position of the spirocyclohexyl ring connecting a substituent that is most preferably a weak base. The invention embraces achiral, achiral diastereomers, racemic mixtures, as well as enantiomeric forms of the compounds.

The trioxolanes of this invention possess excellent potency and efficacy against *Plasmodium* parasites, and a low degree of neurotoxicity. In addition, several of the trioxolanes are suitable for both oral and non-oral administration. Moreover, in comparison to artemisinin semisynthetic derivatives, the compounds of this invention are structurally simple, easy and inexpensive to synthesize, and can be used effectively alone or in conjunction with other antimalarials.

DETAILED DESCRIPTION OF THE PREFERRED EMBODIMENT

The present invention relates to the development of spiro and dispiro 1,2,4-trioxolanes for use in the prophylaxis and treatment of malaria. The present invention is predicated upon the unexpected discovery that trioxolanes that are relatively sterically hindered on at least one side of the trioxolane heterocycle provide metabolic and chemical stability to the trioxolane ring, thereby providing better in vivo activity, especially with respect to oral administration.

As used herein the term "prophylaxis-effective amount" refers to a concentration of compound of this invention that is effective in inhibiting or preventing infection and subsequent disease by malarial parasites. Likewise, the term "treatment-effective amount" refers to a concentration of compound that is effective in treating malaria in terms of preventing an increase in the concentration of malarial parasites, decreasing the concentration of malarial parasites, and/or "curing" a malaria infection, i.e. survival for 30 days post-infection.

Tetrasubstituted trioxolanes are relatively stable peroxidic compounds based on literature precedent (Griesbaum et al., 1997a; 1997b). This may be due, in part, to the lack of α-hydrogen atoms. The present inventors have synthesized new compounds in the trioxolane class having both superior antimalarial potency and oral efficacy. Furthermore, the compounds of this invention have low toxicity, and half-lives conducive to treatment of malaria which are believed will permit short-term treatment regimens comparing favorably to other artemisinin-like drugs. These compounds may also be used in malaria prophylaxis.

In previous application, the present inventors disclosed certain novel tetrasubstituted trioxolanes having the following structural formula:

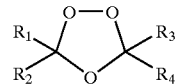

wherein $R_1$, $R_2$, $R_3$, and $R_4$ represent combinations of ring systems, acyclic systems, and functional groups that provide sufficient steric hindrance about the trioxolane ring in order to give the ring chemical and metabolic stability. $R_1$, $R_2$, $R_3$ and $R_4$ may be the same or different, and may be a linear or branched alkyl, aryl, or alkaryl group which is optionally substituted. In the alternative, $R_1$ and $R_2$ taken together and/or $R_3$ and $R_4$ taken together may form an alicyclic group which is optionally interrupted by one or more oxygen, sulfur or nitrogen atoms and which group is optionally substituted. In no event may any of $R_1$, $R_2$, $R_3$ or $R_4$ be hydrogen.

In one embodiment, the compounds include those whereby $R_1$ and $R_2$ taken together and/or $R_3$ and $R_4$ taken together is a mono- or di-substituted $C_5$–$C_{12}$ spirocycloalkyl group which is optionally interrupted by one or more oxygen, sulfur, or nitrogen atoms, and which group is optionally substituted. In another embodiment, $R_1$ and $R_2$ taken together or $R_3$ and $R_4$ is spiroadamantane.

The present invention discloses a new embodiment of trioxolane compounds having the following structure:

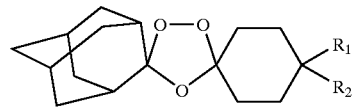

The spirocyclohexyl ring may be optionally interrupted by one or more oxygen, sulfur or nitrogen atoms. In this regard, $R_1$ and $R_2$ may be the same or different, and may be hydrogen, substituted or unsubstituted linear or branched alkyl, aryl, and alkaryl groups and substituted or unsubstituted alicyclic groups that may be interrupted by one or more oxygen, sulfur or nitrogen atoms, substituted or unsubstituted aromatic or heterocyclic groups that may be interrupted by one or more oxygen, sulfur or nitrogen atoms, a hydroxy group, or a halogen. In one embodiment, $R_1$ or $R_2$ is an amide. It has been unexpectedly found that amide-containing substituents at the 4-position provide antimalarial compounds with good oral absorption, good antimalarial activity, and good pharmacokinetics, i.e. rates of absorption, metabolism, and elimination that are suitable and advantageous for the prophylaxis and treatment of malaria.

In another embodiment, the compounds of this invention have the following structural formula:

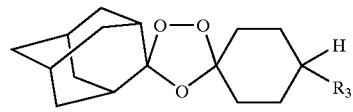

whereby $R_3$ is $(CH_2)_n$—Y. In this formula, Y represents a functional group that, in one embodiment, is non-acidic, and in another embodiment is a weak base. The Y functional group may be an alkyl, ketone, acid, alcohol, amine, amide, sulfonamide, guanidine, ether, ester, oxime, urea, oxime ether, sulfone, lactone, carbamate, semicarbazone, phenyl, or heterocycle. In one embodiment, n=1. The alkyl "bridge" group has been found to improve the metabolically stability (i.e. oral activity and pharmacokinetics) of the antimalarial compounds of this invention.

In another embodiment of the invention, the trioxolanes are weak bases, which provide an ideal combination of high intrinsic potency and good oral activity. Two promising trioxolane structural subtypes are weak base amides of trioxolane amine OZ209 and trioxolane acid OZ78. These compounds have one of the following two structural formulas:

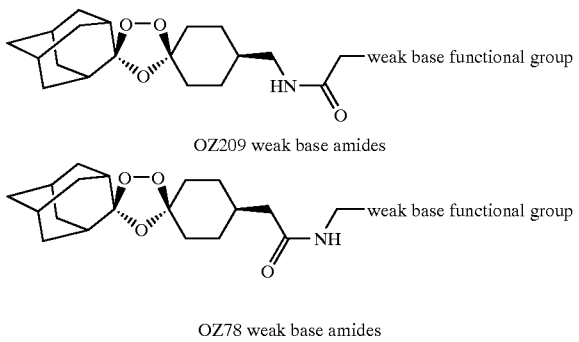

OZ209 weak base amides

OZ78 weak base amides

Other substituents at the 4-position of the spirocyclohexyl ring are also possible that fall within the scope of this invention. The spirocyclohexyl ring may also be substituted at other positions besides the 4-position. For instance, the inventors have synthesized several compounds substituted at the 2-position of the spirocyclohexyl ring that provide excellent antimalarial potency.

In another embodiment of this invention, the compounds include an alkyl group connecting the substituent at the 4-position to the spirocyclohexyl ring. In one embodiment, the alkyl group is methyl or ethyl. In another embodiment, the alkyl group is methyl. The substituent may also be directly attached to the 4-position of the spirocyclohexyl ring.

The present inventors have identified two orally active lead dispiro-1,2,4-trioxolanes, OZ03 and OZ05:

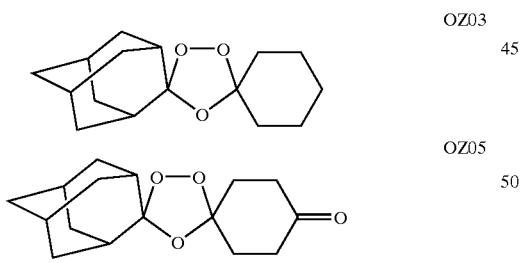

OZ03

OZ05

These trioxolanes have $IC_{50}$s between 1 and 5 ng/ml against *P. falciparum* in vitro, and presumably possess good therapeutic indices as no toxicity is evidence for either compound in a neuroblastoma cell line or at single 640 mg/kg doses in mice in the Rane test. These results contrast with published data (de Almeida Barbosa et al., 1992; 1996) disclosing the weak in vitro antimalarial potency of several tricyclic trioxolanes, the best of which has an $IC_{50}$ of 2000 ng/ml against *P. falciparum* in vitro.

A notable feature of these trioxolanes in comparison to the artemisinin semisynthetic derivatives is their structural simplicity. A potential advantage of trioxolanes over both trioxanes (Jefford, 1997; Cumming et al., 1997) and tetraoxanes (Vennerstrom et al., 2000) is a more convenient access to structurally diverse, non-symmetrical, and in many cases, achiral compounds.

Below are several dispiro 1,2,4-trioxolanes synthesized in accordance with the teachings of this invention. "OZ" is an internal designation for these compounds that will be used throughout the remainder of the application for convenience. The structures of OZ01-OZ90 have been previously disclosed in prior application U.S. Ser. No. 09/886,666 (U.S. Pat. No. 6,486,199), and are therefore not repeated here.

OZ Series 11 (OZ91–OZ99)

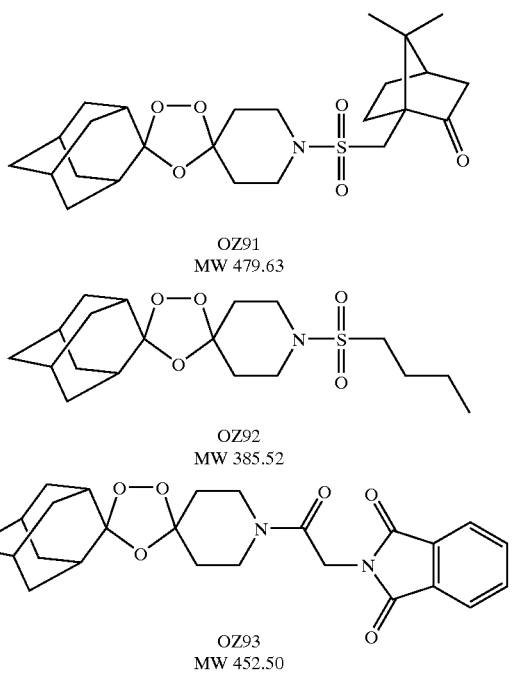

OZ91
MW 479.63

OZ92
MW 385.52

OZ93
MW 452.50

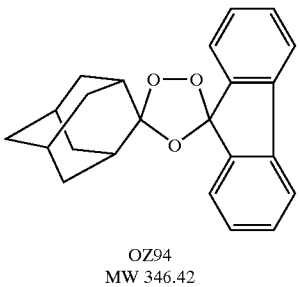

OZ94
MW 346.42

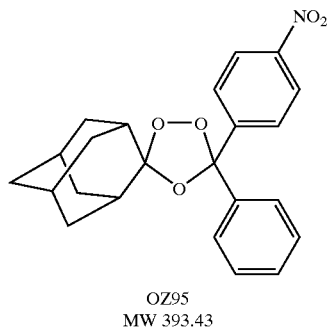

OZ95
MW 393.43

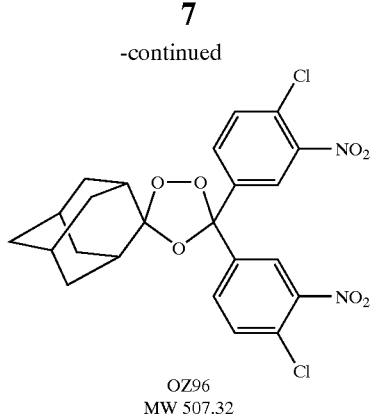
OZ96
MW 507.32
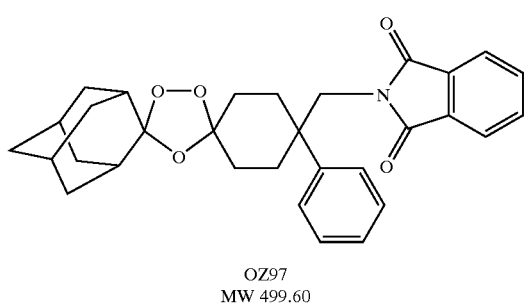
OZ97
MW 499.60
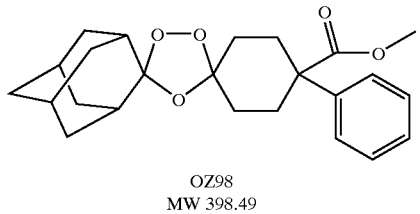
OZ98
MW 398.49
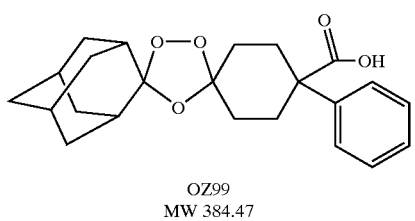
OZ99
MW 384.47
OZ Series 12 (OZ100–OZ108)
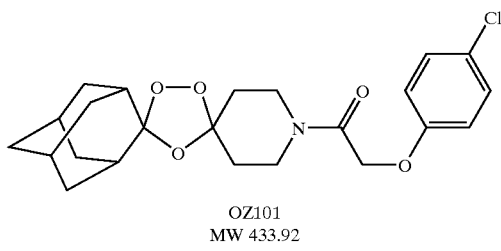
OZ100
MW 370.44
OZ101
MW 433.92
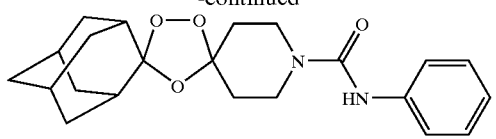
OZ102
MW 384.47
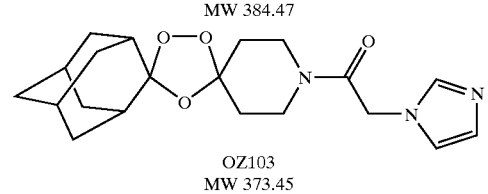
OZ103
MW 373.45
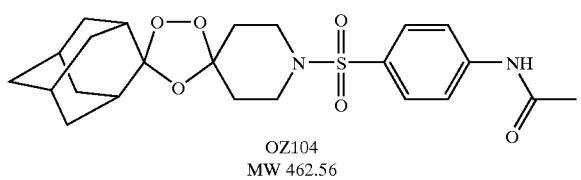
OZ104
MW 462.56
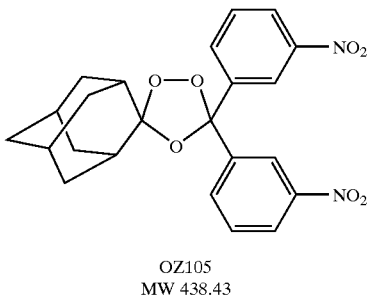
OZ105
MW 438.43
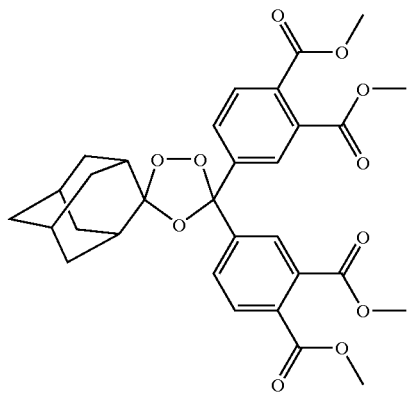
OZ106
MW 580.58
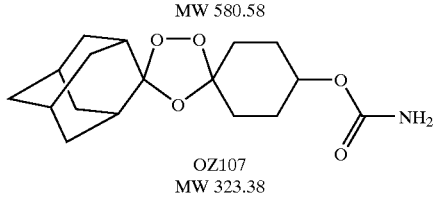
OZ107
MW 323.38
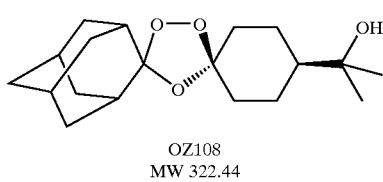
OZ108
MW 322.44

OZ Series 13 (OZ109–OZ117)

OZ109
MW 415.44

OZ110
MW 363.45

OZ111
MW 363.49

OZ112
MW 381.42

OZ113
MW 337.41

OZ114
MW 456.56

OZ115
MW 441.63

OZ116
MW 323.38

OZ117
MW 405.96

OZ Series 14 (OZ118–OZ126)

OZ118
MW 336.42

OZ119
MW 294.39

OZ120
MW 480.55

OZ121
MW 396.47

OZ122
MW 424.44

OZ123
MW 357.28

OZ124
MW 373.44

-continued
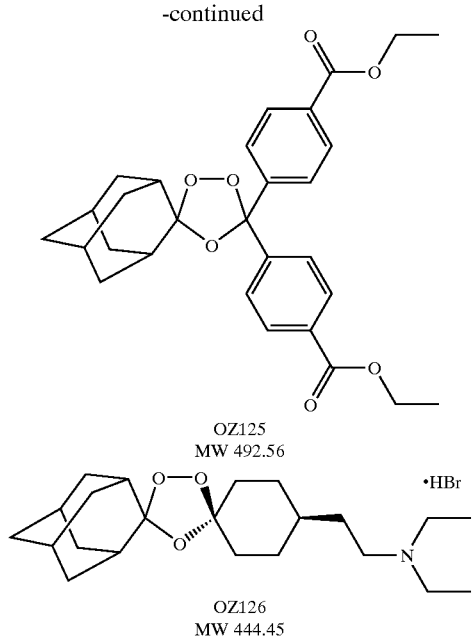
OZ125
MW 492.56
OZ126
MW 444.45
OZ Series 15 (OZ127–OZ135)
OZ127
MW 323.38
OZ128
MW 348.43
OZ129
MW 379.49
OZ130
MW 350.41
OZ131
MW 419.54
-continued
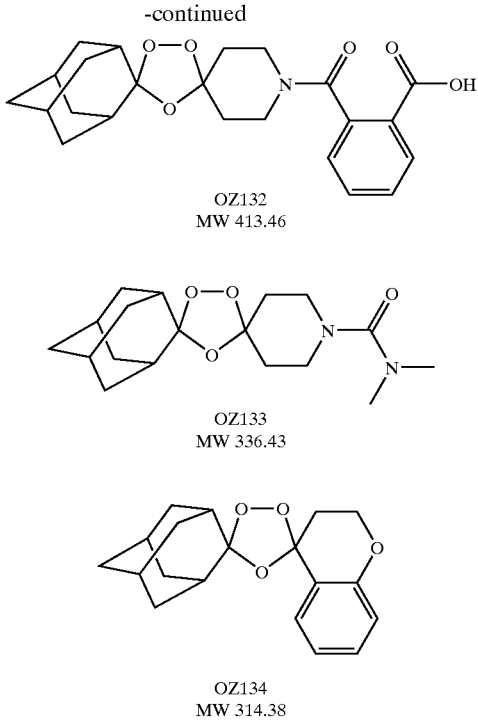
OZ132
MW 413.46
OZ133
MW 336.43
OZ134
MW 314.38
OZ135
MW 436.45
OZ Series 16 (OZ136–OZ144)
OZ136
MW 409.47
OZ137
MW 315.84

-continued
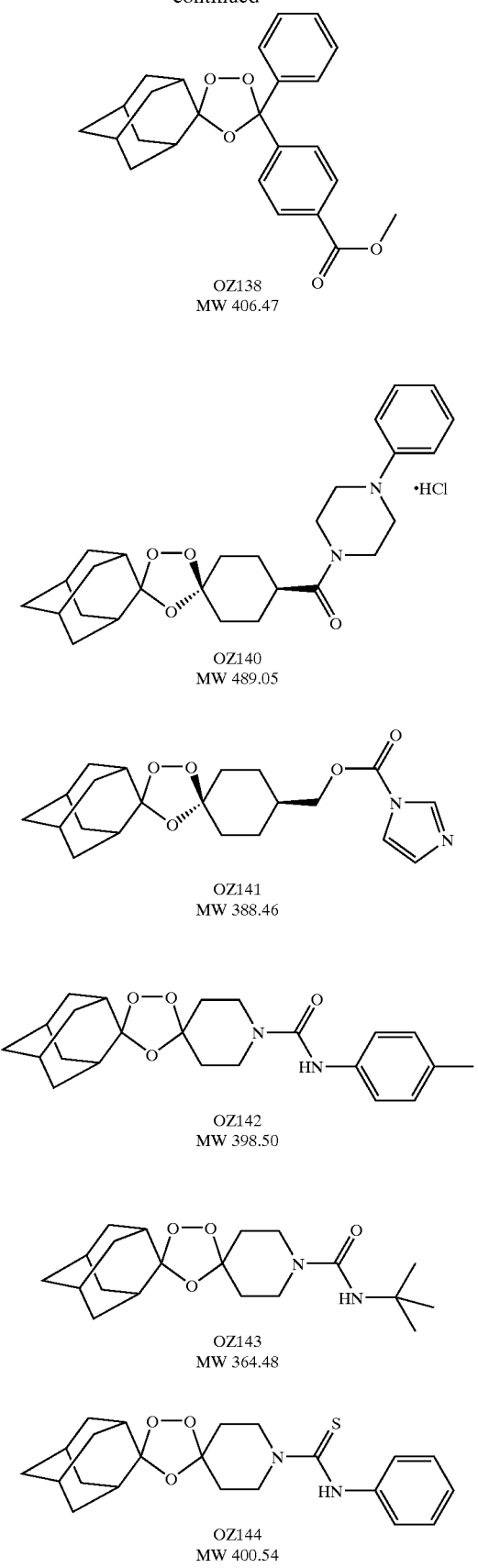
OZ Series 17 (OZ145–OZ153)
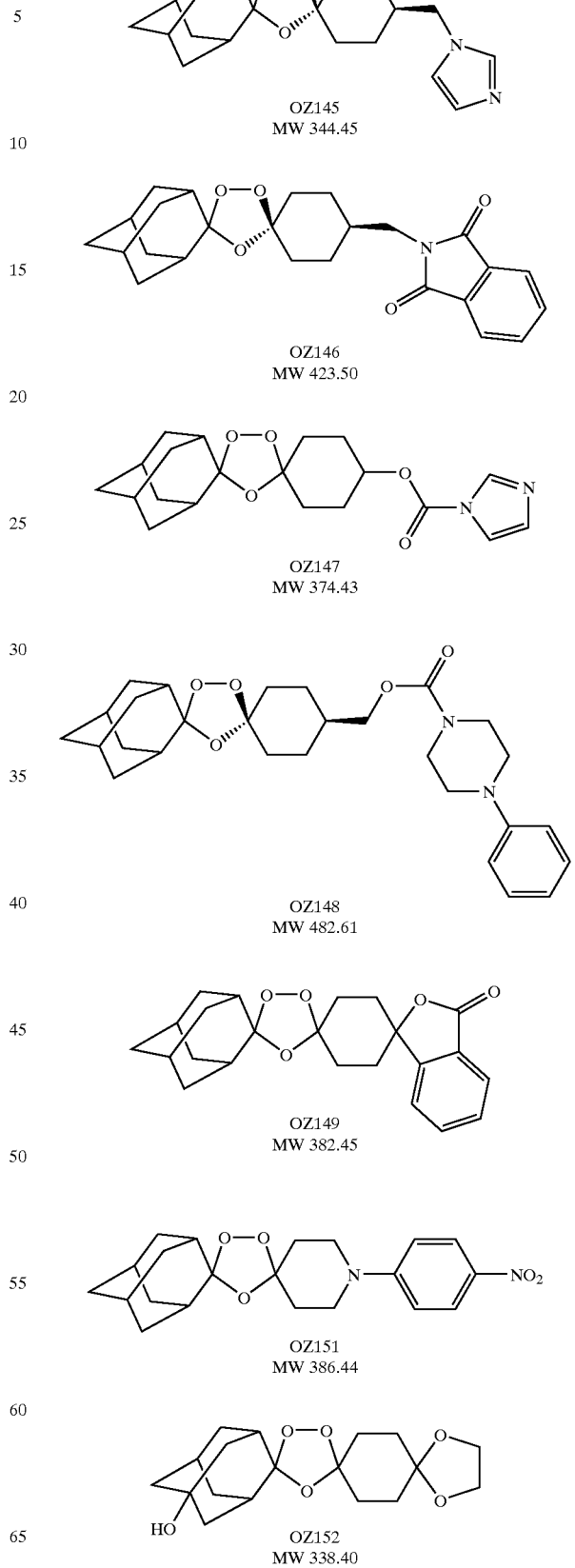

-continued
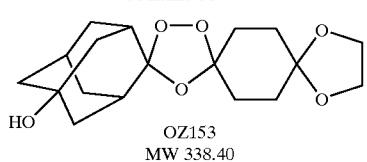
OZ153
MW 338.40
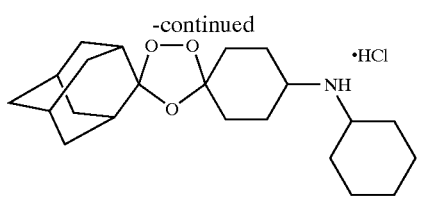
OZ162
MW 397.98
OZ Series 18 (OZ154–OZ162)
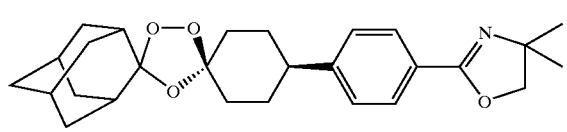
OZ154
MW 437.57
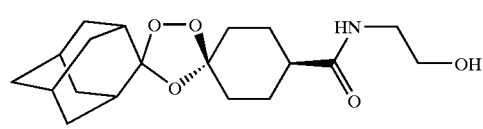
OZ155
MW 351.44
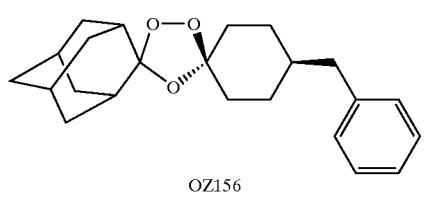
OZ156
MW 354.48
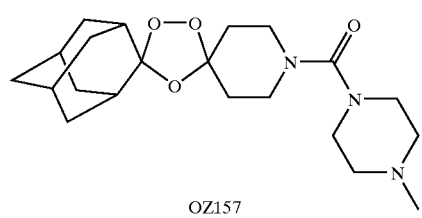
OZ157
MW 391.50
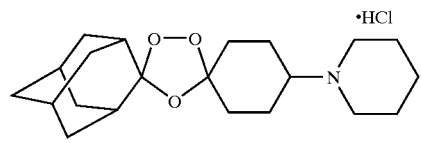
OZ159
MW 383.95
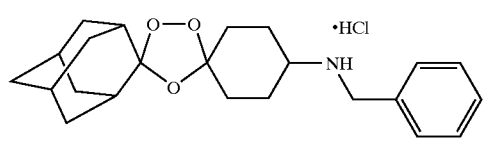
OZ160
MW 405.96
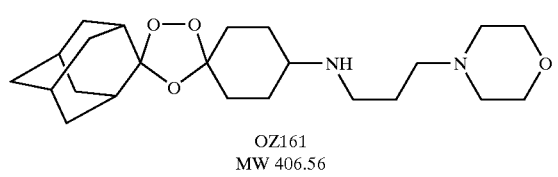
OZ161
MW 406.56
OZ Series 19 (OZ163–OZ171)
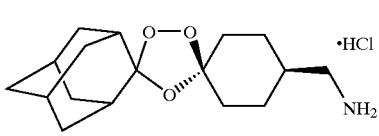
OZ163
MW 329.86
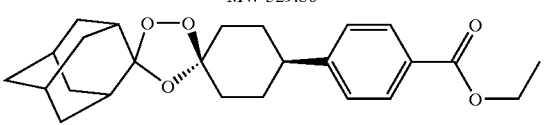
OZ164
MW 412.52
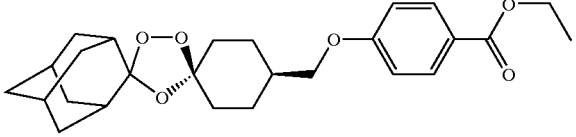
OZ165
MW 384.47
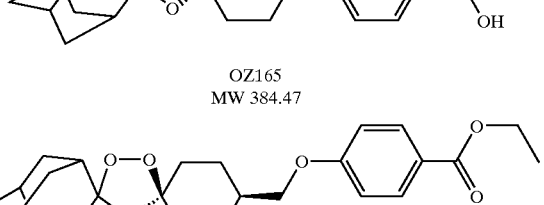
OZ166
MW 442.54
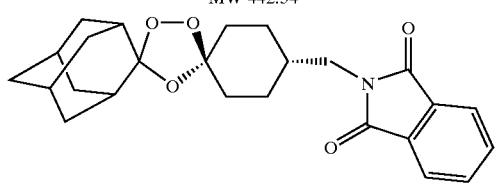
OZ167
MW 423.50
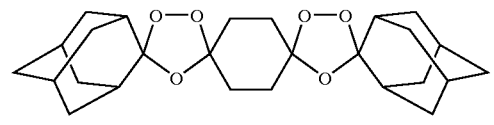
OZ169
MW 444.56
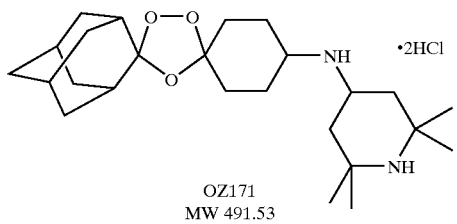
OZ171
MW 491.53

OZ Series 20 (OZ172–OZ180)
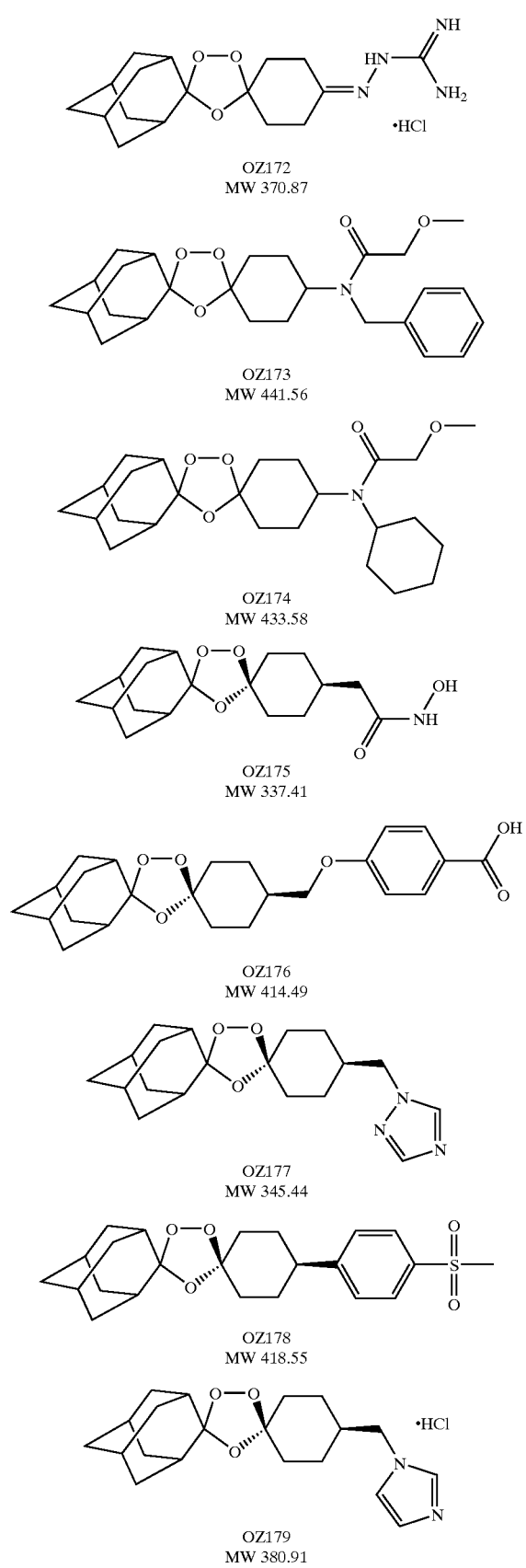
-continued
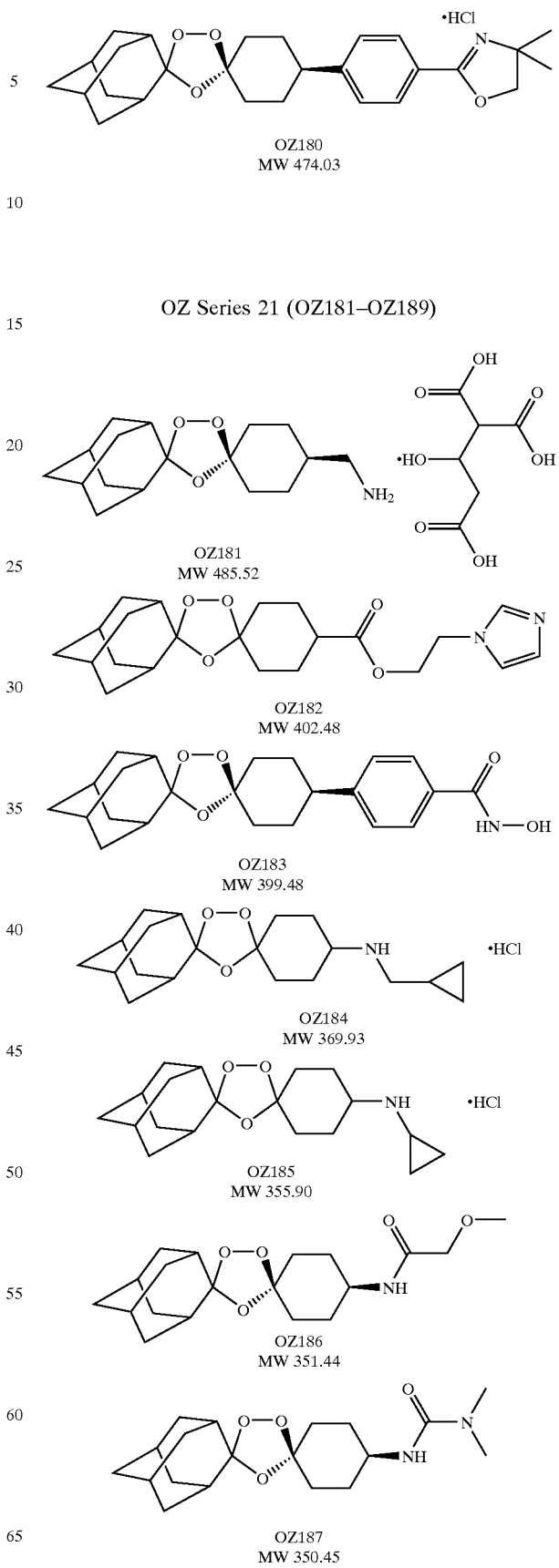
OZ Series 21 (OZ181–OZ189)

-continued
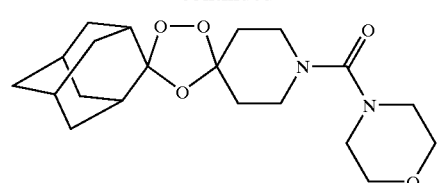
OZ188
MW 378.46
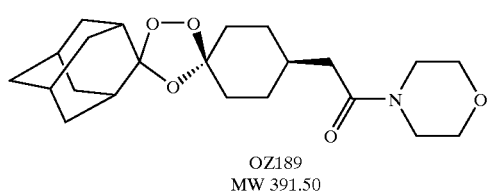
OZ189
MW 391.50
OZ Series 22 (OZ190–OZ198)
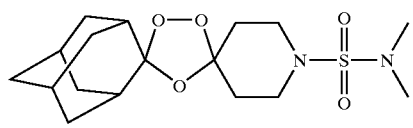
OZ190
MW 372.48
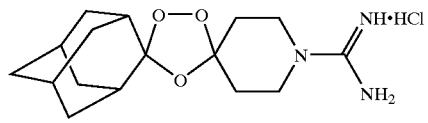
OZ191
MW 343.85
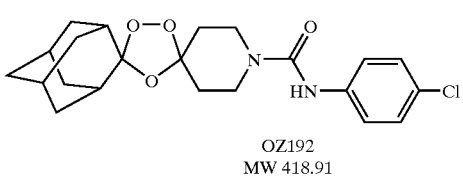
OZ192
MW 418.91
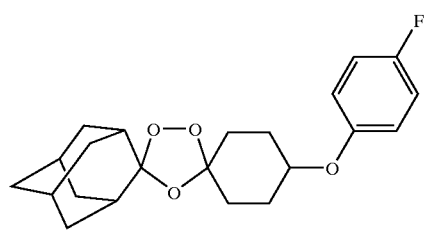
OZ193
MW 374.45
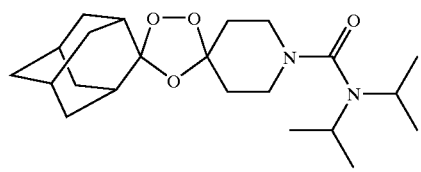
OZ194
MW 392.53
-continued
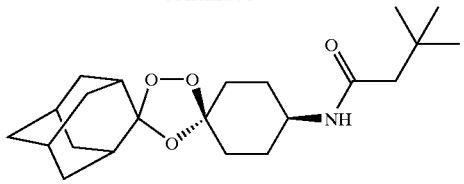
OZ195
MW 377.52
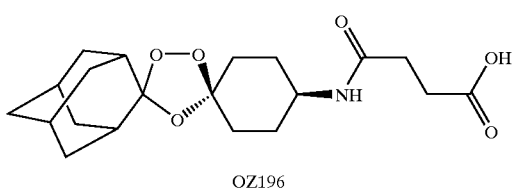
OZ196
MW 379.45
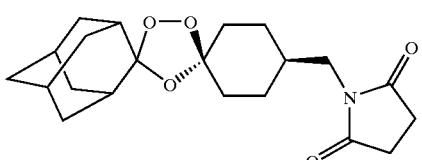
OZ197
MW 375.46
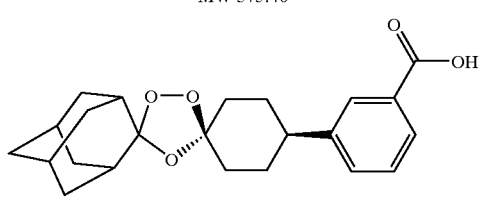
OZ198
MW 384.47
OZ Series 23 (OZ199–OZ207)
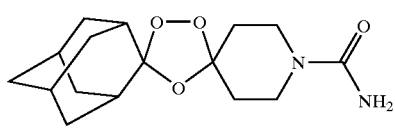
OZ199
MW 308.37
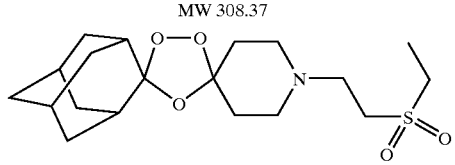
OZ200
MW 385.52
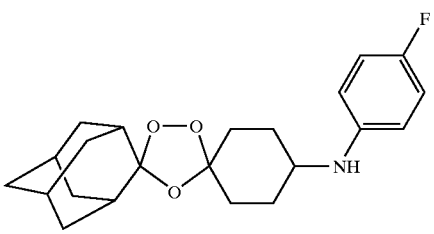
OZ201
MW 373.46

OZ202
MW 407.50

OZ203
MW 362.46

OZ204
MW 412.52

OZ205
MW 336.47

OZ206
MW 376.45

OZ207
MW 465.60

OZ Series 24 (OZ208–OZ216)

OZ208
MW 412.52

OZ209
MW 389.51

OZ210
MW 418.55

OZ211
MW 344.45

OZ212
MW 459.56

OZ213
MW 351.44

OZ214
MW 398.49

OZ215
MW 437.53

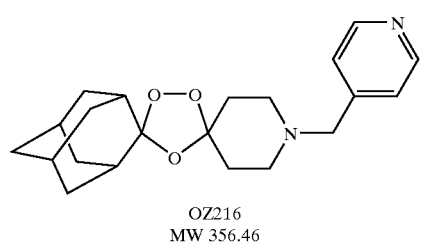
OZ216
MW 356.46
OZ Series 25 (OZ217–OZ225)
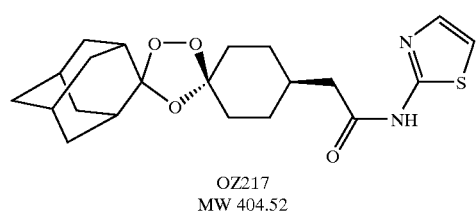
OZ217
MW 404.52
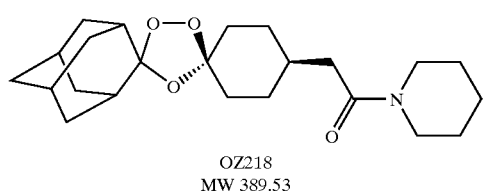
OZ218
MW 389.53
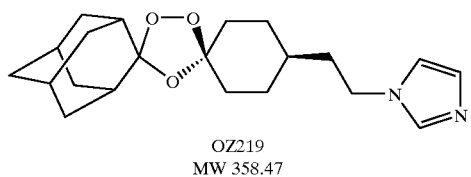
OZ219
MW 358.47
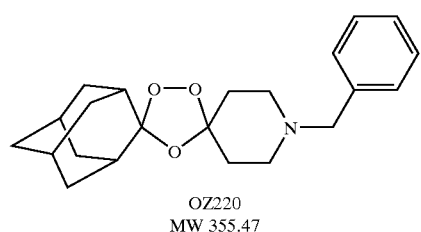
OZ220
MW 355.47
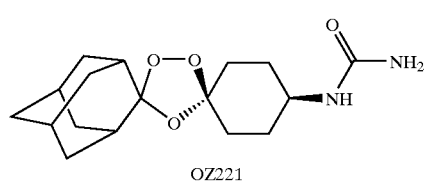
OZ221
MW 322.40
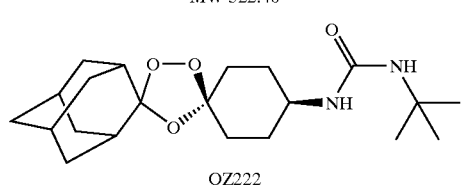
OZ222
MW 378.51
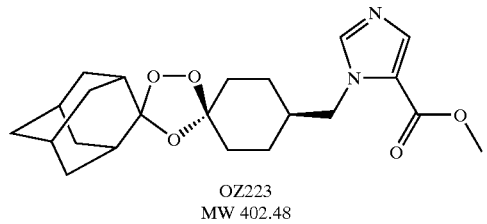
OZ223
MW 402.48
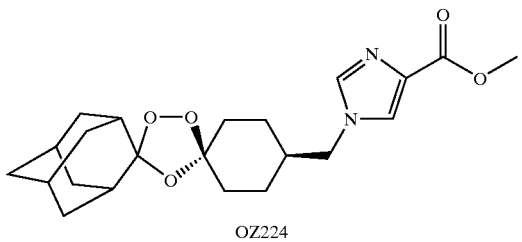
OZ224
MW 402.48
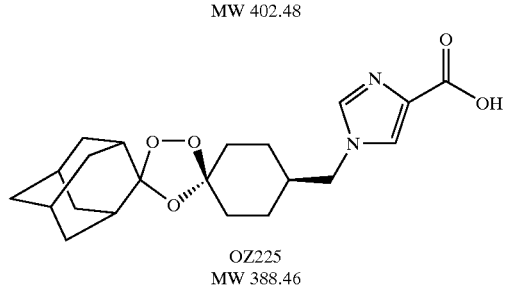
OZ225
MW 388.46
OZ Series 26 (OZ226–OZ234)
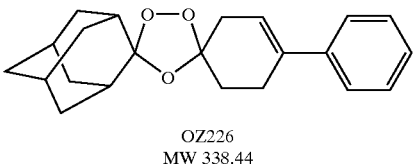
OZ226
MW 338.44
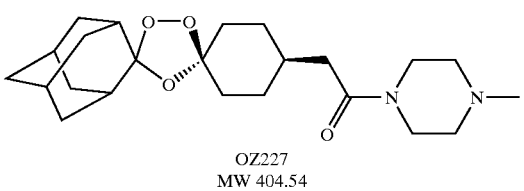
OZ227
MW 404.54
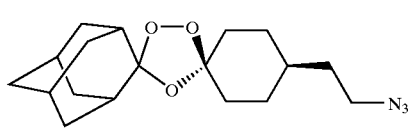
OZ228
MW 333.43
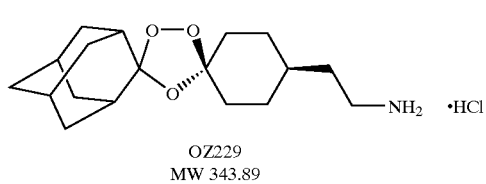
OZ229
MW 343.89

-continued
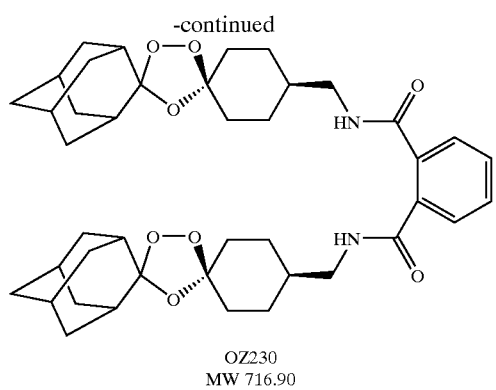
OZ230
MW 716.90
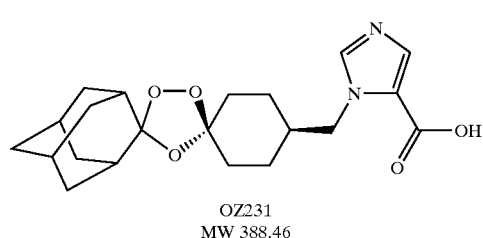
OZ231
MW 388.46
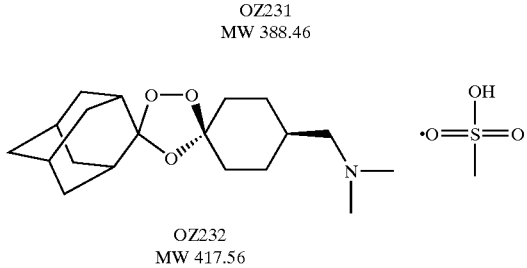
OZ232
MW 417.56
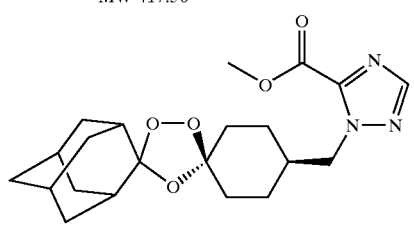
OZ233
MW 403.47
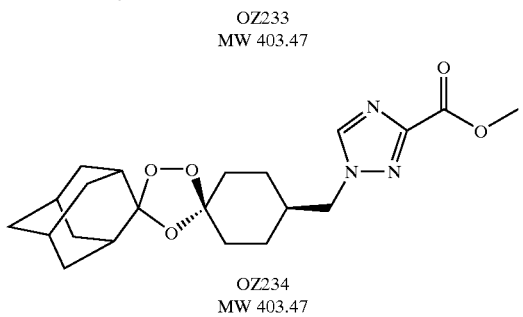
OZ234
MW 403.47
OZ Series 27 (OZ235–OZ243)
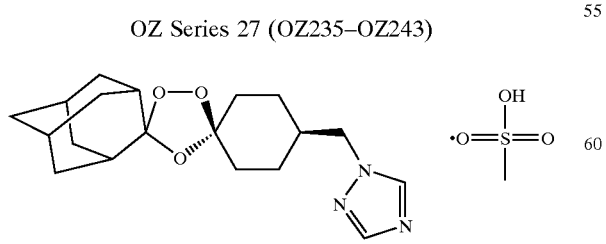
OZ235 (OZ177b)
MW 441.54
-continued
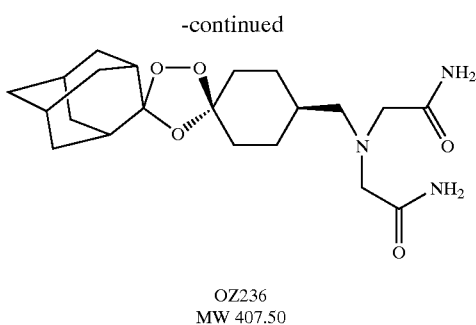
OZ236
MW 407.50
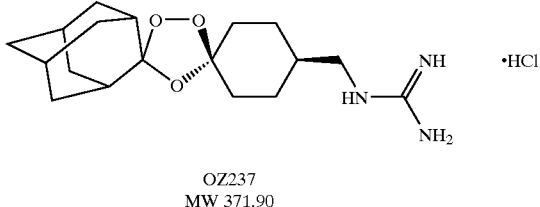
OZ237
MW 371.90
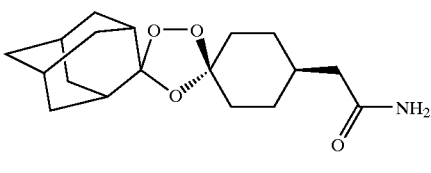
OZ243
MW 321.41
OZ Series 28 (OZ244–OZ252)
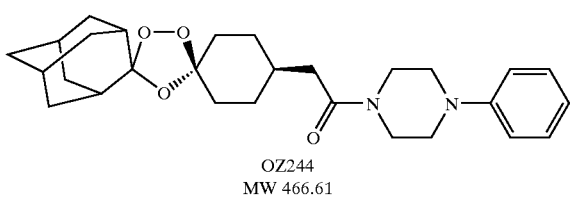
OZ244
MW 466.61
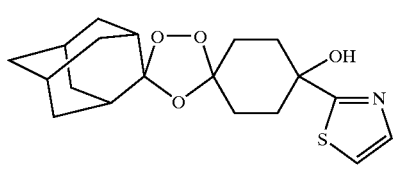
OZ247
MW 363.47
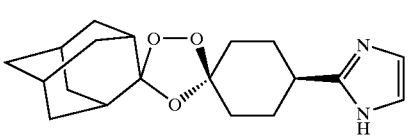
OZ251
MW 330.42

-continued
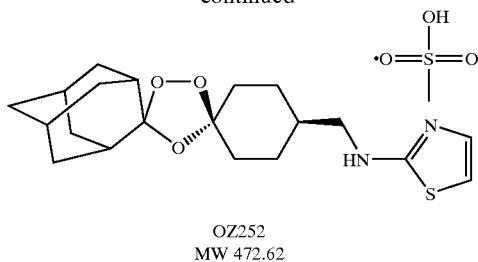
OZ252
MW 472.62
OZ Series 29 (OZ253–OZ261)
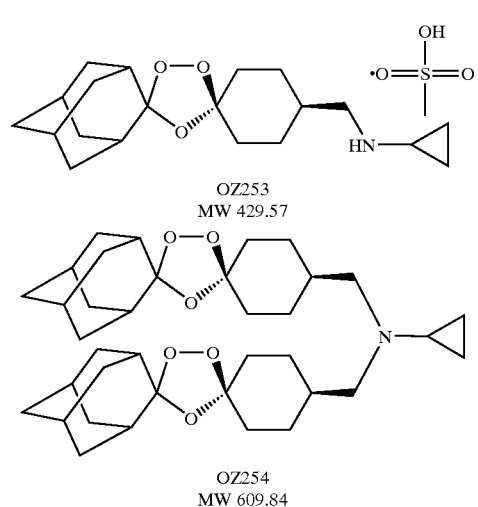
OZ253
MW 429.57
OZ254
MW 609.84
OZ255
MW 398.50
OZ256
MW 350.45
OZ257
MW 371.49
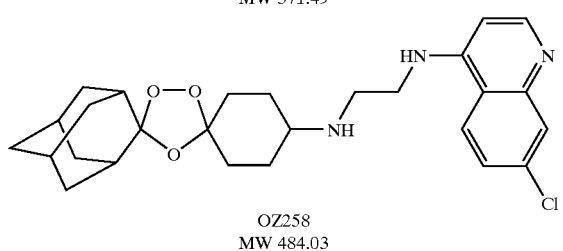
OZ258
MW 484.03
-continued
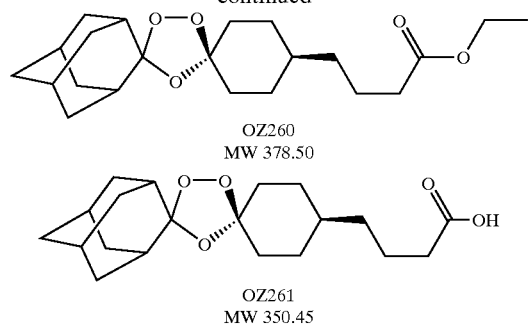
OZ260
MW 378.50
OZ261
MW 350.45
OZ Series 30 (OZ262–OZ270)
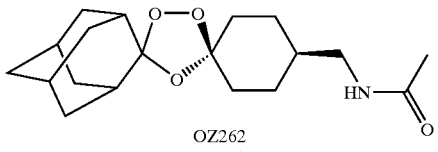
OZ262
MW 335.44
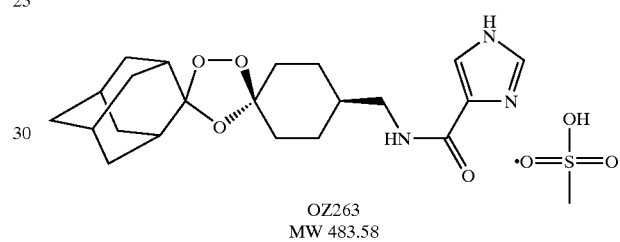
OZ263
MW 483.58
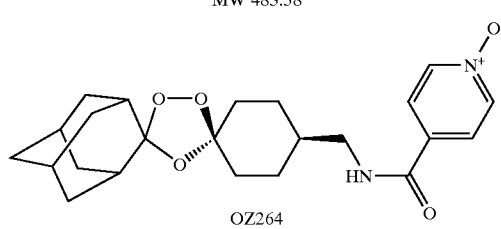
OZ264
MW 414.49
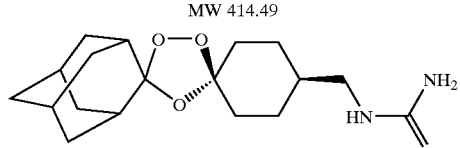
OZ265
MW 336.43
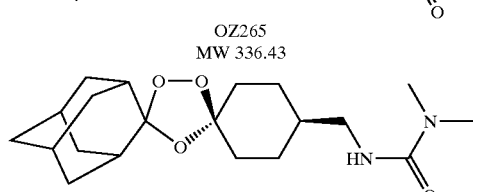
OZ266
MW 364.48
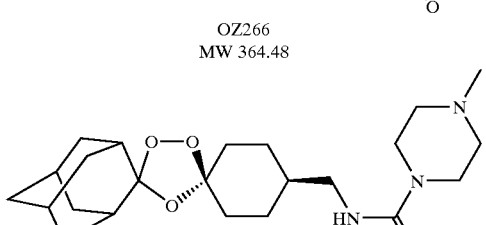
OZ267
MW 419.56

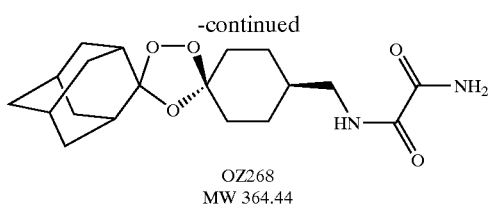
OZ268
MW 364.44
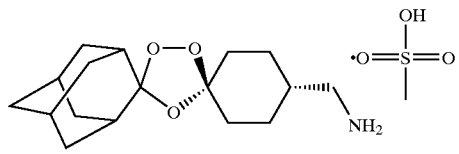
OZ269
MW 389.51
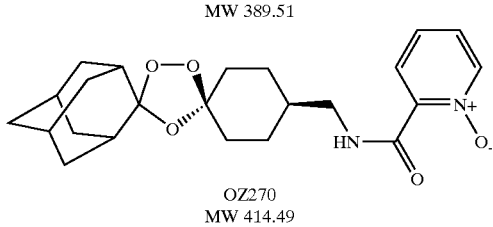
OZ270
MW 414.49
OZ Series 31 (OZ271–OZ279)
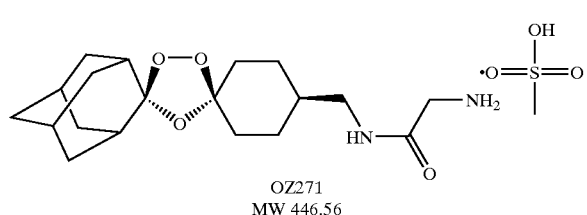
OZ271
MW 446.56
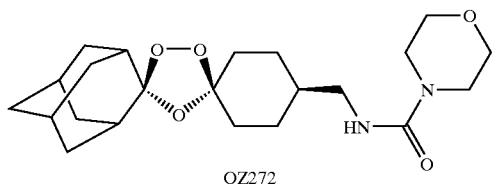
OZ272
MW 406.52
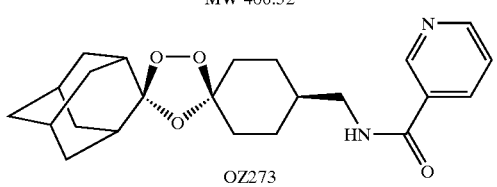
OZ273
MW 398.50
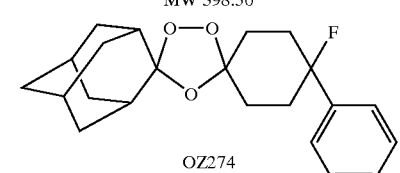
OZ274
MW 358.45
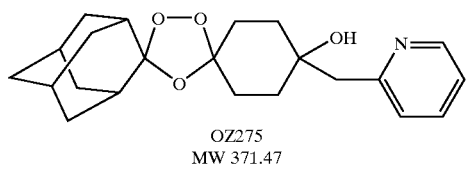
OZ275
MW 371.47
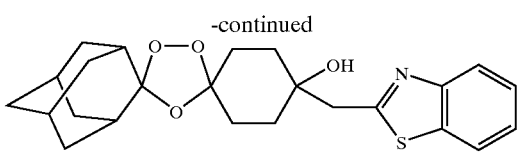
OZ276
MW 427.56
OZ277
MW 564.73
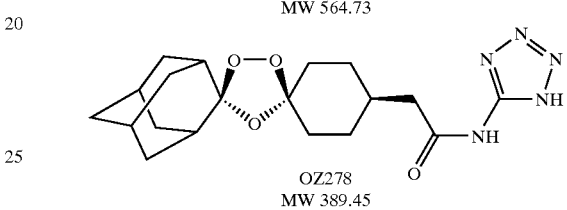
OZ278
MW 389.45
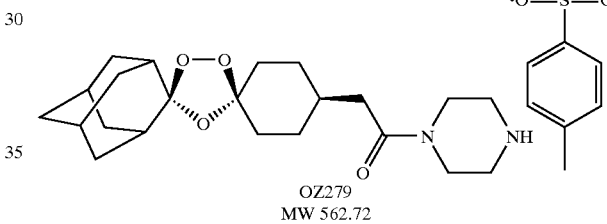
OZ279
MW 562.72
OZ Series 32 (OZ280–OZ288)
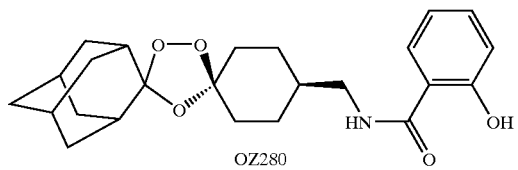
OZ280
MW 413.51
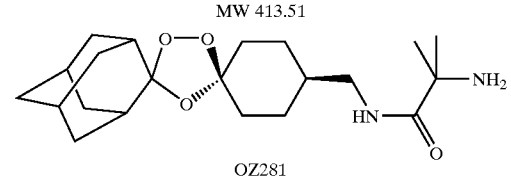
OZ281
MW 378.51
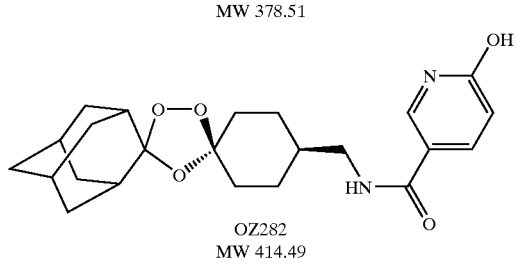
OZ282
MW 414.49

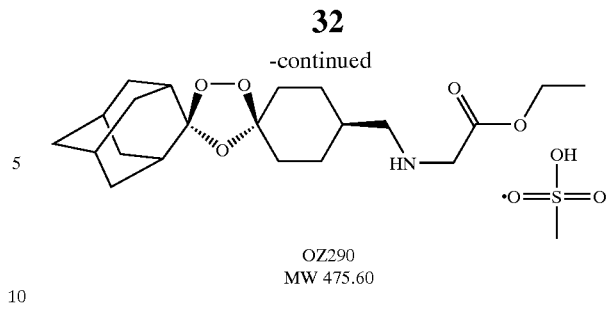
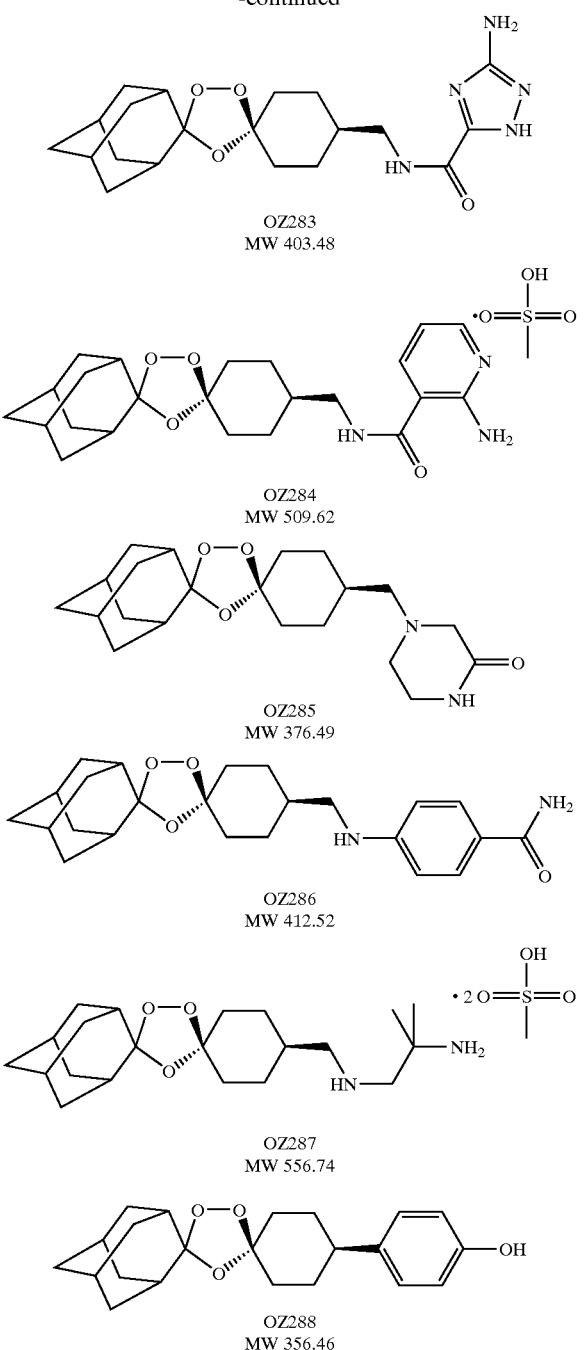
OZ Series 33 (OZ289–OZ297)
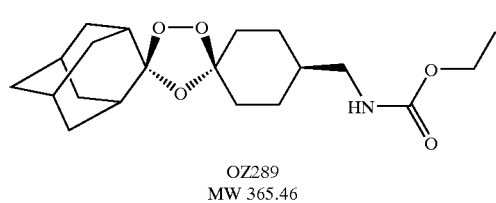

OZ Series 34 (OZ298–OZ306)
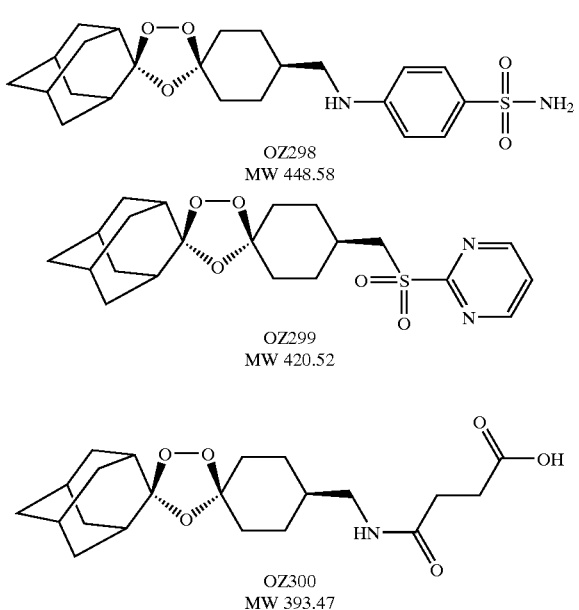
OZ298
MW 448.58
OZ299
MW 420.52
OZ300
MW 393.47
OZ301
MW 467.58
OZ302
MW 371.47
OZ303
MW 390.52
OZ304
MW 398.50
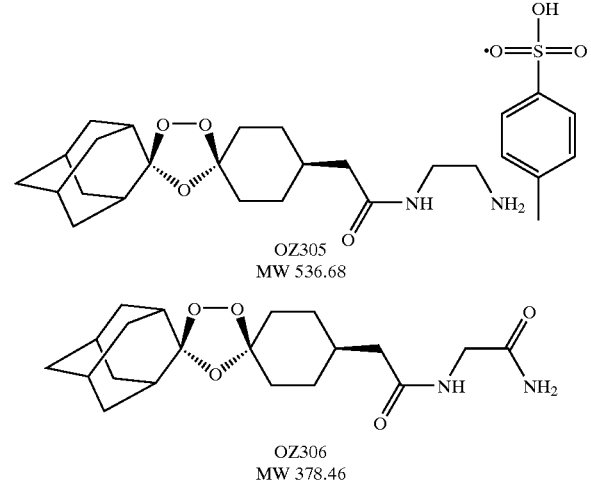
OZ305
MW 536.68
OZ306
MW 378.46
OZ Series 35 (OZ307–OZ315)
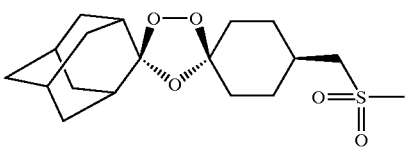
OZ307
MW 356.48
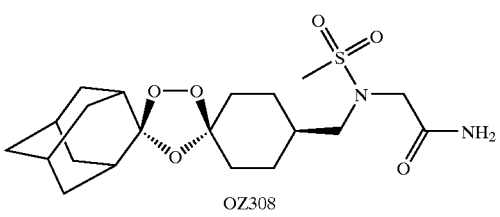
OZ308
MW 428.54
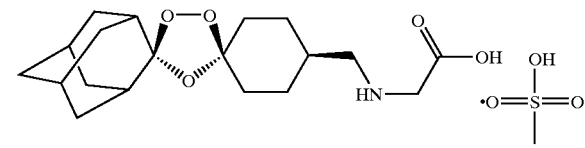
OZ309
MW 447.54
OZ310
MW 422.54
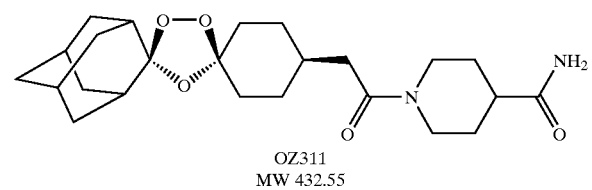
OZ311
MW 432.55

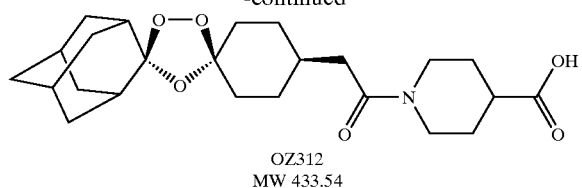
OZ312
MW 433.54
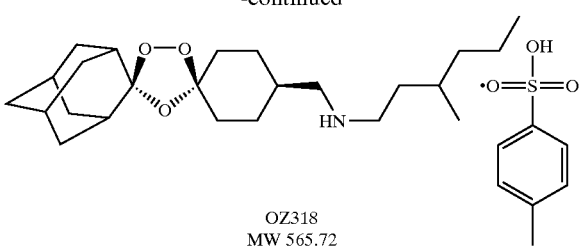
OZ318
MW 565.72
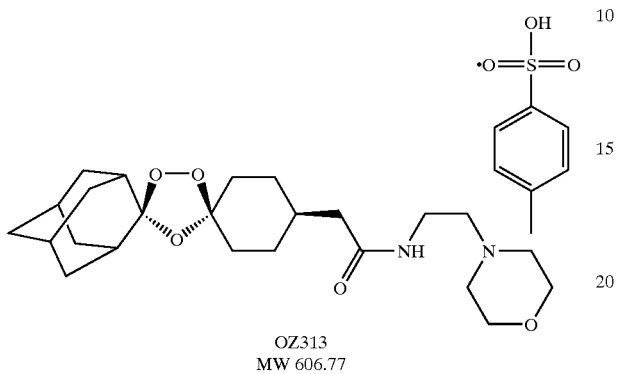
OZ313
MW 606.77
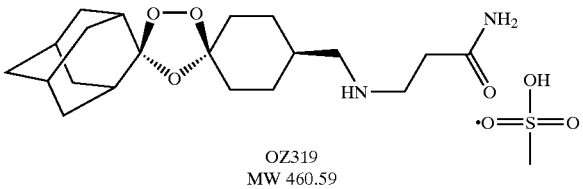
OZ319
MW 460.59
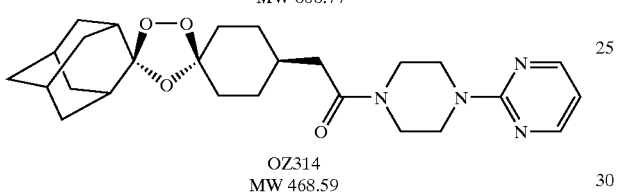
OZ314
MW 468.59
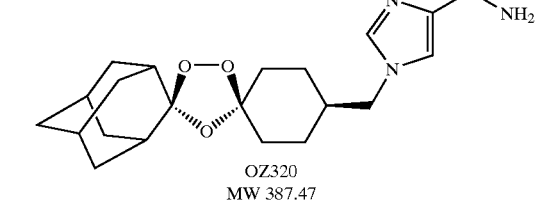
OZ320
MW 387.47
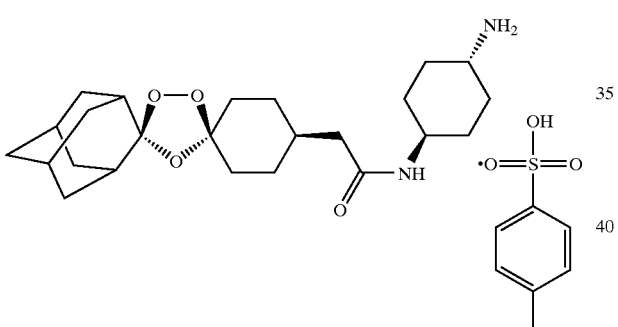
OZ315
MW 590.77
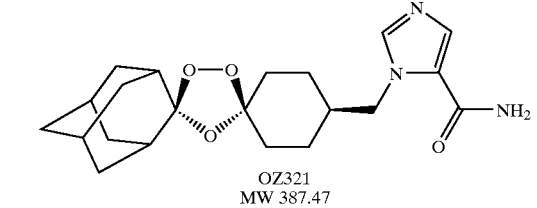
OZ321
MW 387.47
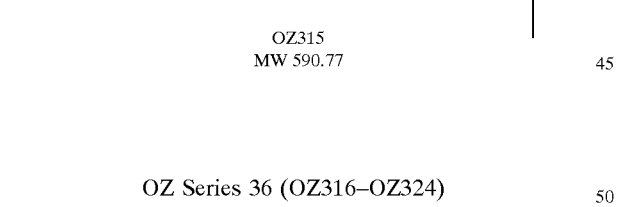
OZ322
MW 378.46
OZ Series 36 (OZ316–OZ324)
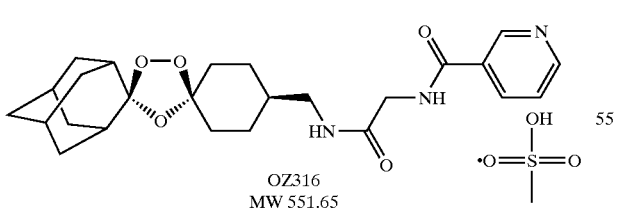
OZ316
MW 551.65
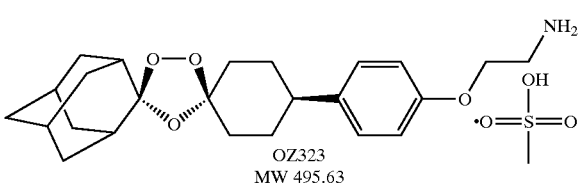
OZ323
MW 495.63
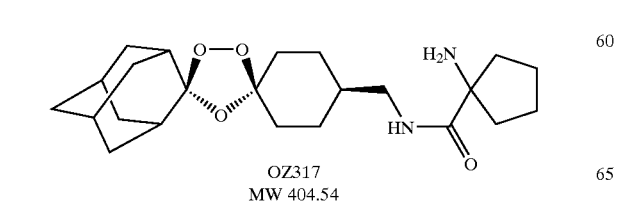
OZ317
MW 404.54
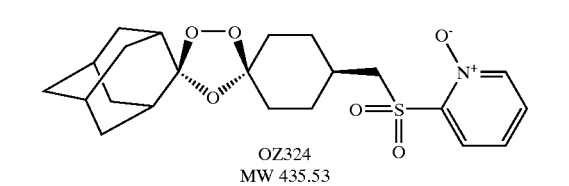
OZ324
MW 435.53

37
OZ Series 37 (OZ325–OZ333)
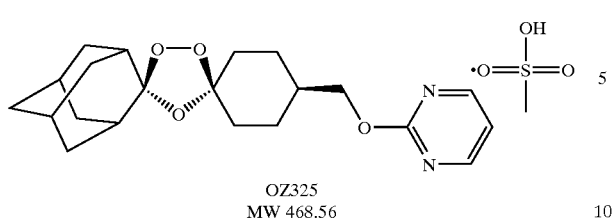
OZ325
MW 468.56
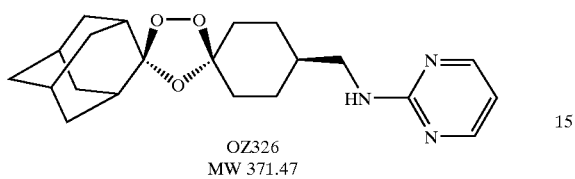
OZ326
MW 371.47
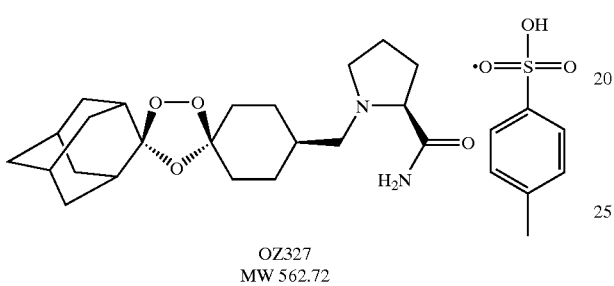
OZ327
MW 562.72
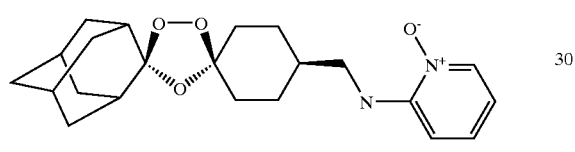
OZ328
MW 403.54
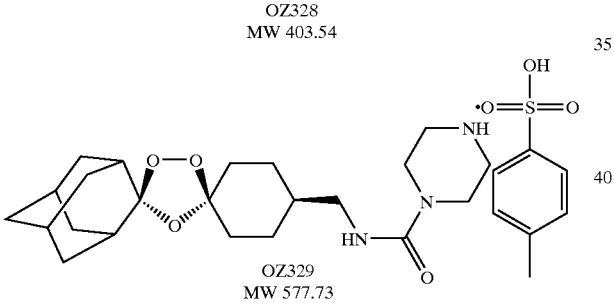
OZ329
MW 577.73
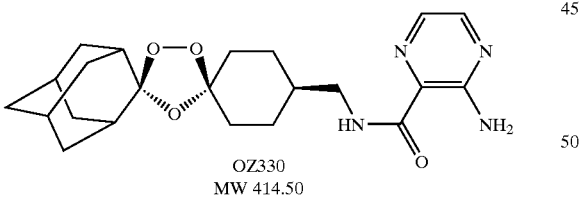
OZ330
MW 414.50
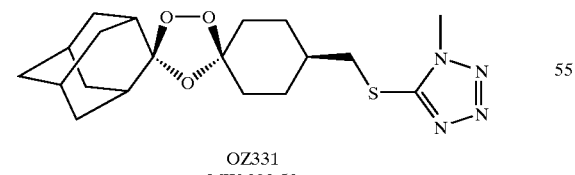
OZ331
MW 392.52
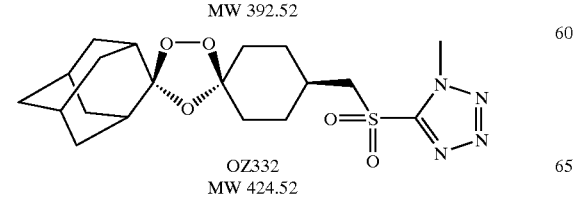
OZ332
MW 424.52
38
-continued
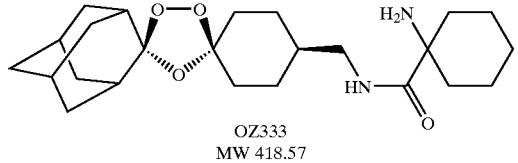
OZ333
MW 418.57
OZ Series 38 (OZ334–OZ342)
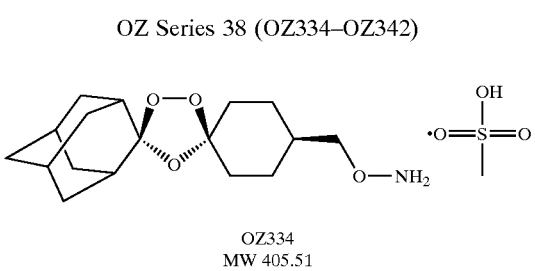
OZ334
MW 405.51
OZ335
MW 364.48
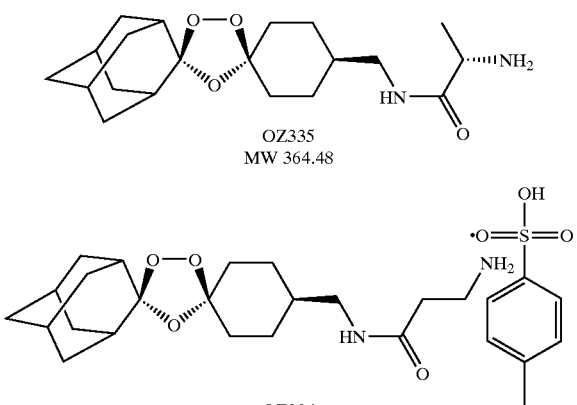
OZ336
MW 536.68
OZ337
MW 390.52
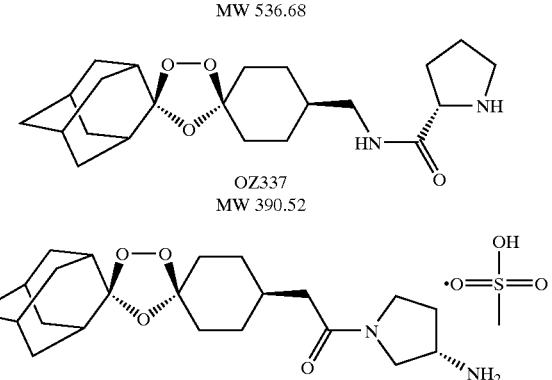
OZ338
MW 486.62
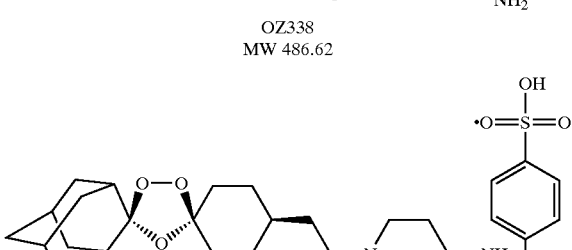
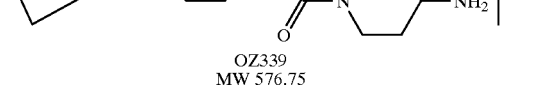
OZ339
MW 576.75

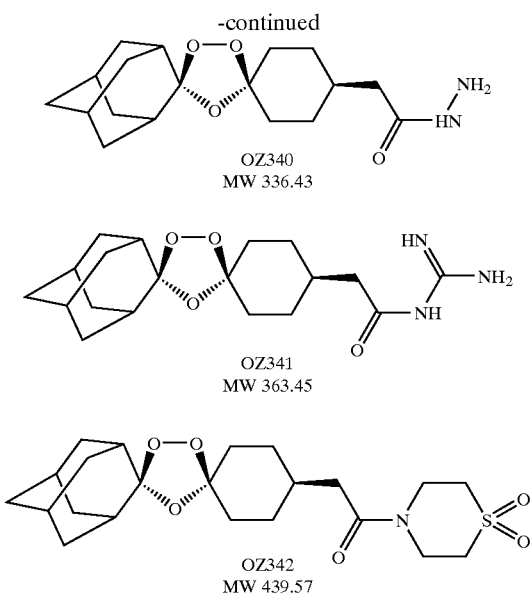

OZ340
MW 336.43

OZ341
MW 363.45

OZ342
MW 439.57

The prototype trioxolanes of this invention are OZ03 and OZ05. Preferred compounds identified thus far include OZ03, OZ05, OZ11, OZ25, OZ27, OZ61, OZ71, OZ78, OZ127, OZ145, OZ156, OZ163, OZ175, OZ177, OZ179, OZ181, OZ189, OZ205, OZ207, OZ209, OZ210, OZ219, OZ227, OZ229, OZ235, OZ255, OZ256, OZ257, OZ263, OZ264, OZ265, OZ266, OZ267, OZ268, OZ269, OZ270, OZ271, OZ277, OZ281, OZ279, OZ288, OZ289, OZ290, OZ296, OZ297, OZ298, OZ301, OZ305, OZ309, OZ315, OZ317OZ319, OZ320, OZ323, OZ329, OZ333, OZ335, OZ336, OZ337, OZ338, and OZ339. The most preferred compounds are OZ78, OZ163, OZ181, OZ207, OZ209, OZ255, OZ256, OZ257, OZ263, OZ264, OZ267, OZ271, OZ277, OZ279, OZ301, OZ305, OZ315, OZ317, OZ319, OZ323, OZ329, OZ338, and OZ339, with OZ277 and OZ279 being the best of those compounds identified thusfar. In general, the highest in vitro potency against malarial parasites is obtained for trioxolanes functionalized or substituted at the 4-position of the spirocyclohexyl ring. As a general rule, non-symmetrical, achiral trioxolanes are also preferred.

Notable features of these spiro and dispiro 1,2,4-trioxolanes in comparison to the artemisinin seminsynthetic derivatives are their structural simplicity and ease of synthesis.

For example, dispiro trioxolanes may be easily synthesized by the coozonolysis of the O-methyl oximes of cycloalkanones in the presence of the requisite cycloalkanone derivatives according to the method of Griesbaum et al. (1997a; 1997b) as illustrated below for the symmetrical dispiro cyclohexyl trioxolane:

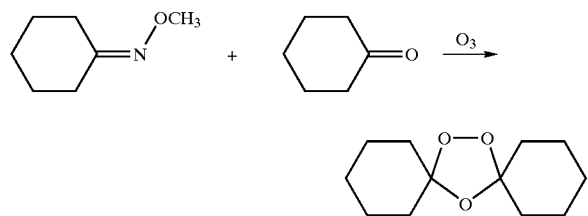

If yields are low in this coozonolysis reaction, yields can improve dramatically when the O-methyloxime and ketone are "reversed." This novel procedure provides a uniquely convenient method to synthesize spiro and dispiro trioxolanes. The trioxolanes may be purified by crystallization or by flash column chromatography. Their structures and purity may be confirmed by analytical HPLC, $^1$H and $^{13}$C NMR, IR, melting point and elemental analysis.

Recently, Griesbaum et al. (1997b) discovered that tetrasubstituted 1,2,4-trioxolanes are conveniently obtained by ozonolysis of O-alkyl ketone oximes in the presence of carbonyl compounds. Advantages of the oxime ether route over the alkene approach include convenient synthesis of starting materials (oxime ethers vs. tetrasubstituted alkenes), higher yield and selectivity of formation of desired trioxolanes by the judicious selection of paired reaction substrates.

Formation of a trioxolane from an oxime ether and a ketone is presumed to be a three-step process. The sequence begins by the electrophilic addition of ozone to the oxime double bond to form a primary ozonide. Second, the very unstable primary adduct fragments to a reactive carbonyl oxide driven in part by the concomitant expulsion of the relatively stable methyl nitrite. Third, the carbonyl oxide undergoes a [3+2] cycloaddition with a ketone to give the secondary ozonide or 1,2,4-trioxolane. It remains to be

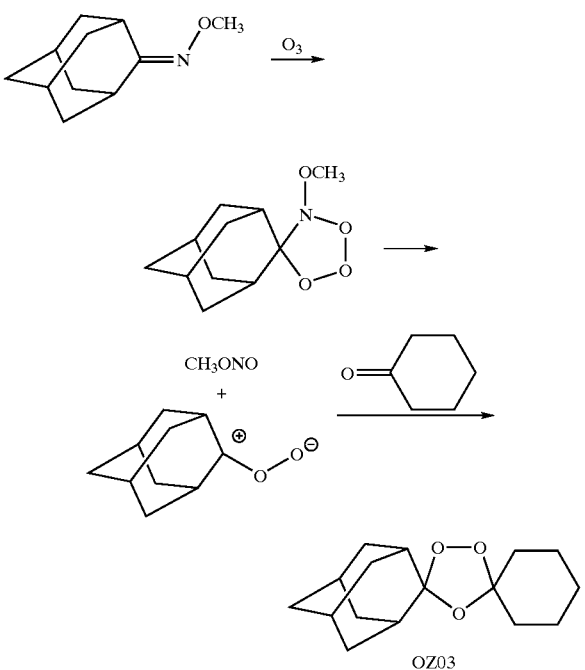

determined whether this is a stepwise or a concerted recombination process.

As illustrated above by the synthesis of OZ03, all of the new target dispiro trioxolanes contain a spiroadamantane and can be synthesized by the coozonolysis of adamantanone O-methyl oxime in the presence of the requisite cycloalkanone derivative. The preferred reaction solvents for the coozonolysis reactions are hydrocarbon solvents such as pentane or cyclohexane; more polar solvents tend to decrease the yield of the reaction. When ketones are not readily soluble in pentane or cyclohexane, a mixed solvent (pentane/methylene chloride) or methylene chloride alone may be used. Several factors govern the ratio of oxime ether to ketone. In some reactions, in order to avoid diperoxide (1,2,4,5-tetraoxane) formation, to preclude diozonide formation from diketones, and to promote the reaction with readily pentane soluble ketones, excess ketone (2:1) is used. Most commonly in the discovery synthesis stage, and especially in cases where ketones are not readily soluble in pentane, expensive, or difficult to remove in the reaction workup, a 1:1 ratio of ketone to oxime ether may be used. In large scale trioxolane syntheses, a 1.5-fold excess of oxime ether can be used to achieve higher conversions of ketones into the desired product trioxolanes without causing purification problems.

There are several examples of where post-ozonolysis transformations were used to obtain trioxolane target compounds difficult, or in some cases, impossible to obtain directly (Kashima et al., 1987) by the coozonolysis method. Trioxolane tertiary alcohols OZ90 and

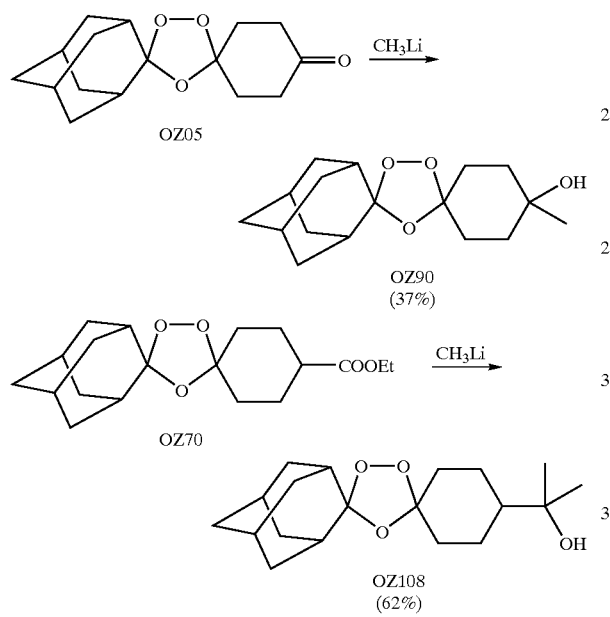

OZ108 can be obtained by methyllithium treatment of trioxolane ketone OZ05 and trioxolane ester OZ70, respectively. In other reactions, trioxolane lactone OZ17 and trioxolane alcohol OZ32 were obtained by treatment of OZ05 with m-CPBA and sodium borohydride, respectively. In addition, various oxime ethers, hydrazones, ketals, and amines (reductive amination with sodium triacetoxyborohydride) were also obtained from trioxolane ketone OZ05 in good to excellent yields. In the examples noted above, it is evident that trioxolane ketone OZ05 is a key intermediate as its ketone functional group provides a convenient means for functional group transformation.

Further evidence of the stability of these trioxolanes to reducing agents is shown by the reduction of trioxolane esters OZ70 and OZ61 into their corresponding trioxolane alcohols OZ119 and OZ89 with a mixture of lithium borohydride and lithium triethylborohydride, and the hydrazinolysis of the trioxolane phthalimides OZ136 and

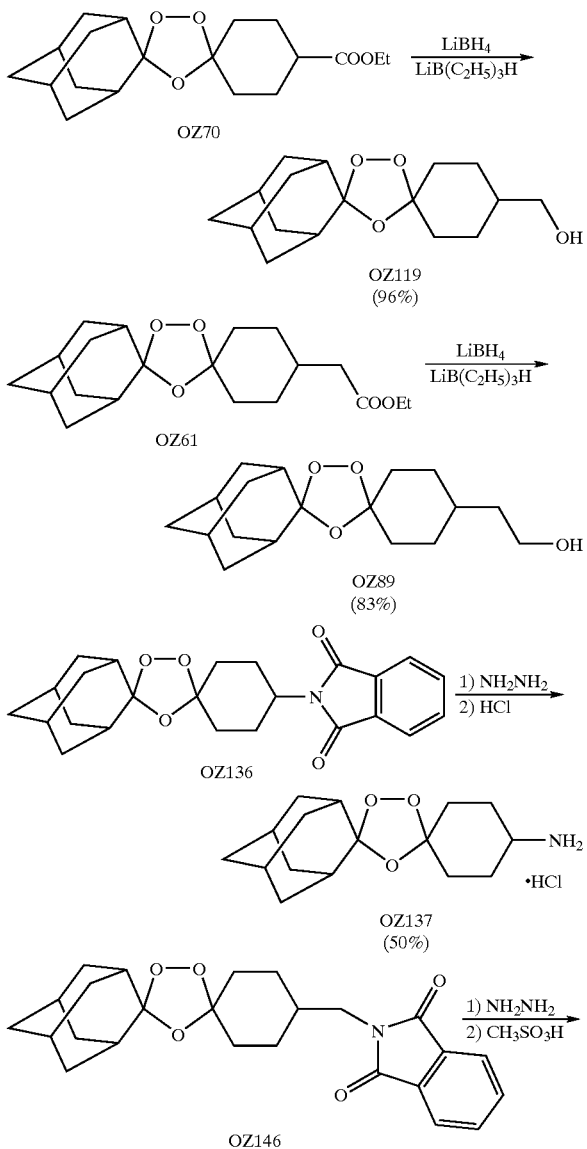

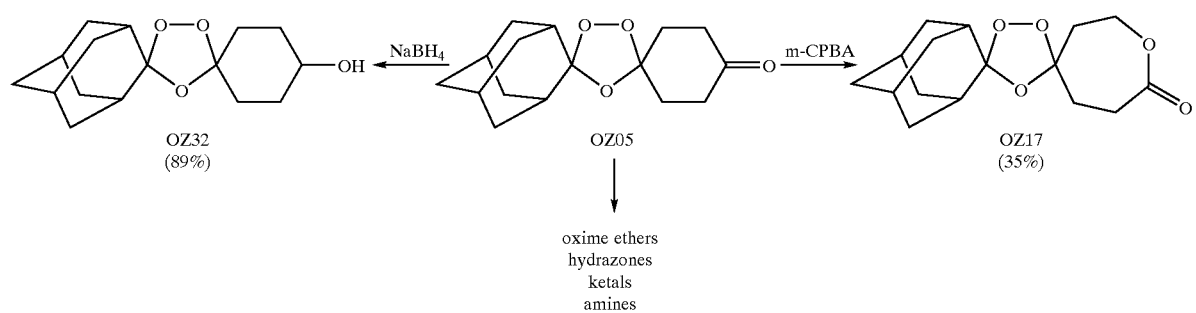

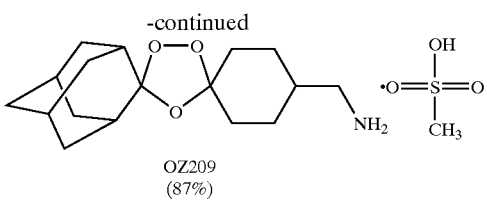

OZ209
(87%)

OZ146 into their corresponding trioxolane amines OZ137 and OZ209.

As shown in the examples below, trioxolane esters can be conveniently converted into their corresponding trioxolane acids.

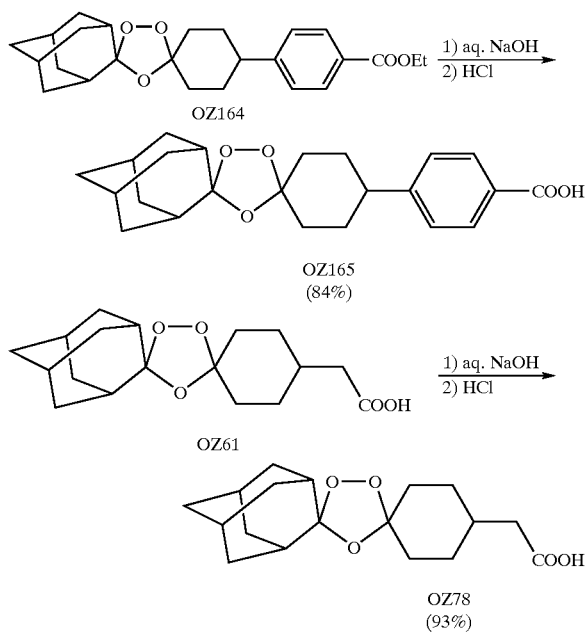

In addition to trioxolane ketone OZ05, trioxolane amine mesylate OZ209, trioxolane ester OZ61 and trioxolane acid OZ78, trioxolane alcohols OZ119 and OZ89 have and will continue to be key intermediates for post-ozonolysis synthetic transformations. A recent example is the

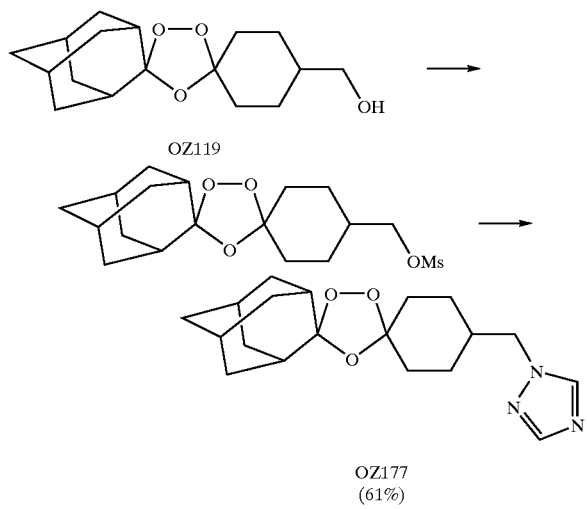

synthesis of trioxolane triazole OZ177 in a reaction between the mesylate derivative of OZ119 and the sodium salt of 1,2,4-triazole.

It has been found that the coozonolysis method using oxime methyl ethers offers a rapid, flexible, and predictable access to structurally diverse trioxolanes. In fact, several key trioxolanes that have served as important building blocks have been prepared in large scale including OZ05 (100 mmol), OZ61 (100 mmol), and OZ146 (60 mmol), with no decrease in reaction yields over the usual 5–10 mmol scale. Furthermore, both OZ61 and OZ146 can be conveniently isolated as white solids by addition of ethanol to the crude reaction mixtures.

Differential scanning calorimetry (DSC) experiments (Cammenga, and Epple, 1995) reveal that these compounds have good thermal stability, comparable to artemisinin. The average Tm, dec was 160±15° C. compared to a Tm, dec of 181° C. for artemisinin. It is presumed that thermal decomposition of these trioxolanes was initiated by formation of a 1,5 diradical produced by homolytic cleavage of the peroxide bond of the trioxolane ring.

Since most of the target trioxolanes contain the symmetrical spiroadamantane structural framework, their stereochemistry is largely a function of the starting material ketone structure or reagents used in post-ozonolysis reactions. For OZ27 and other similarly 1,4-substituted trioxolanes, two achiral diastereomers are possible. However, as exemplified by OZ27, the majority of these trioxolanes were isolated as single achiral diastereomers rather than as mixtures of two achiral diastereomers. For example, in OZ27, no chirality is present since the trioxolane ring and phenyl substituent are in a 1,4 relationship in a six membered ring. Such compounds possess a plane of symmetry.

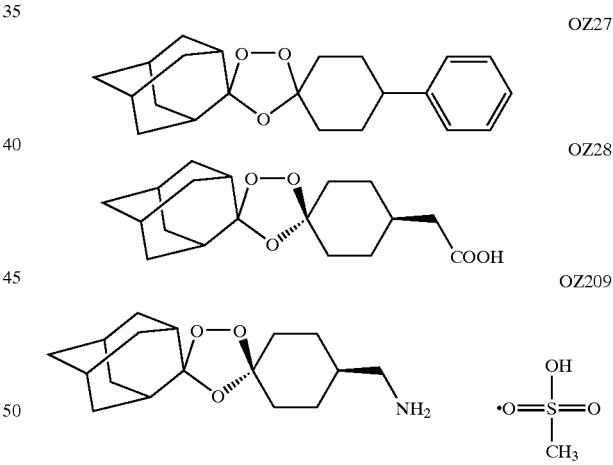

As determined by X-ray crystallography, the assignment of stereochemistry for OZ78, OZ209 and their derivatives was determined to be cis where the peroxide oxygens are in an axial position.

The starting material 2-adamantanone may be obtained from Aldrich Chemical Co. or from TCI American Organic Chemicals or may also be synthesized. Persons skilled in the art can readily ascertain other appropriate means of synthesizing the starting materials and compounds in accordance with this invention.

The spiro and dispiro trioxolane compositions of the present invention may be generally used for the prophylaxis and treatment of malaria. The trioxolane compositions of the present invention are administered along with a pharmaceutically acceptable carrier. Any pharmaceutically acceptable carrier may be generally used for this purpose, provided that the carrier does not significantly interfere with the stability or bioavailability of the trioxolane compounds of this invention.

The trioxolanes of this invention can be administered in any effectively pharmaceutically acceptable form to warm blooded animals, including human and other animal subjects, e.g. in topical, lavage, oral, suppository, parenteral, or infusible dosage forms, as a topical, buccal, sublingual, or nasal spray or in any other manner effective to deliver the agents. The route of administration will preferably be designed to optimize delivery and/or localization of the agents to target cells.

In addition to the active compounds i.e. the trioxolanes, the pharmaceutical compositions of this invention may contain suitable excipients and auxiliaries which facilitate processing of the active compounds into preparations which can be used pharmaceutically. Oral dosage forms encompass tablets, capsules, and granules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, drageemaking, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

In addition to administration with conventional carriers, active ingredients may be administered by a variety of specialized delivery drug techniques which are known to those of skill in the art, such as portable infusion pumps.

The trioxolane compositions of the present invention are administered along with a pharmaceutically acceptable carrier in an amount sufficient to prevent malarial infection and/or treat an active infection. The trioxolane compounds of this invention have extremely low toxicity and a low degree of side effects even at high doses. The dosing range of the trioxolane compositions will vary depending on a number of factors, such as whether it is used for prophylaxis or treatment of an active infection, route of administration, dosing schedule, etc. In general, the therapeutic dose of trioxolane may range between about 0.1–1000 mg/kg/day, with between about 1–100 mg/kg/day being preferred. The foregoing doses may be administered as a single dose or may be divided into multiple doses for administration. The trioxolane compositions may be administered once to several times daily. For malaria prevention, a typical dosing schedule could be, for example, 2.0–1000 mg/kg weekly beginning 1–2 weeks prior to malaria exposure taken up until 1–2 weeks post-exposure.

The spiro and dispiro trioxolanes of this invention have been found to be effective in the treatment of schistosomiasis. Schistosomiasis ranks second behind malaria in terms of socioeconomic and public health importance in tropical and subtropical areas. The disease is endemic in 74 developing countries, infecting more than 200 million people in rural agricultural and peri-urban areas. An estimated 500–600 million people worldwide are at risk from the disease.

The major forms of human schistosomiasis are caused by five species of water-borne flatworm, or blood flukes, called schistosomes. One of these species is *Schistosoma mansoni*, which has been reported in 53 countries in Africa, the Eastern Mediterranean, the Caribbean, and South America. The parasites enter the body through contact with infested surface water, primarily among people engaged in agriculture and fishing. The parasites normally infect the host during the cercaria, or larval stage. Once inside the host, the cercaria develop into adults or schistosomes.

Current treatments for schistosomiasis have focused primarily on prophylaxis, i.e. prevention of host infection by cercaria. Currently, praziquantel is the most widely used drug for treatment of schistosomiasis. While artemether has demonstrated activity in the prophylaxis of schistosomiasis, it has not shown any activity against adult S. mansoni.

It has now been unexpectedly discovered that the spiro and dispiro trioxolanes of this invention are active against both cercaria and adult S. mansoni, S. japonicum when administered in the dosages and manner outlined above with respect to treatment of malarial parasites. It is also believed the trioxolanes of this invention will be active against S. haematobium. Preferred compounds identified for use in the treatment of schistosomiasis include OZ05, OZ11, OZ23, OZ25, OZ28, OZ32, OZ71, OZ78, OZ89, OZ90, OZ119, OZ145, OZ179, OZ205, OZ207, and OZ209. Most preferred compounds are OZ78, OZ207, and OZ209. Preferred dosing levels of the spiro and dispiro trioxolanes are about 100–200 mg/kg/day orally. The prototype trioxolanes of this invention are OZ03 and OZ05.

The spiro and dispiro trioxolanes of this invention may also have effectiveness in the treatment of cancer. Compounds having an endoperoxide moiety that is reactive with heme and iron have shown an ability to kill cancer cells. (See e.g. U.S. Pat. No. 5,578,637, the disclosure of which is hereby incorporated by reference). As noted with respect to artemisinin, trioxolanes' mechanism of action against malarial parasites is based on the ability of trioxolane compounds to react with the iron in free heme molecules in malaria parasites, with the generation of free radicals leading to cellular destruction. Similarly, trioxolanes are selective against cancer cells due to the higher concentration of transferrin receptors on cancer cell membranes that pick up iron at a higher rate than normal cells. In the presence of the trioxolanes of this invention, the cancer cells will accumulate high concentrations of free radicals, leading to cell death. For cancer treatment, the trioxolanes of this invention may be administered in the doses and manner outlined above.

Other drugs besides trioxolanes which are compatible with the carrier ingredients may also be incorporated into the carrier. Such drugs may be readily ascertained by those of ordinary skill in the art and may include, for instance, antibiotics, other antimalarials, antiinflammatory agents, etc.

It is understood that the present invention contemplates the use of not only the above-stated trioxolane compounds themselves, but their prodrugs which metabolize to the compound and the analogues and biologically active salt forms thereof, as well as optical isomers which provide the same pharmaceutical results.

The following examples are offered to illustrate but not limit the invention. Thus, they are presented with the understanding that various formulation modifications as well as method of delivery modifications may be made and still be within the spirit of the invention.

EXAMPLE 1

General Procedure for the Preparation of 1,2,4-Trioxolanes

In the priority applications (U.S. Pat. No. 6,486,199 and PCT App. No. US02/19767, the disclosures of which have been expressly incorporated by reference), detailed information regarding the synthesis of the starting materials for the OZ compounds was provided. This information is therefore not repeated herein.

General procedure for the preparation of 1,2,4-trioxolanes. Ozone was produced with an OREC ozone generator (0.6 L/min $O_2$, 60 V), passed through an empty gas washing bottle that was cooled to −78° C., and bubbled through a solution of an O-methyl ketone oxime and a ketone in pentane/$CH_2Cl_2$ at 0° C. The O-methyl oxime of 2-adamantanone was consumed within 3 min. After completion, the solution was flushed with oxygen for 5 min before being concentrated in vacuo at room temperature to give a residue that was purified by crystallization or flash chromatography.

In the priority applications (U.S. Pat. No. 6,486,199 and PCT App. No. US02/19767), the disclosures of which have been expressly incorporated by reference), detailed information regarding the synthesis of OZ01–OZ90 has already been provided. This information is therefore not repeated herein.

Adamantane-2-spiro-3'-8'-[(1'S)-10'-camphorsulfonyl]-1',2',4'-trioxa-8'-azaspiro[4.5]decane (OZ91). A solution of O-methyl 2-adamantanone oxime (895 mg, 5 mmol) and 1-[(1S)-10-camphorsulfonyl]-4-piperidone (1.56 g, 4.98 mmol) in pentane (50 ml) and $CH_2Cl_2$ (50 ml) was treated with ozone according to the general procedure. The crude product was purified by flash chromatography (silica gel, 30% ether in hexanes) to afford trioxolane OZ91 (860 mg, 36%) as a colorless solid. mp 72–74° C. (methanol); $^1$H NMR (500 MHz, $CDCl_3$) δ 0.88 (s, 3H), 1.13 (s, 3H), 1.38–1.51 (m, 1H), 1.55–2.21 (m, 22H), 2.32–2.46 (m, 1H), 2.47–2.61 (m, 1H), 2.76 (d, J=14.6 Hz, 1H), 3.35 (d, J=14.6 Hz, 1H), 3.34–3.59 (m, 4H); $^{13}$C NMR (125.7 MHz, $CDCl_3$) δ 19.72, 19.94, 25.12, 26.46, 26.84, 26.89, 34.49, 34.72, 34.80, 36.40, 36.71, 42.54, 42.91, 43.84, 43.86, 45.84, 47.82, 58.25, 106.16, 112.26, 214.78. Anal. Calcd for $C_{25}H_{37}NO_6S$: C, 62.60; H, 7.78; N, 2.92. Found: C, 62.80; H, 7.60; N, 2.92.

Adamantane-2-spiro-3'-8'-(1'-butanesulfonyl)-1',2',4'-trioxa-8'-azaspiro[4.5]decane (OZ92). A solution of O-methyl 2-adamantanone oxime (895 mg, 5 mmol) and 1-(1-butanesulfonyl)-4-piperidone (1.12 g, 5.11 mmol) in pentane (50 ml) and $CH_2Cl_2$ (50 ml) was treated with ozone according to the general procedure. The crude product was purified by flash chromatography (silica gel, 30% ether in hexanes) to afford trioxolane OZ92 (700 mg, 36%) as a colorless solid. mp 62–64° C. (methanol); $^1$H NMR (500 MHz, $CDCl_3$) δ 0.95 (t, J=7.6 Hz, 3H), 1.32–1.57 (m, 2H), 1.59–2.21 (m, 20H), 2.81–3.02 (m, 2H), 3.22–3.59 (m, 4H); $^{13}$C NMR (125.7 MHz, $CDCl_3$) δ 13.48, 21.68, 25.24, 26.50, 26.90, 34.67, 34.78, 34.87, 36.48, 36.75, 43.94, 50.09, 106.20, 112.38. Anal. Calcd for $C_{19}H_{31}NO_5S$: C, 59.19; H, 8.10; N, 3.63. Found: C, 59.38; H, 7.99; N, 3.45.

Adamantane-2-spiro-3'-8'-(phthalimidoacetyl)-1',2',4'-trioxa-8'-azaspiro[4.5]decane (OZ93). To a solution of OZ87 (342 mg, 1 mmol) in acetonitrile (10 ml) was added potassium phthalimide (200 mg, 1.08 mmol). The reaction solution was heated at 60–65° C. for 36 h and cooled to rt. The solvent was removed by evaporation, and the residue was triturated with water (20 ml) and filtered. Recrystallization of the solid from methanol gave trioxolane OZ93 (379 mg, 84%) as a colorless solid. mp 152–154° C. (methanol); $^1$H NMR (500 MHz, $CDCl_3$) δ 1.59–2.11 (m, 18H), 3.45–3.71 (m, 3H), 3.72–3.89 (m, 1H), 4.51 (s, 2H), 7.65–7.79 (m, 2H), 7.82–7.97 (m, 2H); $^{13}$C NMR (125.7 MHz, $CDCl_3$) δ

26.47, 26.86, 33.94, 34.75, 36.44, 36.72, 38.96, 40.38, 42.62, 106.49, 112.36, 123.43, 132.38, 133.93, 163.88, 167.87. Anal. Calcd for $C_{25}H_{28}N_2O_6$: C, 66.36; H, 6.24; N, 6.19. Found: C, 66.19; H, 6.07; N, 6.19.

Adamantane-2-spiro-3'-1',2',4'-trioxolane-5'-spiro-9"-fluorene (OZ94). A solution of O-methyl 2-adamantanone oxime (895 mg, 5 mmol) and 9-fluorenone (1.80 g, 10 mmol) in pentane (80 ml) and $CH_2Cl_2$ (20 ml) was treated with ozone according to the general procedure. The crude product was purified by flash chromatography (silica gel, 1% ether in hexanes) to afford trioxolane OZ94 (650 mg, 38%) as a colorless solid. mp 150–152° C. (methanol/ether 9:1); $^1H$ NMR (500 MHz, $CDCl_3$) δ 1.62–2.25 (m, 12H), 2.47 (s, 2H), 7.27 (dd, J=7.6, 7.6 Hz, 2H), 7.38 (dd, J=7.6, 7.6 Hz, 2H), 7.53 (d, J=7.3 Hz, 2H), 7.57 (d, J=7.3 Hz, 2H); $^{13}C$ NMR (125.7 MHz, $CDCl_3$) δ 26.61, 26.99, 34.89, 35.10, 36.51, 36.87, 111.76, 112.99, 120.02, 125.22, 128.42, 130.81, 140.29, 140.99. Anal. Calcd for $C_{23}H_{22}O_3$: C, 79.74; H, 6.40. Found: C, 79.56; H, 6.23.

Adamantane-2-spiro-3'-5'-(4'-nitrophenyl)-5'-phenyl-1',2',4'-trioxolane (OZ95). A solution of O-methyl 2-adamantanone oxime (1.79 g, 10 mmol) and 4-nitrobenzophenone (2.27 g, 10 mmol) in pentane (70 ml) and $CH_2Cl_2$ (80 ml) was treated with ozone according to the general procedure. The crude product was purified by flash chromatography (silica gel, 10% ether in hexanes) to afford trioxolane OZ95 (1.60 g, 41%) as a colorless solid. mp 114–116° C. (ether); $^1H$ NMR (500 MHz, $CDCl_3$) δ 1.60–2.26 (m, 14H), 7.32–7.41 (m, 3H), 7.42–7.49 (m, 2H), 7.75 (d, J=8.8 Hz, 2H), 8.22 (d, J=8.8 Hz, 2H); $^{13}C$ NMR (125.7 MHz, $CDCl_3$) δ 26.46, 26.88, 34.61, 34.78, 34.81, 35.42, 36.04, 36.24, 36.71, 108.77, 114.65, 123.37, 126.86, 127.62, 128.43, 129.39, 137.62, 148.00, 148.26. Anal. Calcd for $C_{23}H_{23}NO_5$: C, 70.21; H, 5.89; N, 3.56. Found: C, 70.12; H, 5.66; N, 3.58.

Adamantane-2-spiro-3'-5',5'-bis(4'-chloro-3'-nitrophenyl)-1',2',4'-trioxolane (OZ96). A solution of O-methyl 2-adamantanone oxime (1.79 g, 10 mmol) and 4,4'-dichloro-3,3'-dinitrobenzophenone (2.09 g, 10 mmol) in pentane (80 ml) and $CH_2Cl_2$ (75 ml) was treated with ozone according to the general procedure. The crude product was purified by flash chromatography (silica gel, 10% ether in hexanes) to afford trioxolane OZ96 (2.03 g, 40%) as a pale yellow solid. mp 113–115° C. (ether); $^1H$ NMR (500 MHz, $CDCl_3$) δ 1.60–2.25 (m, 14H), 7.50–7.71 (m, 4H), 8.04 (d, J=2.0 Hz, 2H); $^{13}C$ NMR (125.7 MHz, $CDCl_3$) δ 26.30, 26.68, 34.75, 34.92, 36.06, 36.49, 106.72, 116.10, 123.73, 128.27, 131.00, 132.31, 139.19, 148.02. Anal. Calcd for $C_{23}H_{20}Cl_2N_2O_7$: C, 54.45; H, 3.97; N, 5.52. Found: C, 54.46; H, 4.09; N, 5.53.

Adamantane-2-spiro-3'-8'-phenyl-8'-phthalimidomethyl-1',2',4'-trioxaspiro[4.5]decane (OZ97). A solution of O-methyl 2-adamantanone oxime (0.75 g, 4.2 mmol) and 4-phenyl-4-phthalimidomethylcyclohexanone (1.40 g, 4.2 mmol) in pentane (100 ml) and $CH_2Cl_2$ (50 ml) was treated with ozone according to the general procedure. The crude product was purified by flash chromatography (silica gel, 12% ethyl acetate in hexanes) to afford trioxolane OZ97 (0.62 g, 30%) as a colorless solid. mp 150–152° C. (ethanol); $^1H$ NMR NMR (500 MHz, $CDCl_3$) δ 1.50–1.99 (m, 20H), 2.40 (app d, J=14.2 Hz, 2H), 3.63 (s, 2H), 7.18–7.30 (m, 1H), 7.31–7.40 (m, 2H), 7.41–7.50 (m, 2H), 7.65–7.72 (m, 2H), 7.73–7.85 (m, 2H); $^{13}C$ NMR (125.7 MHz, $CDCl_3$) δ 26.52, 26.88, 30.80, 30.88, 34.79, 36.43, 36.82, 43.90, 108.57, 111.33, 123.22, 126.67, 127.10, 128.78, 132.02, 133.84, 141.13, 168.44. Anal. Calcd for $C_{31}H_{33}NO_5$: C, 74.53; H, 6.66; N, 2.80. Found: C, 74.54; H, 6.71; N, 2.80.

Adamantane-2-spiro-3'-8'-methoxycarbonyl-8'-phenyl-1',2',4'-trioxaspiro[4.5]decane (OZ98). A solution of O-methyl 2-adamantanone oxime (2.15 g, 12 mmol) and 4-methoxycarbonyl-4-phenylcyclohexanone (2.79 g, 12 mmol) in pentane (100 ml) and $CH_2Cl_2$ (50 ml) was treated with ozone according to the general procedure. The crude product was purified by flash chromatography (silica gel, 10% ether in hexanes) to afford trioxolane OZ98 (1.07 g, 22%) as a colorless solid. mp 127–129° C. (ethanol/$CH_2Cl_2$ 9:1); $^1H$ NMR (500 MHz, $CDCl_3$) δ 1.62–2.15 (m, 20H), 2.53 (app d, J=13.2 Hz, 2H), 3.67 (s, 3H), 7.20–7.44 (m, 5H); $^{13}C$ NMR (125.7 MHz, $CDCl_3$) δ 26.54, 26.94, 31.93, 31.98, 34.82, 34.87, 36.48, 36.85, 50.06, 52.22, 108.03, 111.58, 125.78, 127.06, 128.59, 142.39, 174.86. Anal. Calcd for $C_{24}H_{30}O_5$: C, 72.34; H, 7.59. Found: C, 72.12; H, 7.48.

Adamantane-2-spiro-3'-8'-carboxy-8'-phenyl-1',2',4'-trioxaspiro[4.5]decane (OZ99). A mixture of OZ98 (0.42 g, 1.05 mmol), KOH (1.00 g, 17.85 mmol), ethanol (30 ml), THF (25 ml), and water (10 ml) was heated at 50° C. for 5 h. The reaction mixture was cooled to rt, concentrated to 10 ml, diluted with water (20 ml), acidified with conc. HCl (2.0 ml), and extracted with $CHCl_3$ (3×25 ml). The combined extracts were dried over $MgSO_4$, filtered, and concentrated. Recrystallization of the residue from hexanes/$CH_2Cl_2$ (7:3) afforded trioxolane OZ99 (0.31 g, 77%) as a colorless solid. mp 153–156° C. (hexanes/$CH_2Cl_2$ 7:3); $^1H$ NMR (500 MHz, $CDCl_3$) δ 1.62–2.19 (m, 20H), 2.54 (app d, J=11.7 Hz, 2H), 7.20–7.53 (m, 5H); $^{13}C$ NMR (125.7 MHz, $CDCl_3$) δ 26.58, 26.98, 31.54, 31.83, 34.84, 34.90, 36.51, 36.88, 49.62, 107.96, 111.67, 126.04, 127.34, 128.68, 141.44, 180.55. Anal. Calcd for $C_{23}H_{28}O_5$: C, 71.85; H, 7.34. Found: C, 71.66; H, 7.32.

Adamantane-2-spiro-3'-8'-(4'-pyridinylcarbonyl)-1',2',4'-trioxa-8'-azaspiro[4.5]decane (OZ100). To a solution of OZ80 (225 mg, 0.85 mmol) in $CH_2Cl_2$ (10 ml) was added triethylamine (258 mg, 2.55 mmol). The solution was then cooled to 0–5° C., and isonicotinoyl chloride hydrochloride (180 mg, 1.01 mmol) was added. The resulting mixture was stirred at rt for 16 h before evaporation to dryness. The residue was triturated with water and filtered. Recrystallization of the solid from methanol at –20° C. gave trioxolane OZ100 (190 mg, 69%) as a colorless solid. mp 140–142° C. (methanol); $^1H$ NMR (500 MHz, $CDCl_3$) δ 1.58–2.16 (m, 18H), 3.31–3.58 (m, 2H), 3.68–3.85 (m, 1H), 3.86–4.06 (m, 1H), 7.19–7.37 (m, 2H), 8.60–8.80 (m, 2H); $^{13}C$ NMR (125.7 MHz, $CDCl_3$) δ 26.47, 26.87, 34.13, 34.76, 34.87, 35.18, 36.45, 36.71, 40.03, 45.20, 106.47, 112.49, 120.96, 143.47, 150.37, 167.77. Anal. Calcd for $C_{21}H_{26}N_2O_4$: C, 68.09; H, 7.07; N, 7.56. Found: C, 68.22; H, 7.06; N, 7.68.

Adamantane-2-spiro-3'-8'-(4'-chlorophenoxyacetyl)-1',2',4'-trioxa-8'-azaspiro[4.5]decane (OZ101). A solution of O-methyl 2-adamantanone oxime (895 mg, 5 mmol) and 1-(4-chlorophenoxyacetyl)-4-piperidone (1.34 g, 5 mmol) in pentane (50 ml) and $CH_2Cl_2$ (50 ml) was treated with ozone according to the general procedure. The crude product was purified by flash chromatography (silica gel, 30% ether in hexanes) to afford trioxolane OZ101 (300 mg, 14%) as a colorless solid. mp 148–150° C. (methanol); $^1H$ NMR (500 MHz, $CDCl_3$) δ 1.59–2.19 (m, 18H), 3.48–3.71 (m, 3H), 3.72–3.87 (m, 1H), 4.67 (AB system, 2H), 6.80–6.95 (m, 2H), 7.15–7.35 (m, 2H); $^{13}C$ NMR (125.7 MHz, $CDCl_3$) δ 26.47, 26.86, 34.15, 34.75, 34.93, 35.19, 36.43, 36.71, 40.21, 43.13, 68.16, 106.54, 112.38, 115.99, 126.80, 129.55, 156.57, 166.03. Anal. Calcd for $C_{23}H_{28}ClNO_5$: C, 63.66; H, 6.50; N, 3.23. Found: C, 63.82; H, 6.46; N, 3.30.

Adamantane-2-spiro-3'-8'-(phenylaminocarbonyl)-1',2',4'-trioxa-8'-azaspiro[4.5]decane (OZ102). To a solution of OZ80 (301 mg, 1 mmol) and triethylamine (101 mg, 1 mmol) in $CH_2Cl_2$ (10 ml) at 0–5° C. was added phenyl isocyanate (140 mg, 1.2 mmol). The reaction mixture was stirred at rt for 3 h, diluted with $CH_2Cl_2$ (10 ml), and washed with water (10 ml), 10% aq. $NaHCO_3$ (10 ml), 2 M HCl (10 ml), water (10 ml) and brine (10 ml). The organic layer was dried over $MgSO_4$ and concentrated. The residue was triturated with hexanes (20 ml), filtered, and dried to afford trioxolane OZ102 (370 mg, 96%) as a colorless solid. mp 146–148° C. (hexanes); $^1$H NMR (500 MHz, $CDCl_3$) δ 1.62–2.11 (m, 18H), 3.42–3.76 (m, 4H), 6.46.(s, 1H), 7.04 (dd, J=7.3, 7.3 Hz, 1H), 7.15–7.44 (m, 4H); $^{13}$C NMR (125.7 MHz, $CDCl_3$) δ 26.52, 26.91, 34.42, 34.80, 34.89, 36.49, 36.77, 42.44, 106.80, 112.28, 120.13, 123.29, 128.91, 139.00, 154.88. Anal. Calcd for $C_{22}H_{28}N_2O_4$: C, 68.73; H, 7.34; N, 7.29. Found: C, 68.78; H, 7.14; N, 7.50.

Adamantane-2-spiro-3'-8'-(1'H-imidazol-1'-ylacetyl)-1', 2',4'-trioxa-8'-azaspiro[4.5]decane (OZ103). To a solution of OZ87 (342 mg, 1 mmol) in acetonitrile (10 ml) was added imidazole (201 mg, 3 mmol). The mixture was heated at 60–65° C. for 36 h before evaporation to dryness. The crude product was purified by flash chromatography (silica gel, 5% methanol in dichloromethane) and by subsequent recrystallization from hexanes/ether (9:1) to give trioxolane OZ103 (132 mg, 35%) as a colorless solid. mp 138–140° C. (hexanes/ether 9:1); $^1$H NMR (500 MHz, $CDCl_3$) δ 1.59–2.21 (m, 18H), 3.43–3.60 (m, 2H), 3.61–3.72 (m, 1H), 3.73–3.91 (m, 1H), 4.79 (s, 2H), 6.97 (br s, 1H), 7.12 (br s, 1H), 7.52 (br s, 1H); $^{13}$C NMR (125.7 MHz, $CDCl_3$) δ 26.46, 26.86, 33.98, 34.76, 34.95, 36.44, 36.70, 40.41, 43.02, 48.09, 106.22, 112.54, 120.04 (br s), 129.67, 138.10 (br s), 164.47. Anal. Calcd for $C_{20}H_{27}N_3O_4$: C, 64.32; H, 7.29; N, 11.25. Found: C, 64.12; H, 7.02; N, 11.09.

Adamantane-2-spiro-3'-8'-[[4-(acetylamino)phenyl]sulfonyl]-1',2',4'-trioxa-8'-azaspiro[4.5]decane (OZ104). To a solution of OZ80 (300 mg, 1 mmol) in $CH_2Cl_2$ (10 ml) was added triethylamine (303 mg, 3 mmol). The solution was then cooled to 0–5° C., and 4-acetamidobenzenesulfonyl chloride (280 mg, 1.2 mmol) was added. The resulting mixture was stirred at rt for 16 h before evaporation to dryness. The residue was triturated with water (15 ml) and filtered. Recrystallization of the solid from methanol/$CH_2Cl_2$ (9:1) at −20° C. gave trioxolane OZ104 (300 mg, 65%) as a colorless solid. mp 122–124° C. (methanol/$CH_2Cl_2$); $^1$H NMR (500 MHz, $CDCl_3$) δ 1.50–2.12 (m, 18H), 2.19 (s, 3H), 2.90–3.08 (m, 2H), 3.15–3.37 (m, 2H), 7.65 (d, J=8.8 Hz, 2H), 7.68 (d, J=8.8 Hz, 2H), 7.93–8.16 (m, 1H); $^{13}$C NMR (125.7 MHz, $CDCl_3$) δ 24.51, 26.46, 26.83, 34.05, 34.74, 34.76, 36.39, 36.70, 44.26, 105.86, 112.41, 119.44, 128.73, 131.51, 142.35, 168.72. Anal. Calcd for $C_{23}H_{30}N_2O_6S$: C, 59.72; H, 6.54; N, 6.06. Found: C, 59.58; H, 6.60; N, 5.81. Adamantane-2-spiro-3'-5',5'-bis(3'-nitrophenyl)-1',2',4'-trioxolane (OZ105). A solution of O-methyl 2-adamantanone oxime (1.79 g, 10 mmol) and 3,3'-dinitrobenzophenone (2.72 g, 10 mmol) in pentane (60 ml) and $CH_2Cl_2$ (40 ml) was treated with ozone according to the general procedure. The crude product was purified by flash chromatography (silica gel, 90% ether in hexanes) to afford trioxolane OZ105 (0.90 g, 21%) as a colorless solid. mp 131–134° C. (ether); $^1$H NMR (500 MHz, $CDCl_3$) δ 1.60–2.45 (m, 14H), 7.59 (dd, J=7.8, 7.8 Hz, 2H), 7.81–7.88 (m, 2H), 8.22–8.28 (m, 2H), 8.41 (dd, J=2.0, 2.0 Hz, 2H); $^{13}$C NMR (125.7 MHz, $CDCl_3$) δ 26.37, 26.76, 34.77, 34.95, 36.09, 36.58, 107.55, 115.64, 121.71, 124.10, 129.67, 132.47, 141.33, 148.46. Anal. Calcd for $C_{23}H_{22}N_2O_7$: C, 63.01; H, 5.06; N, 6.39. Found: C, 63.26; H, 5.00; N, 6.47.

Adamantane-2-spiro-3'-5',5'-bis[3',4'-di(methoxycarbonyl)phenyl]-1',2',4'-trioxolane (OZ106). A solution of O-methyl 2-adamantanone oxime (1.79 g, 10 mmol) and 3,3',4,4'-tetra(methoxycarbonyl)benzophenone (4.14 g, 10 mmol) in pentane (70 ml) and $CH_2Cl_2$ (80 ml) was treated with ozone according to the general procedure. The crude product was purified by flash chromatography (silica gel, 80% ether in hexanes) to afford trioxolane OZ106 (2.03 g, 35%) as a colorless solid. mp 52–54° C. (ether); $^1$H NMR (500 MHz, $CDCl_3$) δ 1.60–2.35 (m, 14H), 3.907 (s, 6H), 3.909 (s, 6H), 7.66 (dd, J=8.0, 1.5 Hz, 2H), 7.70 (d, J=8.0 Hz, 2H), 7.87 (d, J=1.5 Hz, 2H); $^{13}$C NMR (125.7 MHz, $CDCl_3$) δ 26.38, 26.77, 34.75, 34.91, 35.99, 36.62, 52.64, 52.66, 107.85, 115.18, 127.10, 129.03, 129.29, 132.05, 132.71, 142.41, 167.29, 167.55. Anal. Calcd for $C_{31}H_{32}O_{11}$: C, 64.13; H, 5.56. Found: C, 64.28; H, 5.46.

Adamantane-2-spiro-3'-8'-[(aminocarbonyl)oxy]-1',2',4'-trioxaspiro[4.5]decane (OZ107). A solution of trichloroacetyl isocyanate (0.44 g, 2.25 mmol) and OZ32 (0.42 g, 1.50 mmol) in $CH_2Cl_2$ (5 ml) was stirred at 0° C. for 4 h. The reaction mixture was warmed up to rt, concentrated, dissolved in methanol (20 ml), and cooled to 0° C. To this cooled solution was added 5% aq. $Na_2CO_3$ solution (20 ml). The resulting mixture was stirred at 0° C. for 0.1 h, warmed up to rt, and stirred at rt overnight. The reaction solution was diluted with water (50 ml) and extracted with $CHCl_3$ (3×40 ml). The combined organic layers were washed with water (30 ml) and brine (30 ml), dried over $MgSO_4$, and concentrated. Recrystallization of the residue from hexanes/chloroform (3:1) gave trioxolane OZ107 (250 mg, 52%, 10:1 mixture of two diastereomers) as a colorless solid. mp 160–162° C. (hexanes/chloroform 3:1); $^1$H NMR (500 MHz, $CDCl_3$) δ 1.50–2.25 (m, 22H), 4.72–4.98 (m, 3H); $^{13}$C NMR (125.7 MHz, $CDCl_3$) δ 26.52, 26.93, 28.60, 31.01, 34.80, 34.88, 36.39, 36.82, 70.81, 107.85, 111.69, 156.34. Anal. Calcd for $C_{17}H_{25}NO_5$: C, 63.14; H, 7.79; N, 4.33. Found: C, 62.91; H, 7.56; N, 4.31.

cis-Adamantane-2-spiro-3'-8'-(1'-hydroxy-1'-methylethyl)-1',2',4'-trioxaspiro[4.5]decane (OZ108). To a solution of methyllithium (3.80 ml, 1.4 M in ether, 5.4 mmol) in ether (5 ml) at −78° C. was added a solution of OZ70 (0.70 g, 2.1 mmol) in ether (20 ml). The reaction was stirred at −78° C. for 3 h before being quenched with saturated aq. ammonium chloride (20 ml). The mixture was extracted with ether (3×30 ml), and the organic layers were washed with water (30 ml) and brine (30 ml), dried over $MgSO_4$, filtered, and concentrated. The crude product was purified by flash chromatography (silica gel, 20% ether in hexanes) to afford trioxolane OZ108 (0.42 g, 62%) as a colorless solid. mp 126–128° C. (ethanol/$H_{20\ 4:1}$); $^1$H NMR (500 MHz, $CDCl_3$) δ 1.17 (s, 6H), 1.06–1.55 (m, 3H), 1.58–2.30 (m, 20H); $^{13}$C NMR (125.7 MHz, $CDCl_3$) δ 24.85, 26.59, 26.99, 27.02, 34.50, 34.85, 36.50, 36.90, 47.76, 72.51, 108.70, 111.28. Anal. Calcd for $C_{19}H_{30}O_4$: C, 70.77; H, 9.38. Found: C, 70.64; H, 9.15.

Adamantane-2-spiro-3'-8'-[(3'-carboxypyrazinyl)carbonyl]-1',2',4'-trioxa-8'-azaspiro[4.5]decane (OZ109). To a solution of OZ80 (301 mg, 1 mmol) in $CH_2Cl_2$ (5 ml) at 0–5° C. were added triethylamine (101 mg, 1 mmol) and 2,3-pyrazinedicarboxylic anhydride (156 mg, 1 mmol). The resulting mixture was stirred at rt for 16 h before evaporation to dryness. The residue was triturated with water (10 ml) and filtered. Recrystallization of the solid from methanol gave trioxolane OZ109 (300 mg, 72%) as a colorless solid. mp 128–130° C. (methanol); $^1$H NMR (500 MHz, $CDCl_3$) δ 1.52–2.21 (m, 18H), 3.21–3.43 (m, 2H), 3.79–3.96 (m, 1H), 3.97–4.14 (m, 1H), 8.71 (s, 1H); $^{13}$C NMR (125.7 MHz, $CDCl_3$) δ 26.54, 26.92, 33.73, 34.32, 34.78, 34.83, 34.84, 34.96, 36.48, 36.52, 36.79, 39.94, 44.80, 106.79, 112.42, 140.16, 143.16, 146.96, 151.73, 163.03, 165.23. Anal. Calcd for $C_{21}H_{25}N_3O_6$: C, 60.71; H, 6.07; N, 10.11. Found: C, 60.46; H, 5.93; N, 9.96.

Adamantane-2-spiro-3'-1',2',4'-trioxolane-5'-spiro-3"-8"-ethoxycarbonyl-8"-azabicyclo[3.2.1]octane (OZ110). A solution of O-methyl 2-adamantanone oxime (895 mg, 5.0 mmol) and N-carboethoxytropinone (1.01 g, 5.2 mmol) in pentane (80 ml) and $CH_2Cl_2$ (20 ml) was treated with ozone according to the general procedure. The crude product was purified by flash chromatography (silica gel, 15% ether in hexanes) to afford trioxolane OZ110 (300 mg, 17%, 2:1 mixture of two diastereomers) as a colorless solid. mp 98–100° C.; $^1$H NMR (500 MHz, $CDCl_3$) δ 1.27 (t, J=7.1 Hz, 3H), 1.58–2.39 (m, 22H), 4.15 (q, J=6.8 Hz, 2H), 4.18–4.45 (m, 2H); $^{13}$C NMR (125.7 MHz, $CDCl_3$) δ 14.67 26.45, 26.50, 26.86, 26.89, 27.16, 27.60 (br s), 33.22, 34.68, 34.82, 35.06, 36.37, 36.41, 36.74, 36.77, 37.05, 40.42 (br s), 52.44, 52.75, 52.78, 60.88, 60.93, 60.96, 106.98, 107.71, 110.39, 112.46, 153.70. Anal. Calcd for $C_{20}H_{29}NO_5$: C, 66.09; H, 8.04; N, 3.85. Found: C, 66.12; H, 7.90; N, 3.82.

Adamantane-2-spiro-3'-8'-(3',3'-dimethylbutanoyl)-1',2',4'-trioxa-8'-azaspiro[4.5]decane (OZ111). To a solution of OZ80 (302 mg, 1 mmol) in $CH_2Cl_2$ (10 ml) at 0–5° C. were added triethylamine (303 mg, 3 mmol) and trimethylacetyl chloride (185 mg, 1.5 mmol). The resulting mixture was stirred at rt for 16 h, then diluted with $CH_2Cl_2$ (10 ml), and washed with water (10 ml) and brine (10 ml). The organic phase was separated, dried over $MgSO_4$, and concentrated. Crystallization of the residue from methanol gave trioxolane OZ111 (140 mg, 39%) as a colorless solid. mp 98–100° C. (methanol); $^1$H NMR (500 MHz, $CDCl_3$) δ 1.05 (s, 9H), 1.58–2.11 (m, 18H), 2.27 (AB system, 2H), 3.46–3.69 (m, 3H), 3.75–3.90 (m, 1H); $^{13}$C NMR (125.7 MHz, $CDCl_3$) δ 26.60, 26.99, 30.06, 31.39, 34.37 (br s), 34.85, 35.34 (br s), 36.57, 36.85, 39.44 (br s), 44.40 (br s), 44.75, 106.92, 112.25, 170.30. Anal. Calcd for $C_{21}H_{33}NO_4$: C, 69.39; H, 9.15; N, 3.85. Found: C, 69.52; H, 8.89; N, 3.72.

Adamantane-2-spiro-3'-8'-[(carboxymethoxy)acetyl]-1', 2',4'-trioxa-8'-azaspiro[4.5]decane (OZ112). To a solution of OZ80 (302 mg, 1 mmol) in $CH_2Cl_2$ (10 ml) was added triethylamine (101 mg, 1 mmol). The solution was then cooled to 0–5° C., and diglycolic anhydride (116 mg, 1 mmol) was added. The resulting mixture was stirred at rt for 16 h before evaporation to dryness. The residue was triturated with water (10 ml) and filtered. Recrystallization of the solid from methanol gave trioxolane OZ112 (250 mg, 66%) as a colorless solid. mp 126–128° C. (methanol); $^1$H NMR (500 MHz, $CDCl_3$). δ 1.59–2.18 (m, 18H), 3.29–3.49 (m, 2H), 3.63–3.77 (m, 1H), 3.79–3.91 (m, 1H), 4.22 (s, 2H), 4.42 (s, 2H); $^{13}$C NMR (125.7 MHz, $CDCl_3$) δ 26.44, 26.84, 33.91, 34.72, 34.80, 34.97, 36.45, 36.68, 40.56, 42.21, 70.94, 72.00, 106.08, 112.64, 169.20, 171.40. Anal. Calcd for $C_{19}H_{27}NO_7$: C, 59.83; H, 7.14; N, 3.67. Found: C, 59.67; H, 7.16; N, 3.56.

Adamantane-2-spiro-3'-8'-methoxyacetyl-1',2',4'-trioxa-8'-azaspiro[4.5]decane (OZ113). To a solution of OZ80 (301 mg, 1 mmol) in $CH_2Cl_2$ (10 ml) was added triethylamine (303 mg, 3 mmol). The solution was then cooled to 0–5° C., and methoxyacetyl chloride (163 mg, 1.5 mmol) was added. The resulting mixture was stirred at rt for 16 h and washed with water (5 ml) and brine (5 ml). The organic phase was separated, dried over $MgSO_4$, and concentrated to give trioxolane OZ113 (325 mg, 96%) as a colorless solid. mp 76–78° C.; $^1$H NMR (500 MHz, $CDCl_3$) δ 1.59–2.17 (m, 18H), 3.42 (s, 3H), 3.43–3.73 (m, 3H), 3.75–3.89 (m, 1H), 4.11 (AB system, 2H); $^{13}$C NMR (125.7 MHz, $CDCl_3$) δ 26.57, 26.97, 34.32 (br s), 34.83, 34.92, 35.25 (br s), 36.55, 36.82, 39.98 (br s), 42.87 (br s), 58.96, 72.21, 106.78, 112.30, 167.54. Anal. Calcd for $C_{18}H_{27}NO_5$: C, 64.07; H, 8.07; N, 4.15. Found: C, 63.94; H, 8.03; N, 4.30.

Adamantane-2-spiro-3'-8'-(8'-quinolinesulfonyl)-1',2',4'-trioxa-8'-azaspiro[4.5]decane (OZ114). To a solution of OZ80 (151 mg, 0.5 mmol) in $CH_2Cl_2$ (5 ml) was added triethylamine (150 mg, 1.49 mmol). The solution was then cooled to 0–5° C., and 8-quinolinesulfonyl chloride (115 mg, 0.5 mmol) was added. The resulting mixture was stirred at rt for 12 h before evaporation to dryness. The residue was triturated with water (5 ml) and filtered. Recrystallization of the solid from methanol gave trioxolane OZ114 (215 mg, 94%) as a colorless solid. mp 142–144° C. (methanol); $^1$H NMR (500 MHz, $CDCl_3$) δ 1.55–2.21 (m, 18H), 3.40–3.61 (m, 2H), 3.62–3.85 (m, 2H), 7.51 (dd, J=8.2, 3.9 Hz, 1H), 7.61 (dd, J=8.2, 8.2 Hz, 1H), 8.02 (d, J=7.8 Hz, 1H), 8.23 (dd, J=8.3, 1.5 Hz, 1H), 8.47 (dd, J=7.3, 1.5 Hz, 1H), 9.05 (dd, J=3.9, 1.5 Hz, 1H); $^{13}$C NMR (125.7 MHz, $CDCl_3$) δ 26.58, 26.97, 34.82, 34.88, 34.90, 36.54, 36.83, 44.37, 106.74, 112.16, 121.98, 125.47, 129.12, 132.68, 133.24, 136.30, 137.86, 144.33, 151.10. Anal. Calcd for $C_{24}H_{28}N_2O_5S$: C, 63.14; H, 6.18; N, 6.14. Found: C, 62.94; H, 6.16; N, 6.00.

Adamantane-2-spiro-3'-8'-(1'-octanesulfonyl)-1',2',4'-trioxa-8'-azaspiro[4.5]decane (OZ115). To a solution of OZ80 (200 mg, 0.66 mmol) and triethylamine (200 mg, 1.98 mmol) in $CH_2Cl_2$ (5 ml) at 0–5° C. was added 1-octanesulfonyl chloride (170 mg, 0.8 mmol). The resulting mixture was stirred at rt for 12 h before evaporation to dryness. The residue was triturated with water (10 ml) and filtered. Recrystallization of the solid from methanol gave trioxolane OZ115 (160 mg, 55%) as a colorless solid. mp 54–56° C. (methanol); $^1$H NMR (500 MHz, $CDCl_3$) δ 0.88 (t, J=6.8 Hz, 3H), 1.17–1.49 (m, 10H), 1.61–2.21 (m, 20H), 2.90 (t, J=8.1 Hz, 2H), 3.24–3.39 (m, 2H), 3.41–3.57 (m, 2H); $^{13}$C NMR (125.7 MHz, $CDCl_3$) δ 13.95, 22.56, 23.26, 26.55, 26.95, 28.49, 28.93, 29.04, 31.71, 34.71, 34.82, 34.91, 36.53, 36.79, 43.97, 50.46, 106.24, 112.41. Anal. Calcd for $C_{23}H_{39}NO_5S$: C, 62.55; H, 8.90; N, 3.17. Found: C, 62.38; H, 8.76; N, 3.25., cis-Adamantane-2-spiro-3'-8'-[(hydroxyamino)carbonyl]-1',2',4'-trioxaspiro[4.5]decane (OZ116). A solution of ethyl chloroformate (0.26 g, 2.4 mmol), OZ72 (0.62 g, 2.0 mmol), and triethylamine (0.27 g, 2.6 mmol) in ether (6 ml) was stirred at 0° C. for 10 min. The solid was removed by filtration, and the filtrate was added to a freshly prepared solution of hydroxylamine. [To a suspension of KOH (168 mg, 3.0 mmol) in methanol (1 ml) at 0° C. was added a solution of hydroxylamine hydrochloride (0.20 g, 3 mmol) in methanol (3 ml). The reaction mixture was stirred at 0° C. for 15 min and filtered to remove solid by-products. The filtrate was used as such.] The resulting mixture was stirred at rt for 1 h and concentrated. The crude product was purified by flash chromatography (silica gel, 8% methanol in chloroform) to afford trioxolane OZ116 (0.23 g, 36%) as a colorless solid. mp 130–132° C. (ethanol/water 1:2); $^1$H NMR (500 MHz, DMSO-$d_6$) δ 1.40–2.19 (m, 23H), 8.60 (s, 1H), 10.35 (s, 1H); $^{13}$C NMR (125.7 MHz, DMSO-$d_6$) δ 25.87, 26.27, 26.50, 33.03, 34.28, 34.30, 35.84, 36.15, 39.04, 107.85, 110.64, 171.30. Anal. Calcd for $C_{17}H_{25}NO_5$: C, 63.14; H, 7.79; N, 4.33. Found: C, 62.97; H, 7.57; N, 4.26.

Adamantane-2-spiro-3'-8'-(aminomethyl)-8'-phenyl-1',2',4'-trioxaspiro[4.5]decane hydrochloride (OZ117). A solution of OZ97 (1.60 g, 3.2 mmol) and hydrazine monohydrate (325 mg, 6.5 mmol) in chloroform (27 ml) and methanol (3 ml) was heated at 50° C. for 36 h. The reaction mixture was cooled to rt and filtered to remove solid by-products. The filtrate was washed with water (20 ml) and brine (20 ml), dried over MgSO$_4$, filtered, and concentrated. The solid was dissolved in ether (30 ml), treated with 1 M ethereal HCl (6 ml), and filtered. Recrystallization from hexanes/chloroform (2:1) gave trioxolane OZ117 (0.22 g, 17%) as a colorless solid. mp 156° C. dec (hexanes/chloroform 2:1); $^1$H NMR (500 MHz, DMSO-d$_6$) δ 1.42–2.05 (m, 20H), 2.32 (apparent d, J=13.7 Hz, 2H), 2.89 (s, 2H), 7.26–7.39 (m, 1H), 7.41–7.62 (m, 4H), 7.80 (br s, 3H); $^{13}$C NMR (125.7 MHz, DMSO-d$_6$) δ 25.82, 26.19, 30.08, 34.24, 35.76, 36.09, 49.37, 107.89, 110.70, 126.97, 127.14, 128.98, 139.82. Anal. Calcd for C$_{23}$H$_{32}$ClNO$_3$: C, 68.05; H, 7.95; N, 3.45. Found: C, 67.92; H, 7.69; N, 3.72.

cis-Adamantane-2-spiro-3'-8'-acetoxymethyl-1',2',4'-trioxaspiro[4.5]decane (OZ118). A solution of O-methyl 2-adamantanone oxime (1.34 g, 7.5 mmol) and 4-acetoxymethylcyclohexanone (1.28 g, 7.5 mmol) in pentane (100 ml) and CH$_2$Cl$_2$ (20 ml) was treated with ozone according to the general procedure. The crude product was purified by flash chromatography (silica gel, 10% ether in hexanes) to afford trioxolane OZ118 (1.15 g, 46%) as a colorless solid. mp 39–41° C. (ethanol/H$_{20\ 7:3}$); $^1$H NMR (500 MHz, CDCl$_3$) δ 1.18–1.31 (m, 2H), 1.59–2.19 (m, 21H), 2.05 (s, 3H), 3.90 (d, J=6.3 Hz, 2H); $^{13}$C NMR (125.7 MHz, CDCl$_3$) δ 20.77, 26.62, 26.77, 27.02, 33.71, 34.86, 34.88, 35.67, 36.54, 36.91, 68.49, 108.57, 111.40, 170.90. Anal. Calcd for C$_{19}$H$_{28}$O$_5$: C, 67.83; H, 8.39. Found: C, 67.70; H, 8.32.

cis-Adamantane-2-spiro-3'-8'-hydroxymethyl-1',2',4'-trioxaspiro[4.5]decane (OZ119). A solution of OZ70 (0.81 g, 2.4 mmol), lithium borohydride (1.2 ml, 2.4 mmol, 2 M in THF), and lithium triethylborohydride (0.24 ml, 0.24 mmol, 1 M in THF) in ether (2.5 ml) was stirred at rt for 3 h. The reaction mixture was diluted with ether (5 ml), washed with 3 M aq. NaOH (2×5 ml), water (2×5 ml) and brine (5 ml), dried over MgSO$_4$, filtered, and concentrated in vacuo to afford trioxolane OZ119 (0.68 g, 96%) as a colorless solid. mp 97–99° C. (ethanol/H$_2$O 1:1); $^1$H NMR (500 MHz, CDCl$_3$) δ 1.09–127 (m, 2H), 1.42–2.19 (m, 21H), 3.47 (d, J=6.5 Hz, 2H); $^{13}$C NMR (125.7 MHz, CDCl$_3$) δ 26.63, 26.66, 27.03, 33.86, 34.87, 34.90, 36.56, 36.93, 38.97, 67.63, 108.91, 111.32. Anal. Calcd for C$_{17}$H$_{26}$O$_4$: C, 69.36; H, 8.90. Found: C, 69.58; H, 8.63.

Adamantane-2-spiro-3'-11',11'-bis(ethoxycarbonyl)-1',2',4',9',13'-pentaoxadispiro[4.2.5.2]pentadecane (OZ120). A solution of O-methyl 2-adamantanone oxime (2.69 g, 15 mmol) and 3,3-bis(ethoxycarbonyl)-1,5-dioxaspiro[5.5]undecan-9-one (4.71 g, 15 mmol) in pentane (100 ml) and CH$_2$Cl$_2$ (50 ml) was treated with ozone according to the general procedure. The crude product was purified by flash chromatography (silica gel, 10% ether in petroleum ether) to afford trioxolane OZ120 (3.60 g, 50%) as a colorless solid. mp 74–77° C. (ethanol); $^1$H NMR (500 MHz, CDCl$_3$) δ 1.27 (t, J=7.1 Hz, 6H), 1.61–2.18 (m, 22H), 4.24 (q, J=7.2 Hz, 4H), 4.28 (s, 4H); $^{13}$C NMR (125.7 MHz, CDCl$_3$) δ 13.91, 26.55, 26.95, 29.35, 30.45, 34.77, 34.87, 36.43, 36.83, 39.26, 53.95, 61.77, 62.10, 97.54, 108.22, 111.56, 167.84. Anal. Calcd for C$_{25}$H$_{36}$O$_9$: C, 62.48; H, 7.55. Found: C, 62.62; H, 7.32.

Adamantane-2-spiro-3'-11',11'-bis(hydroxymethyl)-1',2',4',9',13'-pentaoxadispiro[4.2.5.2]pentadecane (OZ121). A solution of OZ120 (1.00 g, 2.18 mmol), lithium borohydride (2.10 ml, 4.20 mmol, 2 M in THF), and lithium triethyl-borohydride (0.42 ml, 0.42 mmol, 1 M in THF) in ether (5 ml) was stirred at rt for 3 h. The reaction mixture was diluted with ether (10 ml) and washed with 3 M aq. NaOH (2×10 ml), water (2×10 ml), and brine (10 ml). The combined aqueous layers were extracted with CHCl$_3$ (3×50 ml), and the chloroform extract was washed with water (2×50 ml) and brine (50 ml). The ether extract and chloroform extract were combined, dried over MgSO$_4$, filtered, and concentrated. The residue was purified by flash chromatography (silica gel, 5% methanol in chloroform) to afford trioxolane OZ121 (0.40 g, 46%) as a colorless solid. mp 146–148° C. (ethanol/H$_{20\ 3:2}$); $^1$H NMR (500 MHz, DMSO-d$_6$) δ 1.60–2.15 (m, 22H), 3.36 (d, J=4.9 Hz, 4H), 3.61 (s, 2H), 3.62 (s, 2H), 4.49 (t, J=5.4 Hz, 2H); $^{13}$C NMR (125.7 MHz, DMSO-d$_6$) δ 25.86, 26.26, 29.34, 30.21, 34.27, 34.36, 35.77, 36.13, 39.07, 60.69, 61.44, 61.48, 96.00, 108.15, 110.84. Anal. Calcd for C$_{21}$H$_{32}$O$_7$.0.077CHCl$_3$: C, 62.40; H, 7.97. Found: C, 62.76; H, 7.77.

Adamantane-2-spiro-3'-11',11'-dicarboxy-1',2',4',9',13'-pentaoxadispiro[4.2.5.2]pentadecane (OZ122). A solution of OZ120 (0.73 g, 1.5 mmol), 15% aq. KOH (4.2 ml) in methanol (30 ml) was heated at 50° C. for 2 h. After being cooled to rt, the reaction mixture was concentrated to 5 ml, acidified with conc. HCl, and extracted with CHCl$_3$ (5×50 ml). The combined organic layers were washed with water (2×50 ml) and brine (50 ml), dried over MgSO$_4$, filtered, and concentrated to afford trioxolane OZ122 (0.38 g, 58%) as a colorless solid. mp 151–153° C. (water); $^1$H NMR (500 MHz, DMSO-d$_6$) δ 1.51–2.14 (m, 22H), 4.13 (s, 2H), 4.15 (s, 2H); $^{13}$C NMR (125.7 MHz, DMSO-d$_6$) δ 25.86, 26.26, 29.16, 30.16, 34.27, 34.37, 35.77, 36.13, 52.89, 61.65, 96.49, 107.99, 110.92, 169.11. Anal. Calcd for C$_{21}$H$_{28}$O$_9$: C, 59.43; H, 6.65. Found: C, 59.42; H, 6.66.

cis-Adamantane-2-spiro-3'-8'-bromomethyl-1',2',4'-trioxaspiro[4.5]decane (OZ123). A solution of O-methyl 2-adamantanone oxime (2.15 g, 12 mmol) and 4-bromomethylcyclohexanone (2.30 g, 12 mmol) in pentane (100 ml) and CH$_2$Cl$_2$ (50 ml) was treated with ozone according to the general procedure. The crude product was purified by flash chromatography (silica gel, 3% ether in hexanes) to afford trioxolane OZ123 (1.62 g, 38%) as a colorless solid. mp 138–140° C. (ethanol); $^1$H NMR (500 MHz, CDCl$_3$) δ 1.21–1.41 (m, 2H), 1.51–2.21 (m, 21H), 3.28 (d, J=6.3 Hz, 2H); $^{13}$C NMR (125.7 MHz, CDCl$_3$) δ 26.64, 27.04, 28.83, 33.73, 34.88, 34.90, 36.55, 36.93, 38.63, 38.76, 108.41, 111.47. Anal. Calcd for C$_{17}$H$_{25}$BrO$_3$: C, 57.15; H, 7.05. Found: C, 57.20; H, 6.99.

Adamantane-2-spiro-3'-5'-(4'-cyanophenyl)-5'-phenyl)-1',2',4'-trioxolane (OZ124). A solution of O-methyl 2-adamantanone oxime (0.86 g, 4.80 mmol) and 4-cyanobenzophenone (1.00 g, 4.80 mmol) in pentane (50 ml) and CH$_2$Cl$_2$ (60 ml) was treated with ozone according to the general procedure. The crude product was purified by flash chromatography (silica gel, 10% ether in hexanes) to afford trioxolane OZ124 (0.30 g, 17%) as a colorless solid. mp 136–137° C. (ether); $^1$H NMR (500 MHz, CDCl$_3$) δ 1.60–2.35 (m, 14H), 7.31–7.39 (m, 3H), 7.40–7.48 (m, 2H), 7.62–7.73 (m, 4H); $^{13}$C NMR (125.7 MHz, CDCl$_3$) δ 26.50, 26.92, 34.70, 34.80, 34.84, 35.39, 36.08, 36.25, 36.76, 108.84, 112.50, 114.57, 118.43, 126.85, 127.42, 128.38, 129.27, 131.97, 137.97, 146.30. Anal. Calcd for C$_{24}$H$_{23}$NO$_3$: C, 77.19; H, 6.21; N, 3.75. Found: C, 77.58; H, 6.32; N, 3.76.

Adamantane-2-spiro-3'-5',5'-bis[4'-(ethoxycarbonyl)phenyl]-1',2',4'-trioxolane (OZ125). A solution of O-methyl 2-adamantanone oxime (1.79 g, 10 mmol) and 4,4'-bis(ethoxycarbonyl)benzophenone (3.26 g, 10 mmol) in pentane (60 ml) and CH$_2$Cl$_2$ (40 ml) was treated with ozone according to the general procedure. The crude product was purified by flash chromatography (silica gel, 10% ether in hexanes) to afford trioxolane OZ125 (1.77 g, 36%) as a colorless solid. mp 143–145° C. (ether); $^1$H NMR (500 MHz, CDCl$_3$) δ 1.38 (t, J=7.1 Hz, 6H), 1.60–2.07 (m, 12H), 2.20 (app d, J=12.2 Hz, 2H), 4.37 (q, J=7.2 Hz, 4H), 7.58 (d, J=8.3 Hz, 4H), 8.03 (d, J=8.3 Hz, 4H); $^{13}$C NMR (125.7 MHz, CDCl$_3$) δ 14.28, 26.52, 26.94, 34.84, 35.06, 36.17, 36.78, 61.01, 108.84, 114.60, 126.69, 129.52, 131.10, 144.22, 166.06. Anal. Calcd for C$_{29}$H$_{32}$O$_7$: C, 70.71; H, 6.55. Found: C, 70.52; H, 6.32.

cis-Adamantane-2-spiro-3'-8'-[2'-(diethylamino)ethyl]-1', 2',4'-trioxaspiro[4.5]decane hydrobromide (OZ126). Step 1. A solution of O-methyl 2-adamantanone oxime (716 mg, 4 mmol) and 4-(2-bromoethyl)cyclohexanone (820 mg, 4 mmol) in pentane (72 ml) and CH$_2$Cl$_2$ (8 ml) was treated with ozone according to the general procedure. The crude product was purified by flash chromatography (silica gel, 1% ether in hexanes) to afford cis-Adamantane-2-spiro-3'-8'-(2'-bromoethyl)-1',2',4'-trioxaspiro[4.5]decane (800 mg, 54%) as a colorless solid. mp 62–64° C.; $^1$H NMR (500 MHz, CDCl$_3$) δ 1.18–1.22 (m, 2H), 1.72–2.10 (m, 23H), 3.42 (t, 2H, J=6.8 Hz). Step 2. To a solution of the above bromide (371 mg, 1 mmol) in acetonitrile (5 ml) were added diethylamine (140 mg, 2 mmol) and triethylamine (101 mg, 1 mmol). The mixture was heated at 60–65° C. for 60 h before removal of solvents. The residue was triturated with water (5 ml) and filtered. Recrystallization of the solid from ethanol gave trioxolane OZ126 (170 mg, 43%) as a colorless solid. mp 152–154° C. (ethanol); $^1$H NMR (500 MHz, CDCl$_3$) δ 1.20–1.34 (m, 2H), 1.41 (t, J=7.3 Hz, 6H), 1.60–2.25 (m, 23H), 2.95–3.04 (m, 2H), 3.05–3.19 (m, 4H), 12.17 (s, 1H); $^{13}$C NMR (125.7 MHz, CDCl$_3$) δ 8.69, 26.61 27.00, 29.13, 29.84, 33.90, 34.34, 34.86, 34.88, 36.54, 36.90, 46.55, 49.51, 108.27, 111.54. Anal. Calcd for C$_{22}$H$_{37}$NO$_3$·0.5HBr: C, 65.41; H, 9.36; N, 3.47. Found: C, 65.24; H, 9.54; N, 3.46.

trans-Adamantane-2-spiro-3'-8'-[(hydroxyamino) carbonyl]-1',2',4'-trioxaspiro[4.5]decane (OZ127). A solution of ethyl chloroformate (0.13 g, 1.2 mmol), OZ71 (0.31 g, 1.0 mmol), and triethylamine (0.13 g, 1.3 mmol) in ether (5 ml) was stirred at 0° C. for 10 min. The solid was removed by filtration, and the filtrate was added to a freshly prepared solution of hydroxylamine. [To a suspension of KOH (84 mg, 1.5 mmol) in methanol (1 ml) at 0° C. was added a solution of hydroxylamine hydrochloride (0.10 g, 1.5 mmol) in methanol (2 ml). The reaction mixture was stirred at 0° C. for 15 min and filtered to remove solid by-products. The filtrate was used as such.] The resulting mixture was stirred at rt for 1 h and concentrated. The crude product was purified by crystallization from hexanes/chloroform (5:1) to afford trioxolane OZ127 (0.15 g, 47%) as a colorless solid. mp 136–138° C. (hexanes/chloroform 5:1); $^1$H NMR (500 MHz, DMSO-d$_6$) δ 1.42–2.23 (m, 23H), 8.60 (s, 1H), 10.36 (s, 1H); $^{13}$C NMR (125.7 MHz, DMSO-d$_6$) δ 25.87, 26.26, 26.40, 32.95, 34.26, 34.42, 35.81, 36.13, 39.26, 107.88, 110.95, 171.35. Anal. Calcd for C$_{17}$H$_{25}$NO$_5$: C, 63.14; H, 7.79; N, 4.33. Found: C, 62.89; H, 7.59; N, 4.40.

Adamantane-2-spiro-3'-11'-methylene-1',2',4',9',13'-pentaoxadispiro[4.2.5.2]pentadecane (OZ128). Step 1. A mixture of OZ05 (1.12 g, 4 mmol), TFA (0.70 ml), CH$_2$Cl$_2$ (10 ml), and methanol (70 ml) was stirred at rt for 16 h. The reaction was quenched with NaHCO$_3$ (2.0 g) and stirred for additional 1 h before evaporation to dryness. The residue was dissolved in CH$_2$Cl$_2$ (20 ml), washed with water and brine, dried over MgSO$_4$, filtered, and concentrated to afford dimethyl ketal of OZ05 (1.31 g, 100%) as a colorless oil. $^1$H NMR (500 MHz, CDCl$_3$) δ 1.66–2.02 (m, 22H), 3.18 (s, 3H), 3.19 (s, 3H). Step 2. A mixture of the above ketal (1.30 g, 4 mmol), 2-methylene-1,3-propanediol (0.70 g, 8 mmol), and p-TsOH (0.5 g) in CH$_2$Cl$_2$ (70 ml) and THF (10 ml) was stirred at rt for 16 h. The reaction was quenched with NaHCO$_3$ (1.0 g), stirred for additional 1 h, and diluted with water (70 ml). After separation of the organic layer, the aqueous layer was extracted with CH$_2$Cl$_2$ (2×50 ml). The combined organic layers were washed with water and brine, dried over MgSO$_4$, filtered, and concentrated. The crude product was purified by flash chromatography (silica gel, 8% ether in hexanes) to afford trioxolane 128 (0.87 g, 63%) as a colorless solid. mp 58–59° C. (hexanes); $^1$H NMR (500 MHz, CDCl$_3$) δ 1.59–2.21 (m, 22H), 4.31 (s, 4H), 4.86 (s, 2H); $^{13}$C NMR (125.7 MHz, CDCl$_3$) δ 26.60, 27.02, 29.97, 30.69, 34.84, 34.94, 36.49, 36.90, 63.63, 97.60, 107.92, 108.38, 111.59, 141.15. Anal. Calcd for C$_{20}$H$_{28}$O$_5$: C, 68.94; H, 8.10. Found: C, 68.77; H, 7.93.

cis-Adamantane-2-spiro-3'-8'-[(2'-hydroxy-1',1'-dimethylethylamino)carbonyl]-1',2',4'-trioxaspiro[4.5] decane (OZ129). A solution of OZ72 (0.77 g, 2.50 mmol), DCC (0.78 g, 3.75 mmol), HOBT (0.51 g, 3.75 mmol), and 2-amino-2-methyl-1-propanol (0.33 g, 3.75 mmol) in DMF (20 ml) was heated at 50–60° C. for 6 h. After being cooled to rt, the reaction mixture was acidified with 1 M aq. HCl (100 ml) and extracted with ethyl acetate (4×60 ml). The combined extracts were washed with water and brine, dried over MgSO$_4$, filtered, and concentrated. The crude product was purified by flash chromatography (silica gel, 50% ethyl acetate in hexanes) to afford trioxolane 129 (0.44 g, 46%) as a colorless solid. mp 163–164° C. (ethanol); $^1$H NMR (500 MHz, CDCl$_3$) δ 1.27 (s, 6H), 1.60–2.24 (m, 23H), 3.56 (s, 2H), 4.80 (s, 1H); $^{13}$C NMR (125.7 MHz, CDCl$_3$) δ 24.77, 26.62, 27.03, 27.21, 33.64, 34.86, 34.90, 36.55, 36.91, 44.24, 55.95, 70.66, 107.78, 111.60, 175.63. Anal. Calcd for C$_{21}$H$_{33}$NO$_5$: C, 66.46; H, 8.76; N, 3.69. Found: C, 66.41; H, 8.56; N, 3.76.

Adamantane-2-spiro-3'-11'-oxo-1',2',4',9',13'-pentaoxadispiro[4.2.5.2]pentadecane (OZ130). A solution of OZ128 (0.65 g, 1.9 mmol) in CH$_2$Cl$_2$ (80 ml) at −78° C. was treated with ozone for 10 min, flashed with oxygen for 5 min before addition of triphenylphosphine (0.49 g, 1.9 mmol). The reaction mixture was warmed up to rt and stirred at rt for 1 h before evaporation to dryness. The crude product was purified by flash chromatography (silica gel, 10% ether in hexanes) to afford trioxolane OZ130 (0.37 g, 57%) as a colorless solid. mp 76–79° C. (hexanes); $^1$H NMR (500 MHz, CDCl$_3$) δ 1.61–2.21 (m, 22H), 4.17 (s, 4H); $^{13}$C NMR (125.7 MHz, CDCl$_3$) δ 26.61, 27.03, 29.80, 30.81, 34.85, 34.96, 36.52, 36.89, 66.92, 66.94, 99.14, 107.96, 111.82, 207.00. Anal. Calcd for C$_{19}$H$_{26}$O$_6$: C, 65.13; H, 7.48. Found: C, 65.38; H, 7.58.

Adamantane-2-spiro-3'-8'-phenylmethanesulfonyl-1',2', 4'-trioxa-8'-azaspiro[4.5]decane (OZ131). To a solution of OZ80 (301 mg, 1.0 mmol) and p-toluenesulfonyl chloride (192 mg, 1.0 mmol) in CH$_2$Cl$_2$ (10 ml) at 0–5° C. was added triethylamine (303 mg, 3.0 mmol). The resulting mixture was stirred at rt for 16 h before evaporation to dryness. The residue was triturated with water, filtered, and crystallized from ethanol to give trioxolane OZ131 (320 mg, 76%) as a colorless solid. mp 148–150° C. (ethanol); $^1$H NMR (500 MHz, CDCl$_3$) δ 1.59–2.21 (m, 18H), 3.06–3.24 (m, 2H), 3.25–3.41 (m, 2H), 4.22 (s, 2H), 7.27–7.60 (m, 5H); $^{13}$C NMR (125.7 MHz, CDCl$_3$) δ 26.53, 26.94, 34.77, 34.79, 34.89, 36.50, 36.78, 44.20, 57.79, 106.20, 112.28, 128.79, 129.12, 130.67. Anal. Calcd for C$_{22}$H$_{29}$NO$_5$S: C, 62.98; H, 6.97; N, 3.34. Found: C, 63.16; H, 6.79; N, 3.46.

Adamantane-2-spiro-3'-8'-(2'-carboxybenzoyl)-1',2',4'-trioxa-8'-azaspiro[4.5]decane (OZ132). To a solution of OZ80 (301 mg, 1.0 mmol) and triethylamine (101 mg, 1.0 mmol) in CH$_2$Cl$_2$ (10 ml) at 0–5° C. was added phthalic anhydride (148 mg, 1.0 mmol). The resulting mixture was stirred at rt for 24 h before evaporation to dryness. The residue was triturated, filtered, and crystallized from ethanol to give trioxolane OZ132 (285 mg, 69%) as a colorless solid. mp 162–164° C. (ethanol); $^1$H NMR (500 MHz, DMSO-d$_6$) δ 1.57–2.21 (m, 18H), 3.01–3.32 (m, 2H), 3.35–4.04 (m, 2H), 7.33 (d, J=7.3 Hz, 1H), 7.52 (dd, J=7.8, 7.8 Hz, 1H), 7.64 (dd, J=7.3, 7.3 Hz, 1H), 7.93 (d, J=7.8 Hz, 1H), 13.14 (br s, 1H); $^{13}$C NMR (125.7 MHz, DMSO-d$_6$) δ 25.84, 26.23, 33.29, 33.54, 34.25, 34.34, 35.74, 35.79, 36.07, 38.82, 44.26, 107.05, 111.35, 126.62, 128.43, 128.63, 130.03, 132.42, 138.38, 166.90, 168.45. Anal. Calcd for C$_{23}$H$_{27}$NO$_6$: C, 66.81; H, 6.58; N, 3.39. Found: C, 67.02; H, 6.65; N, 3.40.

Adamantane-2-spiro-3'-8'-[(dimethylamino)carbonyl]-1',2',4'-trioxa-8'-azaspiro[4.5]decane (OZ133). To a solution of OZ80 (301 mg, 1.0 mmol) and triethylamine (101 mg, 1.0 mmol) in CH$_2$Cl$_2$ (10 ml) at 0–5° C. was added dimethylcarbamoyl chloride (115 mg, 1.07 mmol). The resulting mixture was stirred at rt for 16 h before evaporation to dryness. The residue was triturated, and filtered, and crystallized from methanol to give trioxolane OZ133 (260 mg, 77%) as a colorless solid. mp 106–108° C. (methanol); $^1$H NMR (500 MHz, CDCl$_3$) δ 1.60–2.11 (m, 18H), 2.82 (s, 6H), 3.21–3.47 (m, 4H); $^{13}$C NMR (125.7 MHz, CDCl$_3$) δ 26.61, 27.01, 34.52, 34.84, 34.94, 36.59, 36.87, 38.53, 44.69, 107.28, 111.95, 164.66. Anal. Calcd for C$_{18}$H$_{28}$N$_2$O$_4$: C, 64.26; H, 8.39; N, 8.33. Found: C, 64.49; H, 8.36; N, 8.42.

Adamantane-2-spiro-3'-1',2',4'-trioxolane-5'-spiro-4''-2'',3''-dihydro-4''H-1''-benzopyran (OZ134). A solution of O-methyl 2-adamantanone oxime (895 mg, 5 mmol) and 4-chromanone (740 mg, 5 mmol) in cyclohexane (80 ml) and CH$_2$Cl$_2$ (20 ml) was treated with ozone according to the general procedure. The crude product was purified by flash chromatography (silica gel, 2% ether in hexanes) to afford trioxolane OZ134 (590 mg, 38%) as a colorless solid. mp 136–138° C. (methanol); $^1$H NMR (500 MHz, CDCl$_3$) δ 1.61–2.38 (m, 14H), 2.39–2.61 (m, 2H), 4.234.51 (m, 2H), 6.83 (d, J=8.3 Hz, 1H), 6.96 (dd, J=8.3, 8.3 Hz, 1H), 7.27 (ddd, J=8.6, 8.6, 1.6 Hz, 1H), 7.53 (dd, J=7.8, 1.6 Hz, 1H); $^{13}$C NMR (125.7 MHz, CDCl$_3$) δ 26.61, 27.03, 33.46, 33.97, 34.89, 34.94, 35.78, 36.43, 36.91, 37.08, 64.65, 103.93, 112.95, 117.04, 120.68, 128.26, 131.42, 157.71. Anal. Calcd for C$_{19}$H$_{22}$O$_4$: C, 72.59; H, 7.05. Found: C, 72.48; H, 6.87.

Adamantane-2-spiro-3'-5',5'-bis(4'-carboxyphenyl)-1',2',4'-trioxolane (OZ135). A mixture of OZ125 (0.44 g, 0.89 mmol), THF (7 ml), and 40% aq. KOH (4.5 ml) was heated at 50° C. for 5 days. The reaction mixture was cooled to rt and extracted with ether (5×20 ml). The aqueous layer was acidified to pH=3 with conc. HCl. The resulting precipitate was filtered and recrystallized from ethanol/water (2:1) to afford trioxolane OZ135 (0.35 g, 90%) as a colorless solid. mp 170° C. (EtOAc) dec; $^1$H NMR (500 MHz, CDCl$_3$) δ 1.60–2.05 (m, 12H), 2.13 (app d, J=11.7 Hz, 2H), 7.60 (d, J=8.8 Hz, 4H), 7.98 (d, J=8.8 Hz, 4H); $^{13}$C NMR (125.7 MHz, CDCl$_3$) δ 25.79, 26.19, 34.25, 34.42, 35.56, 35.99, 108.40, 113.95, 126.42, 129.46, 131.47, 143.44, 166.69. Anal. Calcd for C$_{25}$H$_{24}$O$_7$: C, 68.80; H, 5.54. Found: C, 68.64; H, 5.34.

cis-Adamantane-2-spiro-3'-8'-phthalimido-1',2',4'-trioxaspiro[4.5]decane (OZ136). A solution of O-methyl 2-adarmantanone oxime (1.79 g, 10 mmol) and 4-phthalimidocyclohexanone (2.43 g, 10 mmol) in pentane (60 ml) and CH$_2$Cl$_2$ (80 ml) was treated with ozone according to the general procedure. The crude product was purified by flash chromatography (silica gel, 80% ether in hexanes) to afford trioxolane OZ136 (1.20 g, 29%) as a colorless solid. mp 156–158° C. (ether); $^1$H NMR NMR (500 MHz, CDCl$_3$) δ 1.60–2.19 (m, 20H), 2.45–2.63 (m, 2H), 4.18 (tt, J=12.4, 3.9 Hz, 1H), 7.64–7.76 (m, 2H), 7.77–7.89 (m, 2H); $^{13}$C NMR (125.7 MHz, CDCl$_3$) δ 26.60, 26.89, 27.00, 33.81, 34.85, 36.45, 36.89, 49.35, 107.43, 111.50, 123.06, 132.13, 133.75, 168.01. Anal. Calcd for C$_{24}$H$_{27}$NO$_5$: C, 70.40; H, 6.65; N, 3.42. Found: C, 70.16; H, 6.43; N, 3.43.

cis-Adamantane-2-spiro-3'-8'-amino-1',2',4'-trioxaspiro[4.5]decane hydrochloride (OZ137). A solution of OZ136 (0.81 g, 1.98 mmol) and hydrazine monohydrate (198 mg, 3.96 mmol) in chloroform (16 ml) and methanol (2 ml) was heated under nitrogen at 50° C. for 24 h. The reaction mixture was cooled to rt, filtered to remove solid by-products, and concentrated. The solid residue was dissolved in CHCl$_3$, washed with water and brine, dried over MgSO$_4$, filtered, and concentrated. The oily amine was dissolved in ether (2 ml), treated with 1 M ethereal HCl (7 ml), and filtered to give trioxolane OZ137 (0.31 g, 50%) as a colorless solid. mp 132° C. dec (ether); $^1$H NMR (500 MHz, DMSO-d$_6$) δ 1.41–1.59 (m, 2H), 1.60–2.15 (m, 20H), 3.10 (br s, 1H), 8.12 (br s, 3H); $^{13}$C NMR (125.7 MHz, DMSO-d$_6$) δ 25.83, 26.23, 27.46, 31.33, 34.27, 34.30, 35.73, 36.10, 47.31, 107.24, 110.96. Anal. Calcd for C$_{16}$H$_{26}$ClNO$_3$: C, 60.85; H, 8.30; N, 4.43. Found: C, 60.64; H, 8.16; N, 4.70.

Adamantane-2-spiro-3'-5'-[4'-(methoxycarbonyl)phenyl]-5'-phenyl-1',2',4'-trioxolane (OZ138). A solution of O-methyl 2-adamantanone oxime (1.79 g, 10 mmol) and 4-(methoxycarbonyl)benzophenone (2.40 g, 10 mmol) in pentane (40 ml) and CH$_2$Cl$_2$ (90 ml) was treated with ozone according to the general procedure. The crude product was purified by flash chromatography (silica gel, 10% ether in hexanes) to afford trioxolane OZ138 (1.00 g, 25%) as a colorless solid. mp 144–146° C. (ether); $^1$H NMR (500 MHz, CDCl$_3$) δ 1.60–2.29 (m, 14H), 3.91 (s, 3H), 7.31–7.39 (m, 3H), 7.43–7.52 (m, 2H), 7.63 (d, J=8.3 Hz, 2H), 8.03 (d, J=8.5 Hz, 2H); $^{13}$C NMR (125.7 MHz, CDCl$_3$) δ 26.58, 26.99, 33.32, 34.86, 34.88, 35.31, 36.13, 36.31, 36.86, 51.99, 109.28, 114.26, 126.76, 126.96, 128.22, 128.97, 129.42, 130.37, 138.83, 145.73, 166.69. Anal. Calcd for C$_{25}$H$_{26}$O$_5$: C, 73.87; H, 6.45. Found: C, 74.07; H, 6.55.

cis-Adamantane-2-spiro-3'-8'-[(4'-phenyl-1'-piperazinyl)carbonyl]-1',2',4'-trioxaspiro[4.5]decane hydrochloride (OZ140). A solution of OZ72 (0.31 g, 1.0 mmol), DCC (0.27 g, 1.3 mmol), and HOBT (0.16 g, 1.3 mmol) in CHCl$_3$ (15 ml) was stirred at 0° C. for 15 min before 1-phenylpiperazine (0.21 g, 1.3 mmol) was added. The mixture was then warmed to rt, stirred overnight, and concentrated. The residue was purified by flash chromatography (silica gel, 1% methanol in chloroform) to afford a solid, which was dissolved in chloroform (20 ml) and filtered. The filtrate was concentrated, redissolved in chloroform (15 ml) and ether (30 ml), and filtered. The filtrate was treated with 1 M ethereal HCl (1.5 ml) to afford trioxolane OZ140 (0.36 g, 74%) as a colorless solid. mp. 155–158° C. (chloroform/ether, 1:2); $^1$H NMR (500 MHz, CDCl$_3$) δ 1.42–2.23 (m, 22H), 2.44–2.62 (m, 1H), 3.51 (br s, 4H), 4.28 (br s, 4H), 7.42–7.60 (m, 3H), 7.79–7.95 (m, 2H); $^{13}$C NMR (125.7 MHz, CDCl$_3$) δ 26.59, 26.80, 27.01, 33.54, 34.84, 34.89, 36.54, 36.87, 38.53, 39.32, 55.25, 107.61, 111.61, 121.22, 130.05, 130.57, 142.36, 173.49. Anal. Calcd for C$_{27}$H$_{37}$ClN$_2$O$_4$: C, 66.31; H, 7.63; N, 5.73. Found: C, 66.26; H, 7.45; N, 5.83.

cis-Adamantane-2-spiro-3'-1',2',4'-trioxaspiro[4.5]decane-8'-methyl imidazole-1-carboxylate (OZ141). To a solution of OZ119 (0.29 g, 1 mmol) in CH₃CN(10 ml) and THF (3 ml) was added 1,1'-carbonyldiimidazole (0.21 g, 1.3 mmol). The mixture was stirred at rt for 2 h before being quenched with cold water (50 ml). The resulting precipitate was collected by filtration, washed with water, and dried to afford trioxolane OZ141 (0.34 g, 91%) as a colorless solid. mp 110–112° C. (water); $^1$H NMR (500 MHz, CDCl₃) δ 1.25–150 (m, 2H), 1.51–2.21 (m, 21H), 4.25 (d, J=6.3 Hz, 2H), 7.07 (s, 1H), 7.42 (s, 1H), 8.13 (s, 1H); $^{13}$C NMR (125.7 MHz, CDCl₃) δ 26.61, 27.02, 33.54, 34.86, 34.88, 35.66, 36.57, 36.90, 72.07, 108.17, 111.59, 117.03, 130.76, 137.07, 148.71. Anal. Calcd for $C_{21}H_{28}N_2O_5$: C, 64.93; H, 7.27; N, 7.21. Found: C, 65.12; H, 7.12; N, 7.25.

Adamantane-2-spiro-3'-8'-p-tolylaminocarbonyl)-1',2',4'-trioxa-8'-azaspiro[4.5]decane (OZ142). To a solution of OZ80 (301 mg, 1 mmol) and triethylamine (101 mg, 1 mmol) in CH₂Cl₂ (10 ml) at 0° C. was added p-tolyl isocyanate (133 mg, 1 mmol). The mixture was stirred at rt for 3 h before removal of solvents. The residue was triturated with water (10 ml) and filtered. Recrystallization of the solid from 95% ethanol gave trioxolane OZ142 (280 mg, 70%) as a colorless solid. mp 150–152° C. (95% ethanol); $^1$H NMR (500 MHz, CDCl₃) δ 1.61–2.19 (m, 18H), 2.29 (s, 3H), 3.43–3.71 (m, 4H), 6.44 (s, 1H), 7.08 (d, J=8.0 Hz, 2H), 7.21 (d, J=8.3 Hz, 2H); $^{13}$C NMR (125.7 MHz, CDCl₃) δ 20.65, 26.60, 26.99, 34.46, 34.84, 34.94, 36.58, 36.84, 42.46, 106.90, 112.25, 120.44, 129.40, 132.85, 136.53, 155.13. Anal. Calcd for $C_{23}H_{30}N_2O_4$: C, 69.32; H, 7.59; N, 7.03. Found: C, 69.10; H, 7.50; N, 7.08.

Adamantane-2-spiro-3'-8'-(t-butylaminocarbonyl)-1',2',4'-trioxa-8'-azaspiro[4.5]decane (OZ143). To a solution of OZ80 (301 mg, 1 mmol) and triethylamine (101 mg, 1 mmol) in CH₂Cl₂ (10 ml) at 0° C. was added tert-butyl isocyanate (100 mg, 1 mmol). The mixture was stirred at rt for 6 h before removal of solvents. The residue was triturated with water (10 ml) and filtered. Recrystallization of the solid from 95% ethanol gave trioxolane OZ143 (185 mg, 51%) as a colorless solid. mp 142–144° C. (95% ethanol); $^1$H NMR (500 MHz, CDCl₃) δ 1.35 (s, 9H), 1.62–2.09 (m, 18H), 3.35–3.59 (m, 4H), 4.34 (s, 1H); $^{13}$C NMR (125.7 MHz, CDCl₃) δ 26.60, 27.00, 29.51, 34.38, 34.84, 34.93, 36.57, 36.86, 42.22, 50.82, 107.13, 112.08, 156.72. Anal. Calcd for $C_{20}H_{32}N_2O_4$: C, 65.91; H, 8.85; N, 7.69. Found: C, 66.19; H, 8.50; N, 7.62.

Adamantane-2-spiro-3'-8'-(phenylaminothiocarbonyl)-1',2',4'-trioxa-8'-azaspiro[4.5]decane (OZ144). To a solution of OZ80 (301 mg, 1 mmol) and triethylamine (101 mg, 1 mmol) in CH₂Cl₂ (10 ml) at 0° C. was added phenyl isothiocyanate (135 mg, 1 mmol). The mixture was stirred at rt for 6 h before removal of solvents. The residue was triturated with water (10 ml) and filtered. Recrystallization of the solid from 95% ethanol gave trioxolane OZ144 (224 mg, 56%) as a colorless solid. mp 136–138° C. (95% ethanol); $^1$H NMR (500 MHz, CDCl₃) δ 1.60–2.19 (m, 18H), 3.78–4.05 (m, 4H), 7.07–7.18 (m, 3H), 7.32 (s, 1H), 7.28–7.37 (m, 2H); $^{13}$C NMR (125.7 MHz, CDCl₃) δ 26.56, 26.96, 34.09, 34.82, 34.92, 36.52, 36.81, 47.59, 106.54, 112.45, 122.59, 125.13, 129.27, 140.42, 184.18. Anal. Calcd for $C_{22}H_{28}N_2O_3S$: C, 65.97; H, 7.05; N, 6.99. Found: C, 65.93; H, 7.15; N, 7.13.

cis-Adamantane-2-spiro-3'-8'-(1'H-imidazol-1'-ylmethyl)-1',2',4'-trioxaspiro[4.5]decane (OZ145). Step 1. To a solution of OZ119 (0.29 g, 1 mmol) and triethylamine (0.15 g, 1.5 mmol) in CH₂Cl₂ (5 ml) at 0° C. was added dropwise a solution of methanesulfonyl chloride (0.14 g, 1.2 mmol) in CH₂Cl₂ (1 ml). The mixture was stirred at rt for 1 h before being quenched with water (5 ml). After separation of the aqueous layer, the organic layer was washed with water (5 ml) and brine (5 ml), dried over MgSO₄, filtered, and concentrated to afford the methanesulfonate (0.34 g, 92%) as a colorless solid. mp 82–84° C. (75% ethanol); $^1$H NMR (500 MHz, CDCl₃) δ 1.25–1.34 (m, 2H), 1.66–2.02 (m, 21H), 3.00 (s, 3H), 4.04 (d, J=6.3 Hz, 2H). Step 2. To a suspension of 60% NaH (0.08 g, 2 mmol) in DMF (4 ml) under nitrogen at 0° C. was added a solution of imidazole (0.14 g, 2 mmol) in DMF (4 ml). The mixture was stirred for 30 min before a solution of the above methanesulfonate (0.34 g, 0.9 mmol) in DMF (4 ml) was added dropwise. The mixture was heated at 50° C. for 2 h before being quenched with water (40 ml) and then extracted with ethyl acetate (3×30 ml). The combined extracts were washed with brine (3×30 ml), dried over MgSO₄, filtered, and concentrated. Crystallization of the residue from hexanes/CH₂Cl₂ (4:1) gave trioxolane OZ145 (0.17 g, 55%) as a colorless solid. mp 125–128° C. (hexanes/CH₂Cl₂, 4:1); $^1$H NMR (500 MHz, CDCl₃) δ 1.17–1.39 (m, 2H), 1.55–2.18 (m, 21H), 3.77 (d, J=7.3 Hz, 2H), 6.86 (s, 1H), 7.05 (s, 1H), 7.42 (s, 1H); $^{13}$C NMR (125.7 MHz, CDCl₃) δ 26.59, 26.99, 27.70, 33.58, 34.85, 34.87, 36.53, 36.88, 37.97, 52.49, 108.25, 111.60, 119.16, 129.55, 137.43. Anal. Calcd for $C_{20}H_{28}N_2O_3 \cdot 0.2H_2O$: C, 69.02; H, 8.22; N, 8.05. Found: C, 68.81; H, 8.11; N, 7.96.

cis-Adamantane-2-spiro-3'-8'-phthalimidomethyl-1',2',4'-trioxaspiro[4.5]decane (OZ146). A solution of O-methyl 2-adamantanone oxime (2.23 g, 12.4 mmol) and 4-phthalimidomethylcyclohexanone (3.20 g, 12.4 mmol) in pentane (100 ml) and CH₂Cl₂ (50 ml) was treated with ozone according to the general procedure. The crude product was purified by flash chromatography (silica gel, 25% ether in hexanes) to afford trioxolane OZ146 (1.66 g, 32%) as a colorless solid. mp 147–150° C. (ethanol); $^1$H NMR NMR (500 MHz, CDCl₃) δ 1.23–1.44 (m, 2H), 1.45–2.08 (m, 21H), 3.56 (d, J=7.0 Hz, 2H), 7.69–7.74 (m, 2H), 7.81–7.89 (m, 2H); $^{13}$C NMR (125.7 MHz, CDCl₃) δ 26.61, 27.01, 27.88, 33.66, 34.85, 34.87, 35.70, 36.51, 36.92, 43.12, 108.52, 111.35, 123.22, 132.20, 133.86, 168.47. Anal. Calcd for $C_{25}H_{29}NO_5$: C, 70.90; H, 6.90; N, 3.31. Found: C, 71.16; H, 6.75; N, 3.21.

Adamantane-2-spiro-3'-1',2',4'-trioxaspiro[4.5]decane-8'-yl imidazole-1-carboxylate (OZ147). To a solution of OZ32 (0.28 g, 1 mmol) in CH₃CN (10 ml) and THF (3 ml) was added 1,1'-carbonyldiimidazole (0.21 g, 1.3 mmol). The mixture was stirred at 60–70° C. for 2 h before being cooled to rt and diluted with cold water (50 ml). The resulting precipitate was collected by filtration, washed with water, and dried to afford trioxolane OZ147 (0.32 g, 90%, 1:1 mixture of two diastereomers) as a colorless solid. mp 116–118° C. (water); $^1$H NMR (500 MHz, CDCl₃) δ 1.62–2.21 (m, 22H), 5.05–5.22 (m, 1H), 7.07 (s, 0.5H), 7.08 (s, 0.5H), 7.41 (s, 0.5H), 7.43 (s, 0.5H), 8.13 (s, 0.5H), 8.15 (s, 0.5H); $^{13}$C NMR (125.7 MHz, CDCl₃) δ 26.58, 27.00, 28.05, 28.32, 30.53, 30.88, 34.83, 34.94, 36.48, 36.56, 36.85, 74.61, 75.01, 107.24, 107.30, 112.01, 112.11, 117.01, 117.04, 130.74, 137.08, 148.09, 148.14. Anal. Calcd for $C_{20}H_{26}N_2O_5$: C, 64.15; H, 7.00; N, 7.48. Found: C, 64.22; H, 7.00; N, 7.30.

cis-Adamantane-2-spiro-3'-1',2',4'-trioxaspiro[4.5]decane-8'-methyl 4-phenylpiperazine-1-carboxylate (OZ148). To a solution of OZ141 (310 mg, 0.86 mmol) in THF (10 ml) at 0° C. was added methyl triflate (142 mg, 0.86 mmol). The mixture was stirred at 0° C. for 30 min before 1-phenylpiperazine (140 mg, 0.86 mmol) was added. The reaction was stirred at rt for 18 h before removal of solvents. Crystallization of the residue from ethanol/water (3:1) gave trioxolane OZ148 (323 mg, 83%) as a colorless solid. mp 145–146° C. (ethanol/water, 3:1); $^1$H NMR (500 MHz, CDCl$_3$) δ 1.21–1.42 (m, 2H), 1.58–2.10 (m, 21H), 3.15 (br s, 4H), 3.63 (br s, 4H), 3.96 (d, J=6.2 Hz, 2H), 6.90 (dd, J=7.5, 7.5 Hz, 1H), 6.93 (d, J=7.8 Hz, 2H), 7.28 (dd, J=8.6, 7.4 Hz, 2H); $^{13}$C NMR (125.7 MHz, CDCl$_3$) δ 26.61, 26.79, 27.01, 33.77, 34.87, 34.88, 36.03, 36.55, 36.91, 43.81, 49.46, 69.57, 108.61, 111.39, 116.71, 120.40, 129.20, 151.27, 155.45. Anal. Calcd for C$_{28}$H$_{38}$N$_2$O$_5$: C, 69.68; H, 7.94; N, 5.80. Found: C, 69.83; H, 7.98; N, 5.86.

Adamantane-2-spiro-3'-1',2',4'-trioxaspiro[4.5]decane-8'-spiro-1"-3"-oxo-3"H-isobenzofuran (OZ149). A solution of O-methyl 2-adamantanone oxime (0.54 g, 3 mmol) and spiro[cyclohexane-1,1'(3'H)-isobenzofuran]-3',4-dione (0.65 g, 3 mmol) in pentane (50 ml) and CH$_2$Cl$_2$ (50 ml) was treated with ozone according to the general procedure. The crude product was purified by flash chromatography (silica gel, 25% ether in hexanes) to afford trioxolane OZ149 (0.50 g, 44%) as a colorless solid. mp 160–162° C. (ethanol/water, 3:1); $^1$H NMR NMR (500 MHz, CDCl$_3$) δ 1.65–2.12 (m, 18H), 2.21 (ddd, J=13.8, 13.8, 3.9 Hz, 2H), 2.31 (ddd, J=13.7, 13.7, 4.0 Hz, 2H), 7.38 (d, J=7.5 Hz, 1H), 7.52 (dd, J=7.5, 7.5 Hz, 1H), 7.67 (dd, J=7.5, 7.5 Hz, 1H), 7.88 (d, J=7.5 Hz, 1H); $^{13}$C NMR (125.7 MHz, CDCl$_3$) δ 26.61, 26.97, 30.73, 34.27, 34.85, 34.88, 36.60, 36.86, 84.97, 107.56, 112.05, 120.85, 124.64, 125.96, 129.25, 134.08, 153.70, 169.43. Anal. Calcd for C$_{23}$H$_{26}$O$_5$: C, 72.23; H, 6.85. Found: C, 72.12; H, 6.65.

Adamantane-2-spiro-3'-8'-(4'-nitrophenyl)-1',2',4'-trioxa-8'-azaspiro[4.5]decane (OZ151). To a solution of OZ80 (301 mg, 1 mmol) and triethylamine (101 mg, 1 mmol) in CH$_3$CN (10 ml) was added 4-nitrophenyl triflate (271 mg, 1 mmol). The mixture was stirred at 65° C. for 64 h before removal of solvents. The crude product was purified by flash chromatography (silica gel, 5% ether in hexanes) and by subsequent crystallization from methanol to afford trioxolane OZ151 (120 mg, 31%) as a yellowish solid. mp 140–142° C. (methanol); $^1$H NMR (500 MHz, CDCl$_3$) δ 1.61–2.19 (m, 18H), 3.48–3.75 (m, 4H), 6.83 (d, J=9.3 Hz, 2H), 8.11 (d, J=9.3 Hz, 2H); $^{13}$C NMR (125.7 MHz, CDCl$_3$).26.54, 26.94, 33.84, 34.82, 34.92, 36.55, 36.79, 45.57, 106.63, 112.40, 112.93, 126.05, 138.63, 154.14. Anal. Calcd for C$_{21}$H$_{26}$N$_2$O$_5$: C, 65.27; H, 6.78; N, 7.25. Found: C, 65.40; H, 6.66; N, 7.29.

5-Hydroxyadamantane-2-spiro-3'-1',2',4',9',12'-pentaoxadispiro[4.2.4.2]tetradecane (OZ152). Step 1. A solution of O-methyl 5-acetoxy-2-adamantanone oxime (1.18 g, 5.0 mmol) and 1,4-dioxaspiro[4.5]decan-8-one (790 mg, 5.0 mmol) in pentane (20 ml) and CH$_2$Cl$_2$ (100 ml) was treated with ozone according to the general procedure. The crude product was purified by flash chromatography (silica gel, 30% ether in petroleum ether) to afford 5-acetoxyadamantane-2-spiro-3'-1',2',4',9',12'-pentaoxadispiro[4.2.4.2]tetradecane (0.61 g, 32%) as a colorless oil. $^1$H NMR (500 MHz, CDCl$_3$) δ 1.78–2.28 (m, 24H), 3.95 (s, 4H). Step 2. A mixture of the above acetate trioxolane (1.30 g, 3.42 mmol), EtOH (7 ml), and 30% aq. KOH (6 ml) was heated at 50° C. for 2 h. After removal of the solvent, the residue was diluted with water and extracted with ether. The organic layer was washed with water and brine, dried over MgSO$_4$, and concentrated. The crude product was purified by flash chromatography (silica gel, 80% ether in hexanes) to afford trioxolane OZ152 (100 mg, 9%, minor isomer, eluted first) as a colorless solid and trioxolane OZ153 (414 mg, 36%, major isomer, eluted second) as a colorless solid. For OZ152: mp 132–134° C. (ether); $^1$H NMR (500 MHz, CDCl$_3$) δ 1.56–2.19 (m, 21H), 3.95 (s, 4H); $^{13}$C NMR (125.7 MHz, CDCl$_3$).29.27, 31.65, 32.11, 33.52, 38.10, 42.13, 44.59, 64.39, 67.01, 107.84, 108.47, 110.40. Anal. Calcd for C$_{18}$H$_{26}$O$_6$: C, 63.89; H, 7.74. Found: C, 64.02; H, 7.81.

5-Hydroxyadamantane-2-spiro-3'-1',2',4',9',12'-pentaoxadispiro[4.2.4.2]tetradecane (OZ153). For preparation, see OZ152. mp 112–114° C. (ether); $^1$H NMR (500 MHz, CDCl$_3$) δ 1.54–2.22 (m, 21H), 3.98 (s, 4H); $^{13}$C NMR (125.7 MHz, CDCl$_3$) δ 28.85, 31.72, 32.09, 33.40, 38.31, 42.11, 44.54, 64.36, 67.37, 107.80, 108.50, 110.36. Anal. Calcd for C$_{18}$H$_{26}$O$_6$: C, 63.89; H, 7.74. Found: C, 64.03; H, 7.66.

cis-Adamantane-2-spiro-3'-8'-[4'-(4',5'-dihydro-4',4'-dimethyl-2'-oxazolyl)phenyl]-1',2',4'-trioxaspiro[4.5]decane (OZ154). A solution of O-methyl 2-adamantanone oxime (1.32 g, 7.4 mmol) and 4-[4-(4,5-dihydro-4,4-dimethyl-2-oxazolyl)phenyl]cyclohexanone (2.00 g, 7.4 mmol) in pentane (100 ml) and CH$_2$Cl$_2$ (50 ml) was treated with ozone according to the general procedure. The crude product was purified by flash chromatography (silica gel, 10 to 30% ether in hexanes) to afford trioxolane OZ154 (0.80 g, 25%) as a colorless solid. mp 138–140° C. (ethanol); $^1$H NMR (500 MHz, CDCl$_3$) δ 1.37 (s, 6H), 1.59–2.16 (m, 22H), 2.51–2.68 (m, 1H), 4.08 (s, 2H), 7.24 (d, J=8.0 Hz, 2H), 7.85 (d, J=8.0 Hz, 2H); $^{13}$C NMR (125.7 MHz, CDCl$_3$) δ 26.63, 27.03, 28.38, 31.29, 34.70, 34.88, 34.90, 36.56, 36.93, 42.98, 67.52, 79.15, 108.26, 111.46, 126.22, 126.70, 128.44, 149.58, 162.01. Anal. Calcd for C$_{27}$H$_{35}$NO$_4$: C, 74.11; H, 8.06; N, 3.20. Found: C, 74.35; H, 8.08; N, 3.18.

cis-Adamantane-2-spiro-3'-8'-[[(2'-hydroxyethyl)amino]carbonyl]-1',2',4'-trioxaspiro[4.5]decane (OZ155). A solution of OZ72 (0.31 g, 1.0 mmol), 1-[3-(dimethylamino)propyl]-3-ethylcarbodiimide hydrochloride (0.29 g, 1.5 mmol), HOBT (0.20 g, 1.5 mmol), and 2-aminoethanol (0.09 g, 1.5 mmol) in DMF (10 ml) was stirred at rt for 18h before being quenched with 2 M aq. HCl (30 ml). The mixture was extracted with ethyl acetate (4×30 ml), and the combined extracts were washed with water (2×30 ml) and brine (30 ml), dried over MgSO$_4$, and concentrated. The residue was purified by flash chromatography (silica gel, 5% methanol in CH$_2$Cl$_2$) to afford trioxolane OZ155 (0.16 g, 46%) as a colorless solid. mp 114–116° C. (ether/CH$_2$Cl$_2$ 2:1); $^1$H NMR (500 MHz, CDCl$_3$) δ 1.59–2.08 (m, 22H), 2.17 (br s, 1H), 3.38–3.45 (m, 2H), 3.71 (t, J=4.8 Hz, 2H), 6.13 (s, 1H); $^{13}$C NMR (125.7 MHz, CDCl$_3$) δ 26.44, 26.84, 26.99, 33.58, 34.75, 34.78, 36.35, 36.75, 42.27, 43.58, 62.31, 107.77, 111.53, 176.04. Anal. Calcd for C$_{19}$H$_{29}$NO$_5$: C, 64.93; H, 8.32; N, 3.99. Found: C, 64.68; H, 8.11; N, 3.93.

cis-Adamantane-2-spiro-3'-8'-benzyl-1',2',4'-trioxaspiro[4.5]decane (OZ156). A solution of O-methyl 2-adamantanone oxime (895 mg, 5 mmol) and 4-benzylcyclohexanone (940 mg, 5 mmol) in cyclohexane (80 ml) and CH$_2$Cl$_2$ (20 ml) was treated with ozone according to the general procedure. The crude product was purified by flash chromatography (silica gel, 5% ether in hexanes) and by subsequent recrystallization from ethanol/CH$_2$Cl$_2$ (19:1) to afford trioxolane OZ156 (825 mg, 47%) as a colorless solid. mp 87–89° C. (ethanol/CH$_2$Cl$_2$, 19:1); $^1$H NMR (500 MHz, CDCl$_3$) δ 1.18–1.37 (m, 2H), 1.49–2.20 (m, 21H), 2.50 (d, J=7.2 Hz, 2H), 7.09–7.40 (m, 5H); $^{13}$C NMR (125.7 MHz, CDCl$_3$) δ 26.49, 26.88, 29.93, 34.15, 34.78, 34.79, 36.39, 36.81, 38.16, 42.89, 108.94, 111.19, 125.78, 128.16, 129.07, 140.86. Anal. Calcd for C$_{23}$H$_{30}$O$_5$: C, 77.93; H, 8.53. Found: C, 78.17; H, 8.45.

Adamantane-2-spiro-3'-8'-[(4'-methyl-1'-piperazinyl)carbonyl]-1',2',4'-trioxa-8'-azaspiro[4.5]decane (OZ157). To a solution of OZ80 (301 mg, 1 mmol) and triethylamine (404 mg, 4 mmol) in CH$_2$Cl$_2$ (7 ml) at 0° C. was added 4-methyl-1-piperazinecarbonyl chloride hydrochloride (220 mg, 1.1 mmol). The mixture was stirred at rt for 16 h, diluted with CH$_2$Cl$_2$ (10 ml), washed with water (2×10 ml) and brine (10 ml), dried over MgSO$_4$, and concentrated. Crystallization of the residue from ethanol gave trioxolane OZ157 (105 mg, 27%) as a colorless solid. mp 146–148° C. (ethanol); $^1$H NMR (500 MHz, CDCl$_3$) δ 1.61–2.09 (m, 18H), 2.30 (s, 3H), 2.31–2.48 (m, 4H), 3.21–3.47 (m, 8H); $^{13}$C NMR (125.7 MHz, CDCl$_3$) δ 26.61, 27.01, 34.52, 34.85, 34.95, 36.59, 36.87, 44.77, 46.14, 46.87, 54.91, 107.24, 112.04, 163.68. Anal. Calcd for C$_{21}$H$_{33}$N$_3$O$_4$: C, 64.42; H, 8.50; N, 10.73. Found: C, 64.34; H, 8.37; N, 10.61.

Adamantane-2-spiro-3'-8'-(1'-piperidinyl)-1',2',4'-trioxaspiro[4.5]decane hydrochloride (OZ159). To a solution of OZ05 (555 mg, 2 mmol) in 1,2-dichloroethane (10 ml) were added piperidine (187 mg, 2.2 mmol) and acetic acid (10 drops). The reaction mixture was stirred at rt for 15 min before sodium triacetoxyborohydride (677 mg, 3.2 mmol) was added. The mixture was stirred for 5 h before being quenched with 1 M aq. NaOH (2 ml). The resulting mixture was extracted with CH$_2$Cl$_2$ (40 ml), washed with water (2×10 ml) and brine (2×10 ml), dried over MgSO$_4$, and concentrated. The residue was dissolved in ether (2 ml), treated with excess 2 M ethereal HCl, and filtered to give trioxolane OZ159 (460 mg, 60%, 1:1 mixture of two diastereomers) as a colorless solid. mp 12° C. dec (ether); $^1$H NMR (500 MHz, CDCl$_3$) δ 1.39 (br s, 1H), 1.58–2.20 (m, 23H), 2.21–2.60 (m, 4H), 2.78 (br s, 2H), 3.11 (br s, 1H), 3.28–3.59 (m, 2H), 11.94 (br s, 1H); $^{13}$C NMR (125.7 MHz, CDCl$_3$) δ 22.53, 22.69, 22.73, 23.33, 23.43, 26.37, 26.40, 26.78, 32.65, 32.81, 34.66, 34.69, 34.72, 34.91, 36.28, 36.64, 49.77, 49.98, 63.81, 64.20, 106.50, 106.56, 112.20, 112.37. Anal. Calcd for C$_{21}$H$_{34}$ClNO$_3$·0.25H$_2$O: C, 64.93; H, 8.95; N, 3.61. Found: C, 64.48; H, 8.59; N, 3.63.

Adamantane-2-spiro-3'-8'-(benzylamino)-1',2',4'-trioxaspiro[4.5]decane hydrochloride (OZ160). To a solution of OZ05 (555 mg, 2 mmol) in 1,2-dichloroethane (10 ml) were added benzylamine (236 mg, 2.2 mmol) and acetic acid (10 drops). The reaction mixture was stirred at rt for 15 min before sodium triacetoxyborohydride (677 mg, 3.2 mmol) was added. The mixture was stirred for 5 h before being quenched with 1 M aq. NaOH (2 ml). The resulting mixture was extracted with CH$_2$Cl$_2$ (40 ml), washed with water (2×10 ml) and brine (2×10 ml), dried over MgSO$_4$, and concentrated. The residue was dissolved in ether (2 ml), treated with excess 2 M ethereal HCl, and filtered to give trioxolane OZ160 (567 mg, 70%, 2:1 mixture of two diastereomers) as a colorless solid. mp 160° C. dec (ether); $^1$H NMR (500 MHz, CDCl$_3$) δ 1.42–2.31 (m, 22H), 2.78–2.89 (m, 1H), 3.914.19 (m, 2H), 7.31–7.46 (m, 3H), 7.59–7.71 (m, 2H), 10.00 (br s, 2H); $^{13}$C NMR (125.7 MHz, CDCl$_3$) δ 25.95, 26.53, 26.89, 32.21, 34.78, 34.92, 36.38, 36.45, 36.81, 47.82, 53.65, 106.71, 106.79, 111.72, 112.33, 129.07, 129.12, 129.30, 129.35, 130.25, 130.51, 130.57. Anal. Calcd for C$_{23}$H$_{32}$ClNO$_3$: C, 68.05; H, 7.95; N, 3.45. Found: C, 67.89; H, 7.71; N, 3.35.

Adamantane-2-spiro-3'-8'-[[3'-(4'-morpholinyl)propyl]amino]-1',2',4'-trioxaspiro[4.5]decane (OZ161). To a solution of OZ05 (555 mg, 2 mmol) in 1,2-dichloroethane (10 ml) were added 4-(3-aminopropyl)morpholine (317 mg, 2.2 mmol) and acetic acid (10 drops). The reaction mixture was stirred at rt for 15 min before sodium triacetoxyborohydride (677 mg, 3.2 mmol) was added. The mixture was stirred for 5 h before being quenched with 1 M aq. NaOH (2 ml). The resulting mixture was extracted with CH$_2$Cl$_2$ (40 ml), washed with water (2×10 ml) and brine (2×10 ml), dried over MgSO$_4$, and concentrated. The residue was dissolved in ether (2 ml), treated with excess 2 M ethereal HCl, and filtered to give trioxolane OZ161 (552 mg, 68%, 1:1 mixture of two diastereomers) as a colorless solid. mp 70–72° C. (ether); $^1$H NMR (500 MHz, CDCl$_3$) δ 1.31–2.20 (m, 24H), 2.32–2.60 (m, 7H), 2.61–2.78 (m, 2H), 3.62–3.83 (m, 4H); $^{13}$C NMR (125.7 MHz, CDCl$_3$) δ 26.29, 26.70, 26.77, 26.81, 29.61, 30.02, 31.97, 32.42, 34.55, 34.59, 34.63, 34.70, 36.16, 36.20, 36.61, 43.27, 45.76, 46.00, 53.62, 53.64, 54.62, 54.86, 57.31, 57.42, 66.80, 108.35, 108.39, 111.05, 111.34. Anal. Calcd for C$_{23}$H$_{38}$N$_2$O$_4$: C, 67.95; H, 9.42; N, 6.89. Found: C, 67.84; H, 9.30; N, 6.68.

Adamantane-2-spiro-3'-8'-(cyclohexylamino)-1',2',4'-trioxaspiro[4.5]decane hydrochloride (OZ162). To a solution of OZ05 (555 mg, 2 mmol) in 1,2-dichloroethane (10 ml) were added cyclohexylamine (218 mg, 2.2 mmol) and acetic acid (10 drops). The reaction mixture was stirred at rt for 15 min before sodium triacetoxyborohydride (677 mg, 3.2 mmol) was added. The mixture was stirred for 5 h before being quenched with 1 M aq. NaOH (2 ml). The resulting mixture was extracted with CH$_2$Cl$_2$ (40 ml), washed with water (2×10 ml) and brine (2×10 ml), dried over MgSO$_4$, and concentrated. The residue was dissolved in ether (2 ml), treated with excess 2 M ethereal HCl, and filtered to give OZ162 (516 mg, 65%, 1:1 mixture of two diastereomers) as a colorless solid. mp 240° C. dec (ether); $^1$H NMR (500 MHz, CDCl$_3$) δ 1.26 (br s, 2H), 1.55–2.42 (m, 30H), 2.97–3.21 (m, 2H), 9.33 (br s, 1H), 9.37 (br s, 1H); $^{13}$C NMR (125.7 MHz, CDCl$_3$) δ 24.83, 24.87, 26.56, 26.90, 26.97, 29.45, 32.58, 34.80, 34.82, 34.94, 36.39, 36.51, 36.85, 52.70, 54.89, 55.12, 106.82, 106.91, 111.67, 112.32. Anal. Calcd for C$_{22}$H$_{36}$ClNO$_3$: C, 66.39; H, 9.12; N, 3.52. Found: C, 66.28; H, 8.97; N, 3.54.

cis-Adamantane-2-spiro-3'-8'-(aminomethyl)-1',2',4'-trioxaspiro[4.5]decane hydrochloride (OZ163). A solution of OZ146 (423 mg, 1 mmol) and hydrazine monohydrate (150 mg, 3 mmol) in chloroform (9 ml) and methanol (1 ml) was heated at 55° C. for 48 h. The reaction mixture was cooled to rt and filtered to remove solid by-products. The filtrate was washed with water (10 ml) and brine (10 ml), dried over MgSO$_4$, filtered, and concentrated. The solid was dissolved in ether (10 ml), treated with 1 M ethereal HCl (1.2 ml), and filtered. Recrystallization from ether gave trioxolane OZ163 (80 mg, 24%) as a yellowish solid. mp 146° C. dec (ether); $^1$H NMR (500 MHz, CDCl$_3$) δ 1.23–1.42 (m, 2H), 1.59–2.20 (m, 21H), 2.86 (br s, 2H), 8.35 (br s, 3H); $^{13}$C NMR (125.7 MHz, CDCl$_3$) δ 26.45, 26.86, 27.61, 33.27, 34.45, 34.76, 36.37, 36.77, 39.25, 44.88, 107.92, 111.52. Anal. Calcd for C$_{17}$H$_{28}$ClNO$_3$: C, 61.90; H, 8.56; N, 4.25. Found: C, 59.83; H, 8.21; N, 5.07.

cis-Adamantane-2-spiro-3'-8'-[4'-(ethoxycarbonyl)phenyl]-1',2',4'-trioxaspiro[4.5]decane (OZ164). A solution of O-methyl 2-adamantanone oxime (1.10 g, 6.2 mmol) and 4-[4-(ethoxycarbonyl)phenyl]cyclohexanone (1.70 g, 6.2 mmol) in pentane (100 ml) and CH$_2$Cl$_2$ (50 ml) was treated with ozone according to the general procedure. The crude product was purified by flash chromatography (silica gel, 10% ether in hexanes) to afford trioxolane OZ164 (1.60 g, 63%) as a colorless solid. mp 129–132° C. (hexanes/ether 9:1); $^1$H NMR (500 MHz, CDCl$_3$) δ 1.38 (t, J=7.2 Hz, 3H), 1.63–2.22 (m, 22H), 2.56–2.71 (m, 1H), 4.36 (q, J=7.2 Hz, 2H), 7.27 (d, J=7.8 Hz, 2H), 7.96 (d, J=8.0 Hz, 2H); $^{13}$C NMR (125.7 MHz, CDCl$_3$) δ 14.34, 26.49, 26.89, 31.18, 34.59, 34.80, 36.42, 36.80, 42.99, 60.76, 108.18, 111.51, 126.77, 128.54, 129.74, 151.39, 166.57. Anal. Calcd for C$_{25}$H$_{32}$O$_5$: C, 72.79; H, 7.82. Found: C, 72.83; H, 7.90.

cis-Adamantane-2-spiro-3'-8'-(4'-carboxyphenyl)-1',2',4'-trioxaspiro[4.5]decane (OZ165). A mixture of OZ164 (1.38 g, 3.35 mmol), KOH (1.13 g), THF (30 ml), methanol (30 ml), and water (6 ml) was heated at 50° C. for 2 h. The mixture was concentrated to 10 ml, diluted with water (50 ml), and extracted with ethyl acetate. The aqueous layer was acidified with 1 M aq. HCl to pH=2, and the resulting solid was collected by filtration to give trioxolane OZ165 (1.08 g, 84%) as a colorless solid. mp 157° C. dec; $^1$H NMR (500 MHz, CDCl$_3$) δ 1.63–2.22 (m, 22H), 2.57–2.72 (m, 1H), 7.31 (d, J=8.3 Hz, 2H), 8.03 (d, J=8.1 Hz, 2H); $^{13}$C NMR (125.7 MHz, CDCl$_3$) δ 26.49, 26.90, 31.14, 34.58, 34.81, 36.43, 36.80, 43.10, 108.14, 111.54, 126.99, 127.23, 130.46, 152.54, 171.45. Anal. Calcd for C$_{23}$H$_{28}$O$_5$: C, 71.85; H, 7.34. Found: C, 71.68; H, 7.33.

cis-Adamantane-2-spiro-3'-8'-[[4'-(ethoxycarbonyl)phenoxy]methyl]-1',2',4'-trioxaspiro[4.5]decane (OZ166). To a solution of OZ119 (0.59 g, 2.0 mmol), triphenylphosphine (0.63 g, 2.4 mmol), and ethyl 4-hydroxybenzoate (0.50 g, 3.0 mmol) in THF (12 ml) at 0° C. was added dropwise a solution of diisopropyl azodicarboxylate (0.65 g, 3.2 mmol) in THF (0.5 ml). The mixture was then warmed to rt and stirred at rt for 2 h before removal of solvents. The crude product was purified by flash chromatography (silica gel, 20% ether in hexanes) to afford trioxolane OZ166 (0.65 g, 73%) as a colorless solid. mp 142–143° C. (hexanes/ether 9:1); $^1$H NMR (500 MHz, CDCl$_3$) δ 1.38 (t, J=7.2 Hz, 3H), 1.30–1.58 (m, 2H), 1.60–2.21 (m, 21H), 3.82 (d, J=5.9 Hz, 2H), 4.34 (q, J=7.2 Hz, 2H), 6.88 (d, J=9.0 Hz, 2H), 7.97 (d, J=8.8 Hz, 2H); $^{13}$C NMR (125.7 MHz, CDCl$_3$) δ 14.35, 26.48, 26.85, 26.87, 33.72, 34.78, 34.80, 36.14, 36.40, 36.79, 60.58, 72.43, 108.64, 111.41, 113.97, 122.84, 131.50, 162.75, 166.38. Anal. Calcd for C$_{26}$H$_{34}$O$_6$: C, 70.56; H, 7.74. Found: C, 70.72; H, 7.76.

trans-Adamantane-2-spiro-3'-8'-phthalimidomethyl-1',2',4'-trioxaspiro[4.5]decane (OZ167). For the major isomer (cis), see OZ146. A solution of O-methyl 2-adamantanone oxime (2.23 g, 12.4 mmol) and 4-phthalimidomethylcyclohexanone (3.20 g, 12.4 mmol) in pentane (100 ml) and CH$_2$Cl$_2$ (50 ml) was treated with ozone according to the general procedure. The crude product was purified by flash chromatography (silica gel, 25% ether in hexanes and 40% CH$_2$Cl$_2$ in hexanes) to afford trioxolane OZ167 (0.16 g, 3%) as a colorless solid. mp 140–142° C. (ethanol); $^1$H NMR (500 MHz, CDCl$_3$) δ 1.40–2.17 (m, 23H), 3.60 (d, J=7.5 Hz, 2H), 7.68–7.75 (m, 2H), 7.82–7.88 (m, 2H); $^{13}$C NMR (125.7 MHz, CDCl$_3$) δ 26.63, 27.03 27.69, 33.46, 34.83, 34.99, 35.71, 36.51, 36.93, 42.98, 108.58, 111.74, 123.25, 132.19, 133.91, 168.52. Anal. Calcd for C$_{25}$H$_{29}$NO$_5$: C, 70.90; H, 6.90; N, 3.31. Found: C, 70.75; H, 7.03; N, 3.25.

Adamantane-2-spiro-3'-1',2',4',9',10',12'-hexaoxadispiro[4.2.4.2]tetradecane-11'-spiro-2"-adamantane (OZ169). A solution of O-methyl 2-adamantanone oxime (1.80 g, 10 mmol) and 1,4-cyclohexanedione (2.24 g, 20 mmol) in pentane (60 ml) and CH$_2$Cl$_2$ (40 ml) was treated with ozone according to the general procedure. The crude product was purified by flash chromatography (silica gel, 10% ether in hexanes) to afford trioxolane OZ169 (346 mg, 16%, 2:1 mixture of two diastereomers) as a colorless solid. mp 156–158° C. (hexanes); $^1$H NMR (500 MHz, CDCl$_3$) δ 1.92 (s, 8H), 1.60–2.25 (m, 28H); $^{13}$C NMR (125.7 MHz, CDCl$_3$) δ 26.45, 26.83, 26.86, 31.57, 34.72, 34.75, 34.80, 34.84, 36.29, 36.31, 36.74, 107.65, 107.71, 111.72. Anal. Calcd for C$_{26}$H$_{36}$O$_6$: C, 70.24; H, 8.16. Found: C, 70.18; H, 8.28.

Adamantane-2-spiro-3'-8'-[(2',2',6',6'-tetramethyl-4'-piperidinyl)amino]-1',2',4'-trioxaspiro[4.5]decane dihydrochloride (OZ171). To a solution of OZ05 (555 mg, 2 mmol) in 1,2-dichloroethane (10 ml) were added 4-amino-2,2,6,6-tetramethylpiperidine (344 mg, 2.2 mmol) and acetic acid (10 drops). The reaction mixture was stirred at rt for 15 min before sodium triacetoxyborohydride (677 mg, 3.2 mmol) was added. The mixture was stirred for 5 h before being quenched with 1 M aq. NaOH (2 ml). The resulting mixture was extracted with CH$_2$Cl$_2$ (40 ml), washed with water (2×10 ml) and brine (2×10 ml), dried over MgSO$_4$, and concentrated. The residue was dissolved in ether (2 ml), treated with excess 2 M ethereal HCl, and filtered to give trioxolane OZ171 (650 mg, 66%, 1:1 mixture of two diastereomers) as a colorless solid. mp 165° C. dec (ether); $^1$H NMR (500 MHz, DMSO-d$_6$) δ 1.43 (s, 6H), 1.45 (s, 6H), 1.46–2.37 (m, 26H), 3.14–3.40 (m, 1H), 3.55–3.79 (m, 1H), 8.28–8.45 (m, 1H), 9.25–9.47 (m, 2H), 9.55–9.72 (m, 1H); $^{13}$C NMR (125.7 MHz, DMSO-d$_6$) δ 24.03, 24.07, 25.96, 26.38, 29.78, 31.70, 34.38, 34.43, 34.55, 35.81, 35.88, 36.22, 37.00, 45.66, 45.71, 50.74, 50.93, 56.22, 56.26, 107.42, 107.46, 111.13, 111.41. Anal. Calcd for C$_{25}$H$_{44}$Cl$_2$N$_2$O$_3$·1.5H$_2$O: C, 57.90; H, 9.14; N, 5.40. Found: C, 57.65; H, 8.74; N, 5.36.

Adamantane-2-spiro-3'-8'-oxo-1',2',4'-trioxaspiro[4.5]decane amidinohydrazone hydrochloride (OZ172). To a solution of OZ05 (555 mg, 2 mmol) in THF (11 ml), water (3 ml), and ethanol (3.5 ml) were added 2 M aq. HCl (1.5 ml) and aminoguanidine bicarbonate (299 mg, 2.2 mmol). The mixture was stirred at rt for 30 h before removal of solvents. The residue was triturated with ethanol (10 ml) and the resulting precipitate was collected by filtration and washed with THF to give trioxolane OZ172 (476 mg, 64%) as a colorless solid. mp 150° C. dec (ethanol); $^1$H NMR (500 MHz, CDCl$_3$) δ 1.46–2.27 (m, 18H), 2.42–2.61 (m, 2H), 2.62–2.83 (m, 2H), 6.34 (s, 1H), 7.63 (br s, 2H), 7.91 (s, 1H), 10.95 (s, 1H); $^{13}$C NMR (125.7 MHz, CDCl$_3$) δ 24.83, 26.37, 26.77, 31.72, 32.49, 33.62, 34.70, 34.74, 34.84, 36.23, 36.26, 36.65, 107.26, 112.27, 156.57, 157.93. Anal. Calcd for C$_{17}$H$_{27}$ClN$_4$O$_3$: C, 55.05; H, 7.34; N, 15.11. Found: C, 55.14; H, 7.51; N, 15.30.

Adamantane-2-spiro-3'-8'-[(methoxyacetyl)benzylamino]-1',2',4'-trioxaspiro[4.5]decane (OZ173). To a solution of OZ160 (342 mg, 0.84 mmol) in CH$_2$Cl$_2$ (10 ml) at 0° C. were added triethylamine (255 mg, 2.53 mmol) and methoxyacetyl chloride (137 mg, 1.26 mmol). The resulting mixture was stirred at rt for 16 h, diluted with CH$_2$Cl$_2$ (10 ml), and washed with water (10 ml) and brine (10 ml). The organic layer was separated, dried over MgSO$_4$, and concentrated. The residue was triturated with ether to give trioxolane OZ173 (110 mg, 30%, 3:2 mixture of two diastereomers) as a colorless solid. mp 132–134° C. (ether); $^1$H NMR (500 MHz, CDCl$_3$), δ 1.47–2.20 (m, 22H), 3.38 (s, 1.8H), 3.48 (s, 1.2H), 3.99 (s, 1.2H), 4.23 (s, 0.8H), 4.46 (s, 1.2H), 4.55 (s, 0.8H), 4.42–4.58 (m, 1H), 7.09–7.46 (m, 5H); $^{13}$C NMR (125.7 MHz, CDCl$_3$) δ 26.41, 26.80, 26.87, 27.11, 28.74, 33.31, 33.54, 34.67, 34.74, 34.93, 36.29, 36.72, 44.76, 45.52, 51.71, 55.36, 59.20, 71.54, 72.30, 107.56, 111.65, 125.61, 126.74, 127.10, 127.30, 128.33, 128.78, 137.93, 139.04, 169.30, 169.82. Anal. Calcd for C$_{26}$H$_{35}$NO$_5$: C, 70.72; H, 7.99; N, 3.17. Found: C, 70.76; H, 8.02; N, 3.08.

Adamantane-2-spiro-3'-8'-[(methoxyacetyl)cyclohexylamino]-1',2',4'-trioxaspiro[4.5]decane (OZ174). To a solution of OZ162 (330 mg, 0.83 mmol) in CH$_2$Cl$_2$ (10 ml) at 0° C. were added triethylamine (251 mg, 2.49 mmol) and methoxyacetyl chloride (135 mg, 1.24 mmol). The resulting mixture was stirred at rt for 16 h, diluted with CH$_2$Cl$_2$ (10 ml), and washed with water (10 ml) and brine (10 ml). The organic layer was separated, dried over MgSO$_4$, and concentrated. The residue was triturated with ether to give trioxolane OZ174 (109 mg, 30%, 4:1 mixture of two diastereomers) as a colorless solid. mp 140–142° C. (ether); $^1$H NMR (500 MHz, CDCl$_3$) δ 1.02–2.20 (m, 30H), 2.32–2.72 (m, 2H), 2.81–3.05 (m, 1H), 3.40 (s, 2.4H), 3.42 (s, 0.6H), 3.48–3.69 (m, 1H), 4.02 (s, 1.6H), 4.03 (m, 0.4H); $^{13}$C NMR (125.7 MHz, CDCl$_3$) δ 25.25, 26.00, 26.44, 26.84, 27.89, 29.77, 33.50, 34.21, 34.77, 36.32, 36.73, 55.51, 56.10, 58.84, 73.12, 73.71, 107.39, 107.52, 111.83, 168.17. Anal. Calcd for C$_{25}$H$_{39}$NO$_5$: C, 69.25; H, 9.07; N, 3.23. Found: C, 69.12; H, 9.06; N, 3.23.

cis-Adamantane-2-spiro-3'-8'-(2'-hydroxyamino-2'-oxoethyl)-1',2',4'-trioxaspiro[4.5]decane (OZ175). To a solution of OZ78 (322 mg, 1.0 mmol) in ether (10 ml) at 0° C. were added triethylamine (202 mg, 2 mmol) and ethyl chloroformate (217 mg, 2 mmol). The mixture was stirred at 0° C. for 15 min before a freshly prepared solution of hydroxylamine was added. [A suspension of hydroxylamine hydrochloride (170 mg, 2.48 mmol) and sodium bicarbonate (203 mg, 2.48 mmol) in methanol (5 ml) was stirred at rt for 15 min. The supernatant was used as such.] The resulting mixture was stirred at rt for 12 h, diluted with ether (10 ml), washed with water (10 ml), dried over MgSO$_4$, and concentrated. The crude product was purified by flash chromatography (silica gel, 5% methanol in CH$_2$Cl$_2$) and by subsequent recrystallization from ethanol to afford trioxolane OZ175 (95 mg, 28%) as a colorless solid. mp 138–140° C. (ethanol); $^1$H NMR (500 MHz, DMSO-d$_6$) δ 0.81–1.27 (m, 3H), 1.40–2.19 (m, 22H), 8.65 (s, 1H), 10.33 (s, 1H); $^{13}$C NMR (125.7 MHz, DMSO-d$_6$) δ 25.84, 26.25, 29.40, 32.60, 33.35, 34.26, 35.81, 36.13, 38.68, 108.33, 110.44, 167.91. Anal. Calcd for C$_{18}$H$_{27}$NO$_5$: C, 64.07; H, 8.07; N, 4.15. Found: C, 64.11; H, 8.10; N, 3.97.

cis-Adamantane-2-spiro-3'-8'-[(4'-carboxyphenoxy)methyl]-1',2',4'-trioxaspiro[4.5]decane (OZ176). A mixture of OZ166 (0.30 g, 0.68 mmol), KOH (0.38 g), THF (10 ml), methanol (10 ml), and water (2 ml) was heated at 50° C. for 3 h. The mixture was concentrated to 5 ml, diluted with water (15 ml), and acidified with 1 M aq. HCl (1 ml). The resulting solid was collected by filtration to give trioxolane OZ176 (0.21 g, 75%) as a colorless solid. mp 165–168° C.; $^1$H NMR (500 MHz, DMSO-d$_6$) δ 1.15–1.27 (m, 2H), 1.50–2.17 (m, 21H), 3.88 (d, J=6.2 Hz, 2H), 7.00 (d, J=8.8 Hz, 2H), 7.87 (d, J=8.3 Hz, 2H); $^{13}$C NMR (125.7 MHz, DMSO-d$_6$) δ 25.99, 26.40, 26.53, 33.27, 34.45, 35.35, 35.95, 36.26, 72.09, 108.70, 110.71, 114.41, 123.04, 131.50, 162.47, 167.15. Anal. Calcd for C$_{24}$H$_{30}$O$_6$: C, 69.54; H, 7.30. Found: C, 69.67; H, 7.21.

cis-Adamantane-2-spiro-3'-8'-(1'H-1',2',4'-triazol-1'-ylmethyl)-1',2',4'-trioxaspiro[4.5]decane (OZ177). To a suspension of 60% NaH (0.08 g, 2 mmol) in DMF (4 ml) under nitrogen at 0° C. was added a solution of 1,2,4-triazole (0.14 g, 2 mmol) in DMF (4 ml). The mixture was stirred for 30 min before a solution of the methanesulfonate of OZ119 (0.37 g, 1.0 mmol) in DMF (4 ml) was added dropwise. The mixture was heated at 50° C. for 2 h before being quenched with water (40 ml) and then extracted with ethyl acetate (3×30 ml). The combined extracts were washed with brine (3×30 ml), dried over MgSO$_4$, filtered, and concentrated. Crystallization of the residue from hexanes/ether (4:1) gave trioxolane OZ177 (0.21 g, 61%) as a colorless solid. mp 123–124° C. (hexanes/ether 4:1); $^1$H NMR (500 MHz, CDCl$_3$) δ 1.17–1.42 (m, 2H), 1.50–2.19 (m, 21H), 4.02 (d, J=7.0 Hz, 2H), 7.95 (s, 1H), 8.02 (s, 1H); $^{13}$C NMR (125.7 MHz, CDCl$_3$) δ 26.43, 26.82, 27.48, 33.43, 34.75, 36.35, 36.47, 36.73, 54.84, 108.19, 111.57, 143.35, 152.10. Anal. Calcd for C$_{19}$H$_{27}$N$_3$O$_3$: C, 66.06; H, 7.88; N, 12.16. Found: C, 65.86; H, 8.06; N, 11.89.

cis-Adamantane-2-spiro-3'-8'-[(4'-methylsulfonyl)phenyl]-1',2',4'-trioxaspiro[4.5]decane (OZ178). A solution of O-methyl 2-adamantanone oxime (0.54 g, 3 mmol) and 4-[4-(methylsulfonyl)phenyl]cyclohexanone (0.75 g, 3 mmol) in pentane (50 ml) and CH$_2$Cl$_2$ (50 ml) was treated with ozone according to the general procedure. The crude product was purified by flash chromatography (silica gel, 30% ethyl acetate in hexanes) to afford trioxolane OZ178 (0.22 g, 18%) as a colorless solid. mp 132–135° C. (hexanes/CH$_2$Cl$_2$ 4:1); $^1$H NMR (500 MHz, CDCl$_3$) δ 1.62–2.19 (m, 22H), 2.60–2.74 (m, 1H), 3.04 (s, 3H), 7.40 (d, J=8.3 Hz, 2H), 7.86 (d, J=8.0 Hz, 2H); $^{13}$C NMR (125.7 MHz, CDCl$_3$) δ 26.48, 26.88, 31.14, 34.48, 34.80, 36.43, 36.78, 42.94, 44.53, 107.95, 111.64, 127.59, 127.80, 138.45, 152.59. Anal. Calcd for C$_{23}$H$_{30}$O$_5$S: C, 66.00; H, 7.22. Found: C, 66.08; H, 7.16.

cis-Adamantane-2-spiro-3'-8'-(1'H-imidazol-1'-ylmethyl)-1,2',4'-trioxaspiro[4.5]decane hydrochloride (OZ179). To a solution of OZ145 (1.08 g, 3.1 mmol) in ether (80 ml) was added 1 M ethereal HCl (3.5 ml). The resulting precipitate was collected by filtration to afford trioxolane OZ179 (1.14 g, 97%) as a colorless solid. mp 153–156° C.; $^1$H NMR (500 MHz, CDCl$_3$) δ 1.19–1.46 (m, 2H), 1.50–2.19 (m, 21H), 4.24 (br s, 2H), 7.15 (s, 1H), 7.42 (s, 1H), 9.70 (s, 1H), 15.94 (br s, 1H); $^{13}$C NMR (125.7 MHz, CDCl$_3$) δ 26.38, 26.77, 27.26, 33.20, 34.71, 36.29, 36.68, 37.17, 54.75, 107.85, 111.62, 119.72, 121.22, 135.82. Anal. Calcd for C$_{20}$H$_{29}$ClN$_2$O$_3$: C, 63.06; H, 7.67; N, 7.35. Found: C, 63.21; H, 7.63; N, 7.30.

cis-Adamantane-2-spiro-3'-8'-[4'-(4',5'-dihydro-4',4'-dimethyl-2'-oxazolyl)phenyl]-1',2',4'-trioxaspiro[4.5]decane hydrochloride (OZ180). To a solution of OZ154 (0.21 g, 0.48 mmol) in ether (9 ml) and CH$_2$Cl$_2$ (1 ml) was added 1 M ethereal HCl (0.5 ml). The resulting precipitate was collected by filtration to afford trioxolane OZ180 (0.20 g, 88%) as a colorless solid. mp 143–145° C.; $^1$H NMR (500 MHz, CDCl$_3$) δ 1.58–2.25 (m, 28H), 2.58–2.80 (m, 1H), 4.69 (br s, 2H), 7.44 (br s, 2H), 8.40 (br s, 2H); $^{13}$C NMR (125.7 MHz, CDCl$_3$) δ 26.44, 26.84, 27.19, 30.87, 34.37, 34.76, 36.39, 36.74, 43.21, 63.92, 83.36, 107.83, 111.59, 117.60, 128.16, 131.38, 156.27, 168.98. Anal. Calcd for C$_{27}$H$_{36}$ClNO$_4$: C, 68.41; H, 7.65; N. 2.95. Found: C, 68.26; H, 7.80; N, 2.90.

cis-Adamantane-2-spiro-3'-8'-(aminomethyl)-1',2',4'-trioxaspiro[4.5]decane citrate (OZ181). Step 1. A solution of OZ146 (1.00 g, 2.36 mmol) and hydrazine monohydrate (0.50 g, 10 mmol) in chloroform (22.5 ml) and methanol (2.5 ml) was heated under nitrogen at 55° C. for 25 h. The reaction mixture was cooled to rt and filtered to remove solid by-products. The filtrate was washed with water (10 ml) and brine (10 ml), dried over MgSO$_4$, filtered, and concentrated. The crude product was purified by flash chromatography (silica gel, CHCl$_3$/MeOH/Et$_3$N, 90:10:1) to afford cis-Adamantane-2-spiro-3'-8'-(aminomethyl)-1',2',4'-trioxaspiro[4.5]decane (0.63 g, 91%) as a colorless solid. $^1$H NMR (500 MHz, DMSO-d$_6$) δ 1.14–1.22 (m, 2H), 1.30–1.40 (m, 2H), 1.60–2.10 (m, 21H), 2.55 (d, J=6.6 Hz, 2H). Step 2. To a solution of the above amine (0.40 g, 1.36 mmol) in acetone (10 ml) was added a solution of citric acid (0.25 g, 1.30 mmol) in acetone (10 ml). The mixture was stirred at rt for 30 min and filtered. The filtrate was concentrated and treated with ether (25 ml). The resulting precipitate was collected by filtration, re-dissolved in methanol (5 ml), and concentrated to afford trioxolane OZ181 (0.30 g, 45%) as a colorless solid. mp 76–77° C.; $^1$H NMR (500 MHz, DMSO-d$_6$) δ

1.04–1.21 (m, 2H), 1.56–2.04 (m, 21H), 2.53 (AB system, 4H), 2.69 (d, J=7.3 Hz, 2H), 7.78 (br s, 3H), 11.50 (br s, 2H); $^{13}$C NMR (125.7 MHz, DMSO-d$_6$) δ 25.95, 26.37, 27.10, 33.01, 33.88, 34.40, 34.42, 35.90, 36.23, 43.61, 44.43, 71.35, 108.29, 110.81, 171.39. Anal. Calcd for C$_{23}$H$_{35}$NO$_{10}$·0.4H$_2$O: C, 55.52; H, 7.36; N, 2.82. Found: C, 55.25; H, 7.25; N, 2.66.

Adamantane-2-spiro-3'-8'-[[2'-(1'H-imidazol-1'-yl)ethoxy]carbonyl]-1', 2',4'-trioxaspiro[4.5]decane (OZ182). To a solution of OZ72 (0.31 g, 1.0 mmol), triphenylphosphine (0.26 g, 1.0 mmol), and 1-(2-hydroxyethyl)imidazole (0.11 g, 1.0 mmol) in THF (10 ml) at 0° C. was added dropwise a solution of diisopropyl azodicarboxylate (0.20 g, 1.0 mmol) in THF (2 ml). The mixture was then warmed to rt and stirred at rt for 16 h before removal of solvents. The crude product was purified by flash chromatography (silica gel, 1% methanol in methylene chloride) to afford trioxolane OZ182 (0.21 g, 52%, 3:1 mixture of two diastereomers) as a colorless solid. mp 75–76° C. (ether/hexanes 1:1); $^1$H NMR (500 MHz, CDCl$_3$) δ 1.60–2.18 (m, 22H), 2.25–2.48 (m, 1H), 4.20 (t, J=5.3 Hz, 2H), 4.33 (t, J=5.1 Hz, 2H), 6.94 (s, 1H), 7.09 (s, 1H), 7.57 (s, 1H); $^{13}$C NMR (125.7 MHz, CDCl$_3$) δ 26.11, 26.27, 26.44, 26.47, 26.84, 26.87, 33.21, 33.40, 34.75, 34.76, 34.78, 34.81, 36.35, 36.37, 36.75, 36.78, 41.15, 45.87, 63.06, 107.65, 108.11,111.38, 111.61, 119.02,129.31, 137.33, 174.34. Anal. Calcd for C$_{22}$H$_{30}$N$_2$O$_5$: C, 65.65; H, 7.51; N, 6.96. Found: C, 65.86; H, 7.58; N, 6.78.

cis-Adamantane-2-spiro-3'-8'-[4'-[(hydroxyamino)carbonyl]phenyl]-1',2',4'-trioxaspiro[4.5]decane (OZ183). A mixture of ethyl chloroformate (0.13 g, 1.2 mmol), OZ165 (0.41 g, 1.0 mmol), and triethylamine (0.13 g, 1.3 mmol), ether (5 ml), THF (5 ml), and DMF (5 ml) was stirred at 0° C. for 1 h. The solid was removed by filtration, and the filtrate was added to a freshly prepared solution of hydroxylamine. [To a suspension of KOH (84 mg, 1.5 mmol) in methanol (1 ml) at 0° C. was added a solution of hydroxylamine hydrochloride (0.10 g, 1.5 mmol) in methanol (2 ml). The reaction mixture was stirred at 0° C. for 15 min and filtered to remove solid by-products. The filtrate was used as such.] The resulting mixture was stirred at rt for 1 h and concentrated. The crude product was triturated with chloroform (6 ml) at 45° C. for 10 min and cooled to rt. The precipitate was collected by filtration and recrystallized from chloroform/methanol (2:1) to afford trioxolane OZ183 (0.13 g, 33%) as a colorless solid. mp 167–168° C. (chloroform/methanol 2:1); $^1$H NMR (500 MHz, DMSO-d$_6$) δ 1.40–2.17 (m, 22H), 2.57–2.80 (m, 1H), 7.29 (d, J=7.8 Hz, 2H), 7.67 (d, J=7.8 Hz, 2H), 8.95 (s, 1H), 11.14 (s, 1H); $^{13}$C NMR (125.7 MHz, DMSO-d$_6$) δ 26.03, 26.44, 31.06, 34.21, 34.48, 36.01, 36.30, 41.61, 108.26, 110.83, 126.82, 127.25, 130.92, 149.41, 164.47. Anal. Calcd for C$_{23}$H$_{29}$NO$_5$: C, 69.15; H, 7.32; N, 3.51. Found: C, 68.89; H, 7.30; N, 3.70.

Adamantane-2-spiro-3'-8'-[(cyclopropylmethyl)amino]-1',2',4'-trioxaspiro[4.5]decane hydrochloride (OZ184). To a solution of OZ05 (555 mg, 2 mmol) in 1,2-dichloroethane (10 ml) were added cyclopropanemethylamine (156 mg, 2.2 mmol) and acetic acid (10 drops). The reaction mixture was stirred at rt for 15 min before sodium triacetoxyborohydride (677 mg, 3.2 mmol) was added. The mixture was stirred for 5 h before being quenched with 1 M aq. NaOH (2 ml). The resulting mixture was extracted with CH$_2$Cl$_2$ (40 ml), washed with water (2×10 ml) and brine (2×10 ml), dried over MgSO$_4$, and concentrated. The residue was dissolved in ether (2 ml), treated with excess 2 M ethereal HCl, and filtered to give trioxolane OZ184 (401 mg, 54%, 1:1 mixture of two diastereomers) as a colorless solid. mp 110° C. dec (ether); $^1$H NMR (500 MHz, CDCl$_3$) δ 0.39–0.60 (m, 2H), 0.61–0.85 (m, 2H), 1.22–1.43 (m, 1H), 1.59–2.45 (m, 22H), 2.76–3.02 (m, 2H), 3.08–3.35 (m, 1H), 9.65 (br s, 2H); $^{13}$C NMR (125.7 MHz, CDCl$_3$) δ 4.83, 4.87, 7.06, 7.13, 25.87, 25.94, 26.37, 26.73, 26.77, 32.29, 34.67, 34.70, 34.79, 36.20, 36.28, 36.66, 48.93, 49.25, 54.42, 54.60, 106.74, 106.75, 111.77, 112.28. Anal. Calcd for C$_{20}$H$_{32}$ClNO$_3$: C, 64.94; H, 8.72; N, 3.79. Found: C, 65.18; H, 8.56; N, 3.83.

Adamantane-2-spiro-3'-8'-(cyclopropylamino)-1',2',4'-trioxaspiro[4.5]decane hydrochloride (OZ185). To a solution of OZ05 (555 mg, 2 mmol) in 1,2-dichloroethane (10 ml) were added cyclopropylamine (125 mg, 2.2 mmol) and acetic acid (10 drops). The reaction mixture was stirred at rt for 15 min before sodium triacetoxyborohydride (677 mg, 3.2 mmol) was added. The mixture was stirred for 5 h before being quenched with 1 M aq. NaOH (2 ml). The resulting mixture was extracted with CH$_2$Cl$_2$ (40 ml), washed with water (2×10 ml) and brine (2×10 ml), dried over MgSO$_4$, and concentrated. The residue was dissolved in ether (2 ml), treated with excess 2 M ethereal HCl, and filtered to give trioxolane OZ185 (348 mg, 49%, 1:1 mixture of two diastereomers) as a colorless solid. mp 102–103° C. dec (ether); $^1$H NMR (500 MHz, CDCl$_3$) δ 0.69–1.05 (m, 2H), 1.20–1.45 (m, 2H), 1.59–2.21 (m, 20H), 2.22–2.45 (m, 2H), 2.46–2.69 (m, 1H), 3.01–3.39 (m, 1H), 9.62 (br s, 2H); $^{13}$C NMR (125.7 MHz, CDCl$_3$) δ 3.85, 26.21, 26.24, 26.40, 26.76, 26.80, 27.49, 27.94, 32.35, 34.70, 34.73, 34.86, 36.24, 36.32, 36.70, 56.85, 57.19, 106.76, 106.78, 111.84, 112.34. Anal. Calcd for C$_{19}$H$_{30}$ClNO$_3$: C, 64.12; H, 8.50; N, 3.94. Found: C, 64.00; H, 8.38; N, 3.84.

cis-Adamantane-2-spiro-3'-8'-[(methoxyacetyl)amino]-1', 2',4'-trioxaspiro[4.5]decane (OZ186). To a solution of OZ137 (550 mg, 1.74 mmol) in CH$_2$Cl$_2$ (10 ml) at 0° C. were added triethylamine (350 mg, 3.48 mmol) and methoxyacetyl chloride (198 mg, 1.82 mmol). The resulting mixture was stirred at rt for 16 h, diluted with CH$_2$Cl$_2$ (10 ml), and washed with water (10 ml) and brine (10 ml). The organic layer was separated, dried over MgSO$_4$, and concentrated. The crude product was purified by flash chromatography (silica gel, 85% ether in hexanes) to give trioxolane OZ186 (379 mg, 62%) as a colorless solid. mp 105–106° C. (ether); $^1$H NMR (500 MHz, CDCl$_3$) δ 1.40–1.61 (m, 2H), 1.62–2.21 (m, 20H), 3.41 (s, 3H), 3.86 (s, 2H), 3.80–3.96 (m, 1H), 6.35–6.49 (m, 1H); $^{13}$C NMR (125.7 MHz, CDCl$_3$) δ 26.34, 26.72, 29.67, 32.56, 34.64, 36.20, 36.63, 45.84, 58.94, 71.83, 107.53, 111.47, 168.65. Anal. Calcd for C$_{19}$H$_{29}$NO$_5$: C, 64.93; H, 8.32; N, 3.99. Found: C, 64.81; H, 8.31; N, 3.91.

cis-Adamantane-2-spiro-3'-8'-[[(dimethylamino)carbonyl]amino]-1',2',4'-trioxaspiro[4.5]decane (OZ187). To a solution of OZ137 (550 mg, 1.74 mmol) in CH$_2$Cl$_2$ (10 ml) at 0° C. were added triethylamine (352 mg, 3.48 mmol) and dimethylcarbamoyl chloride (197 mg, 1.82 mmol). The resulting mixture was stirred at rt for 16 h, diluted with CH$_2$Cl$_2$ (10 ml), and washed with water (10 ml) and brine (10 ml). The organic layer was separated, dried over MgSO$_4$, and concentrated. The crude product was purified by flash chromatography (silica gel, 90% ether in hexanes) to give trioxolane OZ187 (346 mg, 57%) as a colorless solid. mp 142–144° C. (ether); $^1$H NMR (500 MHz, CDCl$_3$) δ 1.32–1.55 (m, 2H), 1.62–2.21 (m, 20H), 2.88 (s, 6H), 3.62–3.85 (m, 1H), 4.15–4.29 (m, 1H); $^{13}$C NMR (125.7 MHz, CDCl$_3$) δ 26.42, 26.79, 30.67, 32.86, 34.72, 36.07, 36.28, 36.72, 47.91, 107.94, 111.45, 157.69. Anal. Calcd for C$_{19}$H$_{30}$N$_2$O$_4$: C, 65.12; H, 8.63; N, 7.99. Found: C, 65.30; H, 8.68; N, 8.06.

Adamantane-2-spiro-3'-8'-(4'-morpholinylcarbonyl)-1',2', 4'-trioxa-8'-azaspiro[4.5]decane (OZ188). To a solution of OZ80 (301 mg, 1 mmol) and triethylamine (202 mg, 2 mmol) in $CH_2Cl_2$ (7 ml) at 0° C. was added 4-morpholinecarbonyl chloride (170 mg, 1.1 mmol). The mixture was stirred at rt for 16 h, diluted with $CH_2Cl_2$ (10 ml), washed with water (2×10 ml) and brine (10 ml), dried over $MgSO_4$, and concentrated. Crystallization of the residue from ethanol gave trioxolane OZ188 (310 mg, 82%) as a colorless solid. mp 132–134° C. (ethanol); $^1H$ NMR (500 MHz, $CDCl_3$) δ 1.60–2.21 (m, 18H), 3.18–3.28 (m, 4H), 3.29–3.58 (m, 4H), 3.60–3.82 (m, 4H); $^{13}C$ NMR (125.7 MHz, $CDCl_3$) δ 26.42, 26.82, 34.37, 34.73, 34.82, 36.39, 36.70, 44.59, 47.41, 66.62, 107.03, 112.04, 163.66. Anal. Calcd for $C_{20}H_{30}N_2O_5$: C, 63.47; H, 7.99; N, 7.40. Found: C, 63.24; H, 7.84; N, 7.44.

cis-Adamantane-2-spiro-3'-8'-[2'-(4'-morpholinyl)-2'-oxoethyl]-1',2',4'-trioxaspiro[4.5]decane (OZ189). To a solution of OZ78 (322 mg, 1.0 mmol) in ether (10 ml) at 0° C. were added triethylamine (202 mg, 2 mmol) and ethyl chloroformate (217 mg, 2 mmol). The mixture was stirred at 0° C. for 15 min before morpholine (175 mg, 2 mmol) was added. The resulting mixture was stirred at rt for 12 h, diluted with ether (10 ml), washed with water (10 ml), dried over $MgSO_4$, and concentrated. The crude product was purified by crystallization from ethanol to afford trioxolane OZ189 (290 mg, 74%) as a colorless solid. mp 118–120° C. (ethanol); $^1H$ NMR (500 MHz, $CDCl_3$) δ 1.16–1.35 (m, 2H), 1.60–2.16 (m, 21H), 2.21 (d, J=6.9 Hz, 2H), 3.38–3.54 (m, 2H), 3.55–3.82 (m, 6H); $^{13}C$ NMR (125.7 MHz, $CDCl_3$) δ 26.48, 26.86, 30.28, 33.26, 34.05, 34.79, 36.39, 36.79, 39.01, 41.93, 46.18, 66.66, 66.97, 108.58, 111.35, 170.67. Anal. Calcd for $C_{22}H_{33}NO_5$: C, 67.49; H, 8.50; N, 3.58. Found: C, 67.46; H, 8.39; N, 3.34.

Adamantane-2-spiro-3'-8'-(dimethylaminosulfonyl)-1',2',4'-trioxa-8'-azaspiro[4.5]decane (OZ190). To a stirred solution of OZ80 (301 mg, 1 mmol) in $CH_2Cl_2$ (10 ml) at rt were added triethylamine (0.4 ml, 3 mmol) and dimethylaminosulfonyl chloride (0.13 ml, 1.2 mmol). The mixture was stirred at rt for 3 h before removal of the solvent. The residue was diluted with ether (15 ml), washed with water (2×10 ml), dried over $MgSO_4$, and concentrated. Crystallization of the residue from ether/hexanes (1:1) gave trioxolane OZ190 (301 mg, 81%) as a colorless solid. mp 104–106° C. (ether/hexanes 1:1); $^1H$ NMR (500 MHz, $CDCl_3$) δ 1.62–2.17 (m, 18H), 2.82 (s, 6H), 3.29–3.53 (m, 4H); $^{13}C$ NMR (125.7 MHz, $CDCl_3$) δ 26.40, 26.79, 34.24, 34.71, 34.80, 36.36, 36.67, 38.18, 44.51, 106.23, 112.25. Anal. Calcd for $C_{17}H_{29}N_2O_5S$: C, 54.82; H, 7.58; N, 7.52. Found: C, 54.70; H, 7.38; N, 7.50.

Adamantane-2-spiro-3'-8'-amidino-1',2',4'-trioxa-8'-azaspiro[4.5]decane hydrochloride (OZ191). To a stirred solution of OZ80 (301 mg, 1 mmol) and triethylamine (202 mg, 2 mmol) in DMF (2 ml) and $CH_2Cl_2$ (2 ml) at rt was added N,N-diisopropylethylamine (130 mg, 2 mmol). After 1H-pyrazole-1-carboxamidine hydrochloride (147 mg, 1 mmol) was added, the reaction mixture became a cloudy suspension. The stirring was continued for 3 h during which period the reaction mixture turned into a clear solution. Addition of dry ether (15 ml) to the above solution produced a colorless precipitate, which was then filtered and washed with ether (3×5 ml). The collected solid was recrystallized from ether/$CH_2Cl_2$ (3:1) to give trioxolane OZ191 (302 mg, 88%) as a colorless solid. mp 144–148° C. (ether/$CH_2Cl_2$, 3:1); $^1H$ NMR (500 MHz, DMSO-$d_6$) δ 1.57–2.17 (m, 18H), 3.41–3.69 (m, 4H), 7.72 (s, 4H); $^{13}C$ NMR (125.7 MHz, DMSO-$d_6$) δ 25.93, 26.31, 33.61, 34.38, 34.43, 35.76, 36.15, 43.39, 106.26, 111.74, 156.36. Anal. Calcd for $C_{16}H_{26}ClN_3O_3$: C, 55.89; H, 7.62; N, 12.22. Found: C, 55.73; H, 7.54; N, 12.23.

Adamantane-2-spiro-3'-8'-[(4'-chlorophenylamino)carbonyl]-1',2',4'-trioxa-8'-azaspiro[4.5]decane (OZ192). To a solution of OZ80 (301 mg, 1 mmol) and triethylamine (202 mg, 2 mmol) in $CH_2Cl_2$ (7 ml) at 0–5° C. was added 4-chlorophenyl isocyanate (154 mg, 1 mmol). The reaction mixture was stirred at rt for 16 h, diluted with $CH_2Cl_2$ (10 ml), and washed with water (2×10 ml) and brine (10 ml). The organic layer was dried over $MgSO_4$ and concentrated. The residue was purified by crystallization from methanol to afford trioxolane OZ192 (346 mg, 83%) as a colorless solid. mp 132–134° C. (methanol); $^1$-H NMR (500 MHz, $CDCl_3$) δ 1.61–2.17 (m, 18H), 3.42–3.77 (m, 4H), 6.43 (s, 1H), 7.17–7.37 (m, 4H); $^{13}C$ NMR (125.7 MHz, $CDCl_3$) δ 26.41, 26.81, 34.34, 34.73, 34.82, 36.38, 36.67, 42.34, 106.65, 112.32, 121.19, 128.20, 128.86, 137.53, 154.46. Anal. Calcd for $C_{22}H_{27}ClN_2O_4$: C, 63.08; H, 6.50; N, 6.69. Found: C, 62.95; H, 6.36; N, 6.65.

Adamantane-2-spiro-3'-8'-(4'-fluorophenoxy)-1',2',4'-trioxaspiro[4.5]decane (OZ193). A solution of O-methyl 2-adamantanone oxime (895 mg, 5 mmol) and 4-(4-fluorophenoxy)cyclohexanone (950 mg, 5.1 mmol) in cyclohexane (80 ml) and $CH_2Cl_2$ (20 ml) was treated with ozone according to the general procedure. The crude product was purified by flash chromatography (silica gel, 5% ether in hexanes) and by subsequent recrystallization from ethanol/$CH_2Cl_2$ (19:1) to afford trioxolane OZ193 (250 mg, 13%) as a colorless solid. mp 102–104° C. (ethanol/$CH_2Cl_2$ 19:1); $^1H$ NMR (500 MHz, $CDCl_3$) δ 1.57–2.21 (m, 22H), 4.29–4.41 (m, 1H), 6.79–6.89 (m, 2H), 6.91–7.05 (m, 2H); $^{13}C$ NMR (125.7 MHz, $CDCl_3$) δ 26.48, 26.88, 27.82, 30.06, 34.79, 34.85, 36.43, 36.79, 72.54, 108.22, 111.71, 115.87 (d, J=23.3 Hz), 117.44 (d, J=8.2 Hz), 153.44, 157.34 (d, J=239.0 Hz). Anal. Calcd for $C_{22}H_{27}FO_4$: C, 70.57; H, 7.27. Found: C, 70.71; H, 7.33.

Adamantane-2-spiro-3'-8'-[(diisopropylamino)carbonyl]-1',2',4'-trioxa-8'-azaspiro[4.5]decane (OZ194). To a solution of OZ80 (301 mg, 1 mmol) and triethylamine (303 mg, 3 mmol) in $CH_2Cl_2$ (10 ml) at 0–5° C. was added diisopropylcarbamoyl chloride (164 mg, 1 mmol). The resulting mixture was stirred at rt for 16 h, diluted with $CH_2Cl_2$ (10 ml), and washed with water (2×10 ml) and brine (10 ml). The organic layer was dried over $MgSO_4$ and concentrated. The residue was purified by crystallization from methanol to afford trioxolane OZ194 (290 mg, 74%) as a colorless solid. mp 114–116° C. (methanol); $^1$-H NMR (500 MHz, $CDCl_3$) δ 1.27 (d, J=6.8 Hz, 12H), 1.60–2.21 (m, 18H), 3.11–3.39 (m, 4H), 3.60 (sep, J=6.6 Hz, 2H); $^{13}C$ NMR (125.7 MHz, $CDCl_3$) δ 21.57, 26.44, 26.84, 34.39, 34.72, 34.81, 36.40, 36.73, 45.26, 47.52, 107.29, 111.79, 163.59. Anal. Calcd for $C_{22}H_{36}N_2O_4$: C, 67.32; H, 9.24; N, 7.14. Found: C, 67.14; H, 9.13; N, 7.11.

cis-Adamantane-2-spiro-3'-8'-[(tert-butylacetyl)amino]-1',2',4'-trioxaspiro[4.5]decane (OZ195). To a solution of OZ137 (550 mg, 1.74 mmol) in $CH_2Cl_2$ (10 ml) at 0° C. were added triethylamine (529 mg, 5.22 mmol) and tert-butylacetyl chloride (304 mg, 2.26 mmol). The resulting mixture was stirred at rt for 16 h, diluted with $CH_2Cl_2$ (10 ml), and washed with water (10 ml) and brine (10 ml). The organic layer was separated, dried over $MgSO_4$, and concentrated. The crude product was purified by flash chromatography (silica gel, 75% ether in hexanes) to give trioxolane OZ195 (335 mg, 51%) as a colorless solid. mp 142–144° C. (ether); $^1H$ NMR (500 MHz, $CDCl_3$) δ 1.02 (s, 9H), 1.30–1.51 (m, 2H), 1.52–1.99 (m, 20H), 1.96 (s, 2H), 3.79–3.95 (m, 1H), 5.23–5.28 (m, 1H); $^{13}C$ NMR (125.7 MHz, $CDCl_3$) δ 26.44, 26.82, 29.77, 30.00, 30.79, 32.76, 34.76, 36.31, 36.74, 46.45, 50.69, 107.76, 111.63, 170.97.

Anal. Calcd for $C_{22}H_{35}NO_4$: C, 69.99; H, 9.34; N, 3.71. Found: C, 70.15; H, 9.38; N, 3.65.

cis-Adamantane-2-spiro-3'-8'-[(3'-carboxy-1'-oxopropyl) amino]-1',2',4'-trioxaspiro[4.5]decane (OZ196). To a solution of OZ137 (550 mg, 1.74 mmol) in $CH_2Cl_2$ (10 ml) at 0° C. were added triethylamine (350 mg, 3.48 mmol) and succinic anhydride (176 mg, 1.74 mmol). The resulting mixture was stirred at rt for 24 h, concentrated, and triturated with water (3×10 ml), hexanes (2×10 ml), and THF (5 ml) to give trioxolane OZ196 (350 mg, 53%) as a colorless solid. mp 122–124° C. (THF); $^1$H NMR (500 MHz, DMSO-$d_6$) δ 1.33–1.57 (m, 2H), 1.62–2.19 (m, 20H), 2.31–2.41 (m, 2H), 2.42–2.57 (m, 2H), 3.65–3.82 (m, 1H), 7.83–7.87 (m, 1H); $^{13}$C NMR (125.7 MHz, DMSO-$d_6$) δ 26.00, 26.39, 29.34, 29.43, 32.20, 34.43, 35.88, 36.26, 45.65, 108.07, 110.81, 170.41, 173.99. Anal. Calcd for $C_{20}H_{29}NO_6$: C, 63.31; H, 7.70; N, 3.69. Found: C, 63.46; H, 7.68; N, 3.84.

cis-Adamantane-2-spiro-3'-8'-[(2',5'-dioxo-1'-pyrrolidinyl)methyl]-1',2',4'-trioxaspiro[4.5]decane (OZ197). To a solution of OZ119 (0.29 g, 1 mmol), triphenylphosphine (0.42 g, 1.6 mmol), and succinimide (0.11 g, 1.1 mmol) in THF (6 ml) at 0° C. was added a solution of DIPAD (0.32 g, 1.6 mmol) in THF (1 ml). The mixture was warmed to rt and stirred overnight. After removal of the solvent, the crude product was purified by flash chromatography (silica gel, 25% ether in hexanes) and by subsequent recrystallization from hexanes/$CH_2Cl_2$ (3:1) to give trioxolane OZ197 (0.30 g, 80%) as a colorless solid. mp 147–148° C. (hexanes/$CH_2Cl_2$ 3:1); $^1$H NMR (500 MHz, CDCl$_3$) δ 1.37–1.59 (m, 2H), 1.61–2.35 (m, 21H), 2.92 (s, 4H), 3.59 (d, J=7.1 Hz, 2H); $^{13}$C NMR (125.7 MHz, CDCl$_3$) δ 26.39, 26.79, 27.70, 28.02, 33.46, 34.69, 34.71, 34.74, 36.28, 36.71, 43.75, 108.32, 111.25, 177.26. Anal. Calcd for $C_{21}H_{29}NO_5$: C, 67.18; H, 7.79; N, 3.73. Found: C, 67.12; H, 7.81; N, 3.63.

cis-Adamantane-2-spiro-3'-8'-(3'-carboxyphenyl)-1',2',4'-trioxaspiro[4.5]decane (OZ198). A mixture of OZ208 (0.38 g, 0.92 mmol), KOH (0.36 g), THF (10 ml), methanol (10 ml), and water (2 ml) was heated at 50° C. for 2 h. The mixture was concentrated, diluted with water (10 ml), and acidified with 1 M aq. HCl to pH=2. The resulting solid was collected by filtration and washed with hexanes/ether (10 ml, 2:1) to give trioxolane OZ198 (0.28 g, 79%) as a colorless solid. mp 150–152° C.; $^1$H NMR (500 MHz, CDCl$_3$) δ 1.63–2.22 (m, 22H), 2.58–2.73 (m, 1H), 7.40 (dd, J=7.7, 7.7 Hz, 1H), 7.46 (d, J=7.4 Hz, 1H), 7.95 (d, J=7.7 Hz, 1H), 7.97 (s, 1H); $^{13}$C NMR (125.7 MHz, CDCl$_3$) δ 26.51, 26.91, 31.31, 34.63, 34.82, 36.43, 36.82, 42.72, 108.21, 111.49, 128.13, 128.60, 128.75, 129.46, 132.06, 146.59, 171.58. Anal. Calcd for $C_{23}H_{28}O_5$: C, 71.85; H, 7.34. Found: C, 71.74; H, 7.30.

Adamantane-2-spiro-3'-8'-carbamoyl-1',2',4'-trioxa-8'-azaspiro[4.5]decane (OZ199). To a solution of OZ80 (450 mg, 1.49 mmol) in $CH_2Cl_2$ (12 ml) at rt were added pyridine (1.2 ml, 14.9 mmol), HOAc (0.82 ml, 14.9 mmol), triethylamine (0.4 ml, 2.98 mmol), and potassium cyanate (243 mg, 2.98 mmol). After being stirred for 35 h the reaction mixture was poured into a mixture of ether (50 ml) and water (50 ml). The organic layer was separated, washed with brine (15 ml), dried over MgSO$_4$, and concentrated. Crystallization of the residue from ether/$CH_2Cl_2$ (3:1) afforded trioxolane OZ199 (449 mg, 98%) as a colorless solid. mp 140–142° C. (ether/$CH_2Cl_2$ 3:1); $^1$H NMR (500 MHz, CDCl$_3$) δ 1.57–2.21 (m, 18H), 3.31–3.69 (m, 4H), 4.55 (s, 2H); $^{13}$C NMR (125.7 MHz, CDCl$_3$) δ 26.41, 26.81, 34.27, 34.73, 34.81, 36.37, 36.69, 42.25, 106.72, 112.21, 157.65. Anal. Calcd for $C_{16}H_{24}N_2O_4 \cdot 0.4H_2O$: C, 60.89; H, 7.92; N, 8.88. Found: C, 60.86; H, 7.60; N, 8.84.

Adamantane-2-spiro-3'-8'-[2'-(ethylsulfonyl)ethyl]-1',2', 4'-trioxa-8'-azaspiro[4.5]decane (OZ200). To a stirred solution of OZ80 (450 mg, 1.49 mmol) in $CH_2Cl_2$ (10 ml) and methanol (10 ml) at rt was added triethylamine (0.4 ml, 2.98 mmol) followed by ethyl vinyl sulfone (0.15 ml, 1.49 mmol). The resulting mixture was stirred at rt for 3 h before removal of the solvents. The residue was diluted with ether (15 ml), washed with water (2×10 ml), dried (MgSO$_4$), and concentrated. Crystallization of the crude product from ether/hexanes (1:1) afforded trioxolane OZ200 (415 mg, 72%) as a colorless solid. mp 105–107° C. (ether/hexanes 1:1); $^1$H NMR (500 MHz, CDCl$_3$) δ 1.39 (t, J=7.6 Hz, 3H), 1.57–2.21 (m, 18H), 2.41–2.59 (m, 2H), 2.60–2.78 (m, 2H), 2.89 (t, J=6.5 Hz, 2H), 3.09 (t, J=6.5 Hz, 2H), 3.14 (q, J=7.4 Hz, 2H); $^{13}$C NMR (125.7 MHz, CDCl$_3$) δ 6.59, 26.40, 26.80, 34.33, 34.71, 34.79, 36.34, 36.69, 48.56, 49.74, 50.94, 51.10, 106.54, 111.85. Anal. Calcd for $C_{19}H_{31}NO_5S$: C, 59.19; H, 8.10; N, 3.63. Found: C, 58.98; H, 7.95; N, 3.65.

cis-Adamantane-2-spiro-3'-8'-[(4'-fluorophenyl)amino]-1',2',4'-trioxaspiro[4.5]decane (OZ201). To a solution of OZ05 (555 mg, 2 mmol) in 1,2-dichloroethane (10 ml) were added 4-fluoroaniline (236 mg, 2.12 mmol) and acetic acid (10 drops). The reaction mixture was stirred at rt for 15 min before sodium triacetoxyborohydride (677 mg, 3.2 mmol) was added. The mixture was stirred for 5 h before being quenched with 1 M aq. NaOH (2 ml). The resulting mixture was extracted with $CH_2Cl_2$ (40 ml), washed with water (2×10 ml) and brine (2×10 ml), dried over MgSO$_4$, and concentrated to give an oil (517 mg, 69%, 2:1 mixture of two diastereomers). Trituration with ether and hexanes gave trioxolane OZ201 (280 mg, 37%) as a colorless solid. mp 118–120° C. (hexanes); $^1$H NMR (500 MHz, CDCl$_3$) δ 1.37–1.52 (m, 2H), 1.53–2.21 (m, 20H), 3.19–3.27 (m, 1H), 3.28–3.49 (m, 1H), 6.41–6.63 (m, 2H), 6.77–6.99 (m, 2H); $^{13}$C NMR (125.7 MHz, CDCl$_3$) δ 26.46, 26.87, 30.10, 32.75, 34.77, 34.81, 36.34, 36.76, 50.92, 108.08, 111.58, 114.14 (d, J=7.3 Hz), 115.71 (d, J=22.4 Hz), 143.44, 155.70 (d, J=234.9 Hz). Anal. Calcd for $C_{22}H_{28}FNO_3$: C, 70.75; H, 7.56; N, 3.75. Found: C, 70.85; H, 7.42; N, 3.76.

cis-Adamantane-2-spiro-3'-8'-[(2'-acetoxy-2'-methylpropionyl)amino]-1',2',4'-trioxaspiro[4.5]decane (OZ202). To a solution of OZ137 (550 mg, 1.74 mmol) in $CH_2Cl_2$ (10 ml) at 0° C. were added triethylamine (529 mg, 5.22 mmol) and 2-acetoxy-2-methylpropionyl chloride (430 mg, 2.61 mmol). The resulting mixture was stirred at rt for 16 h, diluted with $CH_2Cl_2$ (10 ml), and washed with water (10 ml) and brine (10 ml). The organic layer was separated, dried over MgSO$_4$, and concentrated. The crude product was purified by trituration with hexanes to give trioxolane OZ202 (350 mg, 49%) as a colorless solid. mp 130–132° C. (hexanes); $^1$H NMR (500 MHz, CDCl$_3$) δ 1.35–1.52 (m, 2H), 1.61 (s, 6H), 1.62–2.06 (m, 20H), 2.07 (s, 3H), 3.75–3.95 (m, 1H), 5.77–5.93 (m, 1H); $^{13}$C NMR (125.7 MHz, CDCl$_3$) δ 21.87, 24.29, 26.43, 26.81, 29.73, 32.68, 34.75, 36.30, 36.73, 46.51, 81.35, 107.66, 111.65, 169.15, 172.35. Anal. Calcd for $C_{22}H_{33}NO_6$: C, 64.84; H, 8.16; N, 3.44. Found: C, 64.80; H, 7.93; N, 3.52.

Adamantane-2-spiro-3'-8'-(1'-pyrrolidinylcarbonyl)-1',2', 4'-trioxa-8'-azaspiro[4.5]decane (OZ203). To a solution of OZ80 (301 mg, 1 mmol) and triethylamine (303 mg, 3 mmol) in $CH_2Cl_2$ (10 ml) at 0° C. was added 1-pyrrolidinecarbonyl chloride (118 mg, 1 mmol). The mixture was stirred at rt for 16 h, diluted with $CH_2Cl_2$ (10 ml), and washed with water (2×10 ml) and brine (10 ml). The organic layer was separated, dried over MgSO$_4$, and concentrated. Crystallization of the residue from methanol gave trioxolane OZ203 (152 mg, 42%) as a colorless solid. mp 130–132° C. (methanol); $^1$H NMR (500 MHz, CDCl$_3$) δ 1.61–2.15 (m, 22H), 3.23–3.57 (m, 8H); $^{13}$C NMR (125.7 MHz, CDCl$_3$) δ 25.53, 26.44, 26.83, 34.51, 34.73, 34.82, 36.40, 36.72, 43.94, 48.38, 107.26, 111.90, 162.56. Anal. Calcd for C$_{20}$H$_{30}$N$_2$O$_4$: C, 66.27; H, 8.34; N, 7.73. Found: C, 66.33; H, 8.30; N, 7.60.

cis-Adamantane-2-spiro-3'-8'-[(4'-methoxycarbonylphenyl)methyl]-1',2',4'-trioxaspiro[4.5]decane (OZ204). A solution of O-methyl 2-adamantanone oxime (895 mg, 5 mmol) and 4-[(4'-methoxycarbonylphenyl)methyl]cyclohexanone (1.27 g, 5 mmol) in cyclohexane (80 ml) and CH$_2$Cl$_2$ (20 ml) was treated with ozone according to the general procedure. The crude product was purified by flash chromatography (silica gel, 5% ether in hexanes) and subsequent recrystallization from ethanol/CH$_2$Cl$_2$ (19:1) to afford trioxolane OZ204 (950 mg, 46%) as a colorless solid. mp 104–106° C. (ethanol/CH$_2$Cl$_2$ 19:1); $^1$H NMR (500 MHz, CDCl$_3$) δ 1.19–1.37 (m, 2H), 1.49–2.07 (m, 21H), 2.56 (d, J=6.9 Hz, 2H), 3.90 (s, 3H), 7.20 (d, J=7.9 Hz, 2H), 7.95 (d, J=7.9 Hz, 2H); $^{13}$C NMR (125.7 MHz, CDCl$_3$) δ 26.48, 26.87, 29.90, 34.08, 34.78, 36.38, 36.80, 38.00, 42.86, 51.95, 108.76, 111.28, 127.91, 129.08, 129.57, 146.42, 167.12. Anal. Calcd for C$_{25}$H$_{32}$O$_5$: C, 72.79; H, 7.82. Found: C, 72.72; H, 7.85.

cis-Adamantane-2-spiro-3'-8'-(2'-hydroxy-2'-methylpropyl)-1',2',4'-trioxaspiro[4.5]decane (OZ205). To a solution of OZ61 (350 mg, 1 mmol) in CH$_2$Cl$_2$ at −78° C. was added methyllithium (3 ml, 1.6 M in ether, 4.8 mmol). The reaction was stirred at −78° C. for 2 h before being quenched with water. The organic layer was separated, and the aqueous layer was extracted with CH$_2$Cl$_2$ (2×10 ml). The combined organic layers were washed with water (10 ml) and brine (10 ml), dried over MgSO$_4$, filtered, and concentrated. The crude product was purified by crystallization from ethanol to afford trioxolane OZ205 (262 mg, 78%) as a colorless solid. mp 96–98° C. (ethanol); $^1$H NMR (500 MHz, CDCl$_3$) δ 1.23 (s, 6H), 1.21–1.37 (m, 2H), 1.40 (d, J=5.5 Hz, 2H), 1.43–1.61 (m, 1H), 1.62–2.09 (m, 20H); $^{13}$C NMR (125.7 MHz, CDCl$_3$) δ 26.49, 26.89, 30.03, 31.99, 32.47, 34.31, 34.78, 34.80, 36.40, 36.82, 49.76, 71.39, 108.62, 111.17. Anal. Calcd for C$_{20}$H$_{32}$O$_4$: C, 71.39; H, 9.59. Found: C, 71.44; H, 9.39.

cis-Adamantane-2-spiro-3'-8'-[(2',4'-dioxo-3'-imidazolidinyl)methyl]-1',2',4'-trioxaspiro[4.5]decane (OZ206). To a solution of OZ119 (0.29 g, 1 mmol), triphenylphosphine (0.42 g, 1.6 mmol), and hydantoin (0.11 g, 1.1 mmol) in DMF (6 ml) and THF (6 ml) at 0° C. was added a solution of DIPAD (0.32 g, 1.6 mmol) in THF (1 ml). The mixture was warmed to rt and stirred overnight. After removal of the solvents, the crude product was purified by flash chromatography (silica gel, 25% acetone in hexanes) and subsequent recrystallization from hexanes/CH$_2$Cl$_2$ (5:1) to give trioxolane OZ206 (0.21 g, 56%) as a colorless solid. mp 158–160° C. (hexanes/CH$_2$Cl$_2$ 5:1); $^1$H NMR (500 MHz, CDCl$_3$) δ 1.21–1.41 (m, 2H), 1.58–2.19 (m, 21H), 3.40 (d, J=6.9 Hz, 2H), 3.99 (s, 2H), 5.81 (s, 1H); $^{13}$C NMR (125.7 MHz, CDCl$_3$) δ 26.47, 26.87, 27.69, 33.54, 34.77, 34.79, 35.10, 36.36, 36.79, 43.76, 46.27, 108.43, 111.36, 158.35, 171.31. Anal. Calcd for C$_{20}$H$_{28}$N$_2$O$_5$: C, 63.81; H, 7.50; N, 7.44. Found: C, 63.68; H, 7.31; N, 7.39.

cis-Adamantane-2-spiro-3'-8'-(aminomethyl)-1',2',4'-trioxaspiro[4.5]decane p-tosylate (OZ207). To a solution of cis-Adamantane-2-spiro-3'-8'-(aminomethyl)-1',2',4'-trioxaspiro[4.5]decane (1.465 g, 5 mmol) in ether (60 ml) and CH$_2$Cl$_2$ (20 ml) was added a solution of p-TsOH (0.96 g, 5 mmol) in ether (80 ml). The resulting mixture was placed at −20° C. overnight. The solid was collected by filtration to afford trioxolane OZ207 (2.24 g, 96%) as a colorless solid. mp 162–164° C.; $^1$H NMR (500 MHz, DMSO-d$_6$) δ 1.01–1.23 (m, 2H), 1.51–2.07 (m, 21H), 2.29 (s, 3H), 2.68 (app t, J=5.7 Hz, 2H), 7.12 (d, J=7.8 Hz, 2H), 7.48 (d, J=8.3 Hz, 2H), 7.68 (br s, 3H); $^{13}$C NMR (125.7 MHz, DMSO-d$_6$) δ 20.93, 25.95, 26.36, 27.08, 32.99, 33.86, 34.40, 34.41, 35.89, 36.22, 43.63, 108.28, 110.80, 125.65, 128.21, 137.77, 145.87. Anal. Calcd for C$_{24}$H$_{35}$NO$_6$S: C, 61.91; H, 7.58; N, 3.01. Found: C, 61.78; H, 7.38; N, 2.97.

cis-Adamantane-2-spiro-3'-8'-[(3'-ethoxycarbonyl)phenyl]-1',2',4'-trioxaspiro[4.5]decane (OZ208). A solution of O-methyl 2-adamantanone oxime (0.65 g, 2.6 mmol) and 4-[3-(ethoxycarbonyl)phenyl]cyclohexanone (0.47 g, 2.6 mmol) in pentane (50 ml) and CH$_2$Cl$_2$ (25 ml) was treated with ozone according to the general procedure. The crude product was purified by flash chromatography (silica gel, 10% ether in hexanes) to afford trioxolane OZ208 (0.50 g, 47%) as a colorless solid. mp 72–73° C. (95% ethanol); $^1$H NMR (500 MHz, CDCl$_3$) δ 1.39 (t, J=7.1 Hz, 3H), 1.61–2.21 (m, 22H), 2.55–2.69 (m, 1H), 4.37 (q, J=7.1 Hz, 2H), 7.35 (dd, J=7.6, 7.6 Hz, 1H), 7.39 (d, J=7.7 Hz, 1H), 7.88 (d, J=7.7 Hz, 1H), 7.89 (s, 1H); $^{13}$C NMR (125.7 MHz, CDCl$_3$) δ 14.35, 26.50, 26.90, 31.33, 34.64, 34.81, 36.43, 36.81, 42.78, 60.90, 108.24, 111.47, 127.48, 127.98, 128.41, 130.62, 131.21, 146.38, 166.70. Anal. Calcd for C$_{25}$H$_{32}$O$_5$: C, 72.79; H, 7.82. Found: C, 72.61; H, 7.60.

cis-Adamantane-2-spiro-3'-8'-(aminomethyl)-1',2',4'-trioxaspiro[4.5]decane mesylate (OZ209). To a solution of cis-Adamantane-2-spiro-3'-8'-(aminomethyl)-1',2',4'-trioxaspiro[4.5]decane (0.30 g, 1.02 mmol) in ether (10 ml) and CH$_2$Cl$_2$ (5 ml) was added a solution of methanesulfonic acid (0.10 g, 1.04 mmol) in ether (30 ml). The resulting mixture was concentrated to 10 ml and placed at −20° C. overnight. The solid was collected by filtration to afford trioxolane OZ209 (0.34 g, 86%) as a colorless solid. mp 146–148° C.; $^1$H NMR (500 MHz, DMSO-d$_6$) δ 1.01–1.23 (m, 2H), 1.51–2.07 (m, 21H), 2.34 (s, 3H), 2.69 (app t, J=6.0 Hz, 2H), 7.70 (br s, 3H); $^{13}$C NMR (125.7 MHz, DMSO-d$_6$) δ 25.95, 26.36, 27.09, 33.01, 33.85, 34.39, 34.41, 35.89, 36.22, 43.61, 108.28, 110.79. Anal. Calcd for C$_{18}$H$_{31}$NO$_6$S: C, 55.50; H, 8.02; N, 3.60. Found: C, 55.41; H, 7.94; N, 3.58.

cis-Adamantane-2-spiro-3'-8'-[(phenylsulfonyl)methyl]-1',2',4'-trioxa-8'-azaspiro[4.5]decane (OZ210). A solution of O-methyl 2-adamantanone oxime (1.79 g, 10 mmol) and 4-[(phenylsulfonyl)methyl]cyclohexanone (1.20 g, 4.76 mmol) in pentane (50 ml) and CH$_2$Cl$_2$ (25 ml) was treated with ozone according to the general procedure. The crude product was purified by flash chromatography (silica gel, 33% ether in hexanes) to afford trioxolane OZ210 (0.78 g, 39%) as a colorless solid. mp 120–122° C. (ether/hexanes 1:1); $^1$H NMR (500 MHz, CDCl$_3$) δ 1.25–1.46 (m, 2H), 1.60–2.21 (m, 21H), 2.99 (d, J=6.3 Hz, 2H), 7.54–7.62 (m, 2H), 7.63–7.70 (m, 1H), 7.88–7.96 (m, 2H); $^{13}$C NMR (125.7 MHz, CDCl$_3$) δ 26.44, 26.83, 30.11, 31.19, 33.69, 34.75, 34.76, 36.35, 36.75, 61.79, 107.77, 111.53, 127.73, 129.32, 133.63, 140.21. Anal. Calcd for C$_{23}$H$_{30}$O$_5$S: C, 66.00; H, 7.22. Found: C, 66.15; H, 7.10.

cis-Adamantane-2-spiro-3'-8'-(1'H-pyrazol-1'-ylmethyl)-1',2',4'-trioxaspiro[4.5]decane (OZ211). To a suspension of 60% NaH (0.08 g, 2 mmol) in DMF (4 ml) under nitrogen at 0° C. was added a solution of pyrazole (0.14 g, 2 mmol) in DMF (4 ml). The mixture was stirred for 30 min before a solution of the methanesulfonate of OZ119 (0.37 g, 1.0 mmol) in DMF (4 ml) was added dropwise. The reaction mixture was heated at 50° C. for 2 h, quenched with water (40 ml), and then extracted with ethyl acetate (3×30 ml). The combined extracts were washed with brine (3×30 ml), dried over $MgSO_4$, filtered, and concentrated. The crude product was purified by flash chromatography (silica gel, 33% ether in hexanes) to afford trioxolane OZ211 (0.28 g, 81%) as a colorless solid. mp 103–106° C. (hexanes/$CH_2Cl_2$, 4:1); $^1H$ NMR (500 MHz, $CDCl_3$) δ 1.19–1.37 (m, 2H), 1.53–2.18 (m, 21H), 3.77 (d, J=7.1 Hz, 2H), 6.22 (s, 1H), 7.33 (s, 1H), 7.51 (s, 1H); $^{13}C$ NMR (125.7 MHz, $CDCl_3$) δ 26.47, 26.85, 27.63, 33.60, 34.77, 36.37, 36.78, 37.16, 57.46, 105.02, 108.52, 111.43, 129.63, 139.41. Anal. Calcd for $C_{20}H_{28}N_2O_3$: C, 69.74; H, 8.19; N, 8.13. Found: C, 69.88; H, 8.18; N, 8.17.

cis-Adamantane-2-spiro-3'-8'-[(1',1'-dioxido-3'-oxo-1',2'-benzisothiazol-2'(3'H)-yl)methyl]-1',2',4'-trioxaspiro[4.5]decane (OZ212). To a solution of OZ119 (0.29 g, 1 mmol), triphenylphosphine (0.42 g, 1.6 mmol), and saccharin (0.20 g, 1.1 mmol) in THF (10 ml) at 0° C. was added a solution of DIPAD (0.32 g, 1.6 mmol) in THF (1 ml). The mixture was warmed to rt and stirred overnight. After removal of the solvent, the crude product was purified by flash chromatography (silica gel, 25% ether in hexanes) and by subsequent recrystallization from hexanes/$CH_2Cl_2$ (4:1) to give trioxolane OZ212 (0.17 g, 37%) as a colorless solid. mp 152–155° C. (hexanes/$CH_2Cl_2$, 4:1); $^1H$ NMR (500 MHz, $CDCl_3$) δ 1.23–1.45 (m, 2H), 1.59–2.18 (m, 21H), 3.63 (d, J=7.4 Hz, 2H), 7.80–7.90 (m, 2H), 7.93 (d, J=7.1 Hz, 1H), 8.06 (d, J=7.4 Hz, 1H); $^{13}C$ NMR (125.7 MHz, $CDCl_3$) δ 26.49, 26.88, 27.79, 33.50, 34.79, 34.80, 35.14, 36.39, 36.81, 44.49, 108.43, 111.39, 120.93, 125.22, 127.33, 134.31, 134.73, 137.64, 159.26. Anal. Calcd for $C_{24}H_{29}NO_6S$: C, 62.73; H, 6.36; N, 3.05. Found: C, 62.74; H, 6.18; N, 3.02.

cis-Adamantane-2-spiro-3'-8'-[[(methoxyamino)carbonyl]methyl]-1',2',4'-trioxaspiro[4.5]decane (OZ213). To a solution of OZ78 (322 mg, 1 mmol) in $CH_2Cl_2$ (10 ml) at 0° C. were added triethylamine (202 mg, 2 mmol) and ethyl chloroformate (217 mg, 2 mmol). After the mixture was stirred at 0° C. for 15 min, methoxylamine was added. [To a suspension of methoxylamine hydrochloride (167 mg, 2 mmol) in methanol (5 ml) was added $NaHCO_3$ (164 mg, 2 mmol). The mixture was stirred at rt for 15 min]. The resulting mixture was stirred at rt for 12 h, diluted with $CH_2Cl_2$ (10 ml), washed with water (10 ml), dried over $MgSO_4$, and concentrated. The crude product was purified by crystallization from methanol to afford trioxolane OZ213 (0.17 g, 48%) as a colorless solid. mp 72–74° C. (methanol); $^1H$ NMR (500 MHz, DMSO-$d_6$) δ 0.99–1.21 (m, 2H), 1.45–2.11 (m, 23H), 3.56 (s, 3H), 10.93 (s, 1H); $^{13}C$ NMR (125.7 MHz, DMSO-$d_6$) δ 25.96, 26.37, 29.54, 32.64, 33.50, 34.40, 35.91, 36.25, 38.86, 63.34, 108.49, 110.64, 168.09. Anal. Calcd for $C_{19}H_{29}NO_5$: C, 64.93; H, 8.32; N, 3.99. Found: C, 64.79; H, 8.13; N, 3.76.

cis-Adamantane-2-spiro-3'-8'-[(4'-carboxyphenyl)methyl]-1',2',4'-trioxaspiro[4.5]decane (OZ214). A mixture of OZ204 (412 mg, 1 mmol), NaOH (120 mg, 3 mmol), methanol (10 ml), and water (10 ml) was stirred at rt for 16 h. After removal of the solvents, the residue was acidified with 6 M aq. HCl (4 ml) to pH=2, and the resulting precipitate was collected by filtration and further crystallized from 95% ethanol to give trioxolane OZ214 (182 mg, 46%) as a colorless solid. mp 160–162° C. (95% ethanol); $^1H$ NMR (500 MHz, $CDCl_3$) δ 1.09–1.39 (m, 2H), 1.43–2.22 (m, 21H), 2.59 (d, J=7.1 Hz, 2H), 7.25 (d, J=7.9 Hz, 2H), 8.04 (d, J=7.9 Hz, 2H); $^{13}C$ NMR (125.7 MHz, $CDCl_3$) δ 26.49, 26.88, 29.92, 34.08, 34.79, 36.39, 36.80, 38.00, 42.95, 108.74, 111.31, 126.98, 129.23, 130.24, 147.48, 171.61. Anal. Calcd for $C_{24}H_{30}O_5$: C, 72.34; H, 7.59. Found: C, 72.16; H, 7.37.

cis-Adamantane-2-spiro-3'-8'-phthalimidoethyl-1',2',4'-trioxaspiro[4.5]decane (OZ215). A solution of O-methyl 2-adamantanone oxime (895 mg, 5 mmol) and 4-phthalimidoethylcyclohexanone (1.35 g, 5 mmol) in cyclohexane (85 ml) and $CH_2Cl_2$ (15 ml) was treated with ozone according to the general procedure. The crude product was purified by flash chromatography (silica gel, 15% ether in hexanes) and by subsequent crystallization from ethanol to afford trioxolane OZ215 (1.33 g, 61%) as a colorless solid. mp 136–138° C. (ethanol); $^1H$ NMR (500 MHz, $CDCl_3$) δ 1.15–1.43 (m, 3H), 1.49–2.21 (m, 22H), 3.70 (d, J=7.5 Hz, 2H), 7.62–7.78 (m, 2H), 7.79–7.97 (m, 2H); $^{13}C$ NMR (125.7 MHz, $CDCl_3$) δ 26.48, 26.87, 29.81, 33.78, 34.04, 34.76, 34.79, 36.05, 36.38, 36.80, 108.73, 111.18, 123.14, 132.16, 133.84, 168.33. Anal. Calcd for $C_{26}H_{31}NO_5$: C, 71.37; H, 7.14; N, 3.20. Found: C, 71.50; H, 6.93; N, 3.16.

Adamantane-2-spiro-3'-8'-(4'-pyridinylmethyl)-1',2',4'-trioxa-8'-azaspiro[4.5]decane (OZ216). To a stirred solution of OZ80 (200 mg, 0.66 mmol) in 1,2-dichloroethane (5 ml) at rt was added triethylamine (0.2 ml, 1.2 mmol) followed by 4-pyridinecarboxaldehyde (71 mg, 0.66 mmol) and sodium triacetoxyborohydride (197 mg, 0.924 mmol). The resulting mixture was stirred at rt for 2 h, quenched with saturated aqueous $NaHCO_3$ (5 ml), and extracted with EtOAc (3×10 ml). The combined organic extracts were dried over $MgSO_4$, filtered, and concentrated. Crystallization of the crude product from ether/methanol (3:1) gave trioxolane OZ216 (167 mg, 71%) as a colorless solid. mp 124–126° C. (ether/methanol 3:1); $^1H$ NMR (500 MHz, $CDCl_3$) δ 1.59–2.19 (m, 18H), 2.37–2.51 (m, 4H), 3.52 (s, 2H), 7.27 (d, J=4.9 Hz, 2H), 8.54 (d, J=5.0 Hz, 2H); $^{13}C$ NMR (125.7 MHz, $CDCl_3$) δ 26.45, 26.87, 34.45, 34.74, 34.83, 36.40, 36.75, 51.24, 61.20, 106.94, 111.70, 123.63, 148.00, 149.81. Anal. Calcd for $C_{21}H_{28}N_2O_3$: C, 70.76; H, 7.92; N, 7.86. Found: C, 70.80; H, 7.77; N, 7.65.

cis-Adamantane-2-spiro-3'-8'-[[[(2'-thiazolyl)amino]carbonyl]methyl]-1',2',4'-trioxaspiro[4.5]decane (OZ217). To a solution of OZ78 (322 mg, 1 mmol) in $CH_2Cl_2$ (10 ml) at 0° C. were added triethylamine (303 mg, 3 mmol) and ethyl chloroformate (217 mg, 2 mmol). The mixture was stirred at 0° C. for 15 min before 2-aminothiazole (100 mg, 1 mmol) was added. The resulting mixture was stirred at rt for 12 h, concentrated, and triturated with water. The crude product was purified by crystallization from ethanol to afford trioxolane OZ217 (0.29 g, 72%) as a colorless solid. mp 160–162° C. (ethanol); $^1H$ NMR (500 MHz, $CDCl_3$) δ 1.19–1.47 (m, 2H), 1.51–2.18 (m, 21H), 2.46 (d, J=6.9 Hz, 2H), 7.02 (d, J=3.6 Hz, 1H), 7.42 (d, J=3.6 Hz, 1H), 12.51 (s, 1H); $^{13}C$ NMR (125.7 MHz, $CDCl_3$) δ 26.46, 26.84, 30.10, 33.23, 33.91, 34.77, 36.37, 36.77, 42.81, 108.35, 111.45, 113.68, 136.10, 159.96, 170.18. Anal. Calcd for $C_{21}H_{28}N_2O_4S$: C, 62.35; H, 6.98; N, 6.93. Found: C, 62.28; H, 6.92; N, 6.87.

cis-Adamantane-2-spiro-3'-8'-[(1'-piperidinylcarbonyl)methyl]-1',2',4'-trioxaspiro[4.5]decane (OZ218). To a solution of OZ78 (322 mg, 1.0 mmol) in $CH_2Cl_2$ (10 ml) at 0° C. were added triethylamine (202 mg, 2 mmol) and ethyl chloroformate (217 mg, 2 mmol). The mixture was stirred at 0° C. for 15 min before piperidine (100 mg, 1.2 mmol) was added. The resulting mixture was stirred at rt for 12 h, concentrated, and triturated with water. The crude product was purified by crystallization from ethanol to afford trioxolane OZ218 (0.24 g, 62%) as a colorless solid. mp 98–100° C. (ethanol); $^1H$ NMR (500 MHz, $CDCl_3$) δ 1.15–1.39 (m, 2H), 1.43–2.17 (m, 27H), 2.21 (d, J=6.8 Hz, 2H), 3.30–3.49 (m, 2H), 3.50–3.65 (m, 2H); $^{13}$C NMR (125.7 MHz, CDCl$_3$) δ 24.57, 25.66, 26.49, 26.60, 26.87, 30.31, 33.43, 34.11, 34.79, 36.39, 36.81, 39.26, 42.69, 46.87, 108.72, 111.29, 170.28. Anal. Calcd for C$_{23}$H$_{35}$NO$_4$: C, 70.92; H, 9.06; N, 3.60. Found: C, 70.83; H, 8.99; N, 3.60.

cis-Adamantane-2-spiro-3'-8'-(1 'H-imidazol-1'-ylethyl)-1',2',4'-trioxaspiro[4.5]decane (OZ219). Step 1. To a solution of OZ89 (924 mg, 3 mmol) and triethylamine (606 mg, 6 mmol) in CH$_2$Cl$_2$ (30 ml) at 0° C. was added methanesulfonyl chloride (516 mg, 4.5 mmol). The mixture was stirred at rt for 1 h, diluted with CH$_2$Cl$_2$ (20 ml), and washed with with water (2×10 ml) and brine (10 ml). The organic layer was dried over MgSO$_4$, filtered, and concentrated to afford the methanesulfonate (1.16 g, 100%) as a colorless solid. Step 2. To a solution of imidazole (100 mg, 1.5 mmol) in DMF (5 ml) was added 60% NaH (75 mg, 1.9 mmol). The mixture was stirred for 15 min before a solution of the above methanesulfonate (0.40 g, 1 mmol) in DMF (2 ml) was added dropwise. The mixture was heated at 50° C. for 3 h, quenched with water (15 ml), and then extracted with ether (3×20 ml). The combined extracts were dried over MgSO$_4$, filtered, and concentrated. Crystallization of the residue from hexanes/ether (19:1) gave trioxolane OZ219 (0.22 g, 61%) as a colorless solid. mp 116–118° C. (hexanes/ether, 19:1); $^1$H NMR (500 MHz, CDCl$_3$) δ 1.11–1.39 (m, 3H), 1.51–2.18 (m, 22H), 3.95 (t, J=8.0 Hz, 2H), 6.89 (s, 1H), 7.06 (s, 1H), 7.46 (s, 1H); $^{13}$C NMR (125.7 MHz, CDCl$_3$) δ 26.46, 26.85, 29.80 33.26, 33.93, 34.77, 36.38, 36.77, 37.35, 44.81, 108.48, 111.40, 118.65, 129.52, 136.95. Anal. Calcd for C$_{21}$H$_{30}$N$_2$O$_3$: C, 70.36; H, 8.44; N, 7.81. Found: C, 70.14; H, 8.27; N, 7.81.

Adamantane-2-spiro-3'-8'-benzyl-1',2',4'-trioxa-8'-azaspiro[4.5]decane (OZ220). To a stirred solution of OZ80 (200 mg, 0.66 mmol) in 1,2-dichloroethane (5 ml) at rt was added triethylamine (0.2 ml, 1.2 mmol) followed by benzaldehyde (70 mg, 0.66 mmol) and sodium triacetoxyborohydride (197 mg, 0.924 mmol). The resulting mixture was stirred at rt for 2 h, quenched with saturated aqueous NaHCO$_3$ (5 ml), and extracted with EtOAc (3×10 ml). The combined organic extracts were dried over MgSO$_4$, filtered, and concentrated. Crystallization of the crude product from ether/methanol (3:1) gave trioxolane OZ220 (177 mg, 75%) as a colorless solid. mp 108–110° C. (ether/methanol 3:1); $^1$H NMR (500 MHz, CDCl$_3$) δ 1.58–2.21 (m, 18H), 2.38–2.52 (m, 2H), 2.53–2.69 (m, 2H), 3.51 (s, 2H), 7.18–7.45 (m, 5H); $^{13}$C NMR (125.7 MHz, CDCl$_3$) δ 26.47, 26.88 34.46, 34.75, 34.83, 36.40, 36.78, 51.09, 62.50, 107.26, 111.56, 126.99, 128.21, 128.96, 138.63. Anal. Calcd for C$_{22}$H$_{29}$NO$_3$: C, 74.33; H, 8.22; N, 3.94. Found: C, 74.52; H, 8.17; N, 4.03.

cis-Adamantane-2-spiro-3'-8'-[(aminocarbonyl)amino]-1',2',4'-trioxaspiro[4.5]decane (OZ221). To a solution of OZ137 (550 mg, 1.74 mmol) in CH$_2$Cl$_2$ (10 ml) at rt were added pyridine (1.38 g, 17.4 mmol), acetic acid (1.01 g, 16.8 mmol), triethylamine (349 mg, 3.45 mmol), and KOCN (278 mg, 3.45 mmol). The resulting mixture was stirred at rt for 48 h, diluted with ether (100 ml), and washed with water (100 ml) and brine (25 ml). The organic layer was separated, dried over MgSO$_4$, and concentrated to give trioxolane OZ221 (166 mg, 30%) as a colorless solid. mp 140–142° C. (ether); $^1$H NMR (500 MHz, CDCl$_3$) δ 1.35–1.52 (m, 2H), 1.62–2.21 (m, 20H), 3.51–3.54 (m, 1H), 4.70 (s, 2H), 4.58–5.03 (m, 1H); $^{13}$C NMR (125.7 MHz, CDCl$_3$) δ 26.43, 26.80, 30.34, 32.61, 34.76, 36.30, 36.73, 47.41, 107.88, 111.66, 158.32. Anal. Calcd for C$_{17}$H$_{26}$N$_2$O$_4$: C, 63.33; H, 8.13; N, 8.69. Found: C, 63.06; H, 8.29; N, 8.49.

cis-Adamantane-2-spiro-3'-8'-[[(tert-butylamino) carbonyl]amino]-1',2',4'-trioxaspiro[4.5]decane (OZ222). To a solution of OZ137 (315 mg, 1 mmol) in CH$_2$Cl$_2$ (10 ml) at 0° C. were added triethylamine (350 mg, 3.48 mmol) and tert-butyl isocyanate (100 mg, 1 mmol). The resulting mixture was stirred at rt for 7 h before removal of solvents. The residue was triturated with water (10 ml) and further purified by crystallization from 95% ethanol to give trioxolane OZ222 (300 mg, 79%) as a colorless solid. mp 130° C. dec (ethanol); $^1$H NMR (500 MHz, CDCl$_3$) δ 1.32 (s, 9H), 1.22–2.21 (m, 22H), 3.64 (s, 1H), 4.28 (s, 1H), 4.37 (s, 1H); $^{13}$C NMR (125.7 MHz, CDCl$_3$) δ 26.44, 26.81, 29.54, 30.64, 32.83, 34.75, 36.30, 36.74, 47.05, 50.29, 108.01, 111.53. Anal. Calcd for C$_{21}$H$_{34}$N$_2$O$_4$: C, 66.64; H, 9.05; N, 7.40. Found: C, 66.65; H, 9.01; N, 7.22.

cis-Adamantane-2-spiro-3'-8'-(5'-methoxycarbonyl-1'H-imidazol-1'-ylmethyl)-1',2',4'-trioxaspiro[4.5]decane (OZ223). To a suspension of 60% NaH (0.24 g, 6 mmol) in DMF (5 ml) under nitrogen at 0° C. was added a solution of methyl 4-imidazolecarboxylate (0.76 g, 6 mmol) in DMF (18 ml). The mixture was stirred for 30 min before a solution of the methanesulfonate of OZ119 (0.96 g, 2.6 mmol) in DMF (6 ml) was added dropwise. The reaction mixture was heated at 55° C. overnight, quenched with water (100 ml), and then extracted with CH$_2$Cl$_2$ (3×50 ml). The combined extracts were washed with water and brine, dried over MgSO$_4$, filtered, and concentrated. The crude product was purified by flash chromatography (silica gel, 40% ethyl acetate in hexanes, then 5% methanol in CH$_2$Cl$_2$) to afford trioxolane OZ223 (0.21 g, 20%, eluted first) as a colorless solid and trioxolane OZ224 (0.36 g, 47%, eluted second) as a colorless solid. For OZ223: mp 148–150° C. (hexanes/CH$_2$Cl$_2$, 4:1); $^1$H NMR (500 MHz, CDCl$_3$) δ 1.17–1.41 (m, 2H), 1.55–2.18 (m, 21H), 3.85 (s, 3H), 4.13 (d, J=7.0 Hz, 2H), 7.52 (s, 1H), 7.75 (s, 1H); $^{13}$C NMR (125.7 MHz, CDCl$_3$) δ 26.43, 26.83, 27.43, 33.45, 34.74, 36.34, 36.74, 36.96, 51.43, 52.08, 108.33, 111.48, 122.20, 138.15, 142.54, 160.70. Anal. Calcd for C$_{22}$H$_{30}$N$_2$O$_5$: C, 65.65; H, 7.51; N, 6.96. Found: C, 65.78; H, 7.41; N, 6.97.

cis-Adamantane-2-spiro-3'-8'-(4'-methoxycarbonyl-1'H-imidazol-1'-ylmethyl)-1',2',4'-trioxaspiro[4.5]decane (OZ224). For the preparation of OZ224, see OZ223. mp 150–152° C. (ethanol); $^1$H NMR (500 MHz, CDCl$_3$) δ 1.15–1.39 (m, 2H), 1.49–2.15 (m, 21H), 3.81 (d, J=7.4 Hz, 2H), 3.89 (s, 3H), 7.44 (s, 1H), 7.57 (s, 1H); $^{13}$C NMR (125.7 MHz, CDCl$_3$) δ 26.42, 26.81, 27.53, 33.39, 34.75, 36.34, 36.72, 37.73, 51.66, 52.95, 108.01, 111.68, 125.29, 133.99, 138.15, 163.25. Anal. Calcd for C$_{22}$H$_{30}$N$_2$O$_5$: C, 65.65; H, 7.51; N, 6.96. Found: C, 65.79; H, 7.34; N, 6.85.

cis-Adamantane-2-spiro-3'-8'-(4'-carboxy-1 'H-imidazol-1'-ylmethyl)-1',2', 4'-trioxaspiro[4.5]decane (OZ225). A mixture of OZ224 (0.16 g, 0.4 mmol), 15% KOH (1.5 ml), and methanol (15 ml) was heated at 55° C. for 4 h. After being cooled to rt, the mixture was concentrated to 3 ml, diluted with water (15 ml), and acidified with acetic acid to pH=5. The solid was collected by filtration to afford trioxolane OZ225 (0.10 g, 64%) as a colorless solid. mp 162° C. dec; $^1$H NMR (500 MHz, DMSO-d$_6$) δ 1.01–1.23 (m, 2H), 1.40–2.05 (m, 21H), 3.87 (d, J=7.3 Hz, 2H), 7.64 (s, 1H), 7.71 (s, 1H); $^{13}$C NMR (125.7 MHz, DMSO-d$_6$) δ 25.96, 26.37, 27.05, 33.03, 34.42, 35.90, 36.25, 36.66, 51.32, 108.54, 110.75, 125.80, 134.59, 138.63, 164.23. Anal. Calcd for C$_{21}$H$_{28}$N$_2$O$_{O5}$H$_2$O: C, 62.05; H, 7.44; N, 6.89. Found: C, 62.36; H, 7.16; N, 6.50.

Adamantane-2-spiro-3'-8'-phenyl-1',2',4'-trioxaspiro[4.5] dec-7'-ene (OZ226). Step 1. Addition of phenyllithium to OZ05. To a stirred solution of OZ05 (1.10 g, 4.0 mmol) in ether (50 ml) at −78° C. was added phenyllithium (2.6 ml, 1.8 M, 4.40 mmol). The reaction mixture was allowed to reach rt during 3 h and quenched with saturated aq. NH$_4$Cl solution (30 ml). After the ether layer was separated, the aqueous layer was extracted with ether (3×40 ml). The combined organic extracts were washed with brine (50 ml), dried over MgSO$_4$, and concentrated. The crude product was purified by flash chromatography (silica gel, 5% EtOAc in hexanes) to afford the trioxolane carbinol intermediate (923 mg, 65%, 1:1 mixture of two diastereomers) as a colorless oil. $^1$H NMR (500 MHz, CDCl$_3$) δ 1.58–2.39 (m, 22H), 7.19–7.28 (m, 1H), 7.29–7.40 (m, 2H), 7.42–7.55 (m, 2H); $^{13}$C NMR (125.7 MHz, CDCl$_3$) δ 26.64, 26.66, 27.06, 27.08, 30.36, 30.46, 34.84, 34.90, 34.91, 35.10, 36.45, 36.51, 36.57, 36.63, 36.92, 36.95, 72.08, 72.38, 108.39, 108.41, 111.52, 111.64, 124.41, 124.57, 126.98, 127.07, 128.32, 128.35, 148.11, 148.30. Step 2. Dehydration of the carbinol intermediate. To a stirred solution of the above carbinol (550 mg, 1.54 mmol) in CH$_2$Cl$_2$ (10 ml) at −10° C. was added triethylamine (1.0 ml, 7.75 mmol) followed by a solution of methanesulfonyl chloride (0.25 ml, 3.10 mmol) in CH$_2$Cl$_2$ (5 ml). The resulting mixture was stirred at 0° C. for 8 h and poured into water (10 ml). After separation of the organic layer, the aqueous layer was extracted with CH$_2$Cl$_2$ (3×15 ml). The combined organic extracts were dried over MgSO$_4$, filtered, and concentrated. The crude product was purified by flash chromatography (silica gel, 1% ether in hexanes) and by subsequent recrystallization from ether/hexanes (1:1) to afford trioxolane OZ226 (435 mg, 83%) as a colorless solid. mp 62–64° C. (ether/hexanes, 1:1); $^1$H NMR (500 MHz, CDCl$_3$) δ 1.42–2.21 (m, 16H), 2.40–2.73 (m, 4H), 5.73–5.99 (m, 1H), 7.02–7.45 (m, 5H); $^{13}$C NMR (125.7 MHz, CDCl$_3$) δ 26.54, 26.71, 27.10, 31.36, 34.81, 34.88, 34.95, 35.12, 35.23, 36.64, 36.70, 36.98, 107.80, 111.81, 120.95, 125.27, 126.96, 128.25, 136.69, 141.52. Anal. Calcd for C$_{22}$H$_{26}$O$_3$: C, 78.07; H, 7.74. Found: C, 78.28; H, 7.81.

cis-Adamantane-2-spiro-3'-8'-[[(4'-methyl-1'-piperazinyl) carbonyl]methyl]-1',2',4'-trioxaspiro[4.5]decane (OZ227). To a solution of OZ78 (322 mg, 1 mmol) in CH$_2$Cl$_2$ (10 ml) at 0° C. were added triethylamine (303 mg, 3 mmol) and ethyl chloroformate (217 mg, 2 mmol). The mixture was stirred at 0° C. for 15 min before 1-methylpiperazine (110 mg, 1.1 mmol) was added. The resulting mixture was stirred at rt for 12 h, diluted with CH$_2$Cl$_2$ (10 ml), washed with water (10 ml), dried over MgSO$_4$, and concentrated. The crude product was purified by crystallization from ethanol to afford trioxolane OZ227 (0.19 g, 47%) as a colorless solid. mp 96–98° C. (ethanol); $^1$H NMR (500 MHz, CDCl$_3$) δ 1.15–1.37 (m, 2H), 1.59–2.18 (m, 21H), 2.21 (d, J=6.9 Hz, 2H), 2.29 (s, 3H), 2.30–2.58 (m, 4H), 3.40–3.57 (m, 2H), 3.58–3.78 (m, 2H); $^{13}$C NMR (125.7 MHz, CDCl$_3$) δ 26.64, 27.02, 30.34, 33.41, 34.13, 34.87, 36.56, 36.93, 39.18, 41.62, 45.75, 45.94, 54.89, 55.31, 108.66, 111.32, 170.46. Anal. Calcd for C$_{23}$H$_{36}$N$_2$O$_4$: C, 68.29; H, 8.97; N, 6.92. Found: C, 68.07; H, 8.69; N, 6.81.

cis-Adamantane-2-spiro-3'-8'-(azidoethyl)-1',2',4'-trioxaspiro[4.5]decane (OZ228). For the preparation of the mesylate of OZ89, see OZ219. To a solution of NaN$_3$ (375 mg, 5 mmol) in DMF (5 ml) was added the mesylate (760 mg, 2 mmol) in DMF (2 ml). The mixture was stirred at 50–55° C. for 16 h before being quenched with water (15 ml). After separation of the organic layer, the aqueous layer was extracted with ether (3×20 ml). The combined organic layers were dried over MgSO$_4$, filtered, and concentrated. The residue was purified by crystallization from ethanol to give trioxolane OZ228 (618 mg, 93%) as a colorless solid. mp 58–60° C. (ethanol); $^1$H NMR (500 MHz, CDCl$_3$) δ 1.11–1.37 (m, 2H), 1.38–1.48 (m, 1H), 1.49–1.61 (m, 2H), 1.62–2.18 (m, 20H), 3.29 (t, J=7.0 Hz, 2H); $^{13}$C NMR (125.7 MHz, CDCl$_3$) δ 26.69, 27.10, 29.91, 33.63, 34.13, 34.92, 34.94, 35.02, 36.62, 36.99, 49.44, 108.69, 111.37. Anal. Calcd for C$_{18}$H$_{27}$N$_3$O$_3$: C, 64.84; H, 8.16; N, 12.60. Found: C, 64.68; H, 7.94; N, 12.47.

cis-Adamantane-2-spiro-3'-8'-(aminoethyl)-1',2',4'-trioxaspiro[4.5]decane hydrochloride (OZ229). To a solution of OZ228 (333 mg, 1 mmol) in THF (7 ml) were added triphenylphosphine (262 mg, 1 mol) and water (1 ml). The mixture was stirred at rt for 16 h and diluted with 2 M aq. HCl (5 ml). The precipitate was filtered, and washed with CH$_2$Cl$_2$ (10 ml), and dried to give trioxolane OZ229 (194 mg, 56%) as a colorless solid. mp 150–152° C.; $^1$H NMR (500 MHz, DMSO-d$_6$) δ 1.00–1.19 (m, 2H), 1.25–2.08 (m, 23H), 2.67–2.89 (m, 2H), 8.04 (s, 3H); $^{13}$C NMR (125.7 MHz, DMSO-d$_6$) δ 25.83, 26.23, 29.33, 32.40, 33.02, 33.37, 34.24, 34.26, 35.81, 36.11, 36.81, 108.36, 110.45. Anal. Calcd for C$_{18}$H$_{30}$ClNO$_3$: C, 62.87; H, 8.79; N, 4.07. Found: C, 63.00; H, 8.58; N, 4.34.

N,N'-Bis[cis-[adamantane-2-spiro-3'-1',2',4'-trioxaspiro [4.5]dec-8'-yl]methyl]-1,2-benzenedicarboxamide (OZ230). A solution of OZ146 (10.40 g, 24.60 mmol) and hydrazine monohydrate (5.00 g, 50 mmol) in chloroform (180 ml) and methanol (20 ml) was heated under nitrogen at 55° C. for 24 h. The reaction mixture was cooled to rt and filtered to remove solid by-products. The filtrate was washed with water (100 ml) and brine (100 ml), dried over MgSO$_4$, filtered, and concentrated. The crude product was purified by flash chromatography (silica gel, CHCl$_3$/MeOH/Et$_3$N, 90:10:1) to afford trioxolane OZ230 (1.60 g, 20%, eluted first) and cis-Adamantane-2-spiro-3'-8'-(aminomethyl)-1',2', 4'-trioxaspiro[4.5]decane (5.10 g, 71%, eluted second). OZ230 was obtained as a colorless solid. mp 164–166° C. (CHCl$_3$/ethanol 9:1); $^1$H NMR (500 MHz, CDCl$_3$) δ 1.19–1.39 (m, 4H), 1.59–2.11 (m, 42H), 3.19–3.35 (m, 4H), 6.75–6.88 (m, 2H), 7.41–7.52 (m, 2H), 7.53–7.65 (m, 2H); $^{13}$C NMR (125.7 MHz, CDCl$_3$) δ 26.48, 26.88, 27.81, 33.77, 34.79, 36.29, 36.39, 36.80, 45.39, 108.54, 111.38, 128.51, 130.27, 134.51, 169.27. Anal. Calcd for C$_{42}$H$_{56}$N$_2$O$_8$: C, 70.37; H, 7.87; N, 3.91. Found: C, 70.50; H, 7.81; N, 3.99.

cis-Adamantane-2-spiro-3'-8'-(5'-carboxy-1'H-imidazol-1'-ylmethyl)-1',2',4'-30 trioxaspiro[4.5]decane (OZ231). A mixture of OZ223 (0.10 g, 0.25 mmol), 15% KOH (1.0 ml), methanol (10 ml), and THF (2 ml) was heated at 55° C. for 4 h. After being cooled to room temperature, the mixture was concentrated to 3 ml, diluted with water (15 ml), and acidified with acetic acid to pH=5. The solid was collected by filtration to afford trioxolane OZ231 (77 mg, 79%) as a colorless solid. mp 164–166° C.; $^1$H NMR (500 MHz, DMSO-d$_6$) δ 1.03–1.37 (m, 2H), 1.38–2.18 (m, 21H), 4.16 (d, J=6.7 Hz, 2H), 7.58 (s, 1H), 7.89 (s, 1H); $^{13}$C NMR (125.7 MHz, DMSO-d$_6$) δ 25.86, 26.26, 26.88, 32.92, 34.29, 35.81, 36.14, 36.44, 50.38, 108.39, 110.62, 122.87 (br s), 137.04 (br s), 143.25 (br s), 161.10. Anal. Calcd for C$_{21}$H$_{28}$N$_2$O$_5$.0.5H$_2$O: C, 63.46; H, 7.35; N, 7.05. Found: C, 63.41; H, 7.11; N, 6.71.

cis-Adamantane-2-spiro-3'-8'-[(dimethylamino)methyl]-1',2',4'-trioxaspiro[4.5]decane mesylate (OZ232). A solution of cis-Adamantane-2-spiro-3'-8'-(aminomethyl)-1',2',4'-trioxaspiro[4.5]decane (293 mg, 1 mmol), formaldehyde (162 mg, 37% aq. solution, 2 mmol), sodium triacetoxyborohydride (612 mg, 2.8 mmol) in 1,2-dichloroethane (15 ml) was stirred at rt for 4 h before being quenched with saturated aq. NaHCO$_3$ (10 ml). After separation of the organic layer, the aqueous layer was extracted with CH$_2$Cl$_2$ (2×20 ml). The combined organic layers were washed with water and brine, dried over MgSO$_4$, and concentrated. The resulting crude product was dissolved in CH$_2$Cl$_2$/ether (1:5, 10 ml) and treated with a solution of methanesulfonic acid (96 mg, 1 mmol) in ether (2 ml). The precipitate was collected by filtration to afford trioxolane OZ232 (230 mg, 55%) as a colorless solid. mp 130° C. dec; $^1$H NMR (500 MHz, DMSO-d$_6$) δ 1.25–1.45 (m, 2H), 1.59–2.16 (m, 21H), 2.82 (s, 3H), 2.87 (app t, J=6.2 Hz, 2H), 2.91 (app d, J=4.6 Hz, 6H), 10.61 (s, 1H); $^{13}$C NMR (125.7 MHz, DMSO-d$_6$) δ 26.57, 26.96, 28.20, 32.46, 33.37, 34.84, 36.50, 36.85, 39.25, 44.35, 64.04, 107.55, 111.77. Anal. Calcd for C$_{20}$H$_{35}$NO$_6$S·0.6H$_2$O: C, 55.92; H, 8.53; N, 3.26. Found: C, 55.71; H, 8.08; N, 3.12.

cis-Adamantane-2-spiro-3'-8'-(5'-methoxycarbonyl-1'H-1',2',4'-triazol-1'-ylmethyl)-1',2',4'-trioxaspiro[4.5]decane (OZ233). To a suspension of 60% NaH (0.20 g, 5 mmol) in DMF (5 ml) under nitrogen at 0° C. was added a solution of methyl 1H-1,2,4-triazole-3-carboxylate (0.64 g, 5 mmol) in DMF (5 ml). The mixture was stirred for 1 h before a solution of the methanesulfonate of OZ119 (0.93 g, 2.5 mmol) in DMF (5 ml) was added dropwise. The reaction mixture was heated at 55° C. overnight, quenched with water (60 ml), and then extracted with CH$_2$Cl$_2$ (3×40 ml). The combined extracts were washed with water and brine, dried over MgSO$_4$, filtered, and concentrated. The crude product was purified by flash chromatography (silica gel, 33% to 66% ethyl acetate in hexanes) to afford trioxolane OZ233 (0.27 g, 27%, eluted first) as a colorless solid and trioxolane OZ234 (0.21 g, 21%, eluted second) as a colorless solid. For OZ233: mp 120–122° C.; $^1$H NMR (500 MHz, CDCl$_3$) δ 1.29–1.49 (m, 2H), 1.52–2.16 (m, 21H), 3.99 (s, 3H), 4.50 (d, J=7.1 Hz, 2H), 7.96 (s, 1H); $^{13}$C NMR (125.7 MHz, CDCl$_3$) δ 26.64, 27.04, 27.46, 33.59, 34.89, 36.57, 36.94, 37.15, 52.90, 55.75, 108.32, 111.53, 150.78, 158.49, 181.90. Anal. Calcd for C$_{21}$H$_{29}$N$_3$O$_5$: C, 62.51; H, 7.24; N, 10.41. Found: C, 62.40; H, 7.11; N, 10.51.

cis-Adamantane-2-spiro-3'-8'-(3'-methoxycarbonyl-1'H-1',2',4'-triazol-1'-ylmethyl)-1',2',4'-trioxaspiro[4.5]decane (OZ234). For the preparation of OZ234, see OZ233. mp 144–146° C.; $^1$H NMR (500 MHz, CDCl$_3$) δ 1.23–1.41 (m, 2H), 1.52–2.16 (m, 21H), 3.99 (s, 3H), 4.07 (d, J=7.2 Hz, 2H), 8.08 (s, 1H); $^{13}$C NMR (125.7 MHz, CDCl$_3$) δ 26.61, 27.00, 27.55, 33.45, 34.87, 36.50, 36.55, 36.89, 52.55, 55.73, 108.07, 111.70, 144.75, 155.30, 160.13. Anal. Calcd for C$_{21}$H$_{29}$N$_3$O$_5$: C, 62.51; H, 7.24; N, 10.41. Found: C, 62.62; H, 7.17; N, 10.52.

cis-Adamantane-2-spiro-3'-8'-(1'H-1',2',4'-triazol-1'-ylmethyl)-1',2',4'-trioxaspiro[4.5]decane mesylate (OZ235). To a solution of OZ177 (1.20 g, 3.5 mmol) in ether (10 ml) was added a solution of methanesulfonic acid (0.40 g, 4.2 mmol) in ether (10 ml). The resulting mixture was placed at –20° C. overnight. The solid was collected by filtration and dried in vaccuo to afford trioxolane OZ235 (1.48 g, 96%) as a colorless solid. mp 139–142° C.; $^1$H NMR (500 MHz, CDCl$_3$) δ 1.26–1.44 (m, 2H), 1.58–2.19)m, 21H), 2.86 (s, 3H), 4.33 (d, J=7.1 Hz, 2H), 8.54 (s, 1H), 10.04 (s, 1H), 12.85 (br s, 1H); $^{13}$C NMR (125.7 MHz, CDCl$_3$) δ 26.58, 26.97, 27.29, 33.34, 34.85, 36.21, 36.51, 36.86, 39.65, 56.71, 107.92, 111.69, 142.30, 144.05. Anal. Calcd for C$_{20}$H$_{31}$N$_3$O$_6$S: C, 54.40; H, 7.08; N, 9.52. Found: C, 54.28; H, 6.92; N, 9.33.

cis-Adamantane-2-spiro-3'-8'-[[bis(2'-amino-2'-oxoethyl)amino]methyl]-1',2',4'-trioxaspiro[4.5]decane (OZ236). A mixture of cis-adamantane-2-spiro-3'-8'-aminomethyl-1',2',4'-trioxaspiro[4.5]decane (293 mg, 1 mmol), 2-bromoacetamide (138 mg, 1 mmol), and potassium carbonate (276 mg, 2 mmol) in acetonitrile (18 ml) was heated at 50° C. for 16 h before being diluted with water (25 ml). The resulting mixture was extracted with chloroform (3×18 ml). The combined extracts were washed with water and brine, dried over MgSO$_4$, and concentrated. The crude product was purified by falsh chromatography (silica gel, 18% methanol in CH$_2$Cl$_2$) and by recrystallization from CHCl$_3$ to afford trioxolane OZ236 (180 mg, 44%) as a colorless solid. mp 157–159° C. (CHCl$_3$); $^1$-H NMR (500 MHz, DMSO-d$_6$) δ 0.89–1.16 (m, 2H), 1.38–2.09 (m, 21H), 2.25 (d, J=7.1 Hz, 2H), 2.97 (s, 4H), 7.13 (s, 2H), 7.50 (s, 2H); $^{13}$C NMR (125.7 MHz, DMSO-d$_6$) δ 25.96, 26.36, 28.13, 33.51, 33.54, 34.40, 34.42, 35.92, 36.25, 59.21, 61.26, 108.90, 110.57, 172.79. Anal. Calcd for C$_{21}$H$_{33}$N$_3$O$_5$: C, 61.90; H, 8.16; N, 10.31. Found: C, 62.04; H, 7.91; N, 10.12.

cis-Adamantane-2-spiro-3'-8'-[[(aminoiminomethyl)amino]methyl]-1',2',4'-trioxaspiro[4.5]decane hydrochloride (OZ237). A mixture of cis-adamantane-2-spiro-3'-8'-aminomethyl-1',2',4'-trioxaspiro[4.5]decane (293 mg, 1 mmol), 1H-pyrazole-1-carboxamidine hydrochloride (147 mg, 1 mmol), N,N-diisopropylethylamine (129 mg, 1 mmol) in DMF (5 ml) was stirred at rt for 16 h before being diluted with ether (50 ml). The solid was collected by filtration and recrystallized from 30% aq. ethanol to afford trioxolane OZ237 (210 mg, 56%) as a colorless solid. mp 146–149° C. (30% aq. ethanol); $^1$-H NMR (500 MHz, DMSO-d$_6$) δ 0.99–1.21 (m, 2H), 1.39–2.05 (m, 21H), 2.98 (app t, J=6.0 Hz, 2H), 6.50–7.89 (m, 5H); $^{13}$C NMR (125.7 MHz, DMSO-d$_6$) δ 25.86, 26.27, 27.00, 33.05, 34.31, 35.28, 35.83, 36.14, 45.59, 108.41, 110.61, 157.17. Anal. Calcd for C$_{18}$H$_{30}$ClN$_3$O$_3$: C, 58.13; H, 8.13; N, 11.30. Found: C, 58.31; H, 8.27; N, 10.96.

cis-Adamantane-2-spiro-3'-8'-(2'-amino-2'-oxoethyl)-1',2',4'-trioxaspiro[4.5]decane (OZ243). To a solution of OZ78 (322 mg, 1 mmol) in CH$_2$Cl$_2$ (10 ml) at 0° C. was added TEA (202 mg, 2 mmol) followed by ethyl chloroformate (217 mg, 2 mmol). After 15 min, ammonia (7 N in methanol, 3 ml) was added, and the stirring was continued for 12 h. The precipitate was filtered and dried to afford trioxolane OZ243 (210 mg, 65%) as a colorless solid. mp 140–142° C.; $^1$H NMR (500 MHz, CDCl$_3$) δ 1.09–1.43 (m, 3H), 1.45–2.15 (m, 20H), 2.11 (d, J=7.1 Hz, 2H), 5.48 (s, 1H), 5.66 (s, 1H); $^{13}$C NMR (125.7 MHz, CDCl$_3$) δ 26.47, 26.85, 29.97, 33.32, 33.95, 34.77, 36.38, 36.78, 42.55, 108.50, 111.35, 174.39. Anal. Calcd for C$_{18}$H$_{27}$NO$_4$: C, 67.26; H, 8.47; N, 4.36. Found: C, 67.40; H, 8.47; N, 4.39.

cis-Adamantane-2-spiro-3'-8'-[[(4'-phenyl-1'-piperazinyl)carbonyl]methyl]-1',2',4'-trioxaspiro[4.5]decane (OZ244). To a solution of OZ78 (322 mg, 1 mmol) in CH$_2$Cl$_2$ (10 ml) at 0° C. was added TEA (202 mg, 2 mmol) followed by ethyl chloroformate (217 mg, 2 mmol). After 15 min, 1-phenylpiperazine (162 mg, 1 mmol) was added, and the stirring was continued for 12 h. The reaction mixture was concentrated, diluted with water, and filtered. The crude product was purified by recrystallization from ethanol to give trioxolane OZ244 (280 mg, 60%) as a colorless solid. mp 140–142° C. (ethanol); $^1$H NMR (500 MHz, CDCl$_3$) δ 1.18–1.38 (m, 2H), 1.55–2.18 (m, 21H), 2.26 (d, J=6.9 Hz, 2H), 3.02–3.29 (m, 4H), 3.55–3.70 (m, 2H), 3.71–3.89 (m, 2H), 6.81–7.02 (m, 3H), 7.20–7.38 (m, 2H); $^{13}$C NMR (125.7 MHz, CDCl$_3$) δ 26.48, 26.86, 30.30, 33.34, 34.06, 34.78, 36.39, 36.79, 39.18, 41.51, 45.69, 49.47, 49.77, 108.59, 111.33, 116.58, 120.51, 129.22, 150.91, 170.50. Anal. Calcd for C$_{28}$H$_{38}$N$_2$O$_4$: C, 72.07; H, 8.21; N, 6.00. Found: C, 72.22; H, 8.16; N, 5.99.

Adamantane-2-spiro-3'-8'-hydroxy-8'-(2'-thiazolyl)-1',2',4'-trioxaspiro[4.5]decane (OZ247). To a stirred solution of 2-bromothiazole (246 mg, 1.5 mmol) in dry THF (4 ml) under $N_2$ at −78° C. was added n-BuLi (1.6 M in hexanes, 1 ml, 1.5 mmol). The resulting bright yellow solution was stirred for 1 h at the same temperature, and then a solution of OZ05 (415 mg, 1.5 mmol) in dry THF (10 ml) was added. The mixture was allowed to reach 0° C., poured into ice-water mixture (15 ml), and extracted with ether (3×25 ml). The combined organic extracts were washed with brine (25 ml), dried over $MgSO_4$, and concentrated. The crude product was purified by flash chromatography (silica gel, 10% EtOAc in hexanes) followed by recrystallization from hexanes/ether (9:1) to afford trioxolane OZ247 (202 mg, 37%, 1:1 mixture of 2 diastereomers) as a colorless solid. mp 64–66° C. (hexanes/ether 9:1); $^1$H NMR (500 MHz, $CDCl_3$) δ 1.60–2.42 (m, 22H), 3.18 (s, 0.5H), 3.40 (s, 0.5H), 7.28 (d, J=3.0 Hz, 0.5H), 7.30 (d, J=3.0 Hz, 0.5H), 7.69 (d, J=3.3 Hz, 0.5H), 7.72 (d, J=3.0 Hz, 0.5H); $^{13}$C NMR (125.7 MHz, $CDCl_3$) δ 26.45, 26.46, 26.85, 29.98, 30.09, 34.73, 34.77, 34.79, 34.86, 36.34, 36.40, 36.48, 36.75, 36.77, 72.44, 73.00, 107.91, 107.97, 111.61, 111.84, 119.02, 141.95, 142.16, 177.99, 178.23. Anal. Calcd for $C_{19}H_{25}NO_4S$: C, 62.78; H, 6.93; N, 3.85. Found: C, 62.94; H, 7.01; N, 3.89.

cis-Adamantane-2-spiro-3'-8'-(1'H-imidazol-2'-yl)-1',2',4'-trioxaspiro[4.5]decane (OZ251). Step 1. To a solution of oxalyl chloride (0.99 g, 7.8 mmol) in $CH_2Cl_2$ (50 ml) at −78° C. was added methyl sulfoxide (1.41 g, 18 mmol) dropwise. The mixture was stirred at −78° C. for 30 min before OZ119 (1.76 g, 6 mmol) in $CH_2Cl_2$ (5 ml) was added. After the resulting mixture was stirred for 45 min, triethylamine (3.03 g, 30 mmol) was added. The mixture was warmed to rt for 2 h and quenched with water (50 ml). The organic layer was washed with water (2×30 ml) and brine, dried over $MgSO_4$, and concentrated. The crude product (1.80 g) was crystallized from 50% ethanol to afford the desired aldehyde, cis-Adamantane-2-spiro-3'-8'-formyl-1',2',4'-trioxaspiro[4.5]decane, (0.82 g, 47%) as a colorless solid. mp 74–76° C. (50% ethanol); $^1$H NMR (500 MHz, $CDCl_3$) δ 1.64–2.02 (m, 22H), 2.20–2.30 (m, 1H), 9.63 (d, J=1.1 Hz, 1H). Step 2. To a solution of the above aldehyde (292 mg, 1 mmol) and 40% glyoxal (145 mg, 1 mmol) in methanol (12 ml) at 0° C. was added ammonia (0.45 ml, 7 N in methanol). The resulting mixture was stirred at rt overnight and concentrated. The crude product was crystallized from hexanes/$CH_2Cl_2$ (3:2) to afford trioxolane OZ251 (240 mg, 73%) as a colorless solid. mp 138–140° C. (hexanes/$CH_2Cl_2$, 3:2); $^1$H NMR (500 MHz, $CDCl_3$) δ 1.58–2.23 (m, 22H), 2.75–2.98 (m, 1H), 6.96 (s, 2H); $^{13}$C NMR (125.7 MHz, $CDCl_3$) δ 26.54, 26.94, 29.11, 33.92, 34.82, 34.86, 36.23, 36.47, 36.84, 108.00, 111.54, 121.10 (br s), 151.00. Anal. Calcd for $C_{19}H_{26}N_2O_3$: C, 69.06; H, 7.93; N, 8.48. Found: C, 69.04; H, 7.93; N, 8.60.

cis-Adamantane-2-spiro-3'-8'-[(2'-thiazolylamino)methyl]-1',2',4'-trioxaspiro[4.5]decane (OZ252). A mixture of cis-Adamantane-2-spiro-3'-8'-formyl-1',2',4'-trioxaspiro[4.5]decane (292 mg, 1.0 mmol), 2-aminothiazole (150 mg, 1.5 mmol), and acetic acid (240 mg, 4.0 mmol) in $CH_2Cl_2$ (10 ml) and $ClCH_2CH_2Cl$ (10 ml) was stirred at rt for 2.5 h before sodium triacetoxyborohydride (422 mg, 2.0 mmol) was added. The resulting mixture was stirred at rt overnight and then quenched with saturated aq. $NaHCO_3$ (50 ml). The organic layer was separated and washed with water and brine, dried over $MgSO_4$, and concentrated. The crude prude was purified by flash chromatography (silica gel, 2% $CH_3OH$ in $CH_2Cl_2$). The enriched product was dissolved in ether/$CH_2Cl_2$ (4:1, 20 ml), treated with methanesulfonic acid (40 mg, 0.4 mmol), and placed at −20° C. overnight. After the solvent was decanted, the residue was washed with ether and dried in vacuo to afford trioxolane OZ252 (110 mg, 23%) as a colorless solid. mp 136–138° C.; $^1$H NMR (500 MHz, $CDCl_3$) δ 1.20–1.41 (m, 2H), 1.50–2.21 (m, 21H), 2.88 (s, 3H), 3.11 (app t, J=6.1 Hz, 2H), 6.54 (d, J=4.1 Hz, 1H), 7.05 (d, J=4.1 Hz, 1H), 10.51 (s, 1H), 14.17 (s, 1H); $^{13}$C NMR (125.7 MHz, $CDCl_3$) δ 26.46, 26.84, 27.88, 33.44, 34.77, 35.66, 36.38, 36.76, 39.45, 54.26, 104.97, 108.18, 111.57, 127.14, 170.79. Anal. Calcd for $C_{21}H_{32}N_2O_6S_2$: C, 53.37; H, 6.82; N, 5.93. Found: C, 53.16; H, 6.76; N, 5.91.

cis-Adamantane-2-spiro-3'-8'-[(cyclopropylamino)methyl]-1',2',4'-trioxaspiro[4.5]decane mesylate (OZ253). To a solution cis-adamantane-2-spiro-3'-8'-formyl-1',2',4'-trioxaspiro[4.5]decane (292 mg, 1.0 mmol), cyclopropylamine (57 mg, 1.0 mmol), and acetic acid (90 mg, 1.5 mmol) in 1,2-dichloroethane (10 ml) was added sodium triacetoxyborohydride (295 mg, 1.4 mmol). The mixture was stirred for 2 h and then quenched with saturated aq. $NaHCO_3$ (20 ml). The organic layer was separated and the aqueous layer was extracted with $CH_2Cl_2$ (2×20 ml). The combined organic extracts were washed with water and brine, dried over $MgSO_4$, and concentrated. The crude product was purified by flash chromatography (silica gel, 20% ether in hexanes, 400 ml; then 10% methanol in $CH_2Cl_2$, 300 ml) to give two fractions. The first fraction (130 mg) was crystallized from $CH_3OH/CH_2Cl_2$ (6:1) to afford trioxolane OZ254 (96 mg, 31%) as a colorless solid. The second fraction (160 mg) was dissolved in ether (3 ml) and treated with a solution of methanesulfonic acid (46 mg) in ether (3 ml). The precipitate was collected by filtration and dried in vacuo to afford trioxolane OZ253 (160 mg, 37%) as a colorless solid. For OZ253: mp 144–147° C. (ether); $^1$H NMR (500 MHz, $CDCl_3$) δ 0.77–0.95 (m, 2H), 1.10–1.22 (m, 2H), 1.23–1.41 (m, 2H), 1.50–2.19 (m, 21H), 2.50–2.69 (m, 1H), 2.73 (s, 3H), 2.82–3.02 (m, 2H), 8.63 (s, 2H); $^{13}$C NMR (125.7 MHz, $CDCl_3$) δ 3.70, 26.46, 27.89, 31.23, 33.10, 33.43, 34.77, 36.38, 36.77, 39.51, 54.07, 107.97, 111.50. Anal. Calcd for $C_{21}H_{35}NO_6S$: C, 58.72; H, 8.21; N, 3.26. Found: C, 58.65; H, 8.15; N, 3.35.

N,N-Bis(cis-adamantane-2-spiro-3'-1',2',4'-trioxaspiro[4.5]decane-8'-methyl)cyclopropylamine (OZ254). For the preparation of trioxolane OZ254, see OZ253. mp 138–140° C. ($CH_3OH/CH_2Cl_2$ 6:1); $^1$H NMR (500 MHz, $CDCl_3$) δ 0.22–0.35 (m, 2H), 0.36–0.48 (m, 2H), 0.97–1.15 (m, 4H), 1.45–2.15 (m, 43H), 2.28 (d, J=7.1 Hz, 4h); $^{13}$C NMR (125.7 MHz, $CDCl_3$) δ 6.80, 26.52, 26.92, 28.68, 34.09, 34.43, 34.80, 34.82, 36.42, 36.85, 38.74, 63.12, 109.31, 111.15. Anal. Calcd for $C_{37}H_{55}NO_6$: C, 72.87; H, 9.09; N, 2.30. Found: C, 72.83; H, 8.95; N, 2.33.

cis-Adamantane-2-spiro-3'-8'-[[(4'-pyridinylcarbonyl)amino]methyl]-1',2',4'-trioxaspiro[4.5]decane (OZ255). To a solution of OZ209 (389 mg, 1.0 mmol) and triethylamine (0.6 g, 6 mmol) in $CH_2Cl_2$ (10 ml) at 0° C. was added a solution of isonicotinoyl chloride hydrochloride (267 mg, 1.5 mmol) in $CH_2Cl_2$ (10 ml). The resulting mixture was stirred at rt overnight before being quenched with water (20 ml). After separation of the organic phase, the aqueous layer was extracted with $CH_2Cl_2$ (20 ml). The combined organic extracts were washed with water and brine, dried over $MgSO_4$, and concentrated. The crude product was crystallized from 40% aq. ethanol to afford trioxolane OZ255 (410 mg, 103%) as a colorless solid. mp 145–146° C. (40% aq. ethanol); $^1$H NMR (500 MHz, $CDCl_3$) δ 1.19–1.41 (m, 2H), 1.55–2.19 (m, 21H), 3.34 (app t, J=6.3 Hz, 2H), 6.36 (br s, 1H), 7.61 (d, J=4.4 Hz, 2H), 8.75 (br s, 2H); $^{13}$C NMR (125.7 MHz, $CDCl_3$) δ 26.46, 26.85, 27.82, 33.71, 34.78, 36.21, 36.38, 36.76, 45.41, 108.46, 111.48, 120.87, 141.70, 150.57, 165.63. Anal. Calcd for $C_{23}H_{30}N_2O_4$: C, 69.32; H, 7.59; N, 7.03. Found: C, 69.18; H, 7.43; N, 7.04.

cis-Adamantane-2-spiro-3'-8'-[[(2'-amino-2'-oxoethyl)amino]methyl]-1',2',4'-trioxaspiro[4.5]decane (OZ256). A mixture of OZ209 (389 mg, 1 mmol) and triethylamine (101 mg, 1 mmol) in acetonitrile (40 ml) was stirred for 15 min before 2-bromoacetamide (138 mg, 1 mmol) and potassium carbonate (276 mg, 2 mmol) were added. The mixture was heated at 50° C. for 16 h, then diluted with water (25 ml), and extracted with $CH_2Cl_2$ (3×20 ml). The combined organic extracts were washed with water and brine, dried over $MgSO_4$, and concentrated. The crude product was purified by flash chromatography (silica gel, 6% $CH_3OH$ in $CH_2Cl_2$) to afford trioxolane OZ256 (90 mg, 26%) as a colorless solid. mp 136–138° C.; $^1H$ NMR (500 MHz, $CDCl_3$) δ 1.05–1.31 (m, 2H), 1.37–2.19 (m, 22H), 2.49 (d, J=6.4 Hz, 2H), 3.25 (s, 2H), 5.95 (s, 1H); $^{13}C$ NMR (125.7 MHz, $CDCl_3$) δ 26.43, 26.83, 28.07, 33.86, 34.74, 34.76, 36.35, 36.52, 36.75, 52.52, 55.72, 108.73, 111.31, 174.84. Anal. Calcd for $C_{19}H_{30}N_2O_4 \cdot 0.25H_2O$: C, 63.80; H, 8.68; N, 7.83. Found: C, 63.68; H, 8.25; N, 7.82.

cis-Adamantane-2-spiro-3'-8'-[[(methanesulfonyl)amino]methyl]-1',2',4'-trioxaspiro[4.5]decane (OZ257). To a solution of OZ209 (389 mg, 1 mmol) and triethylamine (404 mg, 4 mmol) in $CH_2Cl_2$ (10 ml) at 0° C. was added a solution of methanesulfonyl chloride (171 mg, 1.5 mmol) in $CH_2Cl_2$ (1.5 ml). The mixture was stirred at rt for 16 h, washed with water and brine, dried over $MgSO_4$, and concentrated. The crude product was purified by flash chromatography (silica gel, 5% $CH_3OH$ in $CH_2Cl_2$) to afford trioxolane OZ257 (290 mg, 78%) as a colorless solid. mp 124–126° C.; $^1H$ NMR (500 MHz, $CDCl_3$) δ 1.15–1.33 (m, 2H), 1.45–2.17 (m, 21H), 2.95 (s, 3H), 2.99 (app t, J=6.7 Hz, 2H), 4.31 (br s, 1H); $^{13}C$ NMR (125.7 MHz, $CDCl_3$) δ 26.47, 26.86, 27.55, 33.60, 34.78, 34.79, 36.38, 36.77, 40.36, 48.54, 108.40, 111.50. Anal. Calcd for $C_{18}H_{29}NO_5S$: C, 58.20; H, 7.87; N, 3.77. Found: C, 58.32; H, 7.74; N, 3.83.

Adamantane-2-spiro-3'-8'-[[2'-[(7'-chloro-4'-quinolinyl)amino]ethyl]amino]-1',2',4'-trioxaspiro[4.5]decane (OZ258). To a stirred solution of OZ05 (75 mg, 0.27 mmol) in $CH_2Cl_2$ (5 ml) at rt under $N_2$ was added $N^2$-(7-chloro-4-quinolinyl)-1,2-diaminoethane (176 mg, 0.34 mmol) followed by sodium triacetoxyborohydride (72 mg, 0.34 mmol). The resulting mixture was stirred at rt for 24 h before being poured into water (10 ml). The organic layer was separated, dried, and concentrated. Recrystallization of the crude product from ethanol afforded trioxolane OZ258 (86 mg, 66%) as a colorless solid. mp 146–148° C. (ethanol); $^1H$ NMR (500 MHz, $CDCl_3$) δ 1.42–2.21 (m, 23H), 2.55–2.77 (m, 1H), 3.05 (t, J=5.6 Hz, 2H), 3.34 (br s, 2H), 5.90 (br s, 1H), 6.39 (d, J=5.2 Hz, 1H), 7.37 (dd, J=8.8, 1.9 Hz, 1H), 7.70 (d, J=8.8 Hz, 1H), 7.96 (d, J=1.9 Hz, 1H), 8.53 (d, J=5.2 Hz, 1H); $^{13}C$ NMR (125.7 MHz, $CDCl_3$) δ 26.65, 27.08, 30.17, 32.23, 34.86, 35.06, 36.60, 36.94, 42.89, 45.17, 54.43, 99.36, 108.36, 111.80, 121.09, 125.40, 125.46, 128.93, 134.98, 149.20, 150.00, 152.06. Anal. Calcd for $C_{27}H_{34}ClN_3O_3$: C, 67.00; H, 7.08; N, 8.68. Found: C, 67.18; H, 7.12; N, 8.49.

Adamantane-2-spiro-3'-8'-(3'-pyridinylamino)-1',2',4'-trioxaspiro[4.5]decane (OZ259). To afford trioxolane OZ259 (? mg, 83%, 1:1 mixture of 2 diastereomers) as a colorless solid. mp 132–134° C. (?); $^1H$ NMR (500 MHz, $CDCl_3$) δ 1.42–2.23 (m, 22H), 3.25–3.49 (m, 1H), 3.59–3.83 (m, 1H), 6.82–6.90 (m, 1H), 7.02–7.12 (m, 1H), 7.90–7.96 (m, 1H), 7.98–8.04 (m, 1H); $^{13}C$ NMR (125.7 MHz, $CDCl_3$) δ 26.40, 26.81, 26.83, 29.40, 29.86, 32.16, 32.60, 34.69, 34.72, 34.76, 34.87, 36.29, 36.32, 36.71, 49.54, 49.87, 107.86, 11 1.60, 111.81, 118.78, 118.85, 123.67, 136.22, 136.45, 138.57, 138.61, 143.06. Anal. Calcd for $C_{21}H_{28}N_2O_3$: C, 70.76; H, 7.92; N, 7.86. Found: C, 70.88; H, 7.91; N, 7.84.

cis-Adamantane-2-spiro-3'-8'-[3'-(ethoxycarbonyl)propyl]-1',2',4'-trioxaspiro[4.5]decane (OZ260). A solution of O-methyl 2-adamantanone oxime (895 mg, 5 mmol) and 4-[3-(ethoxycarbonyl)propyl]cyclohexanone (710 mg, 3.35 mmol) in cyclohexane (85 ml) and $CH_2Cl_2$ (15 ml) was treated with ozone according to the general procedure. The crude product was purified by flash chromatography (silica gel, 5% ether in petroleum ether) and by subsequent crystallization from ethanol to afford trioxolane OZ260 (660 mg, 52%) as a colorless solid. mp 52–54° C. (ethanol); $^1H$ NMR (500 MHz, $CDCl_3$) δ 1.01–1.37 (m, 5H), 1.25 (t, J=7.1 Hz, 3H), 1.47–2.21 (m, 22H), 2.27 (t, J=7.6 Hz, 2H), 4.12 (q, J=7.1 Hz, 2H); $^{13}C$ NMR (125.7 MHz, $CDCl_3$) δ 14.24, 22.63, 26.51, 26.90, 30.01, 34.19, 34.55, 34.79, 34.81, 35.66, 35.90, 36.41, 36.83, 60.18, 108.99, 111.17, 173.68. Anal. Calcd for $C_{22}H_{34}O_5$: C, 69.81; H, 9.05. Found: C, 69.82; H, 8.96.

cis-Adamantane-2-spiro-3'-8'-(3'-carboxypropyl)-1',2',4'-trioxaspiro[4.5]decane (OZ261). To a solution of OZ260 (250 mg, 0.66 mmol) in 95% ethanol (5 ml) was added 15% NaOH solution (1 ml). The mixture was stirred at 25° C. for 24 h before being concentrated and acidified with 6 M aq. HCl (3 ml). The precipitate was filtered, washed with water, and crystallized from ethanol to give trioxolane OZ261 (186 mg, 81%) as a colorless solid. mp 156–158° C. (ethanol); $^1H$ NMR (500 MHz, $CDCl_3$) δ 1.03–1.39 (m, 5H), 1.45–2.20 (m, 22H), 2.27 (t, J=7.4 Hz, 2H); $^{13}C$ NMR (125.7 MHz, $CDCl_3$) δ 22.33, 26.50, 26.90, 29.98, 34.06, 34.17, 34.81, 35.55, 35.87, 36.40, 36.83, 108.96, 111.19, 179.14. Anal. Calcd for $C_{20}H_{30}O_5$: C, 68.54; H, 8.63. Found: C, 68.41; H, 8.49.

cis-Adamantane-2-spiro-3'-8'-[(acetylamino)methyl]-1',2',4'-trioxaspiro[4.5]decane (OZ262). To a solution of OZ209 (389 mg, 1 mmol) and triethylamine (505 mg, 5 mmol) in $CH_2Cl_2$ (10 ml) at 0° C. was added dropwise a solution of acetyl chloride (140 mg, 1.9 mmol) in $CH_2Cl_2$ (5 ml). The mixture was stirred at rt for 16 h, washed with water and brine, dried over $MgSO_4$, and concentrated. The crude product was purified by flash chromatography (silica gel, 5% $CH_3OH$ in $CH_2Cl_2$) and by crytallization from hexanes/$CH_2Cl_2$ (3:1) to afford trioxolane OZ262 (150 mg, 45%) as a colorless solid. mp 102° C. dec (hexanes/$CH_2Cl_2$, 3:1); $^1H$ NMR (500 MHz, $CDCl_3$) δ 1.15–1.37 (m, 2H), 1.41–2.09 (m, 21H), 1.98 (s, 3H), 3.11 (app t, J=6.3 Hz, 2H), 5.52 (br s, 1H); $^{13}C$ NMR (125.7 MHz, $CDCl_3$) δ 23.34, 26.46, 26.85, 27.72, 33.73, 34.76, 34.77, 36.16, 36.37, 36.77, 44.87, 108.60, 111.38, 170.03. Anal. Calcd for $C_{19}H_{29}NO_4$: C, 68.03; H, 8.71; N, 4.18. Found: C, 68.26; H, 8.70; N, 4.18.

cis-Adamantane-2-spiro-3'-8'-[[[(1'H-imidazol-4'-yl)carbonyl]amino]methyl]-1',2',4'-trioxaspiro[4.5]decane mesylate (OZ263). To a solution of 4-imidazolecarboxylic acid (134 mg, 1.2 mmol), 1-(3-dimethylaminopropyl)-3-ethylcarbodiimide hydrochloride (290 mg, 1.5 mmol), and 1-hydroxybenzotriazole (200 mg, 1.5 mmol) in DMF (40 ml) under $N_2$ was added a solution of OZ209 (389 mg, 1.0 mmol) and triethylamine (101 mg, 1.0 mmol) in DMF (5 ml). The resulting mixture was stirred at r.t. for 48 h before being quenched with water (120 ml). The mixture was extracted with $CH_2Cl_2$ (3×40 ml). The combined organic extracts were washed with water and brine, dried over $MgSO_4$, and concentrated. The crude product was dissolved in $CH_2Cl_2$ (10 ml) and treated with methanesulfonic acid (90 mg). The solid was collected by filtration and recrytallized from ether/$CH_2Cl_2$/$CH_3OH$ (3:1:1) to afford trioxolane OZ263 (72 mg, 15%) as a colorless solid. mp 161–162° C. (ether/CH$_2$Cl$_2$/CH$_3$OH 3:1:1); $^1$H NMR (500 MHz, DMSO-d$_6$) δ 1.02–1.23 (m, 2H), 1.45–2.09 (m, 21H), 2.32 (s, 3H), 3.13 (app t, J=6.3 Hz, 2H), 8.12 (s, 1H), 8.73 (br s, 1H), 9.03 (s, 1H), 14.47 (br s, 2H); $^{13}$C NMR (125.7 MHz, DMSO-d$_6$) δ 25.96, 26.36, 27.64, 33.34, 34.41, 35.77, 35.90, 36.23, 44.06, 108.68, 110.66, 119.91, 120.22, 128.13, 128.22, 135.92, 136.09, 157.40. Anal. Calcd for C$_{22}$H$_{33}$N$_3$O$_7$S: C, 54.64; H, 6.88; N, 8.69. Found: C, 54.72; H, 6.76; N, 8.90.

cis-Adamantane-2-spiro-3'-8'-[[[(1'-oxido-4'-pyridinyl)carbonyl]amino]methyl]-1',2',4'-trioxaspiro[4.5]decane (OZ264). To a solution of isonicotinic acid N-oxide (167 mg, 1.2 mmol), 1-(3-dimethylaminopropyl)-3-ethylcarbodiimide hydrochloride (290 mg, 1.5 mmol), and 1-hydroxybenzotriazole (200 mg, 1.5 mmol) in DMF (10 ml) under N$_2$ was added a solution of OZ209 (389 mg, 1.0 mmol) and triethylamine (101 mg, 1.0 mmol) in DMF (5 ml). The resulting mixture was stirred at rt for 16 h before being quenched with water (50 ml). The precipitate was collected by filtration to afford trioxolane OZ264 (340 mg, 82%) as a colorless solid. mp 152–154° C.; $^1$H NMR (500 MHz, CDCl$_3$) δ 1.21–1.43 (m, 2H), 1.49–2.11 (m, 21H), 3.33 (app t, J=6.2 Hz, 2H), 6.54 (br s, 1H), 7.69 (d, J=6.3 Hz, 2H), 8.20 (d, J=6.0 Hz, 2H); $^{13}$C NMR (125.7 MHz, CDCl$_3$) δ 26.44, 26.84, 27.82, 33.69, 34.77, 36.18, 36.37, 36.75, 45.56, 108.43, 111.52, 124.32, 131.08, 139.29, 163.52. Anal. Calcd for C$_{23}$H$_{30}$N$_2$O$_5$: C, 66.65; H, 7.30; N, 6.76. Found: C, 66.81; H, 7.18; N, 6.55.

cis-Adamantane-2-spiro-3'-8'-[[(aminocarbonyl)amino]methyl]-1',2',4'-trioxaspiro[4.5]decane (OZ265). A mixture of OZ209 (389 mg, 1 mmol), pyridine (790 mg, 10 mmol), acetic acid (600 mg, 10 mmol), triethylamine (303 mg, 3 mmol), and potassium cyanate (164 mg, 2 mmol) in CH$_2$Cl$_2$ (10 ml) was stirred at r.t. for 38 h. The mixture was then washed with water and brine, dried over MgSO$_4$, and concentrated. The crude product was recrytallized from 40% aq. ethanol to afford trioxolane OZ265 (250 mg, 74%) as a colorless solid. mp 138–140° C. (40% aq. ethanol); $^1$H NMR (500 MHz, CDCl$_3$) δ 1.11–1.33 (m, 2H), 1.41–2.18 (m, 21H), 3.02 (app t, J=5.5 Hz, 2H), 4.64 (br s, 2H), 5.09 (br s, 1H); $^{13}$C NMR (125.7 MHz, CDCl$_3$) δ 26.45, 26.84, 27.66, 33.75, 34.76, 36.36, 36.65, 36.76, 45.85 (br s), 108.69, 111.35, 158.96. Anal. Calcd for C$_{18}$H$_{28}$N$_2$O$_4$: C, 64.26; H, 8.39; N, 8.33. Found: C, 64.40; H, 8.15; N, 8.46.

cis-Adamantane-2-spiro-3'-8'-[[[(dimethylamino)carbonyl]amino]methyl]-1',2',4'-trioxaspiro[4.5]decane (OZ266). To a solution of OZ209 (389 mg, 1.0 mmol) and triethylamine (202 mg, 2.0 mmol) in CH$_2$Cl$_2$ (10 ml) at 0° C. was added dimethylcarbamoyl chloride (120 mg, 1.1 mmol). The mixture was stirred at rt for 16 h before being washed with water and brine, dried over MgSO$_4$, and concentrated. The crude product was crystallized from 50% aq. ethanol to afford trioxolane OZ266 (270 mg, 74%) as a colorless solid. mp 153–155° C. (50% aq. ethanol); $^1$H NMR (500 MHz, CDCl$_3$) δ 1.14–1.33 (m, 2H), 1.44–2.17 (m, 21H), 2.91 (s, 6H), 3.09 (app t, J=6.2 Hz, 2H), 4.46 (br s, 1H); $^{13}$C NMR (125.7 MHz, CDCl$_3$) δ 26.49, 26.88, 27.77, 33.84, 34.79, 36.19, 36.39, 36.61, 36.80, 46.25, 108.85, 111.30, 158.43. Anal. Calcd for C$_{20}$H$_{32}$N$_2$O$_4$: C, 65.91; H, 8.85; N, 7.69. Found: C, 66.16; H, 8.80; N, 7.90.

cis-Adamantane-2-spiro-3'-8'-[[[(4'-methyl-1'-piperazinyl)carbonyl]amino]methyl]-1',2',4'-trioxaspiro[4.5]decane (OZ267). To a solution of OZ209 (389 mg, 1.0 mmol)-and triethylamine (404 mg, 4.0 mmol) in CH$_2$Cl$_2$ (10 ml) at 0° C. was added 4-methyl-1-piperazinecarbonyl chloride hydrochloride (240 mg, 1.2 mmol). The mixture was stirred at rt for 16 h before being washed with water and brine, dried over MgSO$_4$, and concentrated. The crude product was crystallized from 60% aq. ethanol to afford trioxolane OZ267 (280 mg, 67%) as a colorless solid. mp 82° C. dec (60% aq. ethanol); $^1$H NMR (500 MHz, CDCl$_3$) δ 1.11–1.30 (m, 2H), 1.43–2.15 (m, 21H), 2.31 (s, 3H), 2.39 (t, J=5.1 Hz, 4H), 3.09 (app t, J=6.2 Hz, 2H), 3.38 (t, J=5.1 Hz, 4H), 4.59 (app t, J=5.5 Hz, 1H); $^{13}$C NMR (125.7 MHz, CDCl$_3$) δ 26.45, 26.84, 27.77, 33.78, 34.76, 36.35, 36.48, 36.76, 43.71, 46.08, 46.18, 54.64, 108.77, 111.29, 157.69. Anal. Calcd for C$_{23}$H$_{37}$N$_3$O$_4$: C, 65.84; H, 8.89; N, 10.02. Found: C, 65.91; H, 8.64; N, 10.07.

N-(cis-Adamantane-2-spiro-3'-1',2',4'-trioxaspiro[4.5]decane-8'-methyl)oxamide (OZ268). To a solution of oxamic acid (107 mg, 1.2 mmol), 1-(3-dimethylaminopropyl)-3-ethylcarbodiimide hydrochloride (290 mg, 1.5 mmol), and 1-hydroxybenzotriazole (200 mg, 1.5 mmol) in DMF (15 ml) under N$_2$ was added a solution of OZ209 (389 mg, 1.0 mmol) and triethylamine (101 mg, 1.0 mmol) in DMF (5 ml). The resulting mixture was stirred at rt for 16 h before being quenched with water (80 ml). The precipitate was collected by filtration to afford trioxolane OZ268 (320 mg, 88%) as a colorless solid. mp 152–155° C.; $^1$H NMR (500 MHz, DMSO-d$_6$) δ 0.95–1.23 (m, 2H), 1.39–2.13 (m, 21H), 2.97 (app t, J=6.5 Hz, 2H), 7.74 (s, 1H), 7.80 (s, 1H), 8.67 (app t, J=6.2 Hz, 1H); $^{13}$C NMR (125.7 MHz, DMSO-d$_6$) δ 25.97, 26.38, 27.55, 33.30, 34.41, 35.47, 35.91, 36.25, 44.03, 108.70, 110.62, 160.50, 162.38. Anal. Calcd for C$_{19}$H$_{28}$N$_2$O$_5$: C, 62.62; H, 7.74; N, 7.69. Found: C, 62.80; H, 7.55; N, 7.89.

trans-Adamantane-2-spiro-3'-8'-(aminomethyl)-1',2',4'-trioxaspiro[4.5]decane mesylate (OZ269). A mixture of OZ167 (2.54 g, 6.0 mmol) and hydrazine monohydrate (1.80 g, 36.0 mmol) in chloroform/ethanol (7:3, 60 ml) was heated at 55–65° C. for 24 h. After being cooled to rt, the solid byproduct was filtered off and the filtrate was washed with water (2×40 ml) and brine (20 ml). The combined aqueous layers were extracted with CH$_2$Cl$_2$ (3×30 ml). The CH$_2$Cl$_2$ extracts were washed with water (50 ml) and brine (50 ml). The combined organic solutions were dried over MgSO$_4$ and concentrated. The residue was dissolved in CH$_2$Cl$_2$ (10 ml) and treated with a solution of methanesulfonic acid (0.6 g) in CH$_2$Cl$_2$ (2 ml). The product was precipitated by addition of ether (40 ml) and collected by filtration to afford trioxolane OZ269 (1.80 g, 77%) as a colorless solid. mp 140–141° C.; $^1$H NMR (500 MHz, CDCl$_3$) δ 1.32–1.52 (m, 2H), 1.54–2.15 (m, 21H), 2.76 (s, 3H), 2.87 (app t, J=6.3 Hz, 2H), 7.60 (s, 3H); $^{13}$C NMR (125.7 MHz, CDCl$_3$) δ 26.44, 26.86, 27.24, 33.23, 34.56, 34.71, 34.90, 36.33, 36.74, 39.29, 44.63, 108.06, 111.81. Anal. Calcd for C$_{18}$H$_{31}$NO$_6$S.0.4H$_2$O: C, 53.84; H, 8.12; N, 3.49. Found: C, 53.51; H, 7.64; N, 3.66.

cis-Adamantane-2-spiro-3'-8'-[[(aminoacetyl)amino]methyl]-1',2',4'-trioxaspiro[4.5]decane mesylate (OZ271). To a solution of N-phthaloylglycine (226 mg, 1.1 mmol), EDCI (290 mg, 1.5 mmol), and HOBt (200 mg, 1.5 mmol) in DMF (30 ml) under N$_2$ was added a solution of OZ209 (cis-Adamantane-2-spiro-3'-8'-(aminomethyl)-1',2',4'-trioxaspiro[4.5]decane mesylate) (389 mg, 1.0 mmol) and triethylamine (101 mg, 1.0 mmol) in DMF (5 ml). The resulting mixture was stirred at rt for 16 h before being quenched with water (80 ml). The precipitate was collected by filtration to afford cis-adamantane-2-spiro-3'-8'-[[(2-phthalimidoacetyl)amino]methyl]-1',2',4'-trioxaspiro[4.5]decane (426 mg, 89%) as a colorless solid. mp 139–142° C.; $^1$H NMR (500 MHz, CDCl$_3$) δ 1.15–1.30 (m, 2H), 1.50–2.00 (m, 21H), 3.14 (t, J=6.6 Hz, 2H), 4.33 (s, 2H), 7.72–7.77 (m, 2H), 7.85–7.90 (m, 2H). Step 2. A mixture of cis-adamantane-2-spiro-3'-8'-[[(2-phthalimidoacetyl)amino]methyl]-1',2',4'-trioxaspiro[4.5]decane (420 mg, 0.88 mmol) and hydrazine monohydrate (300 mg, 5.36 mmol) in chloroform/ethanol (7:3, 10 ml) was heated at 55–60° C. for 24 h. After the mixture was cooled to rt, the solid byproduct was filtered off. The filtrate was washed with water (2×10 ml) and brine (10 ml), dried over MgSO$_4$, and concentrated. The residue was dissolved in CH$_2$Cl$_2$/ether (1:4, 10 ml) and treated with methanesulfonic acid (77 mg, 0.8 mmol). The precipitate was collected by filtration to afford trioxolane OZ271 (260 mg, 66%) as a colorless solid. mp 153° C. dec; $^1$H NMR (500 MHz, DMSO-d$_6$) δ 1.01–1.19 (m, 2H), 1.38–2.11 (m, 21H), 2.32 (s, 3H), 3.00 (app t, J=5.8 Hz, 2H), 3.54 (d, J=4.9 Hz, 2H), 7.94 (s, 3H), 8.31 (t, J=5.2 Hz, 1H); $^{13}$C NMR (125.7 MHz, DMSO-d$_6$) δ 25.96, 26.37, 27.52, 33.35, 34.42, 35.71, 35.91, 36.24, 40.28, 43.96, 108.65, 110.68, 165.95. Anal. Calcd for C$_{20}$H$_{34}$N$_2$O$_7$S: C, 53.79; H, 7.67; N, 6.27. Found: C, 53.60; H, 7.46; N, 6.10.

cis-Adamantane-2-spiro-3'-8'-[[(4'-morpholinylcarbonyl)amino]methyl]-1',2',4'-trioxaspiro[4.5]decane (OZ272). To a solution of OZ209 (cis-Adamantane-2-spiro-3'-8'-(aminomethyl)-1',2',4'-trioxaspiro[4.5]decane mesylate) (389 mg, 1.0 mmol) and triethylamine (404 mg, 4.0 mmol) in CH$_2$Cl$_2$ (10 ml) at 0° C. was added 4-morpholinecarbonyl chloride (225 mg, 1.5 mmol). The mixture was stirred at rt for 16 h, washed with water and brine, dried over MgSO$_4$, and concentrated. The crude product was crystallized from hexanes/ether (4:1) to afford trioxolane OZ272 (290 mg, 71%) as a colorless solid. mp 141–142° C. (hexanes/ether, 4:1); $^1$H NMR (500 MHz, CDCl$_3$) δ 1.06–1.35 (m, 2H), 1.42–2.18 (m, 21H), 3.11 (app t, J=5.9 Hz, 2H), 3.33 (t, J=4.8 Hz, 4H), 3.69 (t, J=4.9 Hz, 4H), 4.54 (s, 1H); $^{13}$C NMR (125.7 MHz, CDCl$_3$) δ 26.48, 26.87, 27.78, 33.80, 34.79, 36.38, 36.51, 36.79, 44.02, 46.17, 66.46, 108.75, 111.36, 157.83. Anal. Calcd for C$_{22}$H$_{34}$N$_2$O$_5$: C, 65.00; H, 8.43; N, 6.89. Found: C, 64.84; H, 8.42; N, 6.91.

cis-Adamantane-2-spiro-3'-8'-[[(3'-pyridinylcarbonyl)amino]methyl]-1',2',4'-trioxaspiro[4.5]decane (OZ273). To a solution of cis-adamantane-2-spiro-3'-8'-aminomethyl-1',2',4'-trioxaspiro[4.5]decane (360 mg, 1.2 mmol) and triethylamine (370 mg, 3.6 mmol) in CH$_2$Cl$_2$ (12 ml) at 0° C. was added nicotinoyl chloride (278 mg, 1.56 mmol). The mixture was stirred at rt for 16 h, washed with water and brine, dried over MgSO$_4$, and concentrated. The crude product was purified by flash chromatography (silica gel, 2% MeOH in CH$_2$Cl$_2$) to afford trioxolane OZ273 (240 mg, 60%) as a colorless solid. mp 70–72° C.; $^1$H NMR (500 MHz, CDCl$_3$) δ 1.18–1.42 (m, 2H), 1.49–2.21 (m, 21H), 3.35 (app t, J=6.3 Hz, 2H), 6.39 (s, 1H), 7.37–7.48 (m, 1H), 8.11 (d, J=8.0 Hz, 1H), 8.73 (s, 1H), 8.96 (s, 1H); $^{13}$C NMR (125.7 MHz, CDCl$_3$) δ 26.45, 26.85, 27.84, 33.72, 34.77, 36.26, 36.37, 36.76, 45.38, 108.51, 111.44, 123.52, 130.35, 135.09, 147.71, 152.20, 165.68. Anal. Calcd for C$_{23}$H$_{30}$N$_2$O$_4$: C, 69.32; H, 7.59; N, 7.03. Found: C, 69.29; H, 7.56; N, 7.01.

Adamantane-2-spiro-3'-8'-fluoro-8'-phenyl-1',2',4'-trioxaspiro[4.5]decane (OZ274). To a stirred solution of phenyl carbinol (178 mg, 0.5 mmol), obtained by addition of phenyllithium to OZ05 (Adamantane-2-spiro-3'-8'-oxo-1',2',4'-trioxaspiro[4.5]decane), in dry CH$_2$Cl$_2$ (5 ml) under N$_2$ at −78° C. was added DAST (88 mg, 0.55 mmol). The reaction mixture was stirred at −78° C. for 1.5 h and poured into ice water (5 ml). The organic layer was separated, and the aqueous layer was then extracted with CH$_2$Cl$_2$ (3×5 ml). The combined organic extracts were washed with water (10 ml), dried over MgSO$_4$, and concentrated. The purification of the crude product by flash chromatography (silica gel, 1% ether in hexanes) followed by recrystallization from 5% ether in hexanes afforded trioxolane OZ274 (97 mg, 54%) as a colorless solid. mp 94–96° C.; $^1$H NMR (500 MHz, CDCl$_3$) δ 51.58–2.43 (m, 22H), 7.21–7.58 (m, 5H); $^{13}$C NMR (125.7 MHz, CDCl$_3$) δ 26.47, 26.92, 30.14 (d, J=2.3 Hz), 34.74, 34.95 (d, J=23.4 Hz), 35.03, 36.39, 36.77, 95.09 (d, J=174.9 Hz), 107.82, 111.82, 123.92 (d, 9.6 Hz), 127.55 (d, J=1.4 Hz), 128.31 (d, J=1.4 Hz), 144.29 (d, J=21.5 Hz). Anal. Calcd for C$_{22}$H$_{27}$FO$_3$: C, 73.72; H, 7.59. Found: C, 73.90; H, 7.47.

Adamantane-2-spiro-3'-8'-hydroxy-8'-(2'-pyridinylmethyl)-1',2',4'-trioxaspiro[4.5]decane (OZ275). To a stirred solution of 2-picoline (279 mg, 3.0 mmol) in dry THF (10 ml) under N$_2$ at −78° C. was added n-BuLi (1.6 M in hexanes, 1.9 ml, 3.0 mmol). The resulting bright yellow solution was stirred at the same temperature for 1 h before a solution of OZ05 (690 mg, 2.5 mmol) in dry THF (15 ml) was added slowly. The mixture was allowed to reach 0° C., and then poured into ice water (50 ml), and extracted with ether (3×50 ml). The combined organic extracts were washed with brine (50 ml), dried over MgSO$_4$, and concentrated. The purification of the crude product by flash chromatography (silica gel, 70% EtOAc in hexanes) followed by recrystallization from ethanol afforded trioxolane OZ275 (385 mg, 41%) as a colorless solid. mp 128–130° C.; $^1$H NMR (500 MHz, CDCl$_3$) δ 1.41–2.25 (m, 22H), 2.88 (s, 2H), 5.82 (s, 1H), 7.11 (d, J=7.7 Hz, 1H), 7.17 (dd, J=7.3, 4.6 Hz, 1H), 7.63 (ddd, J=7.7, 7.7, 1.9 Hz, 1H), 8.49 (d, J=4.1 Hz, 1H); $^{13}$C NMR (125.7 MHz, CDCl$_3$) δ 26.51, 26.89, 29.93, 34.80, 35.03, 36.43, 36.83, 47.30, 70.09, 109.01, 111.30, 121.53, 124.42, 136.89, 148.40, 159.55. Anal. Calcd for C$_{22}$H$_{29}$NO$_4$: C, 71.13; H, 7.87; N, 3.77. Found: C, 71.31; H, 7.94; N, 3.93.

Adamantane-2-spiro-3'-8'-hydroxy-8'-(2'-benzothiazolylmethyl)-1',2',4'-trioxaspiro[4.5]decane (OZ276). To a stirred solution of 2-methylbenzothiazole (244 mg, 1.6 mmol) in dry THF (4 ml) under N$_2$ at −78° C. was added n-BuLi (1.6 M in hexanes, 1.1 ml, 1.8 mmol). The resulting bright yellow solution was stirred at the same temperature for 1 h before a solution of OZ05 (500 mg, 1.8 mmol) in dry THF (10 ml) was added slowly. The mixture was allowed to reach 0° C., and then poured into ice water (15 ml), and extracted with ether (3×25 ml). The combined organic extracts were washed with brine (25 ml), dried over MgSO$_4$, and concentrated. The purification of the crude product by flash chromatography (silica gel, 30% EtOAc in hexanes) followed by recrystallization (ether/hexane 1:1) afforded trioxolane OZ276 (353 mg, 52%) as a colorless solid. mp 130–132° C.; $^1$H NMR (500 MHz, CDCl$_3$) δ 1.58–2.29 (m, 22H), 3.19 (s, 2H), 4.28 (br s, 1H), 7.31–7.43 (m, 1H), 7.44–7.53 (m, 1H), 7.86 (d, J=7.7 Hz, 1H), 7.99 (d, J=8.2 Hz, 1H); $^{13}$C NMR (125.7 MHz, CDCl$_3$) δ 26.49, 26.88, 29.87, 34.71, 34.79, 34.80, 36.41, 36.80, 44.92, 70.19, 108.63, 111.47, 121.44, 122.70, 125.06, 126.17, 134.35, 152.98, 168.22. Anal. Calcd for C$_{24}$H$_{29}$NO$_4$S: C, 67.42; H, 6.84; N, 3.28. Found: C, 67.70; H, 6.76; N, 3.23.

cis-Adamantane-2-spiro-3'-8'-[[[(2'-amino-2'-methylpropyl)amino]carbonyl]methyl]-1',2',4'-trioxaspiro[4.5]decane p-tosylate (OZ277). Step 1. A solution of OZ78 (cis-Adamantane-2-spiro-3'-8'-carboxymethyl-1',2',4'-trioxaspiro[4.5]decane) (12.92 g, 40 mmol), HOBt (6.49 g, 48 mmol), and EDCI (9.20 g, 48 mmol) in DMF (300 ml) under N$_2$ was stirred at rt for 24 h. Under ice cooling, the reaction was quenched with water (150 ml). The precipitate was collected by filtration, washed with 95% ethanol (150 ml), and dried to afford the OZ78 active ester (16.61 g, 95%) as a colorless solid. mp 154–156° C.; $^1$H NMR (500 MHz, CDCl$_3$) δ 1.37–1.51 (m, 2H), 1.63–2.17 (m, 21H), 2.72 (d, J=7.1 Hz, 2H), 7.39 (d, J=78.5 Hz, 1H), 7.43 (dd, J=8.2, 7.2 Hz, 1H), 7.56 (dd, J=8.0, 7.4 Hz, 1H), 8.07 (d, J=8.5 Hz, 1H). Step 2. To a solution of the OZ78 active ester (13.19 g, 30 mmol) in CHCl$_3$ (300 ml) was added rapidly a solution of 1,2-diamino-2-methylpropane (5.29 g, 60 mmol) in CHCl$_3$ (50 ml). The resulting mixture was stirred at rt for 1 h before being quenched with water (500 ml). After separation of the organic layer, the aqueous layer was extracted with CHCl$_3$ (2×100 ml). The combined extracts were washed with water (3×500 ml) and brine (300 ml), dried over MgSO$_4$, and filtered. To the filtrate was added a solution of p-toluenesulfonic acid monohydrate (5.71 g, 30 mmol) in ethanol (30 ml). After evaporation of the solvents, the residue was treated with ethanol (100 ml), filtered, and washed with hexanes (200 ml) to afford trioxolane OZ277 (14.25 g, 84%) as a colorless solid. mp 160–162° C.; $^1$H NMR (500 MHz, DMSO-d$_6$) δ 1.01–1.17 (m, 2H), 1.16 (s, 6H), 1.58–1.99 (m, 21H), 2.05 (d, J=7.1 Hz, 2H), 2.28 (s, 3H), 3.19 (d, J=6.3 Hz, 2H), 7.11 (d, J=8.0 Hz, 2H), 7.48 (d, J=8.0 Hz, 2H), 7.70 (s, 3H), 8.02 (t, J=6.2 Hz, 1H); $^{13}$C NMR (125.7 MHz, DMSO-d$_6$) δ 20.92, 23.47, 25.96, 26.36, 29.68, 32.71, 33.56, 34.40, 35.91, 36.23, 41.97, 46.02, 54.52, 108.52, 110.63, 125.64, 128.20, 137.80, 145.82, 172.49. Anal. Calcd for C$_{29}$H$_{44}$N$_2$O$_7$S: C, 61.68; H, 7.85; N, 4.96. Found: C, 61.46; H, 7.67; N, 4.76.

cis-Adamantane-2-spiro-3'-8'-[[(1'H-tetrazol-5'-ylamino) carbonyl]methyl]-1',2',4'-trioxaspiro[4.5]decane (OZ278). To a solution of OZ78 (322 mg, 1.0 mmol), 5-aminotetrazole (103 mg, 1.0 mmol), and 4-methylmorpholine (304 mg, 3 mmol) in DMF (10 ml) at 0° C. was added benzotriazol-1-yloxy-tris(dimethylamino)phosphonium hexafluorophosphate (531 mg, 1.2 mmol). The resulting mixture was stirred at rt for 3 days and filtered. After the filtrate was concentrated, the residue was crystallized from 40% aq. ethanol followed by recrystallization from CH$_2$Cl$_2$ to afford trioxolane OZ278 (68 mg, 17%) as a colorless solid. mp 150–152° C.; $^1$H NMR (500 MHz, DMSO-d$_6$) δ 1.01–1.23 (m 2H), 1.41–2.07 (m, 21H), 2.35 (d, J=6.9 Hz, 2H), 11.94 (s, 1H), 15.82 (s, 1H); $^{13}$C NMR (125.7 MHz, DMSO-d$_6$) δ 25.95, 26.36, 29.53, 32.80, 33.50, 34.40, 35.90, 36.23, 41.51, 108.40, 110.68, 149.95, 171.13. Anal. Calcd for C$_{19}$H$_{27}$N$_5$O$_4$: C, 58.60; H, 6.99; N, 17.98. Found: C, 58.76; H, 7.05; N, 18.14.

cis-Adamantane-2-spiro-3'-8'-[(1'-piperazinylcarbonyl) methyl]-1',2',4'-trioxaspiro[4.5]decane p-tosylate (OZ279). To a solution of the OZ78 active ester (13.19 g, 30 mmol) in CHCl$_3$ (300 ml) was added rapidly a solution of piperazine (12.92 g, 150 mmol) in CHCl$_3$ (50 ml). The resulting mixture was stirred at rt for 1.5 h before being quenched with water (500 ml). After separation of the organic layer, the aqueous layer was extracted with CHCl$_3$ (2×100 ml). The combined extracts were washed with water (3×500 ml) and brine (300 ml), dried over MgSO$_4$, and filtered. To the filtrate was added a solution of p-toluenesulfonic acid monohydrate (5.71 g, 30 mmol) in ethanol (30 ml). After evaporation of the solvents, the residue was dissolved in CHCl$_3$ (70 ml), and the product was precipitated by adding isopropanol (420 ml), filtered, and washed with isopropanol/CHCl$_3$ (6:1, 210 ml) and hexanes (300 ml). The solid was redissolved in CHCl$_3$ (60 ml), precipitated by adding hexanes (600 ml), filtered, and washed with hexanes (200 ml) to afford trioxolane OZ279 (12.58 g, 75%) as a colorless solid. mp 148–150° C.; $^1$H NMR (500 MHz, CDCl$_3$) δ 1.03–1.29 (m, 2H), 1.49–2.05 (m, 21H), 2.15 (d, J=6.3 Hz, 2H), 2.39 (s, 3H), 3.18 (s, 2H), 3.25 (s, 2H), 3.71 (s, 2H), 3.83 (s, 2H), 7.22 (d, J=7.7 Hz, 2H), 7.71 (d, J=7.4 Hz, 2H), 9.25 (s, 2H); $^{13}$C NMR (125.7 MHz, CDCl$_3$) δ 21.35, 26.47 26.85, 30.19, 33.00, 33.96, 34.77, 36.38, 36.78, 38.19, 38.90, 42.36, 43.68, 43.78, 108.41, 111.37, 125.66, 129.22, 140.94, 141.11, 170.45. Anal. Calcd for C$_{29}$H$_{42}$N$_2$O$_7$S: C, 61.90; H, 7.52; N, 4.98. Found: C, 62.18; H, 7.68; N, 4.95.

cis-Adamantane-2-spiro-3'-8'-[[(2'-hydroxybenzoyl) amino]methyl]-1',2',4'-trioxaspiro[4.5]decane (OZ280). To a mixture of salicylic acid (166 mg, 1.2 mmol), EDCI (290 mg, 1.5 mmol), and HOBt (200 mg, 1.5 mmol) in DMF (10 ml) under N$_2$ was added a solution of OZ209 (cis-Adamantane-2-spiro-3'-8'-(aminomethyl)-1',2',4'-trioxaspiro[4.5]decane mesylate) (389 mg, 1.0 mmol) and triethylamine (101 mg, 1.0 mmol) in DMF (5 ml). The resulting mixture was stirred at rt for 16 h before being quenched with water (70 ml). The precipitate was collected by filtration and recrystallized from ethanol to afford trioxolane OZ280 (175 mg, 42%) as a colorless solid. mp 149–150° C. (ethanol); $^1$H NMR (500 MHz, CDCl$_3$) δ 1.21–1.41 (m, 2H), 1.47–2.07 (m, 21H), 3.32 (app t, J=6.3 Hz, 2H), 6.40 (s, 1H), 6.85 (ddd, J=7.4, 7.4, 1.1 Hz, 1H), 6.99 (dd, J=8.2, 0.8 Hz, 1H), 7.35 (dd, J=8.0, 1.4 Hz, 1H), 7.40 (ddd, J=7.8, 7.8, 1.5 Hz, 1H), 12.31 (s, 1H); $^{13}$C NMR (125.7 MHz, CDCl$_3$) δ 526.43, 26.82, 27.82, 33.69, 34.76, 36.21, 36.34, 36.74, 44.86, 108.49, 111.47, 114.19, 118.60, 118.68, 125.13, 134.23, 161.55, 170.01. Anal. Calcd for C$_{24}$H$_{31}$N$_{O5}$: C, 69.71; H, 7.56; N, 3.39. Found: C, 69.57; H, 7.66; N, 3.48.

cis-Adamantane-2-spiro-3'-8'-[[(2'-amino-2'-methylpropionyl)amino]methyl]-1',2',4'-trioxaspiro[4.5] decane (OZ281). To a mixture of 2-aminoisobutyric acid (618 mg, 6.0 mmol), EDCI (1.16 g, 6.0 mmol), and HOBt (800 mg, 6.0 mmol) in DMF (150 ml) under N$_2$ was added a solution of OZ209 (1.47 g, 3.0 mmol) and triethylamine (404 mg, 4.0 mmol) in DMF (15 ml). The resulting mixture was stirred at rt for 48 h and concentrated. The residue was treated with saturated aq. NaHCO$_3$ (40 ml), diluted with water (40 ml), then basified with 1M aq. NaOH to pH=8, and extracted with CHCl$_3$ (3×60 ml). The combined extracts were washed with water and brine, dried over MgSO$_4$, and concentrated. The crude product was crystallized from 50% aq. ethanol to afford trioxolane OZ281 (0.92 g, 81%) as a colorless solid. mp 153–155° C. (ether/CH$_2$Cl$_2$, 1:1); $^1$H NMR (500 MHz, CDCl$_3$) δ 1.19–1.35 (m, 2H), 1.36 (s, 6H), 1.43–2.09 (m, 23H), 3.09 (app t, J=6.5 Hz, 2H), 7.73 (s, 1H); $^{13}$C NMR (125.7 MHz, CDCl$_3$) δ 26.48, 26.88, 27.75, 29.36, 33.82, 34.79, 36.39, 36.80, 44.36, 54.92, 108.69, 111.32, 177.45. Anal. Calcd for C$_{21}$H$_{34}$N$_2$O$_4$: C, 66.64; H, 9.05; N, 7.40. Found: C, 66.48; H, 9.05; N, 7.52.

cis-Adamantane-2-spiro-3'-8'-[[[(4'-hydroxy-3'-pyridinyl)carbonyl]amino]methyl]-1',2',4'-trioxaspiro[4.5] decane (OZ282). To a mixture of 6-hydroxynicotinic acid (167 mg, 1.2 mmol), EDCI (290 mg, 1.5 mmol), and HOBt (200 mg, 1.5 mmol) in DMF (10 ml) under N$_2$ was added a solution of OZ209 (389 mg, 1.0 mmol) and triethylamine (101 mg, 1.0 mmol) in DMF (5 ml). The resulting mixture was stirred at rt for 16 h before being quenched with water (70 ml). The precipitate was collected by filtration to afford trioxolane OZ282 (390 mg, 94%) as a colorless solid. mp 150–152° C.; $^1$H NMR (500 MHz, CDCl$_3$) δ 1.17–1.39 (m, 2H), 1.47–2.09 (m, 21H), 3.26 (app t, J=6.2 Hz, 2H), 6.54 (d, J=9.3 Hz, 1H), 6.62 (t, J=5.7 Hz, 1H), 7.83 (dd, J=9.5, 2.3 Hz, 1H), 8.06 (d, 1.9 Hz, 1H), 12.62 (br s, 1H); $^{13}$C NMR (125.7 MHz, CDCl$_3$) δ 26.44, 26.83, 27.85, 33.71, 34.77, 36.24, 36.35, 36.75, 45.28, 108.57, 111.44, 114.94, 119.53, 136.62, 139.61, 164.25, 164.76. Anal. Calcd for C$_{23}$H$_{30}$N$_2$O$_5$·0.67H$_2$O: C, 64.77; H, 7.40; N, 6.57. Found: C, 64.30; H, 7.18; N, 6.78.

cis-Adamantane-2-spiro-3'-8'-[[[(3'-amino-1'H-triazol-5'-yl)carbonyl]amino]methyl]-1',2',4'-trioxaspiro[4.5]decane (OZ283). To a mixture of 3-amino-1H-1,2,4-triazole-5-carboxylic acid hemihydrate (164 mg, 1.2 mmol), EDCI (290 mg, 1.5 mmol), and HOBt (200 mg, 1.5 mmol) in DMF (10 ml) under $N_2$ was added a solution of OZ209 (389 mg, 1.0 mmol) and triethylamine (101 mg, 1.0 mmol) in DMF (5 ml). The resulting mixture was stirred at rt for 48 h before being quenched with water (70 ml). The precipitate was collected by filtration to afford trioxolane OZ283 (325 mg, 81%) as a colorless solid. mp 146° C. dec; $^1$H NMR (500 MHz, DMSO-$d_6$) δ 1.01–1.19 (m, 2H), 1.41–2.05 (m, 21H), 3.04 (app t, J=6.6 Hz, 2H), 6.05 (br s, 2H), 7.98 (br s, 1H), 12.37 (br s, 1H); $^{13}$C NMR (125.7 MHz, DMSO-$d_6$) δ 25.98, 26.39, 27.59, 33.37, 34.42, 35.76, 35.92, 36.26, 43.58, 108.79, 110.62, 155.04 (br s), 157.07 (br s), 159.77 (br s). Anal. Calcd for $C_{20}H_{29}N_5O_4$: C, 59.54; H, 7.24; N, 17.36. Found: C, 59.38; H, 7.33; N, 17.57.

cis-Adamantane-2-spiro-3'-8'-[[[(2'-amino-3'-pyridinyl) carbonyl]amino]methyl]-1',2',4'-trioxaspiro[4.5]decane mesylate (OZ284). To a mixture of 2-aminonicotinic acid (168 mg, 1.2 mmol), EDCI (290 mg, 1.5 mmol), and HOBt (200 mg, 1.5 mmol) in DMF (10 ml) under $N_2$ was added a solution of OZ209 (389 mg, 1.0 mmol) and triethylamine (101 mg, 1.0 mmol) in DMF (5 ml). The resulting mixture was stirred at rt for 16 h before being quenched with water (70 ml). The precipitate was collected by filtration, re-dissolved in $CH_2Cl_2$ (3 ml), and treated with a solution of methanesulfonic acid (96 mg, 1.0 mmol) in $CH_2Cl_2$ (21 ml). The solid was collected by filtration to afford trioxolane OZ284 (280 mg, 55%) as a colorless solid. mp 164–165° C. ($CH_2Cl_2$); $^1$H NMR (500 MHz, DMSO-$d_6$) δ 1.03–1.23 (m, 2H) 1.46–1.98 (m, 21H), 2.40 (s, 3H), 3.13 (app t, J=6.1 Hz, 2H), 6.99 (dd, J=7.8, 6.4 Hz, 1H), 8.15 (dd, J=6.3, 1.4 Hz, 1H), 8.42 (dd, J=7.8, 1.5 Hz, 1H), 8.46 (br s, 2H), 8.94 (t, J=5.9 Hz, 1H), 13.48 (br s, 1H); $^{13}$C NMR (125.7 MHz, DMSO-$d_6$) δ 25.98, 26.39, 27.74, 33.40, 34.42, 35.59, 35.92, 36.25, 44.48, 108.70, 110.68, 111.70, 115.29, 140.11, 143.26, 153.34, 164.69. Anal. Calcd for $C_{24}H_{35}N_3O_7S$: C, 56.56; H, 6.92; N, 8.25. Found: C, 56.35; H, 6.96; N, 8.40.

cis-Adamantane-2-spiro-3'-8'-[(3'-oxo-1'-piperazinyl) methyl]-1',2',4'-trioxaspiro[4.5]decane (OZ285). A mixture of cis-adamantane-2-spiro-3'-8'-formyl-1',2',4'-trioxaspiro [4.5]decane (292 mg, 1.0 mmol), piperazine-2-one (114 mg, 1.0 mmol), and acetic acid (60 mg, 1.0 mmol) in 1,2-dichloroethane (15 ml) under $N_2$ was stirred at rt for 10 min before sodium triacetoxyborohydride (322 mg, 1.5 mmol) was added. The resulting mixture was stirred at rt for 4 h and then quenched with saturated aq. $NaHCO_3$ (15 ml). The organic layer was separated, and the aqueous layer was extracted with $CH_2Cl_2$ (2×15 ml). The combined organic extracts were washed with water and brine, dried over $MgSO_4$, and concentrated. The crude product was crystallized from hexanes/$CH_2Cl_2$ (4:1) to afford trioxolane OZ285 (210 mg, 56%) as a colorless solid. mp 157° C. dec; $^1$H NMR (500 MHz, $CDCl_3$) δ 1.07–1.25 (m, 2H), 1.41–2.05 (m, 21H), 2.17–2.27 (m, 2H), 2.61 (br s, 2H), 3.03–3.15 (m, 2H), 3.35 (br s, 2H), 6.55 (br s, 1H); $^{13}$C NMR (125.7 MHz, $CDCl_3$) δ 26.45, 26.85, 28.35, 33.57, 33.91, 34.76, 34.77, 36.35, 36.77, 41.33, 49.67, 57.21, 63.41, 108.91, 111.28, 169.75. Anal. Calcd for $C_{21}H_{32}N_2O_4$: C, 66.99; H, 8.57; N, 7.44. Found: C, 66.78; H, 8.51; N, 7.46.

cis-Adamantane-2-spiro-3'-8'-[[[4'-(aminocarbonyl) phenyl]amino]methyl]-1',2',4'-trioxaspiro[4.5]decane (OZ286). A mixture of cis-adamantane-2-spiro-3'-8'-formyl-1',2',4'-trioxaspiro[4.5]decane (292 mg, 1.0 mmol), 4-aminobenzamide (136 mg, 1.0 mmol), and acetic acid (60 mg, 1.0 mmol) in 1,2-dichloroethane (15 ml) under $N_2$ was stirred at rt for 10 min before sodium triacetoxyborohydride (322 mg, 1.5 mmol) was added. The resulting mixture was stirred at rt for 4 h and then quenched with saturated aq. $NaHCO_3$ (20 ml). The organic layer was separated, and the aqueous layer was extracted with $CH_2Cl_2$ (2×15 ml). The combined organic extracts were washed with water and brine, dried over $MgSO_4$, and concentrated. The crude product was crystallized from 95% aq. ethanol to afford trioxolane OZ286 (120 mg, 29%) as a colorless solid. mp 153–156° C.; $^1$H NMR (500 MHz, DMSO-$d_6$) δ 1.03–1.25 (m, 2H) 1.46–2.08 (m, 21H), 2.91 (br s, 2H), 6.21 (s, 1H), 6.52 (d, J=8.2 Hz, 2H), 6.80 (br s, 1H), 7.50 (br s, 1H), 7.61 (d, J=8.2 Hz, 2H); $^{13}$C NMR (125.7 MHz, DMSO-$d_6$) δ 26.00, 26.40, 27.96, 33.54, 34.45, 35.25, 35.94, 36.28, 48.05, 108.89, 110.67, 120.70, 129.26, 151.68, 168.17. Anal. Calcd for $C_{24}H_{32}N_2O_4 \cdot 1.5H_2O$: C, 65.58; H, 8.03; N, 6.37. Found: C, 65.86; H, 7.82; N; 6.77.

cis-Adamantane-2-spiro-3'-8'-[[(2'-amino-2'-methylpropyl)amino]methyl]-1',2',4'-trioxaspiro[4.5]decane dimesylate (OZ287). A mixture of cis-adamantane-2-spiro-3'-8'-formyl-1',2',4'-trioxaspiro[4.5]decane (292 mg, 1.0 mmol), 1,2-diamino-2-methylpropane (88 mg, 1.0 mmol), and acetic acid (60 mg, 1.0 mmol) in 1,2-dichloroethane (10 ml) under $N_2$ was stirred at rt for 10 min before sodium triacetoxyborohydride (322 mg, 1.5 mmol) was added. The resulting mixture was stirred at rt for 4.5 h and then quenched with saturated aq. $NaHCO_3$ (20 ml). The organic layer was separated and the aqueous layer was extracted with $CH_2Cl_2$ (2×15 ml). The combined organic extracts were washed with water and brine, dried over $MgSO_4$, and concentrated. The crude product was re-dissolved in $CH_2Cl_2$ (3 ml), treated with a solution of methanesulfonic acid (192 mg, 2.0 mmol) in $CH_2Cl_2$ (2 ml), and diluted with ether (20 ml). The solid was obtained by filtration to afford trioxolane OZ287 (236 mg, 42%) as a colorless solid. mp 158° C. dec; $^1$H NMR (500 MHz, DMSO-$d_6$) δ 1.08–1.25 (m, 2H), 1.36 (s, 6H), 1.58–1.99 (m, 21H), 2.40 (s, 6H), 2.89 (br s, 2H), 3.16 (br s, 2H), 8.14 (s, 3H), 8.28 (s, 2H); $^{13}$C NMR (125.7 MHz, DMSO-$d_6$) δ 23.76, 25.97, 26.38, 27.42, 32.53, 33.06, 34.42, 34.43, 35.91, 36.24, 52.24, 53.79, 54.60, 108.22, 110.85. Anal. Calcd for $C_{23}H_{44}N_2O_9S_2 \cdot 0.2CH_2Cl_2$: C, 48.57; H, 7.80; N, 4.88. Found: C, 48.36; H, 7.43; N, 4.91.

cis-Adamantane-2-spiro-3'-8'-(4'-hydroxyphenyl)-1',2',4'-trioxaspiro[4.5]decane (OZ288). Step 1. To a mixture of 4-(4-hydroxyphenyl)cyclohexanone (19.0 g, 0.1 mol) and triethylamine (40.4 g, 0.4 mol) in $CH_2Cl_2$ (700 ml) at 0° C. was added dropwise acetyl chloride (15.7 g, 0.2 mol). After the addition was finished, the reaction mixture was warmed to rt and stirred overnight. The reaction mixture was washed with water and brine, dried over $MgSO_4$, and concentrated. The crude product was crystallized from 95% aq. ethanol to afford 4-(4-acetoxyphenyl)-cyclohexanone (17.6 g, 76%) as a colorless solid. mp 104–106° C. (95% aq. ethanol); $^1$H NMR (500 MHz, $CDCl_3$) δ 1.88–1.98 (m, 2H), 2.20–2.26 (m, 2H), 2.48–2.54 (m, 4H), 2.30 (s, 3H), 3.00–3.07 (m, 1H), 7.03 (d, J=8.7 Hz, 2H), 7.25 (d, J=8.7 Hz, 2H). Step 2. A solution of O-methyl 2-adamantanone oxime (16.0 g, 89 mmol) and 4-(4-acetoxyphenyl)cyclohexanone (13.8 g, 59 mmol) in cyclohexane (400 ml) and $CH_2Cl_2$ (100 ml) was treated with ozone according to the general procedure. The crude product was triturated with ethanol (200 ml) to afford adamantane-2-spiro-3'-8'-(4'-acetoxyphenyl)-1',2',4'-trioxaspiro[4.5]decane (16.4 g, 70%) as a colorless solid. mp 149–151° C. (ethanol); $^1$H NMR (500 MHz, $CDCl_3$) δ 1.64–2.08 (m, 22H), 2.29 (s, 3H), 2.50–2.60 (m, 1H), 7.00 (d, J=8.2 Hz, 2H), 7.20 (d, J=8.2 Hz, 2H). Step 3. A mixture of adamantane-2-spiro-3'-8'-(4'-acetoxyphenyl)-1',2',4'-trioxaspiro[4.5]decane (16.4 g, 41 mmol) and 15% aq. KOH (65 ml) in THF/MeOH (1:2, 500 ml) was heated at 50° C. for 4 h. After being cooled to rt, the reaction mixture was concentrated to 70 ml, diluted with water (70 ml), and acidified with acetic acid (30 ml). The precipitate was collected by filtration to afford trioxolane OZ288 (14.36 g, 98%) as a colorless solid. mp 136–138° C.; $^1$H NMR (500 MHz, CDCl$_3$) δ 1.56–2.18 (m, 22H), 2.41–2.58 (m, 1H), 5.90 (br s, 1H), 6.76 (d, J=8.5 Hz, 2H), 7.05 (d, J=8.5 Hz, 2H); $^{13}$C NMR (125.7 MHz, CDCl$_3$) δ 26.49, 26.89, 31.65, 34.75, 34.80, 36.41, 36.81, 42.05, 108.46, 111.35, 115.22, 127.71, 138.03, 154.26. Anal. Calcd for C$_{22}$H$_{28}$O$_4$: C, 74.13; H, 7.92. Found: C, 73.90; H, 7.85.

cis-Adamantane-2-spiro-3'-8'-[[(ethoxycarbonyl)amino] methyl]-1',2',4'-trioxaspiro[4.5]decane (OZ289). To a solution of OZ209 (272 mg, 0.7 mmol) and triethylamine (271 mg, 2.7 mmol) in CH$_2$Cl$_2$ (15 ml) at 0° C. was added a solution of ethyl chloroformate (109 mg, 1 mmol) in CH$_2$Cl$_2$ (2 ml). After being stirred at rt for 5 h, the reaction mixture was washed with water and brine, dried over MgSO$_4$, and concentrated. The crude product was crystallized from hexanes/ether (9:1) to afford trioxolane OZ289 (160 mg, 63%) as a colorless solid. mp 69–71° C.; $^1$H NMR (500 MHz, CDCl$_3$) δ 1.12–1.39 (m, 5H), 1.42–2.09 (m, 21H), 3.04 (app t, J=6.3 Hz, 2H), 4.10 (q, J=7.4 Hz, 2H), 4.69 (s, 1H); $^{13}$C NMR (125.7 MHz, CDCl$_3$) δ 14.62, 26.47, 26.87, 27.60, 33.76, 34.79, 36.38, 36.61, 36.79, 46.22, 60.73, 108.68, 111.35, 156.70. Anal. Calcd for C$_{20}$H$_{31}$NO$_5$: C, 65.73; H, 8.55; N, 3.83. Found: C, 66.00; H, 8.69; N, 4.00.

cis-Adamantane-2-spiro-3'-8'-[[(2'-ethoxy-2'-oxoethyl) amino]methyl]-1',2',4'-trioxaspiro[4.5]decane mesylate (OZ290). A mixture of cis-adamantane-2-spiro-3'-8'-formyl-1',2',4'-trioxaspiro[4.5]decane (584 mg, 2.0 mmol), glycine ethyl ester hydrochloride (280 mg, 2.0 mmol), and triethylamine (202 mg, 2.0 mmol) in 1,2-dichloroethane (16 ml) under N$_2$ was stirred at rt for 10 min before sodium triacetoxyborohydride (644 mg, 3.0 mmol) was added. The resulting mixture was stirred at rt for 5 h, quenched with saturated aq. NaHCO$_3$ (20 ml), and basified with 1 M aq. NaOH to pH=8. The organic layer was separated, and the aqueous layer was extracted with CH$_2$Cl$_2$ (2×15 ml). The combined organic extracts were washed with water and brine, dried over MgSO$_4$, and concentrated. The crude product was re-dissolved in CH$_2$Cl$_2$/ether (1:3, 10 ml) and treated with a solution of methanesulfonic acid (198 mg, 2.0 mmol) in ether (2 ml). The precipitate was obtained by filtration to afford trioxolane OZ290 (346 mg, 36%) as a colorless solid. mp 109–112° C.; $^1$H NMR (500 MHz, DMSO-d$_6$) δ 1.03–1.21 (m, 2H), 1.23 (t, J=7.0 Hz, 3H), 1.57–1.99 (m, 21H), 2.34 (s, 3H), 2.84 (br s, 2H), 3.97 (s, 2H), 4.21 (q, J=7.1 Hz, 2H), 8.97 (s, 2H); $^{13}$C NMR (125.7 MHz, DMSO-d$_6$) δ 14.11, 25.98, 26.39, 27.36, 32.56, 32.97, 34.42, 34.43, 35.92, 36.25, 47.35, 51.94, 61.90, 108.21, 110.83, 166.76. Anal. Calcd for C$_{22}$H$_{37}$NO$_8$S: C, 55.56; H, 7.84; N, 2.95. Found: C, 55.73; H, 7.71; N, 2.96.

cis-Adamantane-2-spiro-3'-8'-[[[(ethylamino)carbonyl] amino]methyl]-1',2',4'-trioxaspiro[4.5]decane (OZ291). To a solution of OZ209 (272 mg, 0.7 mmol) and triethylamine (71 mg, 0.7 mmol) in CH$_2$Cl$_2$ (10 ml) at 0° C. was added a solution of ethyl isocyanate (60 mg, 0.84 mmol). After being stirred at rt for 2 h, the reaction mixture was washed with water and brine, dried over MgSO$_4$, and concentrated. The crude product was crystallized from 35% aq. ethanol to afford trioxolane OZ291 (155 mg, 61%) as a colorless solid. mp 112–116° C.; $^1$H NMR (500 MHz, CDCl$_3$) δ 1.13 (t, J=7.3 Hz, 3H), 1.15–1.29 (m, 2H), 1.42–2.09 (m, 21H), 3.04 (d, J=5.4 Hz, 2H), 3.20 (q, J=7.3 Hz, 2H), 4.39 (br s, 1H), 4.52 (br s, 1H); $^{13}$C NMR (125.7 MHz, CDCl$_3$), 15.45, 26.46, 26.85, 27.74, 33.79, 34.77, 35.37, 36.37, 36.78, 45.81, 108.74, 111.33, 158.19. Anal. Calcd for C$_{20}$H$_{32}$N$_2$O$_4$: C, 65.91; H, 8.85; N, 7.69. Found: C, 65.73; H, 8.65; N, 7.53.

cis-Adamantane-2-spiro-3'-8'-[[(2'-pyridinylmethyl) amino]methyl]-1',2',4'-trioxaspiro[4.5]decane dimesylate (OZ292). A mixture of cis-adamantane-2-spiro-3'-8'-formyl-1',2',4'-trioxaspiro[4.5]decane (292 mg, 1.0 mmol), 2-(aminomethyl)pyridine (108 mg, 1.0 mmol), and acetic acid (60 mg, 1 mmol) in 1,2-dichloroethane (10 ml) under N$_2$ was stirred at rt for 10 min before sodium triacetoxyborohydride (322 mg, 1.5 mmol) was added. The resulting mixture was stirred at rt for 4 h and then quenched with saturated aq. NaHCO$_3$ (20 ml). The organic layer was separated, and the aqueous layer was extracted with CHCl$_3$ (2×15 ml). The combined organic extracts were washed with water and brine, dried over MgSO$_4$, and concentrated. The crude product was purified by flash chromatography (silica gel, 2–10% MeOH in CH$_2$Cl$_2$) to give the desired amine (250 mg). The free amine was dissolved in ether (5 ml) and treated with a solution of methanesulfonic acid (130 mg) in ether (5 ml). The precipitate was triturated with CH$_2$Cl$_2$ to afford trioxolane OZ292 (145 mg, 25%) as a colorless solid. mp 142–145° C.; $^1$H NMR (500 MHz, DMSO-d$_6$) δ 1.05–1.25 (m, 2H), 1.54–1.99 (m, 21H), 2.40 (s, 6H), 2.88 (d, J=5.2 Hz, 2H), 4.33 (s, 2H), 7.50 (dd, J=6.2, 6.2 Hz, 1H), 7.58 (d, J=8.0 Hz, 1H), 7.97 (dd, J=7.3, 7.3 Hz, 1H), 8.35 (br s, 1H), 8.67 (d, J=4.6 Hz, 1H), 8.99 (s, 2H); $^{13}$C NMR (125.7 MHz, DMSO-d$_6$) δ 25.97, 26.38, 27.40, 32.73, 33.02, 34.42, 34.44, 35.92, 36.25, 50.51, 51.93, 108.24, 110.83, 123.97, 124.16, 138.42, 148.58, 151.47. Anal. Calcd for C$_{25}$H$_{40}$N$_2$O$_9$S$_2$.0.33CH$_2$Cl$_2$: C, 50.29; H, 6.77; N, 4.63. Found: C, 49.86; H, 6.66; N, 4.56.

cis-Adamantane-2-spiro-3'-8'-[(3'-pyridinylamino) methyl-1', 2',4'-trioxaspiro[4.5]decane (OZ293). A mixture of cis-adamantane-2-spiro-3'-8'-formyl-1',2',4'-trioxaspiro [4.5]decane (292 mg, 1.0 mmol), 3-aminopyridine (84 mg, 1.0 mmol), and acetic acid (60 mg, 1 mmol) in 1,2-dichloroethane (10 ml) under N$_2$ was stirred at rt for 10 min before sodium triacetoxyborohydride (322 mg, 1.5 mmol) was added. The resulting mixture was stirred at rt for 4 h, quenched with saturated aq. NaHCO$_3$ (15 ml), and basified with 1 M aq. NaOH to pH=8. The organic layer was separated, and the aqueous layer was extracted with CHCl$_3$ (2×10 ml). The combined organic extracts were washed with water and brine, dried over MgSO$_4$, and concentrated. The crude product was crystallized from CH$_2$Cl$_2$/ether (1:5) to afford trioxolane OZ293 (100 mg, 27%) as a colorless solid. mp 134–138° C.; $^1$H NMR (500 MHz, CDCl$_3$) δ 1.19–1.37 (m, 2H), 1.45–2.09 (m, 21H), 3.01 (d, J=6.6 Hz, 2H), 3.77 (br s, 1H), 6.85 (d, J=8.2 Hz, 1H), 7.08 (dd, J=8.0, 4.7 Hz, 1H), 7.94 (s, 1H), 8.01 (s, 1H); $^{13}$C NMR (125.7 MHz, CDCl$_3$) δ 26.46, 26.86, 28.08, 33.83, 34.78, 34.79, 35.97, 36.38, 36.77, 49.08, 108.66, 111.44, 118.34, 123.74, 135.81, 138.41, 144.27. Anal. Calcd for C$_{22}$H$_{30}$N$_2$O$_3$: C, 71.32; H, 8.16; N, 7.56. Found: C, 71.54; H, 7.87; N, 7.49.

cis-Adamantane-2-spiro-3'-8'-[[(4'-formyl-1'-piperazinyl) carbonyl]methyl]-1',2',4'-trioxaspiro[4.5]decane (OZ294). To a solution of the OZ78 active ester (440 mg, 1.0 mmol) in CHCl$_3$ (20 ml) was added a solution of 1-piperazinecarboxaldehyde (137 mg, 1.2 mmol) in CHCl$_3$ (1 ml). The resulting mixture was stirred at rt for 2 h before removal of the solvent. The residue was crystallized from ethanol/water (1:2) to afford trioxolane OZ294 (242 mg, 58%, 2:1 mixture of rotamers) as a colorless solid. mp 142–144° C.; $^1$H NMR (500 MHz, CDCl$_3$) δ 1.15–1.32 (m, 2H), 1.45–2.09 (m, 21H), 2.20–2.28 (m, 2H), 3.32–3.78 (m, 8H), 8.10 (s, 1H); $^{13}$C NMR (125.7 MHz, CDCl$_3$) δ 26.46, 26.84, 30.27, 33.18, 34.01, 34.77, 36.38, 36.77, 39.26, 39.99, 40.22, 41.02, 42.15, 45.15, 45.33, 45.70, 46.25, 108.49, 111.39, 160.74, 160.92, 170.55, 170.72. Anal. Calcd for C$_{23}$H$_{34}$N$_2$O$_5$: C, 66.00; H, 8.19; N, 6.69. Found: C, 66.16; H, 7.95; N, 6.46.

cis-Adamantane-2-spiro-3'-8'-[[[(2'-pyridinylmethyl)amino]carbonyl]methyl]-1',2',4'-trioxaspiro[4.5]decane mesylate (OZ295). To a solution of the OZ78 active ester (440 mg, 1.0 mmol) in CHCl$_3$ (20 ml) was added a solution of 2-(aminomethyl)pyridine (130 mg, 1.2 mmol) in CHCl$_3$ (2 ml). The resulting mixture was stirred at rt for 2 h before being quenched with water (20 ml). After seperation of the organic layer, the aqueous layer was extracted with CHCl$_3$ (2×20 ml). The combined extracts were washed with water (2×30 ml) and brine (20 ml), dried over MgSO$_4$, filtered, and concentrated. The residue was dissolved in ether (10 ml) and CH$_2$Cl$_2$ (10 ml) and treated with a solution of methanesulfonic acid (96 mg, 1.0 mmol) in CH$_2$Cl$_2$ (1 ml). After evaporation of the solvents, the residue was crystallized from ether/ethanol (10:1) to afford trioxolane OZ295 (450 mg, 88%) as a colorless solid. mp 152–154° C.; $^1$H NMR (500 MHz, CDCl$_3$) δ 1.15–1.34 (m, 2H), 1.55–2.09 (m, 21H), 2.19 (d, J=7.1 Hz, 2H), 2.91 (s, 3H), 4.74 (d, J=6.0 Hz, 2H), 7.81 (dd, J=6.7, 6.7 Hz, 1H), 8.03 (d, J=8.0 Hz, 1H), 8.37 (dd, J=7.8, 7.8 Hz, 1H), 8.55 (t, J=5.9 Hz, 1H), 8.67 (d, J=5.5 Hz, 1H), 16.98 (br s, 1H); $^{13}$C NMR (1225.7 MHz, CDCl$_3$) δ 5 26.42, 26.81, 29.85, 33.24, 33.93, 34.74, 36.30, 36.75, 39.36, 40.87, 42.10, 108.46, 111.20, 125.19, 127.81, 141.32, 145.72, 154.52, 173.54. Anal. Calcd for C$_{25}$H$_{36}$N$_2$O$_7$S: C, 59.03; H, 7.13; N, 5.51. Found: C, 59.11; H, 7.15; N, 5.36.

cis-Adamantane-2-spiro-3'-8'-[[(3'-oxo-1'-piperazinyl)carbonyl]methyl]-1',2',4'-trioxaspiro[4.5]decane (OZ296). To a solution of the OZ78 active ester (440 mg, 1.0 mmol) in CHCl$_3$ (20 ml) was added piperazin-2-one (120 mg, 1.2 mmol). The resulting mixture was stirred at rt for 3 h before removal of the solvent. The residue was crystallized from ethanol/water (1:1) to afford trioxolane OZ296 (207 mg, 51%, 3:2 mixture of rotamers) as a colorless solid. mp 150–152° C.; $^1$H NMR (500 MHz, CDCl$_3$) δ 1.17–1.34 (m, 2H), 1.57–2.09 (m, 21H), 2.21 (d, J=6.8 Hz, 1.2H), 2.24 (d, J=6.8 Hz, 0.8H), 3.39 (s, 1.2H), 3.42 (s, 0.8H), 3.67 (t, J=5.0 Hz, 0.8H), 3.82 (t, J=5.4 Hz, 1.2H), 4.12 (s, 1.2H), 4.25 (s, 0.8H), 6.42 (s, 0.6H), 6.58 (s, 0.4H); $^{13}$C NMR (125.7 MHz, CDCl$_3$) δ 26.47, 26.85, 30.20, 30.26, 32.98, 34.00, 34.78, 36.38, 36.78, 38.31, 39.34, 39.48, 40.83, 41.34, 42.40, 46.06, 49.01, 108.46, 108.50, 111.35, 111.43, 166.60, 167.91, 170.37, 170.62. Anal. Calcd for C$_{22}$H$_{32}$N$_2$O$_5$: C, 65.32; H, 7.97; N, 6.93. Found: C, 65.17; H, 7.78; N, 6.79.

cis-Adamantane-2-spiro-3'-8'-[[(4'-hydroxy-1'-piperidinyl)carbonyl]methyl]-1',2',4'-trioxaspiro[4.5]decane (OZ297). To a solution of the OZ78 active ester (440 mg, 1.0 mmol) in CHCl$_3$ (20 ml) was added 4-hydroxypiperidine (121 mg, 1.2 mmol). The resulting mixture was stirred at rt for 1 h before being quenched with water (20 ml). After separation of the organic layer, the aqueous layer was extracted with CHCl$_3$ (2×20 ml). The combined extracts were washed with water (3×30 ml) and brine (20 ml), dried over MgSO$_4$, filtered, and concentrated. The residue was crystallized from ether/CHCl$_3$ (10:1) to afford trioxolane OZ297 (152 mg, 37%) as a colorless solid. mp 154–156° C.; $^1$H NMR (500 MHz, CDCl$_3$) δ 1.15–1.35 (m, 2H), 1.41–1.59 (m, 2H), 1.60–2.09 (m, 23H), 2.23 (d, J=7.1 Hz, 2H), 3.09–3.31 (m, 2H), 3.68–3.82 (m, 1H), 3.87–4.03 (m, 1H), 4.05–4.21 (m, 1H); $^{13}$C NMR (125.7 MHz, CDCl$_3$) δ 26.49, 26.86, 30.28, 33.39, 34.01, 34.07, 34.66, 34.78, 36.39, 36.80, 38.92, 39.22, 42.97, 67.20, 108.64, 111.32, 170.39. Anal. Calcd for C$_{23}$H$_{35}$NO$_5$: C, 68.12; H, 8.70; N, 3.45. Found: C, 68.19; H, 8.56; N, 3.26.

cis-Adamantane-2-spiro-3'-8'-[[[4'-(aminosulfonyl)phenyl]amino]methyl]-1',2',4'-trioxaspiro[4.5]decane (OZ298). A mixture of cis-adamantane-2-spiro-3'-8'-formyl-1',2',4'-trioxaspiro[4.5]decane (292 mg, 1.0 mmol), sulfanilamide (172 mg, 1.0 mmol), and acetic acid (60 mg, 1 mmol) in 1,2-dichloroethane (10 ml) under N$_2$ was stirred at rt for 10 min before sodium triacetoxyborohydride (322 mg, 1.5 mmol) was added. The resulting mixture was stirred at rt for 4 h, quenched with saturated aq. NaHCO$_3$ (15 ml), and concentrated to 16 ml. The precipitate was collected by filtration and recrystallized from hexanes/ether (5:1) to afford trioxolane OZ298 (220 mg, 49%) as a colorless solid. mp 153–155° C.; $^1$H NMR (500 MHz, CDCl$_3$) δ 1.19–1.41 (m, 2H), 1.55–2.09 (m, 21H), 3.05 (app t, J=6.2 Hz, 2H), 4.28 (s, 1H), 4.69 (s, 2H), 6.57 (d, J=8.5 Hz, 2H), 7.69 (d, J=8.8 Hz, 2H); $^{13}$C NMR (125.7 MHz, CDCl$_3$) δ 26.45, 26.85, 28.04, 33.78, 34.77, 34.78, 35.91, 36.38, 36.76, 48.84, 108.55, 111.51, 111.56, 128.45, 128.61, 151.72. Anal. Calcd for C$_{23}$H$_{32}$N$_2$O$_5$S: C, 61.58; H, 7.19; N, 6.24. Found: C, 61.61; H, 7.35; N, 6.30.

cis-Adamantane-2-spiro-3'-8'-[(2'-pyrimidinylsulfonyl)methyl]-1',2',4'-trioxaspiro[4.5]decane (OZ299). Step 1. To a mixture of OZ119 (cis-Adamantane-2-spiro-3'-8'-hydroxymethyl-1',2',4'-trioxaspiro[4.5]decane) (588 mg, 2 mmol) and triphenylphosphine (628 mg, 2.4 mmol) in benzene (10 ml) at rt under N$_2$ was added dropwise a solution of DIPAD (486 mg, 2.4 mmol) in benzene (2 ml). After 5 min, 2-pyrimidinethol (224 mg, 2 mmol) in benzene (5 ml) was added slowly over a period of 20 min. The stirring was continued for 24 h before removal of the solvent. The crude product was purified by flash chromatography (silica gel, 15% ethyl acetate in hexanes) to give cis-adamantane-2-spiro-3'-8'-[(2'-pyrimidinylthio)methyl]-1',2',4'-trioxaspiro[4.5]decane (420 mg, 54%) as a colorless solid. mp 140–142° C.; $^1$H NMR (500 MHz, CDCl$_3$) δ 1.21–1.42 (m, 2H), 1.60–2.11 (m, 21H), 3.09 (d, J=6.9 Hz, 2H), 6.95 (t, J=4.8 Hz, 1H), 8.50 (d, J=4.7 Hz, 2H). Step 2. To a solution of the above thioether (396 mg, 1.0 mmol) in CH$_2$Cl$_2$ (5 ml) at 0° C. was added dropwise a solution of 3-chloroperoxybenzoic acid (70% reagent, 790 mg, 3.2 mmol) in CHCl$_3$/CH$_2$Cl$_2$ (1:1, 16 ml). After 2 h, the mixture was allowed to warm up to rt and stirred overnight before being quenched with saturated aq. NaHCO$_3$ (40 ml). The organic layer was separated, and the aqueous layer was extracted with CHCl$_3$ (2×20 ml). The combined organic extracts were washed with water and brine, dried over MgSO$_4$, and concentrated. The crude product was purified by flash chromatography (silica gel, 20% to 50% ethyl acetate in hexanes) to afford trioxolane OZ299 (315 mg, 73%) as a colorless solid. mp 152–154° C.; $^1$H NMR (500 MHz, CDCl$_3$) δ 1.32–1.49 (m, 2H), 1.61–2.07 (m, 20H), 2.12–2.29 (m, 1H), 3.47 (d, J=6.8 Hz, 2H), 7.57 (dd, J=4.9, 4.9 Hz, 1H), 8.96 (d, J=4.9 Hz, 2H); $^{13}$C NMR (125.7 MHz, CDCl$_3$) δ 26.44, 26.82, 30.04, 30.87, 33.66, 34.76, 36.35, 36.75, 56.34, 107.78, 111.59, 123.71, 158.66, 166.30. Anal. Calcd for C$_{21}$H$_{28}$N$_2$O$_5$S: C, 59.98; H, 6.71; N, 6.66. Found: C, 60.16; H, 6.78; N, 6.77.

cis-Adamantane-2-spiro-3'-8'-[[(3'-carboxy-1'-oxopropyl)amino]methyl]-1',2',4'-trioxaspiro[4.5]decane (OZ300). To a solution of OZ209 (389 mg, 1 mmol) and triethylamine (101 mg, 1 mmol) in CH$_2$Cl$_2$ (10 ml) at 0° C. was added succinic anhydride (100 mg, 1 mmol). After being stirred at rt overnight, the reaction mixture was washed with water and brine, dried over MgSO$_4$, and concentrated to afford trioxolane OZ300 (160 mg, 41%) as a colorless solid. mp 152–154° C.; $^1$H NMR (500 MHz, DMSO-d$_6$) δ 0.92–1.11 (m 2H) 1.34–2.07 (m, 21H), 2.29 (t, J=7.0 Hz, 2H), 2.39 (t, J=6.8 Hz, 2H), 2.88 (app t, J=6.2 Hz, 2H), 7.82 (t, J=5.6 Hz, 1H), 12.02 (s, 1H); $^{13}$C NMR (125.7 MHz, DMSO-d$_6$) δ 25.97, 26.38, 27.61, 29.37, 30.14, 33.41, 34.41, 35.85, 35.91, 36.25, 43.86, 108.74, 110.59, 171.01, 173.98. Anal. Calcd for C$_{21}$H$_{31}$N$_{O6}$: C, 64.10; H, 7.94; N, 3.56. Found: C, 63.85; H, 7.86; N, 3.54.

cis-Adamantane-2-spiro-3'-8'-[(4'-pyridinyloxy)methyl]-1',2',4'-trioxaspiro[4.5]decane mesylate (OZ301). A mixture of diisopropyl azodicarboxylate (243 mg, 1.2 mmol) and triphenylphosphine (315 mg, 1.2 mmol) in THF (5 ml) under argon was stirred at 0° C. for 30 min before OZ119 (294 mg, 1 mmol) and 4-hydroxypyridine (114 mg, 1.2 mmol) were added. The resulting mixture was stirred at rt for 5 h. After concentration, the crude product was purified by flash chromatography (silica gel, 40% ethyl acetate in hexanes, then 2% to 6% MeOH in CH$_2$Cl$_2$) to give crude cis-adamantane-2-spiro-3'-8'-[(4'-pyridinyloxy)methyl]-1',2',4'-trioxaspiro[4.5]decane (eluted first) and pure trioxolane OZ302 (85 mg, 23%, eluted second) as a colorless solid. The crude cis-adamantane-2-spiro-3'-8'-[(4'-pyridinyloxy)methyl]-1',2',4'-trioxaspiro[4.5]decane was disolved in CH$_2$Cl$_2$/ether (1:3, 8 ml) and treated with a solution of methanesulfonic acid (77 mg, 0.8 mmol) in ether (2 ml). The precipitate was collected by filtration to afford trioxolane OZ301 (172 mg, 37%) as a colorless solid. For OZ301: mp 153–155° C.; $^1$H NMR (500 MHz, CDCl$_3$) δ 1.34–1.49 (m, 2H), 1.61–2.09 (m, 21H), 2.88 (s, 3H), 4.08 (d, J=6.3 Hz, 2H), 7.29 (d, J=7.3 Hz, 2H), 8.72 (d, J=6.89 Hz, 2H); $^{13}$C NMR (125.7 MHz, CDCl$_3$) δ 26.41, 26.48, 26.81, 33.46, 34.76, 35.60, 36.36, 36.71, 39.34, 74.77, 108.08, 111.66,112.64, 143.28, 171.01. Anal. Calcd for C$_{23}$H$_{33}$NO$_7$S: C, 59.08; H, 7.11; N, 3.00. Found: C, 58.89; H, 7.15; N, 3.09.

cis-Adamantane-2-spiro-3'-8'-[(4'-oxo-1'(4'H)-pyridinyl)methyl]-1',2',4'-trioxaspiro[4.5]decane (OZ302). For the preparation of OZ302, see OZ301. mp 138–140° C.; $^1$H NMR (500 MHz, CDCl$_3$) δ 1.17–1.35 (m, 2H), 1.59–2.03 (m, 21H), 3.60 (d, J=7.3 Hz, 2H), 6.39 (d, J=7.8 Hz, 2H), 7.22 (d, J=7.3 Hz, 2H); $^{13}$C NMR (125.7 MHz, CDCl$_3$) δ 26.40, 26.79, 27.33, 33.34, 34.74, 36.33, 36.69, 37.66, 62.30, 107.90, 111.77, 118.67, 139.88, 178.82. Anal. Calcd for C$_{22}$H$_{29}$NO$_4$.0.25CH$_2$Cl$_2$: C, 68.05; H, 7.57; N, 3.57. Found: C, 67.74; H, 7.37; N, 3.69.

cis-Adamantane-2-spiro-3'-8'-[(4'-formyl-1'-piperazinyl)methyl]-1',2',4'-trioxaspiro[4.5]decane (OZ303). A mixture of cis-adamantane-2-spiro-3'-8'-formyl-1',2',4'-trioxaspiro[4.5]decane (292 mg, 1.0 mmol), 1-piperazinecarboxaldehyde (114 mg, 1.0 mmol), and acetic acid (60 mg, 1.0 mmol) in 1,2-dichloroethane (10 ml) under N$_2$ was stirred at rt for 10 min before sodium triacetoxyborohydride (322 mg, 1.5 mmol) was added. The resulting mixture was stirred at rt for 4 h and then quenched with saturated aq. NaHCO$_3$ (15 ml). The organic layer was separated and the aqueous layer was extracted with CH$_2$Cl$_2$ (2×10 ml). The combined organic extracts were washed with water and brine, dried over MgSO$_4$, and concentrated. The crude product was triturated in hexanes/ether (2:1) to afford trioxolane OZ303 (240 mg, 61%) as a colorless solid. mp 140–142° C.; $^1$H NMR (500 MHz, CDCl$_3$) δ 1.08–1.25 (m, 2H), 1.42–2.07 (m, 21H), 2.16 (d, J=7.3 Hz, 2H), 2.35 (t, J=5.7 Hz, 2H), 2.39 (t, J=5.2 Hz, 2H), 3.36 (t, J=4.9 Hz, 2H), 3.54 (t, J=4.9 Hz, 2H), 8.01 (s, 1H); $^{13}$C NMR (125.7 MHz, CDCl$_3$) δ 26.48, 26.87, 28.50, 33.58, 33.99, 34.78, 34.80, 36.38, 36.79, 40.02, 45.69, 52.79, 54.19, 64.25, 108.98, 111.28, 160.67. Anal. Calcd for C$_{22}$H$_{34}$N$_2$O$_4$: C, 67.66; H, 8.78; N, 7.17. Found: C, 67.85; H, 8.62; N, 7.35.

cis-Adamantane-2-spiro-3'-8'-[[(2'-pyridinylcarbonyl)amino]methyl]-1',2',4'-trioxaspiro[4.5]decane (OZ304). To a mixture of picolinic acid (148 mg, 1.2 mmol), EDCI (290 mg, 1.5 mmol), and HOBt (200 mg, 1.5 mmol) in DMF (10 ml) under N$_2$ was added a solution of OZ209 (389 mg, 1.0 mmol) and triethylamine (101 mg, 1.0 mmol) in DMF (5 ml). The reaction mixture was stirred at rt for 16 h before removal of the solvents. The crude product was dissolved in CH$_2$Cl$_2$ (100 ml), washed with water and brine, dried over MgSO$_4$, and concentrated. Crystallization of the residue from acetone/water (1:4) gave trioxolane OZ304 (90 mg, 23%) as a colorless solid. mp 130–133° C.; $^1$H NMR (500 MHz, CDCl$_3$) δ 1.19–1.45 (m, 2H), 1.57–2.09 (m, 21H), 3.35 (app t, J=6.6 Hz, 2H) 7.42 (ddd, J=8.1, 4.4, 1.0 Hz, 1H), 7.85 (ddd, J=7.8,7.8, 1.7 Hz, 1H), 8.15 (br s, 1H), 8.20 (d, J=7.8 Hz, 1H), 8.55 (d, J=4.9 Hz, 1H); $^{13}$C NMR (125.7 MHz, CDCl$_3$) δ 26.47, 26.86, 27.87, 33.80, 34.78, 36.37, 36.51, 36.79, 44.68, 108.69, 111.34, 122.22, 126.09, 137.35, 148.02, 149.94, 164.32. Anal. Calcd for C$_{23}$H$_{30}$N$_2$O$_4$: C, 69.32; H, 7.59; N, 7.03. Found: C, 69.33; H, 7.45; N, 6.86.

cis-Adamantane-2-spiro-3'-8'-[[[(2'-aminoethyl)amino]carbonyl]methyl]-1',2',4'-trioxaspiro[4.5]decane p-tosylate (OZ305). To a solution of the OZ78 active ester (440 mg, 1.0 mmol) in CHCl$_3$ (15 ml) was added rapidly a solution of ethylenediamine (601 mg, 10 mmol) in ethanol (5 ml). The resulting mixture was stirred at rt for 2 h before being quenched with water (20 ml). After separation of the organic layer, the aqueous layer was extracted with CHCl$_3$ (2×20 ml). The combined extracts were washed with water (3×20 ml) and brine (20 ml), dried over MgSO$_4$, filtered, and concentrated. The residue was dissolved in CH$_2$Cl$_2$ (20 ml) and treated with a solution of p-toluenesulfonic acid monohydrate (191 mg, 1.0 mmol) in ethanol (2 ml). After evaporation of the solvents, the residue was treated with ether (20 ml), filtered, and washed with ether (20 ml) to afford trioxolane OZ305 (448 mg, 83%) as a colorless solid. mp 140–142° C.; $^1$H NMR (500 MHz, CDCl$_3$) δ 5.91–1.11 (m, 2H), 1.59–2.07 (m, 23H), 2.37 (s, 3H), 2.99–3.05 (m, 2H), 3.39–3.44 (m, 2H), 7.16 (d, J=7.8 Hz, 2H), 7.47 (s, 1H), 7.69 (d, J=7.8 Hz, 2H), 7.73 (s, 3H); $^{13}$C NMR (125.7 MHz, CDCl$_3$) δ 21.33, 26.48, 26.86, 29.73, 33.08, 33.84, 34.77, 36.37, 36.80, 36.98, 40.16, 42.46, 108.44, 111.15, 111.31, 125.73, 129.32, 140.71, 141.33, 173.94. Anal. Calcd for C$_{27}$H$_{40}$N$_2$O$_7$S: C, 60.42; H, 7.51; N, 5.22. Found: C, 60.47; H, 7.47; N, 4.83.

cis-Adamantane-2-spiro-3'-8'-[[[(2'-amino-2'-oxoethyl)amino]carbonyl]methyl]-1',2',4'-trioxaspiro[4.5]decane (OZ306). To a solution of glycinamide hydrochloride (221 mg, 2.0 mmol), triethylamine (304 mg, 3 mmol), ethanol (5 ml), and water (1 ml) in CHCl$_3$ (10 ml) was added the OZ78 active ester (440 mg, 1.0 mmol). The resulting mixture was stirred at rt for 17 h before being diluted with CHCl$_3$ (20 ml) and water (40 ml). After separation of the organic layer, the aqueous layer was extracted with CHCl$_3$ (3×10 ml). The combined extracts were washed with water (2×20 ml) and brine (2×20 ml), dried over MgSO$_4$, filtered, and concentrated. The residue was crystallized from 30% aq. ethanol to afford trioxolane OZ306 (284 mg, 75%) as a colorless solid. mp 130–132° C.; $^1$H NMR (500 MHz, CDCl$_3$) δ 1.11–1.38 (m, 2H), 1.42–2.07 (m, 21H), 2.15 (d, J=5.4 Hz, 2H), 3.95 (s, 2H), 5.84 (br s, 1H), 6.52 (br s, 1H), 6.73 (br s, 1H); $^{13}$C NMR (125.7 MHz, CDCl$_3$) δ 26.45, 26.84, 29.94, 33.47, 33.88, 34.75, 36.34, 36.77, 42.77, 42.88, 108.50, 111.33, 171.40, 172.88. Anal. Calcd for C$_{20}$H$_{30}$N$_2$O$_5$: C, 63.47; H, 7.99; N, 7.40. Found: C, 63.60; H, 8.10; N, 7.53.

cis-Adamantane-2-spiro-3'-8'-[(methylsulfonyl)methyl]-1',2',4'-trioxaspiro[4.5]decane (OZ307). Step 1. To a solution of sodium thiomethoxide (0.42 g, 6 mmol) in DMF (30 ml) was added dropwise a solution of the methanesulfonate of OZ119 (1.11 g, 3 mmol) in DMF (10 ml). The mixture was heated at 55° C. for 6 h before removal of the solvent. The residue was dissolved in $CH_2Cl_2$ (30 ml) and washed with water and brine, dried over $MgSO_4$, filtered, and concentrated. The crude product was purified by flash chromatography (silica gel, 90% ethyl acetate in hexanes) to afford cis-adamantane-2-spiro-3'-8'-[(methylthio)methyl]-1',2',4'-trioxaspiro[4.5]decane (0.35 g, 36%) as a colorless oil. $^1$H NMR (200 MHz, $CDCl_3$) δ 1.15–1.37 (m, 2H), 1.50–2.02 (m, 21H), 2.10 (s, 3H), 2.40 (d, J=7.0 Hz, 2H). Step 2. To a solution of the above thioether (350 mg, 1.08 mmol) in $CH_2Cl_2$ (5 ml) at 0° C. was added dropwise a solution of 3-chloroperoxybenzoic acid (70% reagent, 790 mg, 3.2 mmol) in $CHCl_3/CH_2Cl_2$ (1:1, 16 ml). After 2 h, the mixture was allowed to warm up to rt and stirred overnight before being quenched with saturated aq. $NaHCO_3$ (50 ml). The resulting mixture was concentrated to 50 ml and filtered. The collected precipitate was purified by flash chromatography (silica gel, 25% ethyl acetate in hexanes; then 5% MeOH in $CH_2Cl_2$) to afford trioxolane OZ307. (245 mg, 64%) as a colorless solid. mp 118–121° C.; $^1$H NMR (500 MHz, $CDCl_3$) δ 1.33–1.52 (m, 2H), 1.59–2.03 (m, 20H), 2.04–2.25 (m, 1H), 2.92 (s, 3H), 2.94 (d, J=6.4 Hz, 2H); $^{13}$C NMR (125.7 MHz, $CDCl_3$) δ 26.43, 26.81, 30.15, 30.78, 33.66, 34.75, 36.35, 36.73,42.16, 60.13, 107.72, 111.61. Anal. Calcd for $C_{18}H_{28}O_5S$: C, 60.65; H, 7.92. Found: C, 60.70; H, 7.75.

cis-Adamantane-2-spiro-3'-8'-[[(2'-amino-2'-oxoethyl)(methylsulfonyl)amino]methyl]-1',2',4'-trioxaspiro[4.5]decane (OZ308). To a solution of OZ256 (220 mg, 0.62 mmol) and triethylamine (202 mg, 2 mmol) in $CH_2Cl_2$ (10 ml) at 0° C. was added a solution of methanesulfonyl chloride (137 mg, 1.2 mmol) in $CH_2Cl_2$ (2 ml). The reaction mixture was stirred at rt for 4 h, diluted with $CH_2Cl_2$ (10 ml), washed with water and brine, dried over $MgSO_4$, filtered, and concentrated. The crude product was crystallized from $CH_2Cl_2$/hexanes (1:4) to afford trioxolane OZ308 (250 mg, 94%) as a colorless solid. mp 132–136° C.; $^1$H NMR (500 MHz, $CDCl_3$) δ 1.17–1.35 (m, 2H), 1.59–2.05 (m, 21H), 2.96 (s, 3H), 3.12 (d, J=7.3 Hz, 2H), 3.89 (s, 2H), 5.60 (s, 1H), 6.17 (s, 1H); $^{13}$C NMR (125.7 MHz, $CDCl_3$) δ 26.44, 26.84, 27.71, 33.55, 34.76, 36.36, 36.75, 37.97, 51.56, 54.89, 108.43, 111.44,170.70. Anal. Calcd for $C_{20}H_{32}N_2O_6S$: C, 56.05; H, 7.53; N, 6.54. Found: C, 56.22; H, 7.63; N, 6.71.

cis-Adamantane-2-spiro-3'-8'-[[(carboxymethyl)amino]methyl]-1',2',4'-trioxaspiro[4.5]decane mesylate (OZ309). A mixture of cis-adamantane-2-spiro-3'-8'-formyl-1',2',4'-trioxaspiro[4.5]decane (588 mg, 2.0 mmol), glycine (2.20 g, 20 mmol), acetic acid (180 mg, 3 mmol), and sodium cyanoborohydride (190 mg, 3 mmol) in methanol (100 ml) under Ar was stirred at rt for 16 h. The reaction mixture was concentrated, and the residue was triturated with water (50 ml). The solid was collected by filtration and washed with water and ether. The solid free base was suspended in methanol (10 ml), treated with a solution of methanesulfonic acid (91 mg, 0.95 mmol) in methanol (2 ml), and concentrated. The residue was crystallized from MeOH/ether (1:9) to afford trioxolane OZ309 (350 mg, 39%) as a colorless solid. mp 144–146° C.; $^1$H NMR (500 MHz, DMSO-$d_6$) δ 0.97–1.21 (m, 2H), 1.54–2.02 (m, 21H), 2.30 (s, 3H), 2.82 (d, J=5.9 Hz, 2H), 3.86 (s, 2H), 8.80 (s, 2H); $^{13}$C NMR (125.7 MHz, DMSO-$d_6$) δ 25.97, 26.37, 27.36, 32.59, 32.96, 34.41, 34.43, 35.91, 36.23, 47.46, 51.83, 108.21, 110.84, 168.26. Anal. Calcd for $C_{20}H_{33}NO_8S \cdot 0.5H_2O$: C, 52.61; H, 7.51; N, 3.07. Found: C, 52.27; H, 7.49; N, 3.15.

cis-Adamantane-2-spiro-3'-8'-[[(1'-methyl-1'H-imidazol-2'-yl)sulfonyl]methyl]-1',2',4'-trioxaspiro[4.5]decane (OZ310). Step 1. To a suspension of 60% NaH (160 mg, 4 mmol) in DMF (5 ml) under $N_2$ at 0° C. was added dropwise a solution of 2-mercapto-1-methylimidazole 456 mg, 4.0 mmol) in DMF (10 ml). The mixture was stirred for 1 h before a solution of the methanesulfonate of OZ119 (744 mg, 2 mmol) in DMF (4 ml) was added dropwise. The mixture was stirred at rt overnight and concentrated. The residue was dissolved in $CH_2Cl_2$ (30 ml), washed with water and brine, dried over $MgSO_4$, filtered, and concentrated. The crude product was purified by flash chromatography (silica gel, 25% ethyl acetate in hexanes) to afford cis-adamantane-2-spiro-3'-8'-[[(1'-methyl-1'H-imidazol-2'-yl)thio]methyl]-1',2',4'-trioxaspiro[4.5]decane (0.24 g, 30%) as a colorless solid. mp 140–142° C. $^1$H NMR (200 MHz, $CDCl_3$), 1.20–1.35 (m, 2H), 1.60–2.00 (m, 21H), 3.00 (d, J=6.8 Hz, 2H), 3.60 (s, 3H), 6.90 (s, 1H), 7.03 (s, 1H). Step 2. To a solution of the above thioether (250 mg, 0.6 mmol) in $CH_2Cl_2$ (5 ml) at 0° C. was added dropwise a solution of 3-chloroperoxybenzoic acid (70% reagent, 400 mg, 1.6 mmol) in $CHCl_3/CH_2Cl_2$ (1:1, 8 ml). After 2 h, the mixture was allowed to warm up to rt, stirred overnight, and concentrated to 3 ml. The residue was diluted with saturated aq. $NaHCO_3$ (20 ml) and extracted with $CH_2Cl_2$ (2×20 ml). The combined extracts were washed with water and brine, dried over $MgSO_4$, filtered, and concentrated. The crude product was purified by flash chromatography (silica gel, 10% to 50% ethyl acetate in hexanes) to afford trioxolane OZ310 (130 mg, 51%) as a colorless solid. mp 151–152° C.; $^1$H NMR (500 MHz, $CDCl_3$) δ 1.31–1.51 (m, 2H), 1.59–2.04 (m, 20H), 2.06–2.25 (m, 1H), 3.41 (d, J=6.3 Hz, 2H), 3.99 (s, 3H), 6.98 (s, 1H), 7.12 (s, 1H); $^{13}$C NMR (125.7 MHz, $CDCl_3$) δ 26.44, 26.84, 29.96, 30.89, 33.68, 34.76, 35.08, 36.35, 36.75, 59.99, 107.77, 111.55, 125.39, 128.96, 142.61. Anal. Calcd for $C_{21}H_{30}N_2O_5S$: C, 59.69; H, 7.16; N, 6.63. Found: C, 59.56; H, 7.10; N, 6.47.

cis-Adamantane-2-spiro-3'-8'-[[[4'-(aminocarbonyl)-1'-piperidinyl]carbonyl]methyl]-1',2',4'-trioxaspiro[4.5]decane (OZ311). To a solution of the OZ78 active ester (220 mg, 0.5 mmol) in $CHCl_3$ (10 ml) and ethanol (10 ml) was added isonipecotamide (128 mg, 1.0 mmol). The resulting mixture was stirred at rt for 4 h before removal of the solvents. The residue was crystallized from ethanol/water (2:1) to afford trioxolane OZ311 (164 mg, 76%) as a colorless solid. mp 149–151° C.; $^1$H NMR (500 MHz, $CDCl_3$) δ 1.161.32 (m, 2H), 1.58–2.06 (m, 25H), 2.22 (d, J=6.8 Hz, 2H), 2.39 (tt, J=11.2, 3.9 Hz, 1H), 2.69 (t, J=11.5 Hz, 1H), 3.06 (t, J=11.7 Hz, 1H), 3.92 (d, J=13.7 Hz, 1H), 4.60 (d, J=13.2 Hz, 1H), 5.54 (s, 2H); $^{13}$C NMR (125.7 MHz, $CDCl_3$) δ 26.46, 26.84, 28.60, 29.02, 30.25, 30.30, 33.31, 34.05, 34.77, 36.37, 36.78, 39.24, 41.04, 42.37, 45.15, 108.61, 111.31, 170.39, 176.16. Anal. Calcd for $C_{24}H_{36}N_2O_5$: C, 66.64; H, 8.39; N, 6.48. Found: C, 66.39; H, 8.46; N, 6.30.

cis-Adamantane-2-spiro-3'-8'-[[(4'-carboxy-1'-piperidinyl)carbonyl]methyl]-1',2',4'-trioxaspiro[4.5]decane (OZ312). To a solution of the OZ78 active ester (220 mg, 0.5 mmol), water (5 ml), and ethanol (10 ml) in $CHCl_3$ (10 ml) was added isonipecotic acid (129 mg, 1.0 mmol). The resulting mixture was stirred at rt for 16.5 h before removal of the solvents. The residue was crystallized from ethanol/water (1:1) to afford trioxolane OZ312 (179 mg, 82%) as a colorless solid. mp 159–161° C.; $^1$H NMR (500 MHz, $CDCl_3$) δ 1.18–1.35 (m, 2H), 1.58–2.06 (m, 25H), 2.24 (d, J=6.8 Hz, 2H), 2.60 (tt, J=10.7, 3.9 Hz, 1H), 2.86 (t, J=11.2 Hz, 1H), 3.14 (t, J=11.2 Hz, 1H), 3.85 (d, J=13.7 Hz, 1H), 4.44 (d, J=13.6 Hz, 1H); $^{13}$C NMR (125.7 MHz, $CDCl_3$) δ

26.48, 26.86, 27.72, 28.33, 30.27, 33.37, 34.06, 34.79, 36.39, 36.80, 39.23, 40.46, 40.93, 44.96, 108.62, 111.34, 170.53, 178.19. Anal. Calcd for $C_{24}H_{35}NO_6$: C, 66.49; H, 8.14; N, 3.23. Found: C, 66.28; H, 8.26; N, 3.13.

cis-Adamantane-2-spiro-3'-8'-[[[[2'-(4'-morpholinyl) ethyl]amino]carbonyl]methyl]-1',2',4'-trioxaspiro[4.5] decane p-tosylate (OZ313). To a solution of the OZ78 active ester (220 mg, 0.5 mmol) in $CHCl_3$ (10 ml) was added a solution of 4-(2-aminoethyl)morpholine (130 mg, 1.0 mmol) in $CHCl_3$ (1 ml). The resulting mixture was stirred at rt for 2 h before being quenched with water (20 ml). After separation of the organic layer, the aqueous layer was extracted with $CHCl_3$ (2×20 ml). The combined extracts were washed with water (3×20 ml) and brine (20 ml), dried over $MgSO_4$, and filtered. To the filtrate was added a solution of p-toluenesulfonic acid monohydrate (76 mg, 0.4 mmol) in ethanol (1 ml). After evaporation of the solvents, the residue was treated with ether (20 ml), filtered, and washed with ether (20 ml) to afford trioxolane OZ313 (191 mg, 62%) as a colorless solid. mp 130–132° C.; $^1$H NMR (500 MHz, $CDCl_3$) δ 1.07–1.29 (m, 2H), 1.55–2.04 (m, 21H), 2.08 (d, J=7.3 Hz, 2H), 2.39 (s, 3H), 2.81–3.05 (m, 2H), 3.27–3.42 (m, 2H), 3.61–3.82 (m, 4H), 3.89–4.09 (m, 4H), 7.23 d, J=7.8 Hz, 2H), 7.75 (d, J=7.8 Hz, 2H), 7.94 (br s, 1H), 10.56 (br s, 1H); $^{13}$C NMR (125.7 MHz, $CDCl_3$) δ 1.33, 26.46, 26.85, 29.77, 33.19, 33.53, 33.90, 34.76, 36.35, 36.78, 42.38, 52.73, 57.20, 63.67, 108.48, 111.17, 125.82, 129.14, 140.96, 174.20. Anal. Calcd for $C_{31}H_{46}N_2O_8S \cdot 0.5H_2O$: C, 60.47; H, 7.69; N, 4.55. Found: C, 60.26; H, 8.03; N, 4.36.

cis-Adamantane-2-spiro-3'-8'-[[[4'-(2'-pyrimidinyl)-1'-piperazinyl]carbonyl]methyl]-1',2',4'-trioxaspiro[4.5]decane (OZ314). To a solution of the OZ78 active ester (220 mg, 0.5 mmol) in $CHCl_3$ (10 ml) was added a solution of 1-(2-pyrimidyl)piperazine (164 mg, 1.0 mmol) in $CHCl_3$ (10 ml). The resulting mixture was stirred at rt for 2 h before removal of the solvent. The residue was crystallized from ethanol to afford trioxolane OZ314 (199 mg, 85%) as a colorless solid. mp 160–162° C.; $^1$H NMR (500 MHz, $CDCl_3$) δ 1.18–1.35 (m, 2H), 1.58–2.08 (m, 21H), 2.27 (d, J=6.8 Hz, 2H), 3.54 (t, J=5.2 Hz, 2H), 3.71 (t, J=5.2 Hz, 2H), 3.73–3.89 (m, 4H), 6.54 (dd, J=4.9, 4.9 Hz, 1H), 8.33 (d, J=4.4 Hz, 2H); $^{13}$C NMR (125.7 MHz, $CDCl_3$) δ 26.47, 26.85, 30.30, 33.32, 34.06, 34.77, 36.37, 36.79, 39.31, 41.40, 43.60, 43.81, 45.51, 108.60, 110.46, 111.32, 157.76, 161.51, 170.73. Anal. Calcd for $C_{26}H_{36}N_4O_4$: C, 66.64; H, 7.74; N, 11.96. Found: C, 67.03; H, 8.25; N, 11.84.

cis-Adamantane-2-spiro-3'-8'-[[[(trans-4'-aminocyclohexyl)amino]carbonyl]methyl]-1',2',4'-trioxaspiro[4.5]decane p-tosylate (OZ315). To a solution of the OZ78 active ester (220 mg, 0.5 mmol) in $CHCl_3$ (10 ml) was added rapidly a solution of trans-1,4-diaminocyclohexane (343 mg, 3.0 mmol) in $CHCl_3$ (10 ml). The resulting mixture was stirred at rt for 1 h and filtered. The filtrate was diluted with water (30 ml). After separation of the organic layer, the aqueous layer was extracted with $CHCl_3$ (2×10 ml). The combined extracts were washed with water (2×20 ml) and brine (20 ml), dried over $MgSO_4$, and filtered. To the filtrate was added a solution of p-toluenesulfonic acid monohydrate (50 mg, 0.26 mmol) in ethanol (1 ml). After evaporation of the solvents, the residue was treated with ether (20 ml), filtered, and washed with ether (20 ml) to afford trioxolane OZ315 (139 mg, 47%) as a colorless solid. mp 140° C. dec; $^1$H NMR (500 MHz, DMSO-$d_6$) δ 0.97–1.43 (m, 6H), 1.54–2.02 (m, 27H), 2.29 (s, 3H), 2.84–3.06 (m, 1H), 3.38–3.52 (m, 1H), 7.12 (d, J=7.8 Hz, 2H), 7.48 (d, J=7.8 Hz, 2H), 7.71 (s, 1H), 7.73 (s, 3H); $^{13}$C NMR (125.7 MHz, DMSO-$d_6$) δ 20.95, 25.97, 26.37, 29.26, 29.57, 30.16, 33.03, 33.58, 34.42, 35.92, 36.25, 42.10, 46.60, 48.75, 108.57, 110.63, 125.65, 128.25, 137.87, 145.76, 170.48. Anal. Calcd for $C_{31}H_{46}N_2O_7S$: C, 63.02; H, 7.85; N, 4.74. Found: C, 62.88; H, 7.68; N, 4.57.

cis-Adamantane-2-spiro-3'-8'-[[2'-[(3'-pyridinylcarbonyl) amino]acetyl]amino]methyl]-1',2',4'-trioxaspiro[4.5]decane mesylate (OZ316). To a solution of nicotinoylglycine (216 mg, 1.2 mmol), EDCI (290 mg, 1.5 mmol), and HOBt (200 mg, 1.5 mmol) in DMF (10 ml) under $N_2$ was added a solution of OZ209 (389 mg, 1.0 mmol) and triethylamine (101 mg, 1.0 mmol) in DMF (5 ml). The resulting mixture was stirred at rt for 16 h before being quenched with water (70 ml) and 1 M aq. NaOH (3 ml). The precipitate was collected by filtration, re-dissolved in $CH_2Cl_2$ (4 ml), and treated with a solution of methanesulfonic acid (94 mg, 0.98 mmol) in ether (12 ml). The precipitate was obtained by filtration to afford trioxolane OZ316 (420 mg, 76%) as a colorless solid. mp 142–145° C.; $^1$H NMR (500 MHz, DMSO-$d_6$) δ 0.95–1.23 (m, 2H), 1.41–1.97 (m, 21H), 2.38 (s, 3H), 2.94 (app t, J=6.3 Hz, 2H), 3.91 (d, J=5.3 Hz, 2H), 7.96 (br s, 1H), 8.02 (dd, J=5.9, 5.9 Hz, 1H), 8.69 (d, J=7.3 Hz, 1H), 8.94 (d, J=5.3 Hz, 1H), 9.19 (s, 1H), 9.22 (t, J=5.6 Hz, 1H); $^{13}$C NMR (125.7 MHz, DMSO-$d_6$) δ 26.00, 26.40, 27.63, 33.43, 34.44, 35.84, 35.94, 36.27, 42.82, 43.94, 108.76, 110.66, 125.99, 131.79, 141.26, 144.34, 147.12, 163.32, 168.40. Anal. Calcd for $C_{26}H_{37}N_3O_8S$: C, 56.61; H, 6.76; N, 7.62. Found: C, 56.51; H, 6.60; N, 7.56.

cis-Adamantane-2-spiro-3'-8'-[[[(1'-aminocyclopentyl) carbonyl]amino]methyl]-1',2',4'-trioxaspiro[4.5]decane (OZ317).

To a solution of 1-amino-1-cyclopentanecarboxylic acid (155 mg, 1.2 mmol), EDCI (290 mg, 1.5 mmol), and HOBt (200 mg, 1.5 mmol) in DMF (10 ml) under $N_2$ was added a solution of OZ209 (389 mg, 1.0 mmol) and triethylamine (101 mg, 1.0 mmol) in DMF (5 ml). The resulting mixture was stirred at rt for 16 h before being quenched with water (70 ml) and 3 M aq. NaOH (2 ml). The precipitate was collected by filtration and triturated with 50% aq. ethanol to afford trioxolane OZ317 (250 mg, 62%) as a colorless solid. mp 160–162° C. (50% aq. ethanol); $^1$H NMR (500 MHz, $CDCl_3$) δ 1.15–1.33 (m, 2H), 1.38–2.07 (m, 27H), 2.19–2.29 (m, 2H), 3.12 (app t, J=6.6 Hz, 2H), 7.90 (br s, 1H); $^{13}$C NMR (125.7 MHz, $CDCl_3$) δ 26.47, 26.86, 27.55, 33.60, 34.78, 34.79, 36.38, 36.77, 40.36, 48.54, 108.40, 111.50. Anal. Calcd for $C_{23}H_{36}N_2O_4$: C, 68.29; H, 8.97; N, 6.92. Found: C, 68.47; H, 8.70; N, 6.72.

cis-Adamantane-2-spiro-3'-8'-[[(3'-ethoxy-3'-oxopropyl) amino]methyl]-1',2',4'-trioxaspiro[4.5]decane p-tosylate (OZ318). To a mixture of cis-adamantane-2-spiro-3'-8'-formyl-1',2',4'-trioxaspiro[4.5]decane (292 mg, 1.0 mmol), β-alanine ethyl ester hydrochloride (154 mg, 1.0 mmol), and triethylamine (101 mg, 1.0 mmol) in 1,2-dichloroethane (15 ml) at rt under $N_2$ was added sodium triacetoxyborohydride (322 mg, 1.5 mmol). The resulting mixture was stirred at rt for 4 h, and then quenched with saturated aq. $NaHCO_3$ (20 ml) and 1 M. aq. NaOH (3 ml). The organic layer was separated, and the aqueous layer was extracted with $CH_2Cl_2$ (2×20 ml). The combined organic extracts were washed with water and brine, dried over $MgSO_4$, and concentrated. The crude product was dissolved in $CH_2Cl_2$ (2 ml) and added to a solution of p-toluenesulfonic acid monohydrate (170 mg, 0.89 mmol) in ether/$CH_2Cl_2$ (4:1, 5 ml). Hexanes (10 ml) was added, and the resulting solid was collected by filtration to afford trioxolane OZ318 (220 mg, 39%) as a colorless solid. mp 128–131° C.; $^1$H NMR (500 MHz, $CDCl_3$) δ 1.10–1.23 (m, 2H), 1.24 (t, J=7.1 Hz, 3H), 1.45–2.07 (m, 21H), 2.37 (s, 3H), 2.76–2.85 (m, 2H), 2.96 (app t, J=7.1 Hz, 2H), 3.25–3.34 (m, 2H), 4.13 (q, J=7.0 Hz, 2H), 7.20 (d, J=8.3 Hz, 2H), 7.71 (d, J=7.8 Hz, 2H), 8.60 (s, 2H); $^{13}$C NMR (125.7 MHz, CDCl$_3$) δ 14.05, 21.28, 26.43, 26.84, 27.66, 30.22, 33.04, 33.11, 34.73, 36.34, 36.74, 44.08, 53.62, 61.28, 107.91, 111.33, 125.78, 128.98, 140.61, 141.54, 170.62. Anal. Calcd for C$_{29}$H$_{43}$NO$_8$S: C, 61.57; H, 7.66; N, 2.48. Found: C, 61.79; H, 7.53; N, 2.50.

cis-Adamantane-2-spiro-3'-8'-[[(3'-amino-3'-oxopropyl)amino]methyl]-1',2',4'-trioxaspiro[4.5]decane mesylate (OZ319). A mixture of β-alaninamide hydrochloride (375 mg, 3 mmol), cis-adamantane-2-spiro-3'-8'-formyl-1',2',4'-trioxaspiro[4.5]decane (292 mg, 1 mmol), and NaBH$_3$CN (100 mg, 1.5 mmol) in methanol (15 ml) was stirred at rt for 2 days and then concentrated. The crude product was triturated with 0.5 M aq. NaOH, and the resulting solid was crystallized from ether/CH$_2$Cl$_2$ (9:1) to afford the trioxolane free amine (200 mg, 55%). To a solution of methanesulfonic acid (50 mg, 0.51 mmol) in ether (5 ml) was added a solution of the above free amine (179 mg, 0.49 mmol) in CH$_2$Cl$_2$ (2 ml). The solid was collected by filtration, washed with ether, and dried to afford trioxolane OZ319 (190 mg, 84%) as a colorless solid. mp 133–136° C.; $^1$H NMR (500 MHz, CDCl$_3$) δ 1.22–1.38 (m, 2H), 1.61–2.05 (m, 21H), 2.75 (s, 3H), 2.81–2.96 (m, 4H), 3.25 (br, s, 2H), 6.76 (s, 1H), 7.58 (s, 1H), 8.59 (br s, 2H); $^{13}$C NMR (125.7 MHz, CDCl$_3$) δ 26.43, 26.83, 27.57, 30.54, 33.28, 33.34, 34.76, 36.36, 36.74, 39.49, 44.94, 53.42, 107.89, 111.59, 173.76. Anal. Calcd for C$_{21}$H$_{36}$N$_2$O$_7$S: C, 54.76; H, 7.88; N, 6.08. Found: C, 54.60; H, 7.61; N, 6.06.

cis-Adamantane-2-spiro-3'-8'-(4'-aminocarbonyl-1'H-imidazol-1'-ylmethyl)-1',2',4'-trioxaspiro[4.5]decane (OZ320). To a mixture of OZ225 (cis-Adamantane-2-spiro-3'-8'-(4'-carboxy-1'H-imidazol-1'-ylmethyl)-1',2',4'-trioxaspiro[4.5]decane) (600 mg, 1.54 mmol), Boc$_2$O (375 mg, 2.02 mmol), ammonium bicarbonate (156 mg, 1.92 mmol) in acetonitrile (60 ml) under N$_2$ was slowly added pyridine (75 mg, 0.95 mmol). After completion of the addition, the reaction mixture was stirred at rt for 16 h before concentration. The crude product was dissolved in CH$_2$Cl$_2$ (50 ml), washed with water and brine, dried over MgSO$_4$, and concentrated to afford the corresponding anhydride of OZ225 (560 mg). A mixture of the above anhydride and ammonia (7 N in methanol, 3 ml) in CH$_2$Cl$_2$ (10 ml) was stirred at rt overnight and then filtered. The filtrate was concentrated and triturated with CH$_2$Cl$_2$/ether (1:2). The resulting solid was collected by filtration and dried to afford trioxolane OZ320 (250 mg, 42%) as a colorless solid. mp 152–155° C.; $^1$H NMR (500 MHz, CDCl$_3$) δ 1.19–1.34 (m, 2H), 1.54–2.07 (m, 21H), 3.81 (d, J=7.3 Hz, 2H), 5.46 (br s, 1H), 6.96 (s, 1H), 7.36 (s, 1H), 7.56 (s, 1H); $^{13}$C NMR (125.7 MHz, CDCl$_3$) δ 26.43, 26.82, 27.52, 33.40, 34.76, 36.34, 36.73, 37.66, 52.98, 108.06, 111.68, 122.65, 136.80, 137.06, 164.62. Anal. Calcd for C$_{21}$H$_{29}$N$_3$O$_4$.0.1CH$_2$Cl$_2$: C, 64.00; H, 7.43; N, 10.61. Found: C, 64.26; H, 7.13; N, 10.34.

cis-Adamantane-2-spiro-3'-8'-(5'-aminocarbonyl-1'H-imidazol-1'-ylmethyl)-1',2',4'-trioxaspiro[4.5]decane (OZ321). To a mixture of OZ231 (cis-Adamantane-2-spiro-3'-8'-(5'-carboxy-1'H-imidazol-1'-ylmethyl)-1',2',4'-trioxaspiro[4.5]decane) (350 mg, 0.9 mmol), Boc$_2$O (275 mg, 1.26 mmol), and ammonium bicarbonate (92 mg, 1.17 mmol) in DMF (2 ml) under N$_2$ was slowly added pyridine (50 mg, 0.6 mmol). After completion of the addition, the reaction mixture was stirred at rt for 16 h before ammonia (7 N in methanol, 1 ml) was added. The resulting mixture was stirred for 3 h and concentrated. The crude product was dissolved in CH$_2$Cl$_2$ (30 ml), washed with water and brine, dried over MgSO$_4$, and concentrated. Crystallization from 40% aq. ethanol/NEt$_3$ (9:1) afforded trioxolane OZ321 (50 mg, 14%) as a colorless solid. mp 148–150° C.; $^1$H NMR (500 MHz, CDCl$_3$) δ 1.18–1.32 (m, 2H), 1.54–2.07 (m, 21H), 4.18 (d, J=8.3 Hz, 2H), 5.68 (br s, 2H), 7.50 (s, 1H), 7.51 (s, 1H); $^{13}$C NMR (125.7 MHz, CDCl$_3$) δ 26.44, 26.83, 27.46, 33.49, 34.75, 36.35, 36.75, 37.03, 52.10, 108.39, 111.47, 124.40, 133.22, 142.17, 161.66. Anal. Calcd for C$_{21}$H$_{29}$N$_3$O$_4$.0.5H$_2$O: C, 63.62; H, 7.63; N, 10.60. Found: C, 63.58; H, 7.68; N, 10.28.

cis-Adamantane-2-spiro-3'-8'-[[[2'-(formylamino)acetyl]amino]methyl]-1',2',4'-trioxaspiro[4.5]decane (OZ322). To a solution of N-formylglycine (124 mg, 1.2 mmol), EDCI (290 mg, 1.5 mmol), and HOBt (200 mg, 1.5 mmol) in DMF (10 ml) under N$_2$ was added a solution of OZ209 (389 mg, 1.0 mmol) and triethylamine (101 mg, 1.0 mmol) in DMF (5 ml). The resulting mixture was stirred at rt for 16 h before being quenched with water (70 ml). The precipitate was collected by filtration and recrystallized from hexane/CH$_2$Cl$_2$ (4:1) to afford trioxolane OZ322 (270 mg, 71%) as a colorless solid. mp 125–129° C.; $^1$H NMR (500 MHz, CDCl$_3$) δ 1.15–1.33 (m, 2H), 1.45–2.07 (m, 21H), 3.14 (app t, J=6.4 Hz, 2H), 3.98 (d, J=4.9 Hz, 2H), 6.52 (s, 1H), 6.77 (s, 1H), 8.23 (s, 1H); $^{13}$C NMR (125.7 MHz, CDCl$_3$) δ 26.44, 26.84, 27.68, 33.68, 34.76, 36.19, 36.35, 36.75, 41.85, 44.86, 108.51, 111.40, 161.50, 168.26. Anal. Calcd for C$_{20}$H$_{30}$N$_2$O$_5$: C, 63.47; H, 7.99; N, 7.40. Found: C, 63.55; H, 8.02; N, 7.27.

cis-Adamantane-2-spiro-3'-8'-[4'-(2'-aminoethoxy)phenyl]-1',2',4'-trioxaspiro[4.5]decane mesylate (OZ323). Step 1. To a solution of OZ288 (1.07 g, 3 mmol), triphenylphosphine (1.26 g, 4.8 mmol), N-(2-hydroxyethyl)phthalimide (0.86 g, 4.5 mmol) in THF (20 ml) at 0° C. was added dropwise diisopropyl azodicarboxylate (0.98 g, 4.8 mmol). The mixture was stirred at rt for 36 h and concentrated. The residue was purified by flash chromatography (silica gel, 10% ethyl acetate in hexanes) followed by crystallization from ethanol/triethylamine (4:1) to afford the desired phthalimide derivative (180 mg, 12%) as a colorless solid. mp 142–144° C.; $^1$H NMR (500 MHz, CDCl$_3$) □ 1.62–2.02 (m, 22H), 2.43–2.48 (m, 1H), 4.09 (t, J=5.9 Hz, 2H), 4.20 (t, J=5.9 Hz, 2H), 6.80 (d, J=8.3 Hz, 2H), 7.07 (d, J=8.3 Hz, 2H), 7.71–7.73 (m, 2H), 7.84–7.86 (m, 2H). Step 2. A mixture of above phthalimide derivative (180 mg, 0.34 mmol) and hydrazine monohydrate (140 mg, 2.5 mmol) in chloroform/ethanol (7:3, 10 ml) was heated at 55–60° C. for 24 h. After being cooled to rt, the solid by-product was filtered off. The filtrate was diluted with CHCl$_3$ (10 ml), washed with water (2×20 ml) and brine (20 ml), dried over MgSO$_4$, and concentrated. The residue was dissolved in ether (4 ml) and then a solution of methanesulfonic acid (34 mg, 0.35 mmol) in ether (4 ml) was added. The solid was collected by filtration to afford trioxolane OZ323 (118 mg, 70%) as a colorless solid. mp 152–155° C.; $^1$H NMR (500 MHz, CDCl$_3$) δ 1.55–2.07 (m, 22H), 2.47 (t, J=12.0 Hz, 1H), 2.67 (s, 3H), 3.28–3.33 (m, 2H), 4.11 (s, 2H), 6.83 (d, J=8.3 Hz, 2H) 7.07 (d, J=8.8 Hz, 2H), 7.73 (s, 3H); $^{13}$C NMR (125.7 MHz, CDCl$_3$) δ 26.50, 26.90, 31.62, 34.69, 34.81, 36.42, 36.82, 39.18, 39.43, 41.99, 63.92, 108.34, 111.35, 114.71, 127.74, 139.44, 156.18. Anal. Calcd for C$_{25}$H$_{37}$NO$_7$S.0.17CH$_2$Cl$_2$: C, 59.29; H, 7.38; N, 2.75. Found: C, 59.49; H, 7.06; N, 2.81.

cis-Adamantane-2-spiro-3'-8'-[[(1'-oxido-2'-pyridinyl)sulfonyl]methyl]-1',2',4'-trioxaspiro[4.5]decane (OZ324). To a solution of OZ328 (280 mg, 0.69 mmol) in CH$_2$Cl$_2$ (5 ml) at 0° C. was added dropwise a solution of 3-chloroperoxybenzoic acid (70% reagent, 400 mg, 1.6 mmol) in CHCl₃/CH₂Cl₂ (1:1, 8 ml). After 2 h of stirring, the mixture was allowed to warm up to rt and stirred overnight before being diluted with saturated aq. NaHCO₃ (50 ml). The mixture was stirred for additional 1.5 h. The aqueous layer was extracted with CHCl₃ (3×15 ml). The combined organic solutions were washed with water and brine, dried over MgSO₄, filtered, and concentrated. The crude product was triturated with ether/hexanes (1:1, 10 ml) to afford trioxolane OZ324 (150 mg, 50%) as a colorless solid. mp 148–151° C.; $^1$H NMR (500 MHz, CDCl₃) δ 1.35–1.52 (m, 2H), 1.53–2.22 (m, 21H), 3.65 (d, J=6.8 Hz, 2H), 7.44 (ddd, J=7.8, 7.8, 1.0 Hz, 1H), 7.51 (ddd, J=6.8, 6.8, 2.0 Hz, 1H), 8.10 (dd, J=8.1, 1.8 Hz, 1H), 8.27 (d, J=6.3 Hz, 1H); $^{13}$C NMR (125.7 MHz, CDCl₃) δ 26.43, 26.83, 29.91, 30.95, 33.64, 34.75, 34.76, 36.34, 36.74, 58.48, 107.73, 111.54, 125.39, 127.57, 129.67, 141.15, 147.35. Anal. Calcd for C₂₂H₂₉NO₆S: C, 60.67; H. 6.71; N, 3.22. Found: C, 60.51; H, 6.63; N, 3.11.

cis-Adamantane-2-spiro-3'-8'-[(2'-pyrimidinyloxy) methyl]-1',2',4'-trioxaspiro[4.5]decane mesylate (OZ325). To a suspension of 60% NaH (80 mg, 2 mmol) in DMF (10 ml) under N₂ at 0° C. was added dropwise a solution of OZ119 (588 mg, 2 mmol) in DMF (20 ml). The mixture was stirred at rt for 1 h and cooled down to 0° C. After 2-chloropyrimidine (241 mg, 2 mmol) was added, the resulting mixture was stirred at rt overnight. Water (70 ml) was added, and the precipitate was collected by filtration. The crude product was dissolved in ether (20 ml) and added to a solution of methanesulfonic acid (170 mg, 1.77 mmol) in ether/CH₂Cl₂ (1:1, 4 ml). The solid was collected by filtration and dried to afford trioxolane OZ325 (530 mg, 57%) as a colorless solid. mp 133–135° C.; $^1$H NMR (500 MHz, CDCl₃) δ 1.27–1.41 (m, 2H), 1.62–2.04 (m, 21H), 2.93 (s, 3H), 4.42 (d, J=7.4 Hz, 2H), 7.31–7.36 (m, 1H), 8.94 (d, J=5.4 Hz, 2H), 11.28 (br s, 1H); $^{13}$C NMR (125.7 MHz, CDCl₃) δ 26.45, 26.51, 26.84, 33.40, 34.77, 35.29, 36.37, 36.75, 39.28, 74.65, 108.31, 111.55, 115.16, 159.43, 160.34. Anal. Calcd for C₂₂H₃₂N₂O₇S: C, 56.39; H, 6.88; N. 5.98. Found: C, 56.16; H, 6.72; N, 5.89.

cis-Adamantane-2-spiro-3'-8'-[(2'-pyrimidinylamino) methyl]-1',2',4'-trioxaspiro[4.5]decane (OZ326). A mixture of OZ209 (389 mg, 1 mmol), triethylamine (101 mg, 1 mmol), K₂CO₃ (276 mg, 2 mmol), and 2-chloropyrimidine (170 mg, 1.5 mmol) in DMF (15 ml) was heated at 50° C. for 20 h. The mixture was cooled to rt and diluted with water (70 ml). The precipitate was collected and triturated with ether/hexanes (1:1, 10 ml). The filtrate was concentrated, and the residue was purified by flash chromatography (silica gel, 1%–5% methanol in CH₂Cl₂) to afford trioxolane OZ326 (75 mg, 20%) as a colorless solid. mp 112–115° C.; $^1$H NMR (500 MHz, CDCl₃) δ 1.15–1.35 (m, 2H), 1.55–2.07 (m, 21H), 3.29 (app t, J=6.6 Hz, 2H), 5.23 (s, 1H), 6.51 (t, J=4.9 Hz, 1H), 8.26 (d, J=4.4 Hz, 2H); $^{13}$C NMR (125.7 MHz, CDCl₃) δ 26.47, 26.87, 27.86, 33.82, 34.78, 34.80, 36.26, 36.38, 36.80, 46.71, 108.81, 110.46, 111.31, 158.00, 162.48. Anal. Calcd for C₂₁H₂₉N₃O₃: C, 67.90; H, 7.87; N, 11.31. Found: C, 67.82; H, 7.82; N, 11.26.

cis-Adamantane-2-spiro-3'-8'-[[(2'S)-2'-aminocarbonyl-1'-pyrrolidinyl]methyl]-1',2',4'-trioxaspiro[4.5]decane p-tosylate (OZ327). A mixture of cis-adamantane-2-spiro-3'-8'-formyl-1',2',4'-trioxaspiro[4.5]decane (292 mg, 1.0 mmol), L-prolinamide (342 mg, 3.0 mmol), and NaBH₃CN (100 mg, 1.5 mmol) in methanol (20 ml) was stirred at rt overnight before removal of the solvent. The residue was diluted with saturated aq. NaHCO₃ (30 ml) and extracted with CHCl₃ (3×25 ml). The combined organic extracts were washed with water and brine, dried over MgSO₄, and concentrated. The crude product was dissolved in ethanol (10 ml) and added to a solution of p-toluenesulfonic acid monohydrate (570 mg, 3 mmol) in 50% aq. ethanol (20 ml). Water (10 ml) was added, and the resulting precipitate was collected by filtration to afford trioxolane OZ327 (235 mg, 42%) as a colorless solid. mp 171–173° C.; $^1$H NMR (500 MHz, CDCl₃) δ 1.03–1.22 (m, 2H), 1.51–1.94 (m, 23H), 1.95–2.06 (m, 1H), 2.28 (s, 3H), 2.32–2.44 (m, 1H), 3.01 (app t, J=5.9 Hz, 2H), 3.05–3.19 (m, 1H), 3.60–3.75 (m, 1H), 4.04 (app q, J=8.1 Hz, 1H), 7.10 (d, J=8.3 Hz, 2H), 7.46 (d, J=7.8 Hz, 2H), 7.81 (s, 1H), 8.05 (s, 1H), 8.96 (s, 1H); $^{13}$C NMR (125.7 MHz, CDCl₃) δ 520.94, 22.58, 25.96, 26.36, 26.59, 27.34, 27.67, 28.93, 32.39, 32.80, 33.00, 34.40, 35.89, 36.22, 54.77, 59.92, 67.78, 108.10, 110.85, 125.65, 128.20, 137.72, 145.98, 169.15. Anal. Calcd for C₂₉H₄₂N₂O₇S: C, 61.90; H, 7.52; N, 4.98. Found: C, 62.07; H, 7.42; N, 4.70.

cis-Adamantane-2-spiro-3'-8'-[[(1'-oxido-2'-pyridinyl) thio]methyl]-1',2',4'-trioxaspiro[4.5]decane (OZ328). To a solution of 2-mercaptopyridine-N-oxide sodium salt hydrate (0.68 g, 4.0 mmol) in DMF (20 ml) was added dropwise a solution of the methanesulfonate of OZ119 (0.8 g, 1.8 mmol) in DMF (5 ml). The mixture was stirred at 50–60° C. overnight and then concentrated. The residue was triturated sequentially with water, ether, and then 80% aq. ethanol. The solid was collected by filtration and dried to afford trioxolane OZ328 (0.25 g, 34%) as a colorless solid. mp 151–153° C.; $^1$H NMR (500 MHz, CDCl₃) δ 1.31–1.47 (m, 2H), 1.59–2.07 (m, 21H), 2.78 (d, J=6.8 Hz, 2H), 7.04 (dd, J=6.3, 6.3 Hz, 1H), 7.10 (d, J=8.3 Hz, 1H), 7.24 (dd, J=7.8, 7.8 Hz, 1H), 8.26 (d, J=6.4 Hz, 1H); $^{13}$C NMR (125.7 MHz, CDCl₃) δ 26.45, 26.84, 30.01, 33.81, 34.76, 35.46, 36.37, 36.55, 36.75, 108.29, 111.51, 120.15, 121.25, 125.58, 138.80, 152.58. Anal. Calcd for C₂₂H₂₉NO₄S: C, 65.48; H, 7.24; N, 3.47. Found: C, 65.40; H, 7.07; N, 3.56.

cis-Adamantane-2-spiro-3'-8'-[[(1'-piperazinylcarbonyl) amino]methyl]-1',2',4'-trioxaspiro[4.5]decane p-tosylate (OZ329). Step 1. A mixture of OZ209 (2.0 g, 5.0 mmol), pyridine (0.8 g, 10 mmol), 4-nitrophenyl chloroformate (2.02 g, 10 mmol) in CH₂Cl₂ (60 ml) was refluxed for 4.5 h, cooled to rt, and then diluted with CH₂Cl₂ (80 ml). The solution was washed with water and brine, dried over MgSO₄, filtered, and concentrated. The crude product was purified by flash chromatography (silica gel, 0–1% methanol in CH₂Cl₂) to afford the desired carbamate (1.36 g, 59%) as a colorless solid. mp 135–138° C.; $^1$H NMR (500 MHz, CDCl₃) δ 1.23–1.33 (m, 2H), 1.58–2.00 (m, 21H), 3.17 (t, J=6.3 Hz, 2H), 5.17 (br s, 1H), 7.31 (d, J=9.3 Hz, 2H), 8.24 (d, J=9.3 Hz, 2H). Step 2. A mixture of above carbamate (0.61 g, 1.3 mmol) and piperazine (1.15 g, 13 mmol) in CHCl₃ (10 ml) was stirred at rt for 2 h. The reaction mixture was diluted with CHCl₃ (25 ml), washed with water, 0.25 M aq. NaOH, water, and brine, dried over MgSO₄, filtered, and concentrated. The crude product was dissolved in ether (10 ml) and added to a solution of p-toluenesulfonic acid monohydrate (380 mg, 2 mmol) in methanol/CH₂Cl₂ (1:10, 11 ml). Ether (30 ml) was added. The precipitate was collected and dried to afford trioxolane OZ329 (530 mg, 71%) as a colorless solid. mp 165–167° C.; $^1$H NMR (500 MHz, DMSO-d₆) δ 0.91–1.09 (m, 2H), 1.32–1.97 (m, 21H), 2.28 (s, 3H), 2.87 (app t, J=6.1 Hz, 2H), 3.04 (br s, 4H), 3.46 (t, J=5.2 Hz, 4H), 6.71 (t, J=5.4 Hz, 1H), 7.11 (d, J=7.8 Hz, 2H), 7.47 (d, J=7.8 Hz, 2H), 8.64 (s, 2H); $^{13}$C NMR (125.7 MHz, DMSO-d₆) δ 20.96, 25.99, 26.40, 27.70, 33.48, 34.43, 35.94, 36.07, 36.27, 40.75, 42.84, 45.57, 108.87, 110.64, 125.67, 128.28, 137.91, 145.73, 157.19. Anal. Calcd for C₂₉H₄₃N₃O₇S: C, 60.29; H, 7.50; N, 7.27. Found: C, 60.37; H, 7.34; N, 7.19.

cis-Adamantane-2-spiro-3'-8'-[[[(3'-amino-2'-pyrazinyl) carbonyl]amino]methyl]-1',2',4'-trioxaspiro[4.5]decane (OZ330). To a solution of 3-amino-pyrazine-2-carboxylic acid (167 mg, 1.2 mmol), EDCI (290 mg, 1.5 mmol), and HOBt (200 mg, 1.5 mmol) in DMF (10 ml) under $N_2$ was added a solution of OZ209 (389 mg, 1.0 mmol) and triethylamine (101 mg, 1.0 mmol) in DMF (5 ml). The resulting mixture was stirred at rt for 16 h before being quenched with water (70 ml). The precipitate was collected by filtration, triturated with ether/hexanes (1:1), and crystallized from 95% aq. ethanol to afford trioxolane OZ330 (86 mg, 21%) as a colorless solid. mp 128–131° C.; $^1$H NMR (500 MHz, CDCl$_3$) δ 1.21–1.39 (m, 2H), 1.51–2.07 (m, 21H), 3.29 (app t, J=6.4 Hz, 2H), 7.78 (d, J=2.5 Hz, 1H), 7.99 (br s, 1H), 8.14 (d, J=2.5 Hz, 1H); $^{13}$C NMR (125.7 MHz, CDCl$_3$) δ 26.47, 26.87, 27.86, 33.78, 34.79, 36.38, 36.50, 36.79, 44.44, 108.63, 111.39, 126.61, 131.58, 146.58, 155.04, 166.04. Anal Calcd for $C_{22}H_{30}N_4O_4 \cdot 0.17CH_2Cl_2$: C, 62.11; H, 7.13; N, 13.07. Found: C, 61.86; H, 6.98; N, 13.40.

cis-Adamantane-2-spiro-3'-8'-[[(1'-methyl-1'H-tetrazol-5'-yl)thio]methyl]-1',2',4'-trioxaspiro[4.5]decane (OZ331). To a solution of 1-methyl-5-mercaptotetrazole, sodium salt dihydrate (0.70 g, 4.0 mmol) in DMF (20 ml) was added a solution of the methanesulfonate of OZ119 (0.90 g, 2.0 mmol) in DMF (5 ml). The mixture was stirred at 50–60° C. overnight and then concentrated. The residue was triturated with water, and the resulting solid was purified by repeated flash chromatography (silica gel, hexanes/ethyl acetate, 6:1; then silica gel, CH$_2$Cl$_2$/MeOH, 50:1) to afford trioxolane OZ331 (0.48 g, 61%) as a colorless solid. mp 146–149° C.; $^1$H NMR (500 MHz, CDCl$_3$) δ 1.26–1.41 (m, 2H), 1.59–2.07 (m, 21H), 3.28 (d, J=6.3 Hz, 2H), 3.91 (s, 3H); $^{13}$C NMR (125.7 MHz, CDCl$_3$) δ 26.43, 26.82, 29.18, 33.29, 33.67, 34.75, 35.81, 36.34, 36.74, 39.10, 108.27, 111.47, 154.42. Anal Calcd for $C_{19}H_{28}N_4O_3S$: C, 58.14; H, 7.19; N, 14.27. Found: C, 58.15; H, 7.04; N, 14.50.

cis-Adamantane-2-spiro-3'-8'-[[(1'-methyl-1'H-tetrazol-5'-yl)sulfonyl]methyl]-1',2',4'-trioxaspiro[4.5]decane (OZ332). To a solution of OZ331 (320 mg, 0.815 mmol) in CH$_2$Cl$_2$ (5 ml) at 0° C. was added dropwise a solution of 3-chloroperoxybenzoic acid (70% reagent, 630 mg, 2.8 mmol) in CHCl$_3$/CH$_2$Cl$_2$ (1:1, 12 ml). After 2 h, the mixture was allowed to warm up to rt, stirred at rt overnight, and diluted with saturated aq. NaHCO$_3$ (25 ml). The mixture was stirred for an additional 1.5 h. The aqueous layer was extracted with CH$_2$Cl$_2$ (2×15 ml). The combined organic solutions were washed with water and brine, dried over MgSO$_4$, filtered, and concentrated. The crude product was triturated with 60% aq. ethanol and recrystallized from CH$_2$Cl$_2$/95% aq. ethanol (1:4) to afford trioxolane OZ332 (260 mg, 75%) as a colorless solid. mp 140–141° C.; $^1$H NMR (500 MHz, CDCl$_3$) δ 1.42–1.56 (m, 2H), 1.64–2.09 (m, 20H), 2.16–2.28 (m, 1H), 3.63 (d, J=6.4 Hz, 2H), 4.36 (s, 3H); $^{13}$C NMR (125.7 MHz, CDCl$_3$) δ 26.42, 26.81, 29.86, 30.94, 33.55, 34.75, 36.05, 36.34, 36.72, 60.88, 107.42, 111.70, 153.70. Anal Calcd for $C_{19}H_{28}N_4O_5S$: C, 53.76; H, 6.65; N, 13.20. Found: C, 53.61; H, 6.46; N, 13.31.

cis-Adamantane-2-spiro-3'-8'-[[[(1'-aminocyclohexyl)carbonyl]amino]methyl]-1',2',4'-trioxaspiro[4.5]decane (OZ333). To a solution of 1-amino-1-cyclohexanecarboxylic acid (172 mg, 1.2 mmol), EDCI (290 mg, 1.5 mmol), and HOBt (200 mg, 1.5 mmol) in DMF (10 ml) under $N_2$ was added a solution of OZ209 (389 mg, 1.0 mmol) and triethylamine (101 mg, 1.0 mmol) in DMF (5 ml). The resulting mixture was stirred at rt for 16 h, quenched with water (70 ml), and basified with 1 M aq. NaOH (4 ml). The precipitate was collected by filtration and recrystallized from 40% aq. ethanol to afford trioxolane OZ333 (330 mg, 79%) as a colorless solid. mp 147–150° C.; $^1$H NMR (500 MHz, CDCl$_3$) δ 1.15–2.08 (m, 33H), 3.10 (app t, J=6.4 Hz, 2H), 7.93 (s, 1H); $^{13}$C NMR (125.7 MHz, CDCl$_3$) δ 21.24, 25.19, 26.46, 26.85, 27.73, 33.81, 34.67, 34.77, 36.37, 36.40, 36.78, 44.24, 57.32, 108.70, 111.28, 177.94. Anal Calcd for $C_{24}H_{38}N_2O_4$: C, 68.87; H, 9.15; N, 6.69. Found: C, 68.94; H, 9.07; N, 6.82.

cis-Adamantane-2-spiro-3'-8'-[(aminooxy)methyl]-1',2',4'-trioxaspiro[4.5]decane mesylate (OZ334). Step 1. To a solution of OZ119 (294 mg, 1 mmol), triphenylphosphine (393 mg, 1.5 mmol), N-hydroxyphthalimide (245 mg, 1.5 mmol) in THF (15 ml) at 0° C. was added dropwise diisopropyl azodicarboxylate (364 mg, 1.8 mmol). After the stirring was continued at rt for 16 h, the mixture was concentrated. The residue was purified by flash chromatography (silica gel, 14% ethyl acetate in hexanes) to afford the desired phthalimide derivative (440 mg, 100%) as a colorless solid. mp 155–157° C.; $^1$H NMR (500 MHz, CDCl$_3$) δ 1.31–1.39 (m, 2H), 1.68–2.00 (m, 21H), 4.02 (d, J=6.8 Hz, 2H), 7.73–7.76 (m, 2H), 7.82–7.84 (m, 2H). Step 2. A mixture of above phthalimide derivative (400 mg, 0.91 mmol) and hydrazine monohydrate (275 mg, 5.5 mmol) in chloroform/ethanol (7:3, 10 ml) was heated at 55–60° C. for 24 h. After being cooled to rt, the solid by-product was filtered off. The filtrate was diluted with CHCl$_3$ (10 ml), washed with water (2×20 ml) and brine (20 ml), dried over MgSO$_4$, and concentrated. The residue was dissolved in ether (8 ml), and then a solution of methanesulfonic acid (88 mg, 0.91 mmol) in CH$_2$Cl$_2$ (2 ml) was added. The resulting mixture was diluted with ether (8 ml), and the precipitate was collected by filtration to afford trioxolane OZ334 (250 mg, 69%) as a colorless solid. mp 125–126° C.; $^1$H NMR (500 MHz, CDCl$_3$) δ 1.19–1.36 (m, 2H), 1.58–2.07 (m, 21H), 2.82 (s, 3H), 3.91 (d, J=5.8 Hz, 2H), 10.21 (s, 3H); $^{13}$C NMR (125.7 MHz, CDCl$_3$) δ 26.43, 26.47, 26.86, 33.44, 34.68, 34.77, 36.37, 36.79, 39.44, 79.49, 108.33, 111.42. Anal Calcd for $C_{18}H_{31}NO_7S \cdot 0.13CH_2Cl_2$: C, 52.31; H, 7.57; N, 3.37. Found: C, 52.57; H, 7.06; N, 3.42.

cis-Adamantane-2-spiro-3'-8'-[[[(2'S)-2'-aminopropionyl]amino]methyl]-1',2',4'-trioxaspiro[4.5]decane (OZ335). To a solution of Fmoc-Ala-OH (375 mg, 1.2 mmol), EDCI (290 mg, 1.5 mmol), and HOBt (200 mg, 1.5 mmol) in DMF (10 ml) under $N_2$ was added a solution of OZ209 (389 mg, 1.0 mmol) and triethylamine (101 mg, 1.0 mmol) in DMF (5 ml). The resulting mixture was stirred at rt for 16 h before being quenched with water (70 ml). The precipitate was collected by filtration and dissolved in 10% piperidine in DMF (20 ml). The resulting mixture was stirred at rt overnight, diluted with water (70 ml), and extracted with CHCl$_3$ (3×30 ml). The combined extracts were washed with water and brine, dried over MgSO$_4$, and concentrated. The residue was triturated with hexanes to afford trioxolane OZ335 (100 mg, 27%) as a colorless solid. mp 115–117° C.; $^1$H NMR (500 MHz, CDCl$_3$) δ 1.15–1.31 (m, 2H), 1.34 (d, J=6.8 Hz, 3H), 1.41–2.05 (m, 23H), 3.12 (app t, J=6.4 Hz, 2H), 3.49 (q, J=7.0 Hz, 1H), 7.39 (s, 1H); $^{13}$C NMR (125.7 MHz, CDCl$_3$) δ 21.91, 26.47, 26.86, 27.75, 33.79, 34.78, 36.33, 36.38, 36.79, 44.16, 50.81, 108.66, 111.33, 175.60. Anal Calcd for $C_{20}H_{32}N_2O_4$: C, 65.91; H, 8.85; N, 7.69. Found: C, 66.08; H, 8.68; N, 7.59.

cis-Adamantane-2-spiro-3'-8'-[[[(3'-aminopropionyl)amino]methyl]-1',2',4'-trioxaspiro[4.5]decane p-tosylate (OZ336). To a solution of Fmoc-β-Ala-OH (375 mg, 1.2 mmol), EDCI (290 mg, 1.5 mmol), and HOBt (200 mg, 1.5 mmol) in DMF (10 ml) under $N_2$ was added a solution of OZ209 (389 mg, 1.0 mmol) and triethylamine (101 mg, 1.0 mmol) in DMF (5 ml). The mixture was stirred at rt for 16 h before being quenched with water (70 ml). The precipitate was collected by filtration and dissolved in 10% piperidine in DMF (20 ml). The resulting mixture was stirred at rt overnight, diluted with water (70 ml), and extracted with CHCl$_3$ (3×30 ml). The combined extracts were washed with water and brine, dried over MgSO$_4$, and concentrated. The residue was triturated with CH$_2$Cl$_2$/hexanes (1:10, 11 ml), and the solid was dissolved in CH$_2$Cl$_2$ (5 ml). After a solution of p-toluenesulfonic acid monohydrate (127 mg, 0.67 mmol) in methanol (2 ml) was added, the mixture was concentrated and triturated with CH$_2$Cl$_2$/ether (1:2, 15 ml) to afford trioxolane OZ336 (220 mg, 41%) as a colorless solid. mp 166° C. dec; $^1$H NMR (500 MHz, DMSO-d$_6$) δ 0.98–1.13 (m, 2H), 1.33–1.95 (m, 21H), 2.28 (s, 3H), 2.43 (t, J=6.8 Hz, 2H), 2.93 (app t, J=6.1 Hz, 2H), 2.94–3.02 (m, 2H), 7.11 (d, J=7.8 Hz, 2H), 7.47 (d, J=8.3 Hz, 2H), 7.64 (s, 3H), 8.08 (t, J=5.7 Hz, 1H); $^{13}$C NMR (125.7 MHz, DMSO-d$_6$) δ 20.95, 25.97, 26.38, 27.67, 32.00, 33.41, 34.42, 35.56, 35.79, 35.92, 36.25, 43.90, 108.71, 110.66, 125.68, 128.23, 137.79, 145.89, 169.53. Anal Calcd for C$_{27}$H$_{40}$N$_2$O$_7$S: C, 60.42; H, 7.51; N, 5.22. Found: C, 60.37; H, 7.31; N, 5.22.

cis-Adamantane-2-spiro-3'-8'-[[[(2'S)-2'-pyrrolidinylcarbonyl]amino]methyl]-1',2',4'-trioxaspiro[4.5]decane (OZ337). To a solution of Fmoc-Pro-OH (410 mg, 1.2 mmol), EDCI (290 mg, 1.5 mmol), and HOBt (200 mg, 1.5 mmol) in DMF (10 ml) under N$_2$ was added a solution of OZ209 (389 mg, 1.0 mmol) and triethylamine (101 mg, 1.0 mmol) in DMF (5 ml). The mixture was stirred at rt for 16 h before being quenched with water (70 ml). The precipitate was collected by filtration and dissolved in 10% piperidine in DMF (20 ml). The resulting mixture was stirred at rt overnight before being diluted with water (70 ml). The precipitate was collected by filtration and triturated twice with hexanes to afford trioxolane OZ337 (180 mg, 46%) as a colorless solid. mp 132–134° C.; $^1$H NMR (500 MHz, CDCl$_3$) δ 1.15–1.34 (m, 2H), 1.44–2.25 (m, 25H), 2.81–2.96 (m, 1H), 2.97–3.06 (m, 1H), 3.10 (app t, J=6.3 Hz, 2H), 3.66–3.80 (m, 1H), 7.72 (s, 1H); $^{13}$C NMR (125.7 MHz, CDCl$_3$) δ 26.20, 26.46, 26.85, 27.73, 30.78, 33.78, 33.79, 34.77, 36.36, 36.78, 44.03, 47.28, 60.64, 108.66, 111.29, 175.11. Anal Calcd for C$_{22}$H$_{34}$N$_2$O$_4$: C, 67.66; H, 8.78; N, 7.17. Found: C, 67.71; H, 8.65; N, 7.19.

cis-Adamantane-2-spiro-3'-8'-[[[(3'S)-3'-amino-1'-pyrrolidinyl]carbonyl]methyl]-1',2',4'-trioxaspiro[4.5]decane mesylate (OZ338). Step 1. To a solution of the OZ78 active ester (880 mg, 2 mmol) in CHCl$_3$ (40 ml) was added (3S)-3-(tert-butoxycarbonylamino)pyrrolidine (447 mg, 2.4 mmol). The resulting mixture was stirred at rt for 1 h before being evaporated. The residue was crystallized from 50% aq. ethanol (40 ml) to give the amide intermediate (577 mg, 59%, 2:1 mixture of rotamers). mp 97–100° C.; $^1$H NMR (500 MHz, CDCl$_3$) δ 1.16–1.32 (m, 2H), 1.45 (s, 9H), 1.60–2.06 (m, 22H), 2.09–2.27 (m, 3H), 3.21–3.41 (m, 1H), 3.43–3.62 (m, 2H), 3.64–3.79 (m, 1H), 4.09–4.28 (m, 1H), 4.49–4.73 (m, 1H); $^{13}$C NMR (125.7 MHz, CDCl$_3$) δ 26.48, 26.85, 28.34, 30.18, 30.23, 30.26, 32.38, 32.95, 33.00, 34.04, 34.05, 34.78, 36.38, 36.79, 40.65, 41.05, 43.56, 44.74, 52.71, 108.63, 108.65, 111.28, 111.32, 155.15, 170.97. Step 2. To a solution of the above amide (491 mg, 1.0 mmol) in ether (30 ml) was added a solution of methanesulfonic acid (481 mg, 5.0 mmol) in ether (20 ml). The resulting mixture was stirred at rt for 48 h. After the solvent was decanted off, the residue was washed with ether (20 ml) and crystallized from EtOAc/EtOH (3:1, 20 ml) to give trioxolane OZ338 (231 mg, 47%, 2:1 mixture of rotamers) as a colorless solid. mp 146° C. dec; $^1$H NMR (500 MHz, CDCl$_3$) δ 1.11–1.34 (m, 2H), 1.45–2.05 (m, 21H), 2.06–2.27 (m, 3H), 2.28–2.41 (m, 1H), 2.74 (s, 3H), 3.43–4.01 (m, 5H), 7.96 (s, 2H), 8.02 (s, 1H); $^{13}$C NMR (125.7 MHz, CDCl$_3$) δ 26.48, 26.87, 28.55, 30.11, 30.14, 30.18, 30.24, 30.31, 32.81, 32.86, 34.02, 34.08, 34.79, 36.39, 36.79, 39.39, 40.74, 40.99, 43.32, 44.32, 49.34, 49.38, 50.20, 50.94, 108.49, 108.60, 111.30, 111.35, 171.20, 171.83. Anal Calcd for C$_{23}$H$_{38}$N$_2$O$_7$S: C, 56.77; H, 7.87; N, 5.76. Found: C, 56.91; H, 7.66; N, 5.67.

cis-Adamantane-2-spiro-3'-8'-[[[(4'-amino-1'-piperidinyl)carbonyl]methyl]-1',2',4'-trioxaspiro[4.5]decane p-tosylate (OZ339). Step 1. To a solution of the OZ78 active ester (880 mg, 2 mmol) in CHCl$_3$ (40 ml) was added 4-(tert-butoxycarbonylamino)piperidine (481 mg, 2.4 mmol). The resulting mixture was stirred at rt for 1 h before being evaporated. The residue was crystallized from 50% aq. ethanol (80 ml) to give the amide intermediate (995 mg, 99%). mp 146–148° C.; $^1$H NMR (500 MHz, DMSO-d$_6$) δ 1.02–1.29 (m, 4H), 1.38 (s, 9H), 1.59–1.94 (m, 23H), 2.19 (d, J=6.8 Hz, 2H), 2.63 (dd, J=11.8, 11.8 Hz, 1H), 3.02 (dd, J=12.2, 12.2 Hz, 1H), 3.39–3.51 (m, 1H), 3.80 (d, J=13.7 Hz, 1H), 4.23 (d, J=13.2 Hz, 1H), 6.84 (d, J=7.8 Hz, 1H). Step 2. A mixture of the above amide (505 mg, 1 mmol) and p-toluenesulfonic acid monohydrate (951 mg, 5 mmol) in EtOAc/isopropanol (9:1, 50 ml) was stirred at rt for 48 h. The precipitate was filtered, washed with EtOAc (20 ml), dissolved in 20% aq. ethanol (90 ml), and basified with 14% aq. KOH (10 ml). The solid was filtered, dissolved in CHCl$_3$, dried over MgSO$_4$, and concentrated. To a solution of the above free base (170 mg) in EtOAc (10 ml) was added a solution of p-toluenesulfonic acid monohydrate (80 mg, 0.42 mmol) in EtOAc (10 ml). The precipitate was collected by filtration, washed with EtOAc (10 ml), and dried to give trioxolane OZ339 (180 mg, 31%) as a colorless solid. mp 154–156° C.; $^1$H NMR (500 MHz, DMSO-d$_6$) δ 1.05–1.18 (m, 2H), 1.20–1.29 (m, 1H), 1.30–1.42 (m, 1H), 1.59–1.97 (m, 23H), 2.22 (d, J=5.4 Hz, 2H), 2.29 (s, 3H), 2.57 (dd, J=11.8, 11.8 Hz, 1H), 3.02 (dd, J=12.2, 12.2 Hz, 1H), 3.24 (br s, 1H), 3.92 (d, J=13.7 Hz, 1H), 4.39 (d, J=13.2 Hz, 1H), 7.12 (d, J=7.8 Hz, 2H), 7.48 (d, J=7.8 Hz, 2H), 7.82 (s, 3H); $^{13}$C NMR (125.7 MHz, DMSO-d$_6$) δ 20.94, 25.97, 26.37, 29.61, 29.77, 30.48, 32.73, 33.67, 34.41, 35.93, 36.25, 38.37, 43.32, 47.66, 47.75, 108.58, 110.62, 125.64, 128.23, 137.81, 145.84, 169.78. Anal Calcd for C$_{30}$H$_{44}$N$_2$O$_7$S: C, 62.47; H, 7.69; N, 4.86. Found: C, 62.57; H, 7.54; N, 4.76.

cis-Adamantane-2-spiro-3'-8'-(2'-oxo-2'-hydrazinoethyl)-1',2',4'-trioxaspiro[4.5]decane (OZ340). To a stirred solution of the methyl ester of OZ78 (0.68 g, 2 mmol) in methanol (10 ml) and THF (5 ml) was added hydrazine monohydrate (3 ml, 60 mmol). The resulting mixture was heated at 50–60° C. for 24 h, then cooled to rt, and concentrated. The residue was dissolved in EtOAc (100 ml), washed with water (50 ml) and brine (50 ml), dried over MgSO$_4$, and filtered. After removal of the solvent, the crude product was purified by crystallization from CH$_2$Cl$_2$/EtOH to afford trioxolane OZ340 (0.56 g, 83%) as a colorless solid. mp 124–126° C.; $^1$H NMR (500 MHz, CDCl$_3$) δ 1.15–1.35 (m, 2H), 1.61–2.02 (m, 21H), 2.03 (d, J=6.8 Hz, 2H), 3.55–4.09 (m, 2H), 6.76 (s, 1H); $^{13}$C NMR (125.7 MHz, CDCl$_3$) δ 26.46, 26.85, 29.99, 33.36, 33.91, 34.77, 36.37, 36.77, 41.23, 108.43, 111.40, 172.77. Anal Calcd for C$_{18}$H$_{28}$N$_2$O$_4$: C, 64.26; H, 8.39; N, 8.33. Found: C, 64.12; H, 8.42; N, 8.12.

cis-Adamantane-2-spiro-3'-8'-(2'-oxo-2'-guanidinoethyl)-1',2',4'-trioxaspiro[4.5]decane (OZ341). A solution of potassium tert-butoxide (0.56 g, 5.0 mmol) and guanidine hydrochloride (0.48 g, 5.0 mmol) in dioxane (20 ml) was heated under N$_2$ at 50° C. for 20 min. After the mixture was cooled to rt, a solution of the OZ78 active ester (0.46 g, 1.05 mmol) in CHCl$_3$ (20 ml) was added dropwise. The mixture was stirred at rt for 4 h and then concentrated. After addition of water (30 ml), the resulting precipitate was collected, washed with water, and dried to give trioxolane OZ341 (0.36 g, 94%) as a colorless solid. mp 146–147° C.; $^1$H NMR (500 MHz, CDCl$_3$) δ 1.19–1.35 (m, 2H), 1.61–2.07 (m, 21H), 2.21 (d, J=7.3 Hz, 2H); $^{13}$C NMR (125.7 MHz, CDCl$_3$) δ 26.49, 26.89, 30.13, 33.71, 34.16, 34.80, 36.39, 36.82, 47.35, 108.87, 111.21, 161.10. Anal Calcd for C$_{19}$H$_{29}$N$_3$O$_4$: C, 62.79; H, 8.04; N, 11.56. Found: C, 63.00; H, 7.88; N, 11.42.

cis-Adamantane-2-spiro-3'-8'-[[(1',1'-dioxido-4'-thiomorpholinyl)carbonyl]methyl]-1',2',4'-trioxaspiro[4.5]decane (OZ342). Step 1. To a solution of the OZ78 active ester (0.5 g, 1.14 mmol) in CHCl$_3$ (15 ml) was added dropwise a solution of thiomorpholine (0.15 g, 1.45 mmol) in CHCl$_3$ (10 ml). The resulting mixture was stirred at rt for 1.5 h and then quenched with water (30 ml). After separation of the organic layer, the aqueous layer was extracted with CHCl$_3$ (2×20 ml). The combined extracts were washed with water (2×20 ml) and brine (20 ml), dried over MgSO$_4$, and filtered. After removal of the solvent, the crude product was purified by crystallization from ether to afford the thioether intermediate (0.45 g, 97%) as a colorless solid. mp 126–127° C.; $^1$H NMR (500 MHz, CDCl$_3$) δ 1.15–1.31 (m, 2H), 1.59–2.05 (m, 21H), 2.20 (d, J=6.8 Hz, 2H), 2.57–2.63 (m, 4H), 3.69–3.78 (m, 2H), 3.85–3.92 (m, 2H), $^{13}$C NMR (125.7 MHz, CDCl$_3$) δ 26.48, 26.86, 27.46, 27.94, 30.31, 33.21, 34.05, 34.79, 36.39, 36.79, 39.36, 44.29, 48.41, 108.59, 111.35, 170.40. Step 2. To a solution of the above thioether intermediate (0.39 g, 0.96 mmol) in CH$_2$Cl$_2$ (10 ml) at 0° C. was added dropwise a solution of m-CPBA (0.52 g, 2.1 mmol) in CH$_2$Cl$_2$ (15 ml). The resulting mixture was stirred at rt for 24 h and then partitioned between CH$_2$Cl$_2$ (20 ml) and saturated aq. NaHCO$_3$ (20 ml). The organic layer was washed with water (20 ml) and brine (20 ml), dried over MgSO$_4$, and filtered. After removal of the solvent, the crude product was purified by crystallization from CH$_2$Cl$_2$/EtOH to afford trioxolane OZ342 (0.34 g, 81%) as a colorless solid. mp 159–160° C.; $^1$H NMR (500 MHz, CDCl$_3$) δ 1.15–1.33 (m, 2H), 1.59–2.03 (m, 21H), 2.26 (d, J=6.8 Hz, 2H), 3.02 (s, 4H), 3.96 (s, 2H); $^{13}$C NMR (125.7 MHz, CDCl$_3$) δ 26.46, 26.85, 30.25, 33.07, 33.96, 34.78, 36.38, 36.77, 39.04, 40.22, 43.90, 52.14, 52.28, 108.35, 111.48, 170.54. Anal Calcd for C$_{22}$H$_{33}$NO$_6$S: C, 60.11; H, 7.57; N, 3.19. Found: C, 60.30; H, 7.43; N, 3.23.

EXAMPLE 2

Antimalarial Activity of OZ01–OZ342

Each trioxolane was screened against the chloroquine-resistant K1 and chloroquine-sensitive NF54 strains of *P. falciparum* in vitro. In the single dose STI in vivo screen, Moro SPF or NMRI mice infected with the ANKA strain of *P. berghei* (groups of three mice) were treated on day one post-infection with trioxolanes dissolved or suspended in 3% ethanol and 7% Tween 80. Trioxolanes were administered as single 10 mg/kg doses sc and po. Trioxolanes were also administered as single 10 mg/kg doses in standard suspending vehicle (SSV). SSV consists of 0.5% w/v CMC, 0.5% v/v benzyl alcohol, 0.4% v/v Tween 80, and 0.9% w/v sodium chloride in water. Antimalarial activity was measured by percent reduction in parasitemia on day three post-infection and survival times compared to an untreated control group. Survival to day 30 post-infection is considered to be a cure. In U.S. Pat. No. 6,486,199, Table 1 presented data for trioxolanes OZ01–OZ90 along with the controls, fenozan, artemisinin, arteether, artemether, and artesunate. The data showed that antimalarial activity falls off both when the trioxolane peroxide bond is too exposed or is sterically inaccessible to iron(II) species. Other factors influencing antimalarial activity include the stability of carbon radicals formed by β-scission subsequent to the initial electron transfer to the peroxide bond and the influence of steric effects remote from the peroxide bond on the interactions between carbon radicals and potential drug targets. The data also demonstrated that trioxolane carboxylic acids are usually less active than their hydrocarbon, ester, and hydroxamic acid counterparts.

Below is the activity data for OZ91–OZ342:

TABLE 1

| Compd | IC$_{50}$ (ng/ml) K1/NF54 | Activity (%) 10 mg/kg po/SSV po/sc | Survival (days) 10 mg/kg po/SSV po/sc |
|---|---|---|---|
| NONE | — | 0 | 6–7 |
| OZ91 | 1.4/0.42 | 20/0/85 | 5.7/6.0/7.3 |
| OZ92 | 1.6/0.40 | 81/35/99.98 | 6.7/6.3/10.0 |
| OZ93 | 3.3/0.92 | 57/3/100 | 6.7/6.0/13.3 |
| OZ94 | 57/28 | 21/0/11 | 6.0/5.7/5.3 |
| OZ95 | 2.8/1.3 | 31/0/49 | 6.0/6.0/6.0 |
| OZ96 | 8.4/>10 | 12/14/19 | 5.7/5.7/5.3 |
| OZ97 | 2.2/1.8 | 59/2/66 | 6.7/5.3/7.0 |
| OZ98 | 2.3/0.9 | 72/11/77 | 6.3/5.3/7.3 |
| OZ99 | 77/27 | 30/40/36 | 6.3/5.7/6.3 |
| OZ100 | 1.4/0.34 | 61/36/80 | 6.7/6.3/7.0 |
| OZ101 | 3.0/1.6 | 44/0/99.97 | 6.3/5.3/13 |
| OZ102 | 1.6/0.45 | 92/73/99.97 | 7.0/6.7/19.7 |
| OZ103 | 0.64/0.17 | 86/63/87 | 7.3/6.7/7.3 |
| OZ104 | 1.4/0.50 | 56/0/99.98 | 6.3/5.7/12.0 |
| OZ105 | 5.4/5.0 | 16/0/28 | 5.7/5.7/6.3 |
| OZ106 | 2.2/1.7 | 0/0/0 | 5.3/5.05.3 |
| OZ107 | 1.0/0.30 | 70/32/99.74 | 6.3/6.3/8.0 |
| OZ108 | 68/29 | 0/0/0 | 5.0/5.0/5.7 |
| OZ109 | 21/24 | 2/0/24 | 5.7/5.7/6.3 |
| OZ110 | 5.3/2.1 | 50/0/97.97 | 6.7/5.3/7.7 |
| OZ111 | 0.92/0.35 | 98/79/99.94 | 7.7/6.3/8.3 |
| OZ112 | >10/>10 | 6/0/36 | 5.7/5.7/6.3 |
| OZ113 | 0.95/0.20 | 92/96/89 | 7.3/8.0/7.3 |
| OZ114 | 3.7/2.2 | 0/0/99.64 | 5.7/6.0/8.7 |
| OZ115 | 11/6.9 | 33/0/97 | 6.3/5.7/7.3 |
| OZ116 | 4.2/3.3 | 97/96/96 | 7.7/8.3/8.0 |
| OZ117 | 2.1/1.2 | 95/96/99.94 | 7.0/7.7/8.7 |
| OZ118 | 1.0/0.24 | 99.0/98/99.57 | 7.0/8.0/8.3 |
| OZ119 | 0.83/0.20 | 99.29/99.15/99.66 | 7.7/8.0/8.3 |
| OZ120 | 1.2/0.59 | 33/8/96 | 6.0/5.7/8.0 |
| OZ121 | 0.96/0.41 | 91/98/99.61 | 7.3/8.0/7.3 |
| OZ122 | >100/>100 | 10/3/0 | 5.7/5.3/5.0 |
| OZ123 | 1.6/1.9 | 99.66/94/99.96 | 8.0/7.0/16 |
| OZ124 | 2.1/1.7 | 72/17/86 | 6.3/5.3/7.0 |
| OZ125 | 68/>100 | 8/0/0 | 5.3/5.7/6.0 |
| OZ126 | 0.20/0.50 | 55/72/99.44 | 7.0/6.7/8.5 |
| OZ127 | 0.61/1.3 | 95/98/97 | 7.0/7.7/7.7 |
| OZ128 | 0.59/1.1 | 99.93/99.95/99.98 | 8.3/8.7/11.7 |
| OZ129 | 10/>10 | 0/4/0 | 5.3/5.7/5.7 |
| OZ130 | 0.62/0.94 | 98.8/98.9/98.6 | 9.0/8.0/7.3 |
| OZ131 | 1.7/4.1 | 21/41/90 | 5.7/6.0/8.0 |
| OZ132 | 9.8/>10 | 38/0/40 | 6.3/5.7/6.3 |
| OZ133 | 0.70/1.1 | 94/97/72 | 7.0/7.3/7.0 |
| OZ134 | 0.88/1.1 | 72/27/99.95 | 6.3/6.0/15.3 |
| OZ135 | >100/>100 | 1/0/0 | 5.3/5.3/5.3 |
| OZ136 | 23/21 | 0/0/0 | 6.0/6.0/6.0 |
| OZ137 | 11/18 | 0/6/61 | 5.7/6.3/7.0 |
| OZ138 | 10/19 | 0/5/7 | 5.7/6.3/6.3 |
| OZ140 | 5.9/8.2 | 0/8/60 | 6.0/6.3/7.0 |
| OZ141 | 1.7/1.9 | 98/97/99.89 | 8.0/8.0/8.7 |
| OZ142 | 2.3/2.3 | 0/2/99.98 | 6.0/6.3/14.3 |
| OZ143 | 0.98/1.8 | 48/44/99.85 | 6.7/6.7/9.7 |
| OZ144 | 1.4/2.1 | 99.45/92/99.94 | 7.3/7.3/16.7 |
| OZ145 | 0.50/0.76 | 99.82/99.21/99.87 | 8.3/10.7/10.7 |
| OZ146 | 2.2/2.7 | 62/40/91 | 7.0/6.3/9.0 |
| OZ147 | 1.1/1.8 | 85/71/99.89 | 8.0/8.0/19.7 |
| OZ148 | 17/16 | 38/58/21 | 7.3/7.7/6.3 |
| OZ149 | 8.0/8.8 | 64/3/87 | 7.7/6.0/14.3 |
| OZ151 | 3.8/4.0 | 71/71/99.63 | 7.3/7.3/11.0 |
| OZ152 | 3.2/7.2 | 0/12/22 | 6.3/6.7/6.7 |
| OZ153 | 7.7/19 | 15/23/20 | 6.3/7.0/6.3 |
| OZ154 | 5.0/6.1 | 99.74/81/59 | 14.7/8.7/7.7 |
| OZ155 | 12/>10 | 53/53/73 | 6.3/7.0/8.3 |
| OZ156 | 2.1/2.1 | 99.98/98.8/99.98 | 17.0/10.3/19.7 |
| OZ157 | 0.20/0.22 | 90/80/97 | 7.3/8.3/8.3 |
| OZ159 | 0.70/0.94 | 34/31/98 | 6.7/6.7/9.0 |

TABLE 1-continued

| Compd | IC$_{50}$ (ng/ml) K1/NF54 | Activity (%) 10/3 mg/kg SSV po | Survival (days) 10/3 mg/kg SSV po |
|---|---|---|---|
| OZ160 | 0.70/0.87 | 45/43/99.94 | 6.3/6.7/12.0 |
| OZ161 | 0.40/0.50 | 59/46/99.96 | 7.0/6.7/12.7 |
| OZ162 | 0.50/0.71 | 41/22/99.55 | 6.3/6.3/9.3 |
| OZ163 | 0.2/0.2 | 99.90/99.94/100 | 8.0/9.0/9.7 |
| OZ164 | 9/>10 | 11/0/7 | 5.7/5.7/6.3 |
| OZ165 | 39/>10 | 18/3/9 | 6.3/6.0/5.7 |
| OZ166 | 28/>10 | 11/0/4 | 6.7/6.3/5.7 |
| OZ167 | 6.7/>10 | 0/6/97 | 6.0/6.0/7.3 |
| OZ169 | 15/>10 | 98/22/99.76 | 7.7/6.7/9.0 |
| OZ171 | 1.3/1.4 | 98/85/99.94 | 9.0/7.0/9.7 |
| OZ172 | 3.5/5.0 | 68/82/100 | 8.0/10.3/10.3 |
| OZ173 | 58/32 | 15/0/80 | 7.0/6.7/9.7 |
| OZ174 | 27/34 | 0/15/90 | 6.7/7.3/10.3 |
| OZ175 | 1.4/2.0 | 99.1/97/92 | 10.0/12.3/8.7 |
| OZ176 | 25/35 | 11/18/24 | 7.0/7.7/7.0 |
| OZ177 | 0.9/1.7 | 99.91/99.88/99.91 | 12.3/12.7/17.7 |
| OZ178 | 21/27 | 32/23/31 | 7.3/7.3/10.0 |
| OZ179 | 1.3/1.1 | 99.91/99.78/99.91 | 11.3/10.3/11.3 |
| OZ180 | 3.7/2.8 | 99.91/97/65 | 13.7/12.7/10.3 |
| OZ181 | 0.58/0.35 | 99.98/99.91/100 | 9.0/10.0/11.0 |
| OZ182 | 4.5/5.5 | 91/96/95 | 8.0/7.3/7.7 |
| OZ183 | 0.80/2.1 | 65/19/81 | 6.0/6.0/8.3 |
| OZ184 | 1.0/1.4 | 54/59/97 | 6.7/7.0/8.7 |
| OZ185 | 1.1/1.4 | 86/56/99.96 | 7.7/6.7/10.7 |
| OZ186 | >10/>10 | 87/96/67 | 8.0/9.0/8.0 |
| OZ187 | 4.0/6.8 | 77/94/77 | 7.7/10.0/7.0 |
| OZ188 | 1.5/3.0 | 93/98/99.87 | 8.7/10.0/9.0 |
| OZ189 | 1.7/3.0 | 95/99.79/98 | 9.3/9.0/10.7 |
| OZ190 | 0.16/1.0 | 98/78/2 | 8.7/7.7/5.7 |
| OZ191 | 6.0/>10 | 7/5/17 | 5.7/5.7/6.0 |
| OZ192 | 2.5/4.4 | 38/45/99.98 | 6.0/7.0/13.7 |
| OZ193 | 5.5/8.3 | 99.75/93/99.92 | 9.3/8.0/11.0 |
| OZ194 | 2.0/6.6 | 87/73/99.95 | 8.3/8.0/20.3 |
| OZ195 | 2.2/3.7 | 98/99.02/99.75 | 9.3/10.7/9.0 |
| OZ196 | >10/>10 | 10/0/17 | 6.0/5.3/5.7 |
| OZ197 | 1.0/2.0 | 87/90/99.54 | 7.7/8.7/10.3 |
| OZ198 | >10/>10 | 4/6/6 | 5.7/6.0/5.7 |
| OZ199 | 0.69/1.1 | 99.48/76/99.44 | 8.3/7.7/8.7 |
| OZ200 | 1.0/2.9 | 81/78/92 | 7.0/7.3/8.0 |
| OZ201 | 2.0/3.1 | 100/100/100 | 13/10.3/25 |
| OZ202 | 6.0/7.9 | 79/51/74 | 7.0/7.3/7.3 |
| OZ203 | 3.9/6.7 | 87/99.42/99.72 | 7.3/8.7/9.7 |
| OZ204 | >10/>10 | 0/0/0 | 6.0/6.3/6.0 |
| OZ205 | 1.5/2.0 | 99.96/99.94/99.96 | 10.0/8.7/9.7 |
| OZ206 | 1.0/2.7 | 93/92/91 | 8.0/8.7/9.7 |
| OZ207 | 0.33/0.57 | 99.96/99.98/99.98 | 9.3/12.0/11.3 |
| OZ208 | 6.0/6.5 | 0/29/10 | 6.3/6.7/5.7 |
| OZ209 | 0.21/0.32 | 99.94/99.96/99.97 | 9.5/10.0/12.5 |
| OZ210 | 1.4/1.6 | 99.23/77/99.94 | 9.3/8.0/10.3 |
| OZ211 | 1.0/1.2 | 82/78/99.90 | 8.0/7.3/8.7 |
| OZ212 | 2.7/2.9 | 66/25/59 | 6.7/6.7/8.0 |
| OZ213 | 2.3/2.8 | 83/74/85 | 8.0/8.0/8.0 |
| OZ214 | >10/>10 | 44/54/65 | 6.3/7.3/7.7 |
| OZ215 | 6.4/7.3 | 96/25/39 | 9.7/6.3/7.0 |
| OZ216 | 0.40/0.67 | 62/69/99.02 | 6.3/7.7/11.0 |
| OZ217 | 2.0/2.0 | 67/8/98 | 7.0/6.0/8.0 |
| OZ218 | 2.0/3.0 | 98/99.30/99.68 | 10.0/14.3/9.0 |
| OZ219 | 0.85/1.6 | 99.89/99.82/99.91 | 8.7/8.0/9.3 |
| OZ220 | 6.9/4.9 | 40/0/99.95 | 6.0/5.3/10.0 |
| OZ221 | >10/>10 | 80/87/97 | 6.3/7.0/8.0 |
| OZ222 | 3.9/6.3 | 87/75/99.76 | 7.7/7.0/10.0 |
| OZ223 | 4.0/>10 | 89/79/99.57 | 7.3/6.3/12.0 |
| OZ224 | 2.0/3.0 | 0/5/20 | 6.0/5.7/5.7 |
| OZ225 | 7.3/>10 | 0/0/17 | 5.7/5.7/6.3 |
| OZ226 | 4.0/4.0 | 0/0/99.92 | 5.0/5.3/11.0 |
| OZ227 | 0.20/0.20 | 99.68/99.90/99.84 | 8.3/9.3/10.7 |
| OZ228 | 2.0/2.1 | 99.94/28/99.94 | 10.3/6.0/14.0 |
| OZ229 | 0.24/0.23 | 99.96/99.08/99.98 | 10.0/8.3/12.7 |
| OZ230 | 3.9/3.6 | 0/0/0 | 5.3/5.7/5.7 |
| OZ231 | >10/>10 | 0/0/0 | 5.3/5.7/6.0 |
| OZ232 | 0.30/0.50 | 76/74/99.94 | 8.0/7.3/8.7 |
| OZ233 | 1.7/1.9 | 69/76/99.66 | 7.0/7.7/8.3 |
| OZ234 | 3.0/3.6 | 12/0/0 | 6.0/6.0/6.3 |
| OZ235 | 1.0/2.0 | 99.92/99.97/97 | 8.7/9.0/8.0 |
| OZ236 | 2.0/2.0 | 89/86/98.61 | 6.3/7.7/7.7 |
| OZ237 | 5.7/7.1 | 5/9/52 | 6.0/6.0/6.7 |
| OZ243 | 0.91/1.1 | 87/97/70 | 7.3/8.7/6.3 |
| OZ244 | 4.0/4.2 | 6/0/18 | 5.7/5.3/6.3 |
| OZ247 | 1.8/2.3 | 57/27/99.85 | 6.3/6.0/9.0 |
| OZ251 | 0.60/0.35 | 29/6/99.87 | 6.7/6.0/9.0 |
| OZ252 | 2.3/2.2 | 98.91/99.49/99.82 | 8.3/9.0/9.3 |
| OZ253 | 0.56/0.45 | 75/59/99.82 | 7.0/6.7/9.3 |
| OZ254 | >100/57 | 27/11/2 | 6.0/5.7/5.7 |
| OZ255 | 2.2/1.1 | 99.61/99.54/99.92 | 9.0/8.7/10.0 |
| OZ256 | 0.3/0.2 | 99.70/99.67/99.95 | 8.7/8.7/9.7 |
| OZ257 | 42/21 | 99.00/99.49/99.84 | 8.3/7.7/9.7 |
| OZ258 | 5.8/5.2 | 75/70/99.95 | 6.0/6.0/10.7 |
| OZ260 | 5.6/4.3 | 72/51/81 | 6.7/7.0/7.7 |
| OZ261 | 39/18 | 61/47/92 | 7.0/7.0/8.0 |
| OZ262 | 0.63/0.84 | 96/98/99.39 | 11.7/12.3/10.0 |
| OZ263 | 0.84/1.1 | 99.53/99.45/99.92 | 13.0/13.3/11.0 |
| OZ264 | 1.2/1.5 | 99.61/99.92/99.97 | 11.0/10.3/13.7 |
| OZ265 | 0.56/1.6 | 99/98/99.67 | 13.0/9.7/11.7 |
| OZ266 | 1.1/1.5 | 99/99.39/99.75 | 13.7/11.7/11.7 |
| OZ267 | 0.20/0.34 | 99.92/99.89/99.97 | 8.3/8.7/9.3 |
| OZ268 | 0.44/0.71 | 99.86/99.47/99.92 | 9.3/13.3/9.7 |
| OZ269 | 0.32/0.61 | 98/86/99.92 | 10.7/11.3/9.0 |
| OZ270 | 0.85/1.3 | 99.17/99.47/99.81 | 13.7/12.3/11.3 |

| Compd | IC$_{50}$ (ng/ml) K1/NF54 | Activity (%) 10/3 mg/kg SSV po | Survival (days) 10/3 mg/kg SSV po |
|---|---|---|---|
| OZ271 | 0.36/0.29 | 99.93/99.52 | 8.7/8.6 |
| OZ272 | 1.1/1.3 | 98/49 | 10.3/6.6 |
| OZ273 | 0.97/1.0 | 99.58/64 | 11.7/7.2 |
| OZ274 | 5.1/5.7 | 11/ND | 7.0/ND |
| OZ275 | 0.66/0.74 | 68/ND | 7.3/ND |
| OZ276 | 0.86/0.94 | 17/ND | 7.3/ND |
| OZ277 | 0.57/0.58 | 99.98/99.28 | 9.3/9.6 |
| OZ278 | 23/39 | 56/ND | 7.3/ND |
| OZ279 | 0.21/0.24 | 99.98/99.42 | 9.3/8.4 |
| OZ280 | 1.2/1.4 | 0/ND | 5.7ND |
| OZ281 | 0.50/0.30 | 99.87/96 | 8.7/10.2 |
| OZ282 | 2.0/2.4 | 98.5/53 | 8.3/7.2 |
| OZ283 | 1.7/2.0 | 99.81/56 | 8.3/8.2 |
| OZ284 | 1.0/1.4 | 97/61 | 9.0/7.8 |
| OZ285 | 1.3/1.8 | 99.81/72 | 8.7/7.6 |
| OZ286 | 0.94/1.6 | 99.73/60 | 8.7/7.0 |
| OZ287 | 0.49/0.83 | 95/68 | 8.3/7.2 |
| OZ288 | 1.7/2.7 | 99.96/82 | 11.0/8.0 |
| OZ289 | 0.40/0.56 | 99.94/92 | 13.4/7.4 |
| OZ290 | 0.42/0.45 | 99.64/95 | 9.0/7.0 |
| OZ291 | 0.52/0.72 | 98/34 | 8.0/6.8 |
| OZ292 | 0.19/0.26 | 74/46 | 7.0/6.6 |
| OZ293 | 0.25/0.34 | 99.58/77 | 8.8/7.4 |
| OZ294 | 0.39/0.63 | 99.79/70 | 8.6/7.4 |
| OZ295 | 0.44/0.75 | 47/35 | 7.0/6.4 |
| OZ296 | 0.60/0.89 | 99.22/90 | 10.0/9.2 |
| OZ297 | 0.49/0.76 | 99.69/83 | 9.8/7.6 |
| OZ298 | 2.0/3.0 | 99.95/98 | 9.4/9.0 |
| OZ299 | 6.8/6.3 | 36/0 | 6.6/6.4 |
| OZ300 | 71/97 | 6/0 | 6.8/7.0 |
| OZ301 | 2.1/2.8 | 100/97 | 11.8/8.4 |
| OZ302 | 1.9/2.9 | 99.60/88 | 9.0/9.0 |
| OZ303 | 1.6/2.4 | 99.01/69 | 8.6/7.6 |
| OZ304 | 1.6/2.3 | 98/61 | 8.2/8.8 |
| OZ305 | 1.8/1.9 | 99.93/96 | 9.2/9.6 |
| OZ306 | 3.9/3.6 | 99.58/87 | 9.2/8.2 |
| OZ307 | 0.62/0.88 | 98/74 | 9.4/7.8 |
| OZ308 | 1.2/1.7 | 86/30 | 7.8/6.6 |
| OZ309 | 11/17 | 99.80/86 | 8.8/7.8 |
| OZ310 | 0.82/1.1 | 81/38 | 7.8/8.2 |
| OZ311 | 1.2/1.8 | 80/40 | 8.6/7.0 |
| OZ312 | 19/27 | 43/13 | 7.2/6.2 |
| OZ313 | 0.55/0.76 | 98.9/58 | 10.4/7.4 |
| OZ314 | 11/17 | 13/11 | 6.6/6.6 |
| OZ315 | 2.8/3.0 | 99.97/92 | 11.2/9.6 |
| OZ316 | 1.0/1.7 | 69/7 | 10.0/8.0 |
| OZ317 | 0.33/0.36 | 99.92/99.20 | 9.8/10.0 |
| OZ318 | 0.56/0.82 | 88/29 | 12.4/7.6 |
| OZ319 | 0.41/0.91 | 99.92/99.14 | 10.6/10.8 |
| OZ320 | 0.68/1.30 | 99.76/92 | 10.4/11.8 |
| OZ321 | 0.58/0.97 | 99.77/64 | 14.0/9.8 |
| OZ322 | 0.90/1.5 | 98/61 | 10.0/9.4 |
| OZ323 | 0.85/1.1 | 99.98/99.92 | 15.6/9.2 |
| OZ324 | 2.4/3.4 | 60/26 | 9.4/7.4 |
| OZ325 | 0.62/1.4 | 99.43/30 | 8.8/6.2 |

TABLE 1-continued

| OZ326 | 0.65/1.2 | 80/7 | 7.4/6.0 |
| --- | --- | --- | --- |
| OZ327 | 0.85/1.1 | 97/72 | 9.8/7.0 |
| OZ328 | 1.4/3.0 | 99.77/75 | 8.6/7.6 |
| OZ329 | 0.43/0.68 | 99.97/99.50 | 11.2/9.2 |
| OZ330 | 0.55/1.2 | 99.96/82 | 12.2/7.2 |
| OZ331 | 0.50/1.2 | 99.47/66 | 9.0/7.0 |
| OZ332 | 1.7/2.5 | 8/0 | 6.0/6.0 |
| OZ333 | 0.24/0.44 | 99.86/96 | 9.2/8.0 |
| OZ334 | 28/20 | 47/13 | 6.8/6.6 |
| OZ335 | 0.29/0.28 | 99.95/97 | 9.2/10.0 |
| OZ336 | 1.4/0.91 | 99.93/98 | 9.2/9.6 |
| OZ337 | 0.29/0.25 | 99.92/97 | 8.6/11.6 |
| OZ338 | 0.38/0.45 | 99.93/99.80 | 9.8/8.0 |
| OZ339 | 0.35/0.39 | 99.95/99.65 | 10.2/9.2 |
| OZ340 | 4.9/2.9 | 93/36 | 9.2/6.4 |
| OZ341 | 2.4/2.0 | 97/32 | 8.0/7.0 |
| OZ342 | 1.8/1.2 | 27/0 | 6.8/6.4 |
| AM | 0.45/0.36 | 99.75/79 | 9.4/8.7 |
| AS | 1.4/1.5 | 87/66 | 7.0/8.0 |
| CQ | 76/4.4 | 99.92/82 | 9.0/8.0 |
| MFQ | 2.2/5.0 | 99.11/9 | 17/6.3 |

As shown in the inventors' earlier studies with OZ01 to OZ90, antimalarial activity falls off when the trioxolane peroxide bond is too exposed or is sterically inaccessible to iron(II) species. Other factors influencing antimalarial activity include the stability of carbon radicals formed by β-scission subsequent to the initial electron transfer to the peroxide bond and the influence of steric effects remote from the peroxide bond on the interactions between carbon radicals and potential drug targets. The new activity data demonstrates that trioxolane carboxylic acids are usually less active than their hydrocarbon, ester, amide, and hydroxamic acid counterparts. The position of ionizable functional groups such as carboxylic acids and amines is also critical to activity. The best combination of high intrinsic potency and good oral activity is found when a weak base functional group is present.

EXAMPLE 3

Onset of Action and Recrudescence of OZ11, OZ27, OZ78, OZ156, OZ175, OZ177, OZ207, OZ209, OZ277, and OZ279

Onset of Action and Recrudescence Experiments

The onset of drug action was determined after a single fixed dose of 100 mg/kg (SSV vehicle) po to groups of five animals on day +3 post-infection (day 0). Parasitemias at this point are usually between 25–40%. The infected controls do not survive beyond day +6 post-infection. The reduction of parasitemia is monitored 12, 24, and 48 h after treatment, and the time of recrudescence (>5% parasitemia) is assessed by daily blood smears for 14 days, followed by intermittent assessment for up to 60 days.

The onset part of this experiment reveals how rapidly a compound reduces parasite load; the recrudescence part of the experiment provides information about the efficacy of the compound against the parasite. A long delay in recrudescence can be due to a very good antiparasitic effect of the compound or to a compound with a long half-life.

Both the trioxolanes and the artemisinins produced a rapid decline in parasitemia, confirming that they are rapidly acting antimalarial agents. In contrast to both chloroquine and these peroxidic antimalarials, mefloquine has a slow onset of action. Recrudescence (>5% parasitemia) occurs quite rapidly for artemisinin and artesunate. The time of recrudescence increased for the more lipophilic artemisinin derivatives artemether and arteether.

In contrast to artemether, recrudescence occured much more slowly for the lipophilic trioxolanes OZ11 and OZ27; the recrudescence time for OZ27 was especially marked, superior to that of mefloquine. However, recrudescence times for the relatively polar trioxolanes OZ78, OZ175, and OZ277 were very similar to that of artemether. The more lipophilic trioxolane (OZ156) of the OZ156/OZ177 pair produced the longest delay in recrudescence, longer than chloroquine, but less than mefloquine. The recrudescence times for OZ177 and OZ279 were roughly equivalent to that of chloroquine.

Strikingly, there was no recrudescence observed for OZ207 and OZ209, two different salt forms (OZ207—tosylate, OZ209—mesylate) of aminomethyl trioxolane OZ163 (hydrochloride). The recrudescence data for these two trioxolanes suggests that they are either more powerful antimalarial agents or have longer half-lives than any of the semisynthetic artemisinins.

TABLE 2

| Compd | Time of Recrudescence (days) |
| --- | --- |
| OZ11 | 22.2 |
| OZ27 | 22.0 (3/5), >60 (2/5) |
| OZ78 | 11.2 |
| OZ156 | 19.0 (4/5), >60 (1/5) |
| OZ175 | 13.0 |
| OZ177 | 18.5 |
| OZ207 | >60 |
| OZ209 | >60 |
| OZ277 | 13.0 |
| OZ279 | 15.0 |
| Artemisinin | 8.4 |
| Artesunate | 8.6 |
| Artemether | 12.0 |
| Arteether | 11.4 |
| Chloroquine | 17.8 |
| Mefloquine | 28.0 |

EXAMPLE 4

Effect of Trioxolanes on Schistosoma Species

Effect of Trioxolane OZ207 on *Schistosoma japonicum*

TABLE 3

Comparative effect of OZ207 and artemether in mice infected with *Schistosoma japonicum*

| Drug | Age of worm | Dose (mg/kg × 1) | Mice without ♀ worm | MTWB/ x ± SD | WRR/% | MFWB/ x ± SD | FWR R/% |
| --- | --- | --- | --- | --- | --- | --- | --- |
| Control | — | — | 0/8 | 26.6 ± 4.2 | — | 11.6 ± 2.4 | — |
| OZ207 | 35 days | 200 | 4/7 | 9.1 ± 3.9 | 66 | 0.6 ± 0.7 | 95 |

TABLE 3-continued

Comparative effect of OZ207 and artemether in mice infected with Schistosoma japonicum

| Drug | Age of worm | Dose (mg/kg × 1) | Mice without ♀ worm | MTWB/ x ± SD | WRR/% | MFWB/ x ± SD | FWR R/% |
|---|---|---|---|---|---|---|---|
| OZ207 | 35 days | 400 | 4/6 | 4.3 ± 1.2 | 84 | 0.7 ± 1.2 | 94 |
| Artemether | 35 days | 400 | 0/7 | 10.1 ± 4.4 | 62 | 3.4 ± 1.6 | 71 |
| OZ207 | 7 days | 200 | 0/8 | 5.4 ± 2.4 | 81 | 2.1 ± 1.0 | 82 |

MTWB, mean total worm burden;
WRR, worm reduction rate
MFWB, mean female worm burden;
FWRR, female worm reduction rate.

Table 3 illustrates that the mean total worm burden and mean female worm burden in OZ207 400 mg/kg group was significantly lower than those in artemether 400 mg/kg group ($P<0.01$). The mean female worm burden in OZ207 200 mg/kg group was also significantly lower than that in artemether group ($P<0.01$).

Effect of Trioxolanes on 21-day-old Schistosomules

Mice were infected with 100 Schistosoma mansoni cercariae on day 21 post-treatment. Each group was treated per os with trioxolanes at a single dose of 200 mg/kg. Untreated mice served as the control. All groups were killed 4 weeks after treatment and the liver and intestine were removed and separated. The liver and intestine were compressed and alive male and female worms could be seen and counted. The effect of the compounds was evaluated by mean total and female worm burden. The results are shown in Table 5.

Effect of Trioxolanes on Adult Schistosomes (49-day-old)

Mice were infected with 100 Schistosoma mansoni cercariae on day 49 post-treatment. Each group was treated per os with OZ compounds at single doses of 200, 400, and 600 mg/kg. Untreated mice served as the control. All groups were killed 4 weeks after treatment and the liver and intestine were removed and separated. The liver and intestine were compressed and alive male and female worms could be seen and counted. The effect of the compounds was evaluated by mean total and female worm burden, and the results are set forth in Table 4.

TABLE 4

IN VIVO ACTIVITY AGAINST SCHISTOSOMA MANSONI (MICE INFECTED)

| OZ COMPOUNDS TESTED | % reduction of schistosomule growth at day 21 after per os application of 200 mg/kg | | % reduction of adult worms growth at day 49 after per os application of ... mg/kg | | |
|---|---|---|---|---|---|
| | TWR (%) | FWR (%) | 200 TWR (%)/ DEAD WORM (%) | 400 | 600 |
| OZ 03 liquid | 74 | 74 | | 29/8 | |
| OZ 04 | 7 | 7 | | 0/0 | |
| OZ 05 | 90 | 88 | 46/12 | 23/32* | 70/58 |
| OZ 10 | 66 | 73 | | 28/13 | 21/23 |
| OZ 11 | 85 | 84 | | 16/4 | |
| OZ 12 | 78 | 79 | | 14/0 | |
| OZ 14 | 7 | 0 | | 0/0 | |
| OZ 15 | 63 | 70 | | 0/10 | |
| OZ 16 | 78 | 77 | | ND | |

TABLE 4-continued

IN VIVO ACTIVITY AGAINST SCHISTOSOMA MANSONI (MICE INFECTED)

| OZ COMPOUNDS TESTED | % reduction of schistosomule growth at day 21 after per os application of 200 mg/kg | | % reduction of adult worms growth at day 49 after per os application of ... mg/kg | | |
|---|---|---|---|---|---|
| | TWR (%) | FWR (%) | 200 TWR (%)/ DEAD WORM (%) | 400 | 600 |
| OZ 17 | 23 | 7 | | 0/5 | |
| OZ 18 | 12 | 9 | | 0/0 | |
| OZ 19 | 77 | 74 | | ND | |
| OZ 20 | 0 | 0 | | 0/0 | |
| OZ 21 | 0 | 0 | | 0/0 | |
| OZ 22 liquid | 75 | 76 | | ND | |
| OZ 23 | 90 | 84 | | 0/4 | |
| OZ 24 | 65 | 61 | | 21/0 | |
| OZ 25 | 86 | 84 | | 46/34 | |
| OZ 26 | 37 | 40 | | ND | |
| OZ 27 | 63 | 58 | | 20/10 | |
| OZ 28 | 81 | 87 | | ND | |
| OZ 29 | 28 | 20 | | 0/0 | |
| OZ 30 | 16 | 12 | | ND | |
| OZ 31 | 60 | 63 | | 4/4 | |
| OZ 32 | 73 | 70 | | 27/28 | |
| OZ 33 | 28 | 14 | | ND | |
| OZ 35 | 73 | 63 | | ND | |
| OZ 36 | 16 | 12 | | 0/0 | |

IN VIVO ACTIVITY AGAINST SCHISTOSOMA MANSONI (MICE INFECTED)

| OZ COMPOUNDS TESTED | % reduction of schistosomule growth at day 21 after per os application of 200 mg/kg | | % reduction of adult worms growth at day 49 after per os application of ... mg/kg | | |
|---|---|---|---|---|---|
| | TWR (%) | FWR (%) | 200 TWR (%)/ DEAD WORM (%) | 400 | 600 |
| OZ 37 | 63 | 53 | | ND | |
| OZ 43 | ND | ND | | 1/0 | |
| OZ 49 | ND | ND | | 17/10 | |

-continued

IN VIVO ACTIVITY AGAINST SCHISTOSOMA MANSONI (MICE INFECTED)

| OZ COMPOUNDS TESTED | % reduction of schistosomule growth at day 21 after per os application of 200 mg/kg | | % reduction of adult worms growth at day 49 after per os application of ... mg/kg | | |
|---|---|---|---|---|---|
| | TWR (%) | FWR (%) | 200 TWR (%)/ DEAD WORM (%) | 400 | 600 |
| OZ 50 | ND | ND | 12/4 | | |
| OZ 56 | 69 | 66 | ND | | |
| OZ 61 | ND | ND | 8/21 | | |
| OZ 67 | ND | ND | 38/0 | | |
| OZ 68 | ND | ND | 17/0* | | |
| OZ 71 | 91 | 85 | 0/16 | | |
| OZ 72 | ND | ND | 0/10 | | |
| OZ 76 | ND | ND | 32/0 | | |
| OZ 78 | 82 | 87 | 24/29 | 0/17 | 0/14 |
| OZ 79 | ND | ND | 4/0 | | |
| OZ 80 | 79 | 75 | 0/3 | ND | |
| OZ 81 | ND | ND | 28/0 | | |
| OZ 83 | ND | ND | 7/19 | | |
| OZ 89 | 86 | 81 | 0/17 | | |
| OZ 90 | 81 | 79 | ND | | |
| OZ 105 | ND | ND | 8/0 | | |
| OZ 107 | ND | ND | 26/4 | | |
| OZ 108 | 30 | 28 | 28/0 | | |
| OZ 111 | 71 | 68 | ND | | |
| OZ 119 | 88 | 87 | ND | | |
| OZ 126 | ND | ND | 0/9 | | |
| OZ 130 | ND | ND | 0/8 | | |
| OZ 140 | ND | ND | 0/3 | | |
| OZ 145 | 80 | 83 | ND | | |
| OZ 148 | ND | ND | 25/0 | | |
| OZ 151 | 19 | 19 | ND | | |
| OZ 152 | 19 | 11 | ND | | |
| OZ 153 | ND | ND | no dead worm* | | |

IN VIVO ACTIVITY AGAINST SCHISTOSOMA MANSONI (MICE INFECTED)

| OZ COMPOUNDS TESTED | % reduction of schistosomule growth at day 21 after per os application of 200 mg/kg | | % reduction of adult worms growth at day 49 after per os application of ... mg/kg | | |
|---|---|---|---|---|---|
| | TWR (%) | FWR (%) | 200 TWR (%)/ DEAD WORM (%) | 400 | 600 |
| OZ 154 | ND | ND | 58/0* | | |
| OZ 156 | ND | ND | 0/6 | | |
| OZ 157 | 65 | 68 | ND | | |
| OZ 159 | 19 | 19 | ND | | |
| OZ 160 | 0 | 0 | ND | | |
| OZ 163 | 84 | 80 | ND | | |
| OZ 169 | 0 | 0 | ND | | |
| OZ 170 | ND | ND | 12/0 | | |
| OZ 189 | ND | ND | 0/30* | | |
| OZ 205 | 84 | 83 | 0/12 | | |
| OZ 207 | 93 | 100 | 32/17 | 35/21 | 11/24++ |
| OZ 209 | ND | ND | 39/34 | 16/28+ | 41/21++ |
| OZ 226 | ND | ND | 52/0* | | |
| OZ 256 | ND | ND | 10/19 | | |
| OZ 271 | ND | ND | 0/6 | | |
| OZ 277 | ND | ND | 0/0 | | |
| OZ 279 | ND | ND | 0/12 | | |
| OZ 281 | ND | ND | 12/15 | | |
| ARTEMETHER | (n2) 81 | (n2) 78 | (n2) 53/29 | | |
| PRAZIQUANTEL | ND | ND | 93/89 | 100/100 | |

TWR = Total worm reduction rate.
FWR = Female worm reduction rate.
DEAD WORM = Percentage of dead worm in the liver.
ND = Not determined
OZ 207 (base):
S. haematobium: 1 × 200 mg/kg p.o. = TWR 73%, DEAD WORM 68%
S. Japonicum: 1 × 200 mg/kg p.o. = TWR 66%, FWR 95% 1 × 400 mg/kg p.o. = TWR 84%, FWR 94%

EXAMPLE 5

Activity of Trioxolanes Against *P. berghei*

In the single dose $ED_{50}/ED_{98}/ED_{99}$ determinations, Moro SPF or NMRI mice (group of three) infected with the ANKA strain of *Plasmodium berghei* were treated on day one post-infection. Trioxolanes were dissolved or suspended in the standard suspending vehicle (SSV)* and administered as single 10, 6, 3, 1, 0.3, and 0.1 mg/kg doses po and sc. The SSV consists of 0.5% w/v CMC, 0.5% v/v benzyl alcohol, 0.4% v/v Tween 80, and 0.9% w/v sodium chloride in water. Antimalarial activity was measured by percent reduction in parasitemia on day three post-infection. The $ED_{50}/ED_{90}$ values were calculated by nonlinear fitting.

TABLE 5

| Compd | $ED_{50}$ (mg/kg) | $ED_{90}$ (mg/kg) | $ED_{99}$ (mg/kg) |
|---|---|---|---|
| OZ05 | 8.7 | 12 | 15 |
| OZ11 | 4.4 | 6.2 | 8.2 |
| OZ27 | 2.9 | 5.7 | 9.9 |
| OZ78 | 4.2 | 9.1 | 17 |
| OZ113 | 3.6 | 9.0 | 19 |
| OZ127 | 2.5 | 7.6 | 19 |
| OZ156 | 1.3 | 2.6 | 4.7 |
| OZ175 | 3.5 | 6.2 | 9.9 |
| OZ177 | 2.1 | 3.7 | 5.8 |
| OZ179 | 1.4 | 3.3 | 6.6 |
| OZ181 | 0.63 | 1.8 | 4.0 |
| OZ205 | 1.6 | 3.3 | 6.0 |
| OZ207 | 0.37 | 1.2 | 3.0 |
| OZ209 | 0.55 | 1.4 | 3.0 |
| OZ219 | 1.6 | 3.0 | 5.2 |
| OZ227 | 2.3 | 4.0 | 6.2 |
| OZ235 | 4.0 | 7.1 | 11 |
| OZ277 | 0.78 | 2.0 | 4.4 |
| OZ279 | 0.63 | 1.8 | 3.9 |
| Artesunate | 4.7 | 19 | 60 |
| Artelinate | 4.8 | 10 | 18 |
| Artemether | 2.2 | 4.2 | 7.1 |

TABLE 5-continued

| Compd | $ED_{50}$ (mg/kg) | $ED_{90}$ (mg/kg) | $ED_{99}$ (mg/kg) |
|---|---|---|---|
| Chloroquine | 1.8 | 3.5 | 5.9 |
| Mefloquine | 4.0 | 5.4 | 6.8 |

Table 5 shows ED50/ED90/ED99 data obtained by po administration of trioxolanes in the SSV formulation. The relatively lipophilic artemether is substantially more active than the more polar artesunate and artelinate. In contrast, the most active trioxolanes (OZ181, OZ207, OZ209)—different salt forms of the same amino trioxolane, and amino and amide trioxolanes OZ277 and OZ279, are relatively polar compounds.

EXAMPLE 6

Dosing of OZ279, OZ277, OZ256, and OZ209

Based on results of dosing OZ279, OZ277, OZ256, and OZ209 in rats and dogs, the inventors determined projected optimal dosing of the same compounds in humans. Artesunate is listed as a reference compound.

TABLE 6

| Parameter | Ideal | Accept | Artes | OZ 279 | OZ 277 | OZ 256 | OZ 209 |
|---|---|---|---|---|---|---|---|
| Rat Data | | | | | | | |
| IV t1/2 (10 mg/kg) | 180 min | 60 min | 40 (DHA) | 100.5 | 77.2 | 94.0 | 150.0 |
| Oral Bioavailability | | | | | | | |
| 10 mg/kg | >30% | >20% | not done | 37.2 | 36.9 | 18.6 | 12.4 |
| 25 mg/kg | >30% | >20% | 21 (DHA) | 71.1 | 44.1 | 51.9 | 22.4 |
| Oral t1/2 (25 mg/kg) | 180 min | 60 min | not done | 166.8 | 90.5 | 73.3 | 101.5 |
| Dog Data | | | | | | | |
| IV t1/2 (10 mg/kg) | 180 min | 60 min | not done | 177.5 | 95.0 | 85.4 | 182.8 |
| Oral Bioavailability | | | | | | | |
| 10 mg/kg | >30% | >20% | not done | 32.8 (V) | 87.9 | 42.0 (V) | 24.5 (V) |
| 25 mg/kg | >30% | >20% | not done | 55.7 (V) | 96.1 | 38.3 (V) | 15.9 (V) |
| Oral t1/2 (10 mg/kg) | 180 min | 60 min | not done | 195.3 | 148.1 | 82.8 | 127.3 |
| Human Data | | | | | | | |
| Projected daily dose mg/day (% BA) | 150 mg | 300 mg | 150–300 (actual) | 105–154 (30%) | 28–56 (30%) | 91–133 (20%) | 35–70 (20%) |

EXAMPLE 7

Effectiveness of Selected OZ Compounds in the Treatment and Prophylaxis of Malarial Infections In vitro Antimalarial Assays Various OZ compounds were tested by the semiautomated microdilution assay against intraerythrocytic forms of *Plasmodium falciparum* derived from asynchronous stock cultures. The culture medium used was RPMI 1640 supplemented with 10% human type $A^+$ serum, 25 mM HEPES, 25 mM $NaHCO_3$ (pH 7.3). Human type $A^+$ erythrocytes served as host cells. The culture was kept at 37° C. in an atmosphere of 3% $O_2$, 4% $CO_2$, and 93% $N_2$ in humidified modular chambers.

Compounds were dissolved in DMSO (10 mg/ml), prediluted in complete culture medium, and titrated in duplicate in serial twofold dilutions over a 64-fold range in 96-well microtiter plates. After addition of the parasite cultures with an initial parasitemia (expressed as the percentage of erythrocytes infected) of 0.75% in a 2.5% erythrocytes suspension, the test plates were incubated under the conditions described above for 72 h. Growth of the parasites cultures was measured by the incorporation of radiolabelled [$^3$H]-hypoxanthine added 16 h prior to termination of the test. Fifty percent inhibitory concentration ($IC_{50}$) were estimated by Logit regression analysis. Compounds were tested against reference *P. falciparum* strains, K1 strain (Thailand resistant to chloroquine) and NF54 strain (an airport strain of unknown origin that is sensitive to standard antimalarials).

In vivo Antimalarial Assays

Moro NMRI male mice (Fu Albino specific pathogen free) weighing 18±2 g were infected intravenously (i.v.) with $2 \times 10^7$ *P. berghei* ANKA strain-infected erythrocytes from donor mice on day 0 of the experiment. From donor mice with circa 30% parasitemia, heparinized blood was taken and diluted in physiological saline to $10^8$ parasitized erythrocytes per ml. An aliquot (0.2 ml) of this suspension was injected i.v. into experimental and control groups of mice. In untreated control mice, parasitemia rose regularly to 40 to 50% by day 3 post-infection and 70 to 80% by day 4 post-infection. The mice died between days 5 and 7 post-infection. Throughout the experiments, mice were kept in groups of three or five animals in Makrolon type II cages in an air-conditioned animal room at 22 to 23° C. A diet with p-aminobenzoic acid (PABA) of 45 mg (NAFAG FUTTER© food N° 9009 PAB-45) per kg of body weight, and tap water is available ad libitum.

OZ compounds were prepared at an appropriate concentration, either as a solution or a suspension containing SSV (0.5% w/v CMC, 0.5% v/v benzyl alcohol, 0.4% v/v Tween 80, and 0.9% w/v sodium chloride in water). They were administered per os (p.o.) in a total volume of 0.01 ml per gram of mouse. The activity of the compound was determined by a variety of methods outlined in subsequent sections. Survival time was also recorded, and survival to day 30 post-infection was considered to be a cure.

Determinations of 50, 90, and 99% effective doses ($ED_{50}$, $ED_{90}$, and $ED_{99}$, respectively) were determined after treatment with a single dose only. Mice were treated once on day 1 post-infection (24 h after infection). On day 3 post-infection (72 h after infection) blood smears of all animals were prepared and stained with Giemsa. Parasitemia was determined microscopically, and the difference between the mean value of the control group (taken as 100%) and those of the experimental groups was calculated and expressed as percent reduction. The $ED_{50}$, $ED_{90}$, and $ED_{99}$ values were calculated by non-linear fitting with statistical program and were expressed in mg/kg.

The first experiment conducted consisted of administration of a divided 3×10 mg/kg p.o. dose administered on days 1, 2, and 3 post-infection vs. a single 1×30 mg/kg po dose administered on day 1 post-infection. On day 4 post-infection, blood smears of all animals were prepared and stained with Giemsa. Parasitemia was determined microscopically, and the difference between the mean value of the control group (taken as 100%) and those of the experimental groups was calculated and expressed as percent reduction. Compounds were administered orally in the SSV vehicle. The results are shown in Table 7 below:

TABLE 7

| | 1 × 30 mg/kg | | | 3 × 10 mg/kg | | |
|---|---|---|---|---|---|---|
| | Activity (%) | Survival (days) | Cures | Activity (%) | Survival (days) | Cures |
| OZ | p.o. SSV | | | p.o. SSV | | |
| 209 | 100 | >30 | 0/5 | 100 | >30 | 3\3 |
| 271 | 99.97 | 14 | 0/5 | 100 | 27.8 | 4\5 |
| 277 | 99.92 | 10.4 | 0/5 | 100 | 27.6 | 4\5 |
| 279 | 99.95 | 14.8 | 0/5 | 100 | 25.4 | 3\5 |
| 301 | NA | NA | NA | 100 | >30 | 5\5 |
| 315 | NA | NA | NA | 100 | >30 | 5\5 |
| CQ | 99.94 | 9.5 | 0/5 | 99.99 | 14.3 | 0/5 |
| MFQ | 99.94 | 20.3 | 0/5 | 99.92 | 23.3 | 0/5 |
| AS | 83.83 | 9 | 0/5 | 98.62 | 11 | 0/5 |

As shown by Table 7, a 3×10 mg/kg dose of these trioxolanes cured between 3/5 and 5/5 of the infected mice. At this same dose, none of the standard antimalarial drugs cured any of the infected mice. At the 1×30 mg/kg dose, all tested trioxolanes showed activities >99.9% on day 3 post-treatment.

The second experiment consists of administration of divided 3×3 mg/kg and 3×1 mg/kg po doses administered on days 1, 2, and 3 post-infection. On day 4 post-infection, blood smears of all animals were prepared and stained with Giemsa. Parasitemia was determined microscopically, and the difference between the mean value of the control group (taken as 100%) and those of the experimental groups was calculated and expressed as percent reduction. Compounds were administered orally in the SSV vehicle. The results are shown in Table 8.

| | 3 × 3 mg/kg | | | 3 × 1 mg/kg | |
|---|---|---|---|---|---|
| | Activity (%) | Survival (days) | | Activity (%) | Survival (days) |
| OZ | p.o. SSV | | Cur s | p. . SSV | |
| 209 | 100 | 16.4 | 0\5 | 99.51 | 9.4 |
| 271 | 99.99 | 16.2 | 0\5 | 87 | 8.8 |
| 277 | 100 | 14 | 0\5 | 83 | 9.4 |
| 279 | 100 | 14.8 | 0\5 | 83 | 8.8 |

-continued

| | 3 × 3 mg/kg | | | 3 × 1 mg/kg | |
|---|---|---|---|---|---|
| | Activity (%) | Survival (days) | | Activity (%) | Survival (days) |
| OZ | p.o. SSV | | Cur s | p. . SSV | |
| 281 | 100 | 12.4 | 0\5 | 92 | 13 |
| 288 | 99 | 10.2 | 0\5 | 49 | 8.4 |
| 289 | 100 | 17.2 | 0\5 | 41 | 7.4 |
| 290 | 93 | 10.6 | 0\5 | 14 | 6.8 |
| 296 | 94 | 9.4 | 0\5 | 49 | 7.8 |
| 297 | 89 | 9.4 | 0\5 | 22 | 6.4 |
| 298 | 99.99 | 16.4 | 0\5 | 93 | 11 |
| 301 | 100 | 23 | 1\5 | 58 | 8.8 |
| 302 | 99.51 | 13.4 | 0\5 | 87 | 13.4 |
| 305 | 99.91 | 12.2 | 0\5 | 87 | 9.6 |
| 306 | 99.75 | 7.6 | 0\5 | 85 | 11 |
| 309 | 99 | 9.2 | 0\5 | 66 | 9.4 |
| 315 | 99.99 | 22 | 0\5 | 81 | 12.2 |
| 317 | 100 | 16.8 | 0\5 | 73 | 11.4 |
| 319 | 99.97 | 11.2 | 0\5 | 92 | 13 |
| 320 | 96 | 9.6 | 0\5 | 50 | 8.6 |
| 323 | 99.95 | 14.4 | 0\5 | 66 | 14.4 |
| 329 | 100 | 27 | 2\5 | 99.86 | 11 |
| 330 | 99 | 12.6 | 0\5 | 45 | 9.2 |
| 333 | 99 | 10.2 | 0\5 | 64 | 9.4 |
| 335 | 99.99 | 15.4 | 0\5 | 98 | 10 |
| 336 | 100 | 20.8 | 0\5 | 99.14 | 10.4 |
| 337 | 99.98 | 14.4 | 0\5 | 96 | 9.4 |
| 338 | 100 | 25.6 | 0\5 | 98 | 9.4 |
| 339 | 100 | 27 | 3\5 | 97 | 9.2 |
| CQ | 99.54 | 10 | 0\5 | 25 | 7.2 |
| MFQ | 98 | 12 | 0\5 | 2 | 6.2 |
| AM | 86 | 9.4 | 0\5 | 51 | 7.2 |
| AS | 78 | 9.4 | 0\5 | 39 | 6.8 |

As shown by Table 8, at the 3×3 mg/kg dose, ten trioxolanes, together with the previously reported OZ209, had activities of 100% and produced high survival numbers. Of these, OZ301, OZ329, and OZ339 cured 1/5, 2/5, and 3/5 of the infected mice, respectively. At the 3×1 mg/kg dose, most of the trioxolanes were more potent than the reference antimalarial drugs; ten of these had activities >90%. OZ209, OZ329, and OZ336 were the only trioxolanes with activities greater than 99% at the 3×1 mg/kg dose.

Prophylactic activities of the compounds were compared after administering po single dose of 100 mg/kg to different groups of five animals at various times before infection. All groups including an untreated control group, were then infected at the same time. Parasitemia was determined for each animal on day 3 post-infection, and percent of reduction of the level of parasitemia compared to levels for animals given no drug is determined. The results are shown in Table 10.

TABLE 9

| | AM | AS | CQ | MFQ | 209 | 256 | 271 | 277 | 279 | 281 |
|---|---|---|---|---|---|---|---|---|---|---|
| | | | Prophylactic Activity (%) | | | | | | | |
| 72 h - | | | | 99.97 | 99.92 | 13 | 99.89 | 9 | 14 | 8 |
| 48 h - | | | 57.49 | 99.92 | 99.9 | 29 | 99.98 | 7 | 27 | 45 |
| 24 h - | 0 | 6.28 | 99.92 | 100 | 100 | 82 | 100 | 25 | 97 | 99.23 |
| 0 h | 100 | 92.44 | 100 | 100 | 100 | 100 | 100 | 100 | 100 | 100 |

The unique prophylactic property of OZ209 (3-day protection, same as MFQ) was found also for OZ271.

It should be appreciated that the Spiro and dispiro 1,2,4-trioxolane compositions of this invention may contain trioxolanes within the scope of the formulas described above, or prodrugs or analogues of these compounds or a racemic mixture of either the D or the L form. The invention is also intended to include all biologically active salt forms of the compounds. Also, minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

All articles cited herein and in the following list are hereby expressly incorporated in their entirety by reference.

CITATIONS de Almeida Barbosa, L.-C. et al., The Design, Synthesis and Biological Evaluation of Some Stable Ozonides With Anti-malarial Activity. *J. Chem. Soc. Perkin Trans. I*, 1996, 1101–1105.

de Almeida Barbosa, L.-C. et al., Synthesis of Some Stable Oozonides With Anti-malarial Activity. *J. Chem. Soc. Perkin Trans. I*, 1992, 3251–3252.

Cammenga, H. K. et al., Basic principles of thermoanalytical techniques and their applications in preparative chemistry. *Angew. Chem. Int. Ed. Engl.* 1995, 34, 1171–1187.

Cumming, J. N. et al., Antimalarial activity of artemisinin (qinghaosu) and related trioxanes: mechanism(s) of action. *Adv. Pharmacol.* 1997. 37, 254–297.

Dhingra, V. K. et al., Current Status of Artemisinin and Its Derivatives As Antimalarial Drugs. *Life Sci.* 2000, 66, 279–300.

Dong, Y.; Vennerstrom, J. L Peroxidic Antimalarials. *Expert Opin. Ther. Patents* 2001, 11, 1753–1760.

Fishwick, J., et al., The Toxicity of Artemisinin and Related Compounds on Neuronal and Glial Cells in Culture. *Chem.-Biol. Interact.* 1995, 96, 263–271.

Griesbaum, K. et al., Diozonides from coozonolyses of suitable O-methyl oximes and ketones. *Tetrahedron* 1997a, 53, 5463–5470.

Griesbaum, K. et al., Ozonolyses of O-alkylated ketoximes in the presence of carbonyl groups: a facile access to ozonides. *Liebigs Ann./Recueil.* 1997b, 1381–1390.

Jefford, C. Peroxidic Antimalarials. *Adv. Drug Res.* 1997, 29, 271–325.

Kashima, C. et al., Ozonolysis of Five-Membered Heterocycles. *J. Het. Chem.* 1987, 24, 637–639.

Meshnick, S. R. et al., Artemisinin and the antimalarial endoperoxides: from herbal remedy to targeted chemotherapy. *Microbiol. Rev.* 1996, 60, 301–315.

Park, B. K. et al., Safety Assessment of Peroxide Antimalarials: Clinical and Chemical Perspectives. *Br. J. Clin. Pharmacol.* 1998, 46, 521–529.

Titulaer, H. A. C., Zuidema, J., and Lugt, C. B. Formulation and pharmacokinetics of artemisinin and its derivatives. *Int. J. Pharmaceut.* 1991, 69, 83–92.

van Agtmael, M. A. et al., Artemisinin Drugs In the Treatment of Malaria: From Medicinal Herb to Registered Medication. *Trends Pharmacol. Sci.* 1999, 20, 199–205.

Vennerstrom, J. L. et al., Synthesis and Antimalarial Activity of Sixteen Dispiro-1,2,4,5-tetraoxane Analogs of WR 148999: Alkyl Substituted 7,8,15,16-Tetraoxadispiro [5.2.5.2]hexadecanes. *J. Med. Chem.* 2000, 43, 2753–2758.

Vroman, J. A. et al., Current Progress in the Chemistry, Medicinal Chemistry and Drug Design of Artemisinin Based Antimalarials. *Curr. Pharm. Design* 1999, 5, 101–138.

Wesche, D. L. et al., Neurotoxicity of artemisinin analogs in vitro. *Antimicrob. Agents. Chemother.* 1994, 38, 1813–1819.

White, N. J. Clinical pharmacokinetics and pharmacodynamics of artemisinin and derivatives. *Trans. R. Soc. Trop. Med. Hyg.* 1994, 88, 41–43.

What is claimed is:

1. A spiro or dispiro 1,2,4-trioxolane having the following structure:

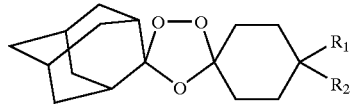

wherein $R_1$ and $R_2$ are the same or different, and are selected from the group consisting of hydrogen, substituted or unsubstituted linear or branched alkyl, aryl, and alkaryl groups and substituted or unsubstituted alicyclic groups that are optionally interrupted by one or more oxygen, sulfur or nitrogen atoms, substituted or unsubstituted aromatic or heterocyclic groups that may be interrupted by one or more oxygen, sulfur or nitrogen atoms, a hydroxy group, and a halogen, and further providing that the spirocyclohexyl ring attaching $R_1$ and $R_2$ are optionally interrupted by one or more oxygen, sulfur, or nitrogen atoms.

2. The trioxolane of claim 1 whereby $R_1$ is hydrogen and $R_1$ is $(CH_2)_n$—Y; whereby Y is a functional group selected from the group consisting of an alkyl, ketone, acid, alcohol, amine, amide, sulfonamide, guanidine, ether, ester, oxime, urea, oxime ether, sulfone, lactone, carbamate, semicarbazone, phenyl, and heterocycle; and n is an integer.

3. The trioxolane of claim 2 whereby Y is a non-acidic functional group.

4. The trioxolane of claim 3 whereby Y is a weak base.

5. The trioxolane of claim 2 whereby n=1.

6. The spiro or dispiro 1,2,4-trioxolane of claim 1 wherein the 1,2,4-trioxolane is selected from the group consisting of OZ271, OZ277, OZ281, OZ279, OZ288, OZ289, OZ290, OZ296, OZ297, OZ298, OZ301, OZ305, OZ309, OZ315, OZ317, OZ319, OZ320, OZ323, OZ329, OZ333, OZ335, OZ336, OZ337, OZ338, and OZ339.

7. The spiro or dispiro 1,2,4-trioxolane of claim 6 wherein the 1,2,4-trioxolane is selected from the group consisting of OZ271, OZ277, OZ279, OZ301, OZ305, OZ315, OZ317, OZ319, OZ323, OZ329, OZ338, and OZ339.

8. Cis-adamantane-2-spiro-3-8'-[[[(2'-amino-2'-methylpropyl)amino]carbonyl]methyl]-1',2',4'-trioxaspiro[4.5]decane p-tosylate.

9. Cis-adamantane-2-spiro-3'-8'-[(1'-piperazinylcarbonyl)methyl]-1',2',4'-trioxaspiro[4.5]decane p-tosylate.

10. Cis-Adamantane-2-spiro-3'-8'-[[(1-piperazinylcarbonyl)amino]methyl]-1',2',4'-trioxaspiro[4.5]decane p-tosylate.

11. Cis-Adamantane-2spiro-3'-8'-[[(4'-amino-1'-piperidinyl)carbonyl[methyl]-1',2',4'-trioxaspiro[4.5]decane p-tosylate.

12. A pharmaceutical composition for prophylaxis and treatment of malaria comprising: a malaria prophylaxis or malaria treatment-effective amount of a spire or dispiro 1,2,4-trioxolane, its prodrugs and optical isomers thereof, and a pharmaceutically acceptable carrier, said trioxolane having the following structure:

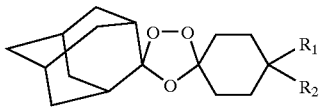

wherein $R_1$ and $R_2$ are the same or different, and are selected from the group consisting of hydrogen, substituted or unsubstituted linear or branched alkyl, aryl, and alkaryl groups and substituted or unsubstituted alicyclic groups that are optionally interrupted by one or more oxygen, sulfur or nitrogen atoms, substituted or unsubstituted aromatic or heterocyclic groups that may be interrupted by one or more oxygen, sulfur or nitrogen atoms, a hydroxy group, and a halogen, and further providing that the spirocyclohexyl ring attaching $R_1$ and $R_2$ are optionally interrupted by one or more oxygen, sulfur, or nitrogen atoms.

13. The pharmaceutical composition of claim 12 whereby $R_1$ is hydrogen and $R_2$ is $(CH_2)_n$—Y; whereby Y is a functional group selected from the group consisting of an alkyl, ketone, acid, alcohol, amine, amide, sulfonamide, guanidine, ether, ester, oxime, urea, oxime ether, sulfone, lactone, carbamate, semicarbazone, phenyl, and heterocycle; and n is an integer.

14. The pharmaceutical composition of claim 13 whereby Y is a non-acidic functional group.

15. The pharmaceutical composition of claim 13 whereby Y is a weak base.

16. The pharmaceutical composition of claim 15 whereby Y is an amide.

17. The pharmaceutical composition of claim 13 whereby n=1.

18. The pharmaceutical composition of claim 12 wherein the trioxolane is selected from the group consisting of OZ271, OZ277, OZ281, OZ279, OZ288, OZ289, OZ290, OZ296, OZ297, OZ298, OZ301, OZ305, OZ309, OZ315, OZ317, OZ319, OZ320, OZ323, OZ329, OZ333, OZ335, OZ336, OZ337, OZ338, and OZ339.

19. The pharmaceutical composition of claim 18 wherein the trioxolane is selected from the group consisting of OZ271, OZ277, OZ279, OZ301, OZ305, OZ315, OZ317, OZ319, OZ323, OZ329, OZ338, and OZ339.

20. The pharmaceutical composition of claim 12 wherein the 1,2,4-trioxolane is cis-adamantane-2-spiro-3'-8'-[[[(2'-amino-2'-methylpropyl)amino]carboxyl]methyl]-1',2',4'-trioxaspiro[4.5]decane p-tosylate.

21. The pharmaceutical composition of claim 12 wherein the 1,2,4-trioxolane is cis-adamantane-2-spiro-3'-8'-[-(1'-piperazinylcarbonyl)methyl]-1',2',4'-trioxaspiro[4.5]decane p-tosylate.

22. The pharmaceutical composition of claim 12 that is suitable for administration by a method selected from the group consisting of oral, subcutaneous, intravenous, intranasal, rectal, sublingual, and buccal.

23. A method of preventing or treating malaria comprising: administrating a malaria prevention or malaria treatment effective amount of a spiro or dispiro 1,2,4-trioxolane in a pharmaceutically acceptable carrier, said trioxolane having the following structure:

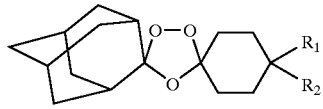

wherein $R_1$ and $R_2$ are the same or different, and are selected from the group consisting of hydrogen, substituted or unsubstituted linear or branched alkyl, aryl, and alkaryl groups and substituted or unsubstituted alicyclic groups that are optionally interrupted by one or more oxygen, sulfur or nitrogen atoms, substituted or unsubstituted aromatic or heterocyclic groups that are optionally interrupted by one or more oxygen, sulfur or nitrogen atoms, a hydroxy group, and a halogen, and further providing that the spirocyclohexyl ring attaching $R_1$ and $R_2$ may be interrupted by one or more oxygen, sulfur, or nitrogen atoms.

24. The method of claim 23 whereby $R_1$ is hydrogen and $R_2$ is $(CH_2)_n$—Y; whereby Y is a functional group selected from the group consisting of an alkyl, ketone, acid, alcohol, amine, amide, sulfonamide, guanidine, ether, ester, oxime, urea, oxime ether, sulfone, lactone, carbamate, semicarbazone, phenyl, and heterocycle; and n is an integer.

25. The method of claim 23 wherein the trioxolane is administered in a dose of between about 0.1–1000 mg/kg/day.

26. The method of claim 25 wherein the trioxolane is administered in a dose of between about 1–100 mg/kg/day.

27. The method of claim 23 wherein the trioxolane is administered in a single dose.

28. The method of claim 23 wherein the trioxolane is administered in divided doses.

29. The method of claim 23 wherein the trioxolane is administered in a malaria-preventive dose beginning 1–2 weeks prior to malaria exposure and ending 1–2 weeks post exposure.

30. A method of claim 23 wherein the trioxolane is administered in a malaria-curative dose over 1–10 days.

31. A method of manufacturing a composition for prophylaxis and treatment of malaria comprising: mixing a malaria prophylaxis or malaria treatment-effective amount of a spiro or dispiro 1,2,4-trioxolane, its prodrugs and optical isomers thereof, with a pharmaceutically acceptable carrier, said trioxolane having the following structure:

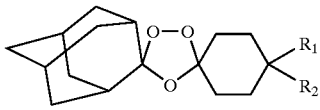

wherein $R_1$ and $R_2$ are the same or different, and are selected from the group consisting of hydrogen, substituted or unsubstituted linear or branched alkyl, aryl, and alkaryl groups and substituted or unsubstituted alicyclic groups that are optionally interrupted by one or more oxygen, sulfur or nitrogen atoms, substituted or unsubstituted aromatic or heterocyclic groups that are optionally interrupted by one or more oxygen, sulfur or nitrogen atoms, a hydroxy group, and a halogen, and further providing that the spirocyclohexyl ring attaching $R_1$ and $R_2$ may be interrupted by one or more oxygen, sulfur, or nitrogen atoms.

32. A method of prophylaxis or treatment of schistosomiasis comprising: administering a schistosomiasis prophylaxis or treatment effective amount or a spiro or dispiro 1,2,4-trioxolane in a pharmaceutically acceptable carrier, said trioxolane having the following structure:

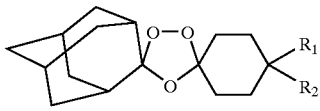

wherein $R_1$ and $R_2$ are the same or different, and are selected from the group consisting of hydrogen, substituted or unsubstituted linear or branched alkyl, aryl, and alkaryl groups and substituted or unsubstituted alicyclic groups that are optionally interrupted by one or more oxygen, sulfur or nitrogen atoms, substituted or unsubstituted aromatic or heterocyclic groups that are optionally interrupted by one or more oxygen, sulfur or nitrogen atoms, a hydroxy group, and a halogen, and further providing that the spirocyclohexyl ring attaching $R_1$ and $R_2$ may be interrupted by one or more oxygen, sulfur, or nitrogen atoms.

33. A method of synthesizing a dispiro 1,2,4-trioxolane comprising: treating a trioxolane having the following structure:

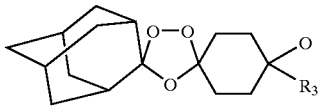

wherein $R_3$ is selected from the group consisting of a ketone, an aldehyde, an ester, and a phthalimide with one or more reagents selected from the group consisting of an oxidizing agent, reducing agent, hydroxylamine, hydrazine, diol, alcohol, heteroaryllithium, aryllithium, alkyllithium, hydrolyzing agent, and deprotecting agent to form a compound selected from the group consisting of lactone, alcohol, oxime ether, hydrazone, ketal, acetal, amine, and acid.

34. The method of claim 33 wherein the trioxolane has a ketone or an aldehyde functional group, and is treated with an oxidizing agent to form a lactone or an acid.

35. The method of claim 34 wherein the trioxolane has a ketone or an aldehyde functional group and is treated with a reducing agent to form an amine or an alcohol.

36. The method of claim 34 wherein the trioxolane has a ketone or an aldehyde functional group, and is treated with a hydroxylamine or a hydrazine to form an oxime ether or a hydrazone, respectively.

37. The method of claim 33 wherein the trioxolane has a ketone or an aldehyde functional group, and is treated with one or more diols and/or alcohols to form a ketal or acetal.

38. The method of claim 34 whereby the trioxolane is OZ05.

39. The method of claim 38 whereby OZ05 is treated with a heteroaryllithium, aryllithium, or alkyllithium reagent to form the corresponding tertiary alcohol.

40. The method of claim 35 wherein the trioxolane has an ester functional group, and is treated with a reducing agent to form an alcohol.

41. The method of claim 40 whereby the trioxolane is selected from the group consisting of OZ70 and OZ61.

42. The method of claim 41 whereby OZ70 is treated with a reducing agent to form OZ119.

43. The method of claim 41 whereby OZ61 is treated with a reducing agent to form OZ89.

44. The method of claim 37 wherein the trioxolane has an ester functional group, and is treated with a hydrolyzing agent to form an acid.

45. The method of claim 44 wherein the hydrolyzing agent is aqueous potassium hydroxide.

46. The method of claim 44 wherein OZ61 is treated with a hydrolyzing agent to form OZ78.

47. The method of claim 33 wherein the trioxolane has a phthalimide functional group, and is treated with a deprotecting reagent to form an amine.

48. The method of claim 47 whereby the phthalimide is selected from the group consisting of OZ136, OZ146, and OZ167.

49. The method of claim 48 whereby OZ136 is treated with a deprotecting reagent to form OZ137.

50. The method of claim 48 whereby OZ146 is treated with a deprotecting reagent to form OZ181.

51. The method of claim 50 whereby OZ167 is treated with a deprotecting reagent to form OZ269.

52. The method of claim 51 wherein the deprotecting reagent is hydrazine.

53. A spiro or dispiro 1,2,4-trioxolane having the following structure:

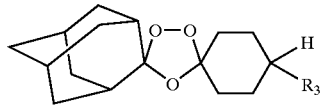

whereby $R_3$ is $(CH_2)_n$—Y, and further providing that Y is a weak base amide; and n is an integer.

54. The trioxolane of claim 53 whereby n=1.

* * * * *